(12) United States Patent
Jeon et al.

(10) Patent No.: US 8,071,227 B2
(45) Date of Patent: Dec. 6, 2011

(54) COMPOUNDS AND ORGANIC LIGHT EMITTING DIODE USING THE SAME

(75) Inventors: Byung-Sun Jeon, Seoul (KR); Wook-Dong Cho, Daejeon Metropolitan (KR); Jeung-Gon Kim, Daejeon Metropolitan (KR); Sang-Young Jeon, Daejeon Metropolitan (KR); Yeon-Hwan Kim, Goyang-si (KR)

(73) Assignee: LG Chem, Ltd., Seoul (KR)

( * ) Notice: Subject to any disclaimer, the term of this patent is extended or adjusted under 35 U.S.C. 154(b) by 389 days.

(21) Appl. No.: 12/312,856

(22) PCT Filed: Dec. 3, 2007

(86) PCT No.: PCT/KR2007/006178
§ 371 (c)(1),
(2), (4) Date: May 29, 2009

(87) PCT Pub. No.: WO2008/066358
PCT Pub. Date: Jun. 5, 2008

(65) Prior Publication Data
US 2010/0065828 A1    Mar. 18, 2010

(30) Foreign Application Priority Data

Dec. 1, 2006  (KR) .................. 10-2006-0120557

(51) Int. Cl.
*H01L 51/54* (2006.01)

(52) U.S. Cl. ........ 428/690; 313/504; 313/505; 313/506; 546/42

(58) Field of Classification Search ................. 428/690; 313/504, 505, 506; 546/42
See application file for complete search history.

(56) References Cited

U.S. PATENT DOCUMENTS

| 6,998,487 B2 | 2/2006 | Kim et al. |
| 7,138,483 B2 | 11/2006 | Wang et al. |
| 2002/0107405 A1 | 8/2002 | Lin et al. |

FOREIGN PATENT DOCUMENTS

EP    1 671 998    6/2006

OTHER PUBLICATIONS

Jiang et. al., Diarylmethylene-bridged 4,4'-(bis(9-carbazoyl))biphenyl :morphological stable host material for highly efficient electrophosphorescene, 2009, J. of Materials Chemistry, vol. 19, pp. 7661-7665.*

* cited by examiner

*Primary Examiner* — Jennifer Chriss
*Assistant Examiner* — Gregory Clark
(74) *Attorney, Agent, or Firm* — McKenna Long & Aldridge LLP

(57) ABSTRACT

Disclosed are new compounds and an organic light emitting diode using the same. The organic light emitting diode using the new compound according to the present invention exhibits excellent characteristics in terms of actuating voltage, light efficiency, and lifespan.

16 Claims, 1 Drawing Sheet

[Fig. 1]
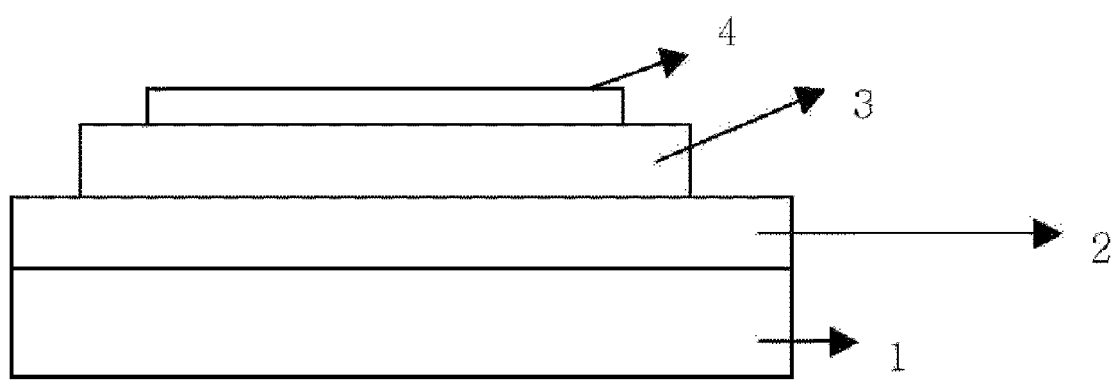
[Fig. 2]
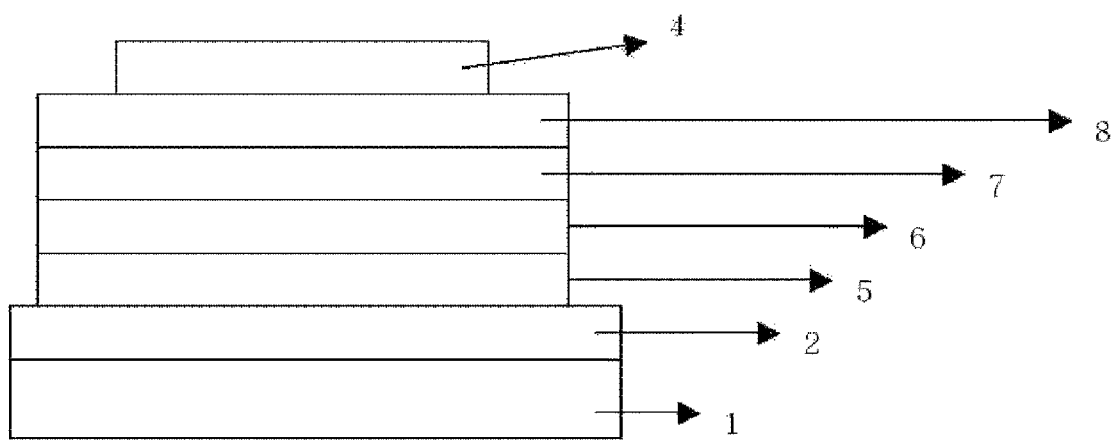

COMPOUNDS AND ORGANIC LIGHT EMITTING DIODE USING THE SAME

TECHNICAL FIELD

The present invention relates to new compounds which are capable of significantly improving a lifespan, efficiency, electrochemical stability and thermal stability of an organic light emitting diode, and an organic light emitting diode in which the compound is contained in an organic compound layer.

This application is a national phase application of International Application No. PCT/KR2007/006178 filed on Dec. 3, 2007, which claims priority to Korean Patent Application No. 10-2006-0120557 filed on Dec. 1, 2006, both of which are incorporated by reference for all purposes, as if fully set forth herein.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting diode which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting diode are mostly pure organic materials or complexes of organic material and metal. The material used in the organic light emitting diode may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting diode further have the following properties.

First, it is preferable that the material used in the organic light emitting diode have excellent thermal stability. The reason is that joule heat is generated by movement of electric charges in the organic light emitting diode. NPB (N,N-di(naphthalene-1-yl)-N,N-diphenyl-benzidene), which has recently been used as the hole transport layer material, has a glass transition temperature of 100° C. or lower, thus it is difficult to apply to an organic light emitting diode requiring a high current.

Second, in order to produce an organic light emitting diode that is capable of being actuated at low voltage and has high efficiency, holes and electrons which are injected into the organic light emitting diode must be smoothly transported to a light emitting layer, and must not be released out of the light emitting layer. To achieve this, a material used in the organic light emitting diode must have a proper band gap and a proper HOMO (highest occupied molecular orbital) or LUMO (lowest unoccupied molecular orbital) energy levels. A LUMO energy level of PEDOT (poly(3,4-ethylenedioxythiophene)):PSS (poly(styrenesulfonate)), which is currently used as a hole transport material of an organic light emitting diode produced using a solution coating method, is lower than that of an organic material used as a light emitting layer material, thus it is difficult to produce an organic light emitting diode having high efficiency and a long lifespan.

Moreover, the material used in the organic light emitting diode must have excellent chemical stability, electric charge mobility, and interfacial characteristic with an electrode or an adjacent layer. That is to say, the material used in the organic light emitting diode must be little deformed by moisture or oxygen. Furthermore, proper hole or electron mobility must be assured so as to balance densities of the holes and of the electrons in the light emitting layer of the organic light emitting diode to maximize the formation of excitons. Additionally, it has to be able to have a good interface with an electrode including metal or metal oxides so as to assure stability of the device.

Accordingly, there is a need to develop an organic material having the above-mentioned requirements in the art.

DISCLOSURE OF INVENTION

Technical Problem

Therefore, an object of the present inventions is to provide a new compound which is capable of satisfying conditions required of a material usable for an organic light emitting diode, for example, a proper energy level, electrochemical stability, and thermal stability, and which has a chemical structure capable of playing various roles required in the organic light emitting diode, depending on a substituent group, and an organic light emitting diode containing the same.

Technical Solution

The present invention provides a new compound represented by the following Formula 1.

[Formula 1]

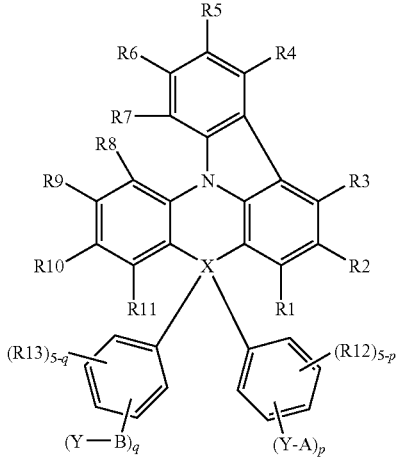

wherein, X is C or Si,

Ys may be the same or different from each other, and may be each independently directly connected to each other; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups, R1 to R11 may be the same or different from each other, and each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R12 and R13 may be the same or different from each other, and each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R7 and R8 may be directly connected to each other, or may form a condensation ring along with a group selected from the group consisting of O, S, NR, PR, C=O, CRR' and SiRR' in which R and R' are the same or different from each other, each in dependently hydrogen, a substituted or unsubstituted alkyl group, a substituted or un-substituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound, p and q may be each independently an integer of 1 to 5, with the proviso that when p is an integer of 2 or more, q is 1, and when q is an integer of 2 or more, p is 1, A is

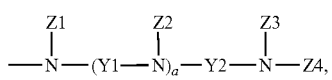

B is

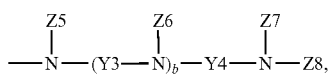

a and b may be each independently an integer of 0 to 10,

Y1 to Y4 may be the same or different from each other, and each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy and amino groups, and Z1 to Z8 may be the same or different from each other, and each independently hydrogen; aliphatic hydrocarbons having 1 to 20 carbon atoms; aromatic hydrocarbons; aromatic hydrocarbons which are substituted with at least one substituent group selected from the group consisting of nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of nitro, nitrile, halogen, alkyl, alkoxy, amino, aromatic hydrocarbon, and heterocyclic groups; a thiophene group which is substituted with aliphatic hydrocarbons having 1 to 20 carbon atoms or aromatic hydrocarbons having 6 to 20 carbon atoms; or a boron group which is substituted with aromatic hydrocarbons.

Further, the present invention provides an organic light emitting diode which comprises a first electrode, at least one organic material layer, and a second electrode, wherein the first electrode, the organic material layer(s), and the second electrode form a layered structure and at least one layer of the organic material layers includes a compound represented by Formula 1 of the present invention.

Advantageous Effects

The compound of the present invention can be used as an organic material layer material, particularly, hole injection and/or transport materials in an organic light emitting diode, and when applied to an organic light emitting diode it is possible to reduce the actuating voltage of the device, to improve the light efficiency thereof, and to improve the lifespan of the device through the thermal stability of the compound.

BRIEF DESCRIPTION OF THE DRAWINGS

FIG. 1 illustrates an example of an organic light emitting diode comprising a substrate 1, an anode 2, a light emitting layer 3, and a cathode 4; and FIG. 2 illustrates an example of an organic light emitting diode comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Substituent groups of Formula 1 will be described in detail, below.

In Y and Y1 to Y4 of Formula 1, examples of the bivalent aromatic hydrocarbons include monocyclic aromatic rings such as phenylene, biphenylene and terphenylene, and multicyclic aromatic rings such as naphthylene, anthracenylene, pyrenylene and perylenylene, but are not limited thereto.

In Y and Y1 to Y4 of Formula 1, examples of the bivalent heterocyclic group include thiophenylene, furylene, pyrrolylene, imidazolylene, thiazolylene, oxazolylene, oxadiazolylene, thiadiazolylene, triazolylene, pyridylene, pyridazylene, pyrazinylene, quinolylene and isoquinolylene, but are not limited thereto.

In Z1 to Z8 of Formula 1, examples of the aromatic hydrocarbons include monocyclic aromatic rings such as phenyl, biphenyl and terphenyl, and multicyclic aromatic rings such as naphthyl, anthracenyl, pyrenyl and perylenyl, but are not limited thereto.

In Z1 to Z8 of Formula 1, examples of the heterocyclic group include thiophene, furan, pyrrole, imidazole, thiazole, oxazole, oxadiazole, thiadiazole, triazole, pyridyl, pyridazyl, pyrazine, quinoline and isoquinoline, but are not limited thereto.

In Z1 to Z8 of Formula 1, aliphatic hydrocarbons having 1 to 20 carbon atoms include straight chain aliphatic hydrocarbons, branched chain aliphatic hydrocarbons, saturated aliphatic hydrocarbons, and unsaturated aliphatic hydrocarbons. They are exemplified by an alkyl group such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond such as styryl; and an alkynyl group having a triple bond such as an acetylene group, but are not limited thereto.

In R1 to R13 of Formula 1, the carbon number of the alkyl, alkoxy, and alkenyl groups is not limited, but is preferably 1 to 20.

The length of the alkyl group contained in the compound does not affect the conjugation length of the compound, but may affect the method of applying the compound to the organic light emitting diode, for example, a vacuum deposition method or a solution coating method.

In R1 to R13 of Formula 1, examples of the aryl group include monocyclic aromatic rings such as a phenyl group, a biphenyl group, a terphenyl group, and a stilbene group, and multicyclic aromatic rings such as a naphthyl group, an anthracenyl group, a phenanthrene group, a pyrenyl group, and a perylenyl group, but are not limited thereto.

In R1 to R11 of Formula 1, examples of the arylamine group include a diphenylamine group, a dinaphthylamine group, a dibiphenylamine group, a phenyl-naphthylamine group, a phenyldiphetylamine group, a ditolylamine group, a phenyl-tolylamine group, a carbazolyl group, and a triphenylamine group, but are not limited thereto.

In R1 to R13 of Formula 1, examples of the heterocyclic group include a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, and an acridyl group, but are limited thereto.

In R1 to R13 of Formula 1, if the alkyl, alkoxy, alkenyl, aryl, arylamine, and heterocyclic groups have other substituent group, the substituent group may be aliphatic hydrocarbons having 1 to 20 carbon atoms, an alkoxy group, an arylamine group, an aryl group, a heterocyclic group, a nitrile group, an acetylene group or the like.

In addition, in R1 to R13 of Formula 1, specific examples of the alkenyl, aryl, arylamine, and heterocyclic groups include compounds shown in the following Formulae, but are not limited thereto.

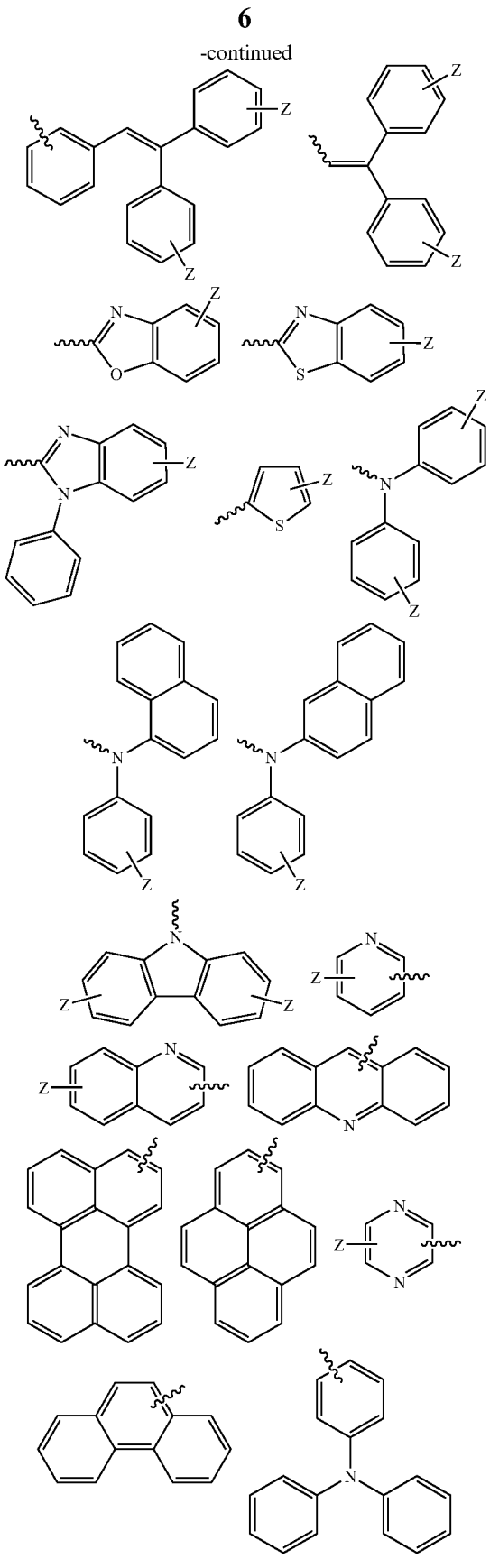

In the above Formulae, Z is a group selected from the group consisting of hydrogen, aliphatic hydrocarbons having 1 to 20 carbon atoms, an alkoxy group, an arylamine group, an aryl group, a heterocyclic group, a nitrile group, and an acetylene group. Specific examples of the arylamine, aryl, and heterocyclic groups of Z are as shown in the above-mentioned substituent groups of R1 to R13.

According to a preferred embodiment of the present invention, in Formula 1, X is C, R7 and R8 may be directly connected to each other, or form a condensation ring along with a group selected from the group consisting of O, S, NR, PR, C=O, CRR' and SiRR' (R and R' are as defined in Formula 1).

According to another preferred embodiment of the present invention, in Formula 1, X is Si, R7 and R8 may be directly connected to each other, or form a condensation ring along with a group selected from the group consisting of O, S, NR, PR, C=O, CRR' and SiRR' (R and R' are as defined in Formula 1).

According to still another preferred embodiment of the present invention, the compound of Formula 1 can be represented by any one of the following Formulae 2 to 7.

[Formula 2]

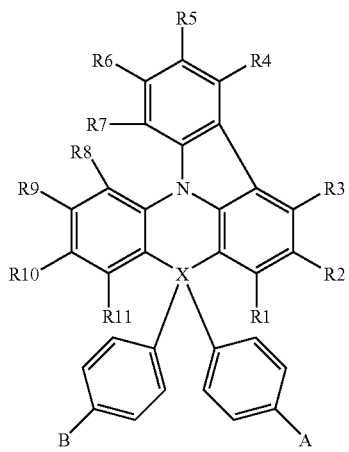

[Formula 3]

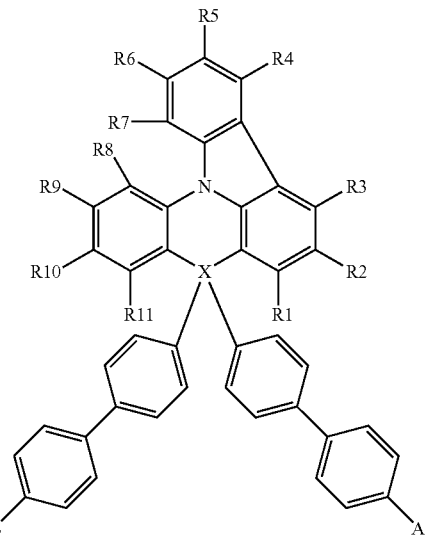

[Formula 4]

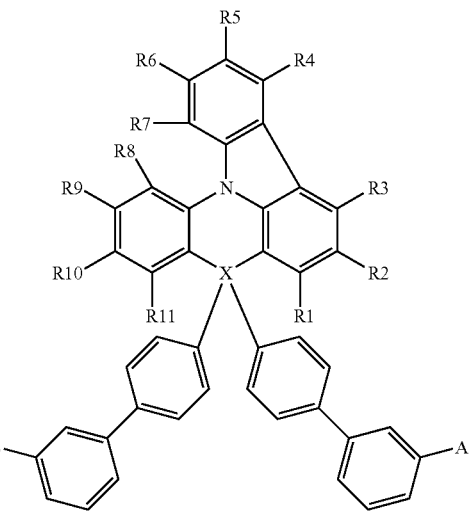

[Formula 5]

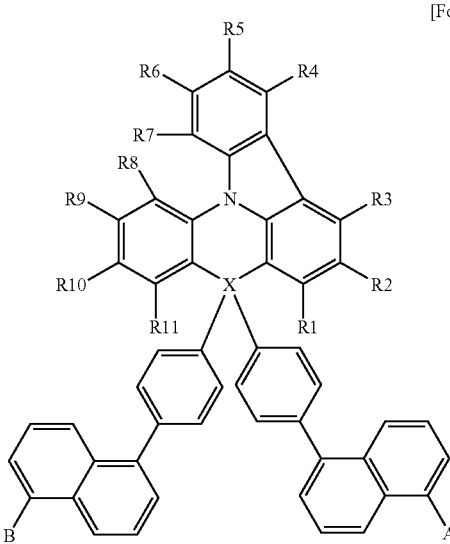

[Formula 6]

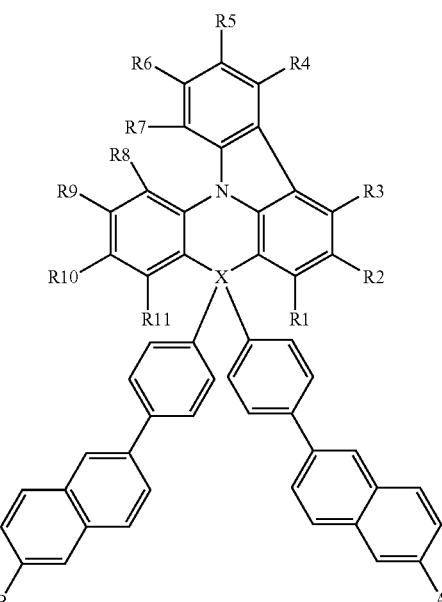

[Formula 7]
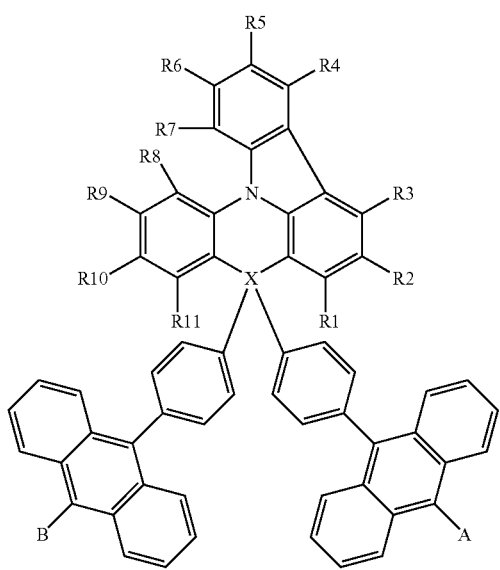
In the above Formulae 2 to 7, X, R1 to R11, A and B are as defined in Formula 1.
Examples of A and B groups of Formula 1 are preferably as follows, but are not limited thereto. Combination of the compounds of Formulae 2 to 7 and the following groups can form various derivative compounds.
1
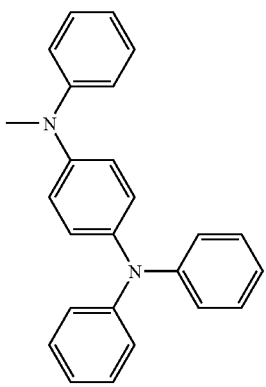
2
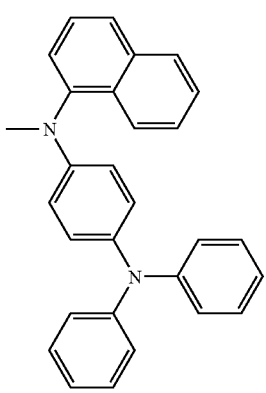
3
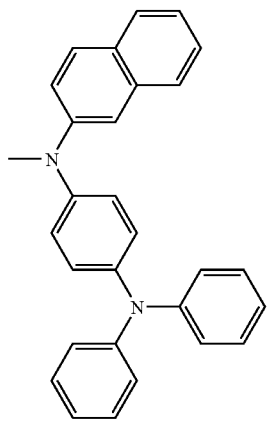
4
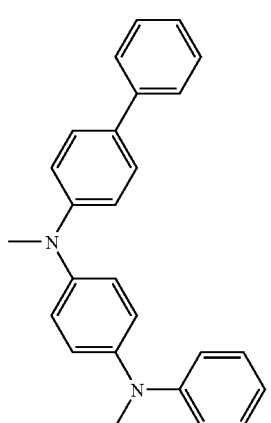
5
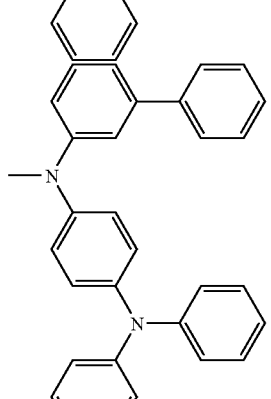
6
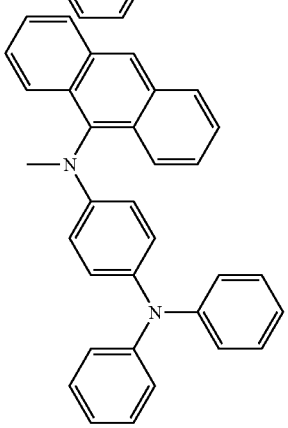

7
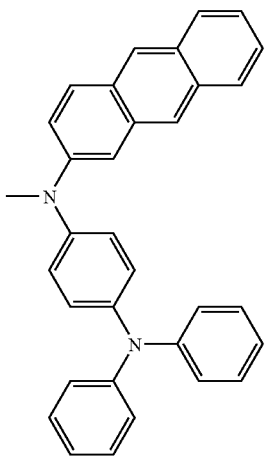
8
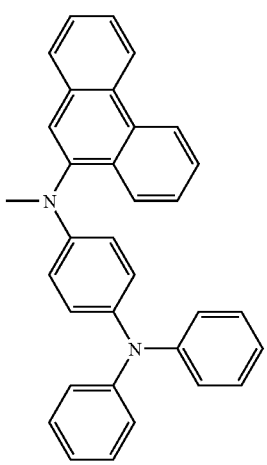
9
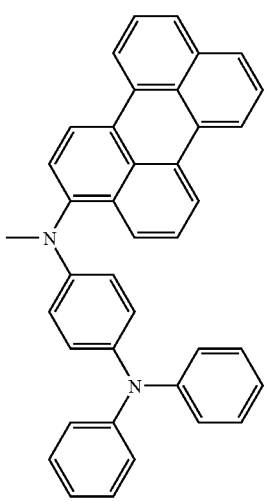
10
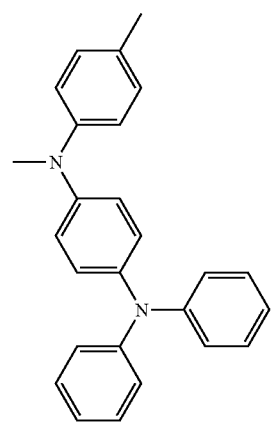
11
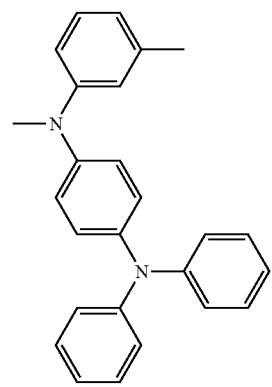
12
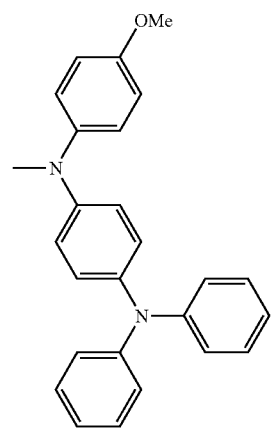
13
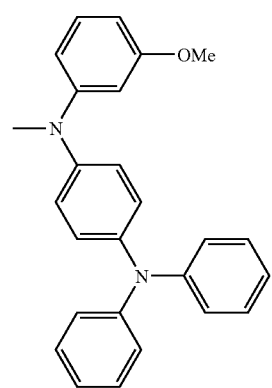

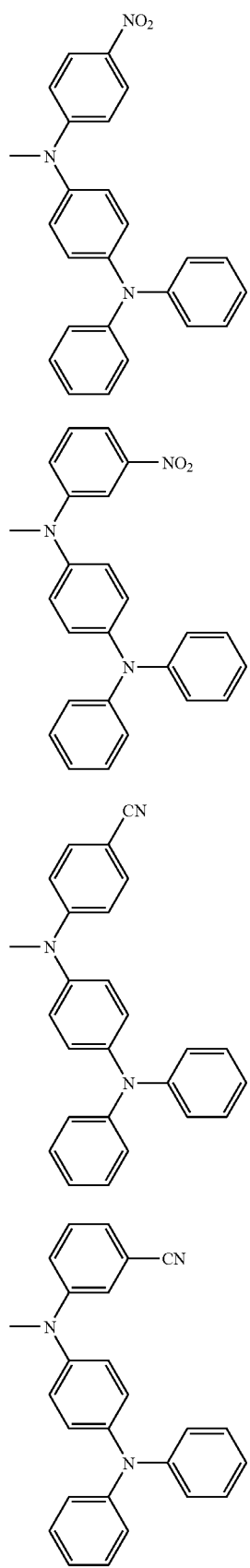
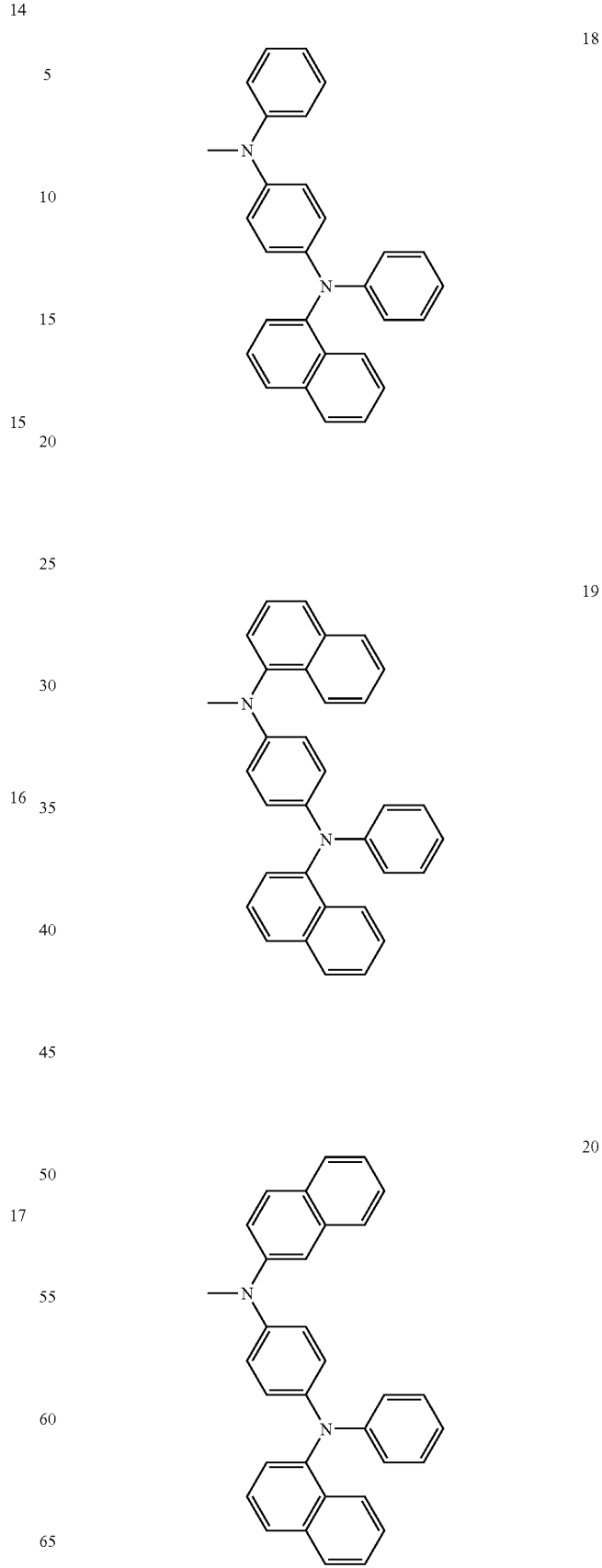

21
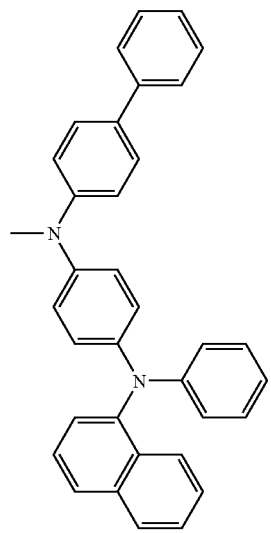
22
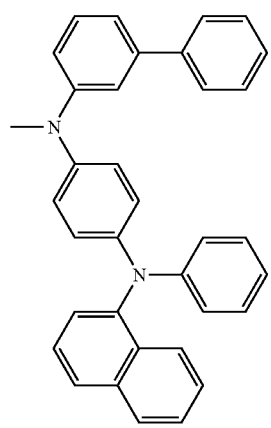
23
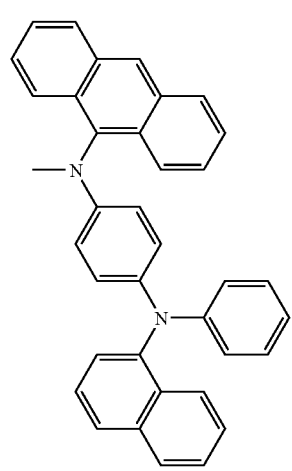
24
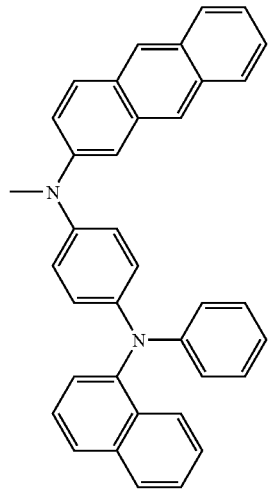
25
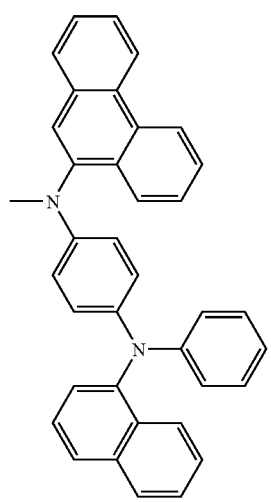
26
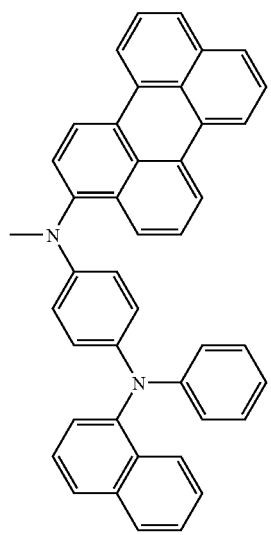

27
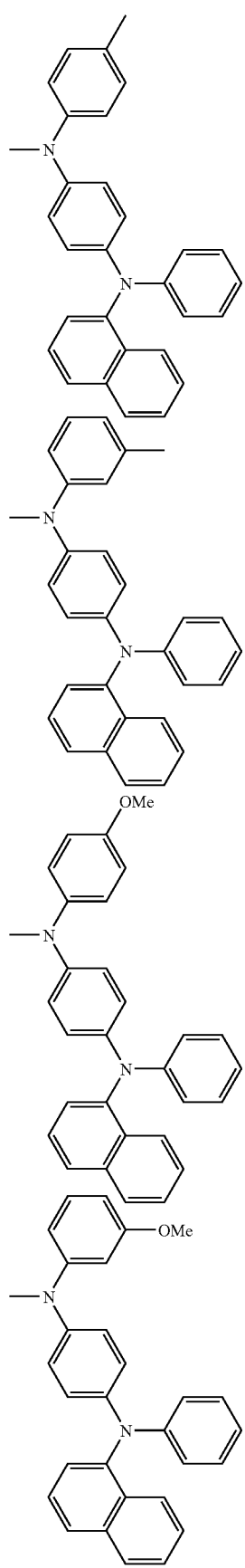
28
29
30
31
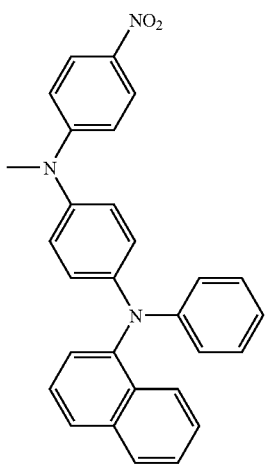
32
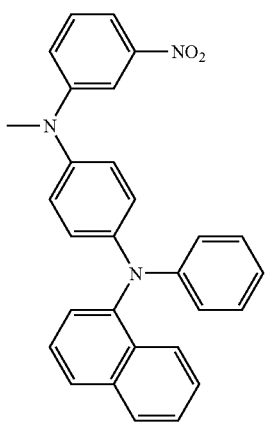
33
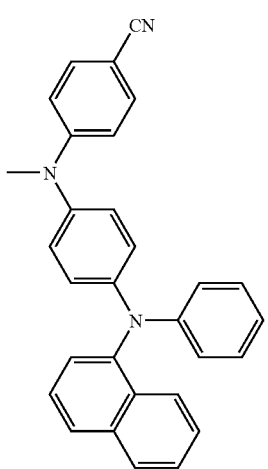

34
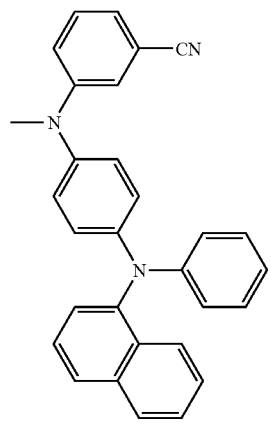
35
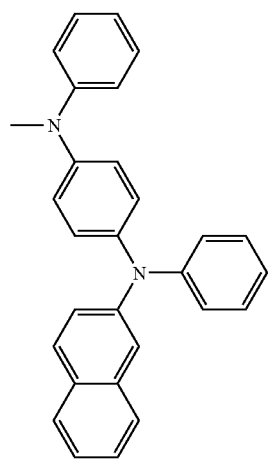
36
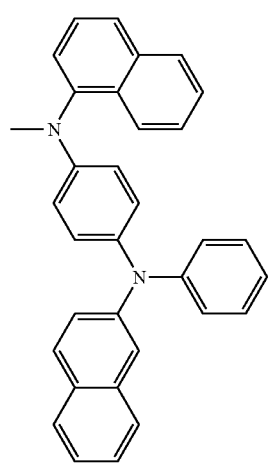
37
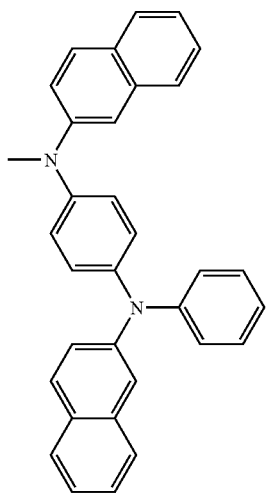
38
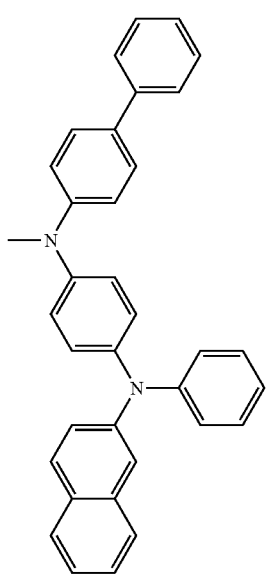
39
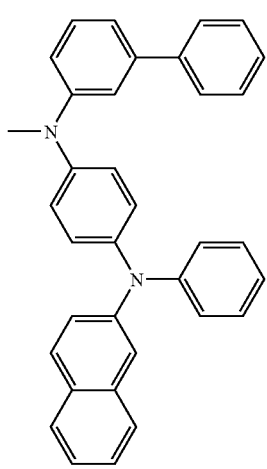

40
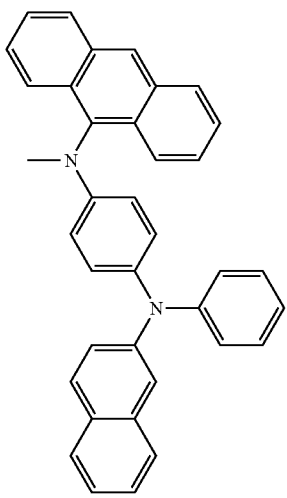
41
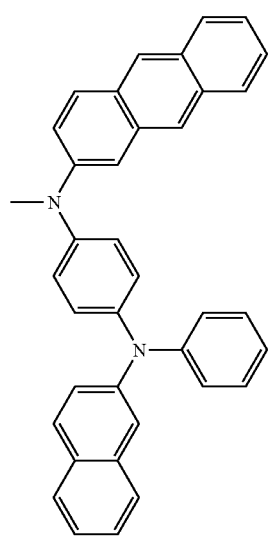
42
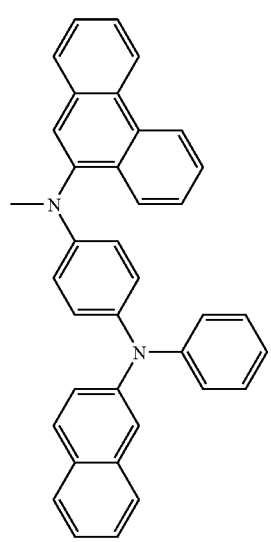
43
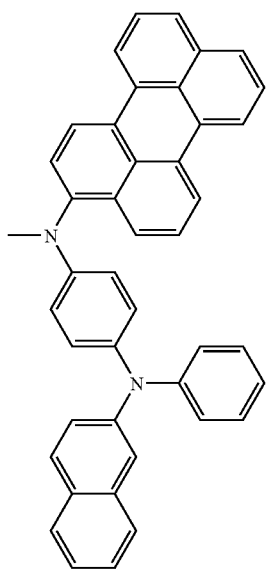
44
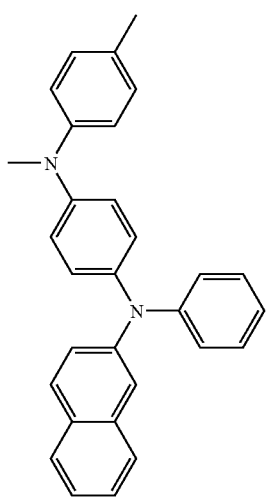
45
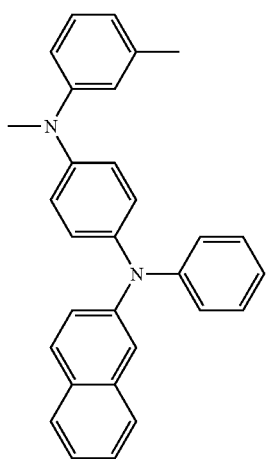

46
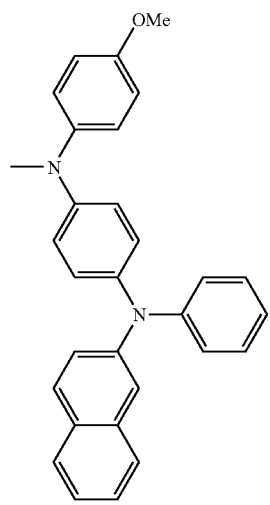
47
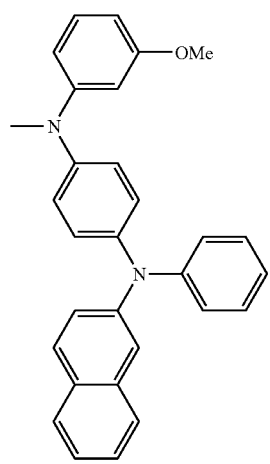
48
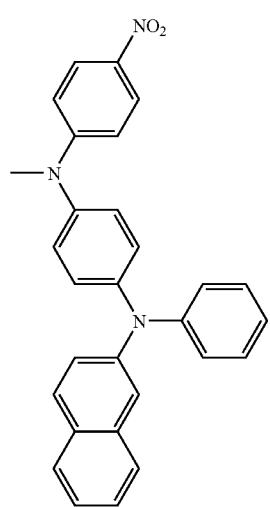
49
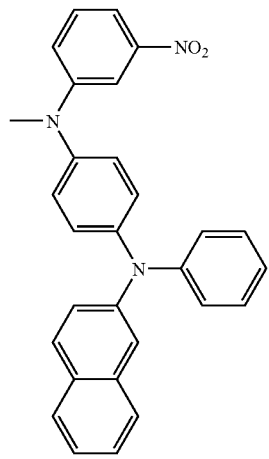
50
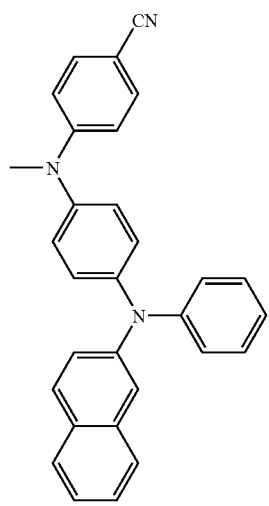
51
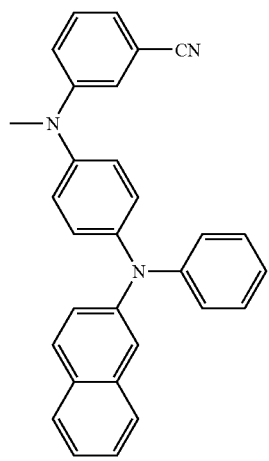

52
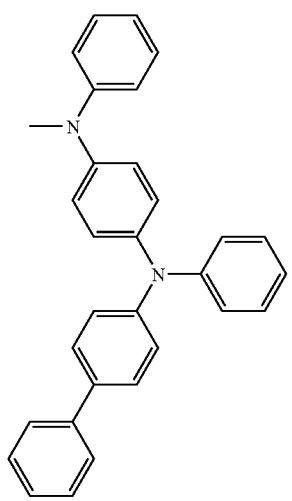
53
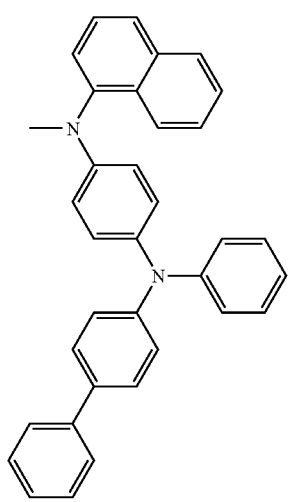
54
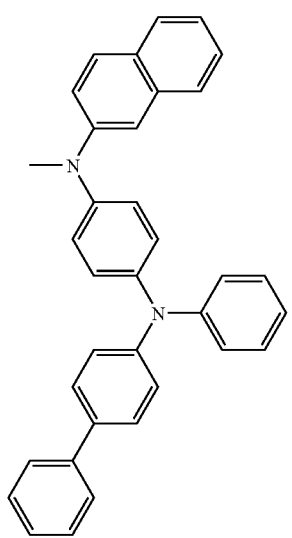
55
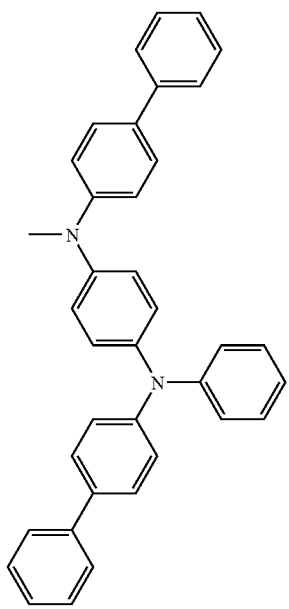
56
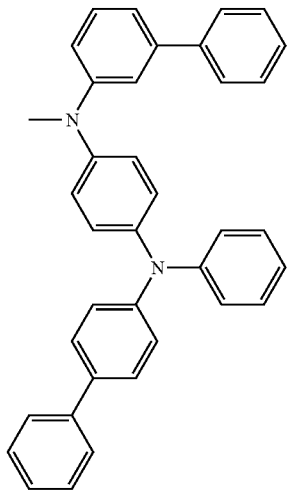
57
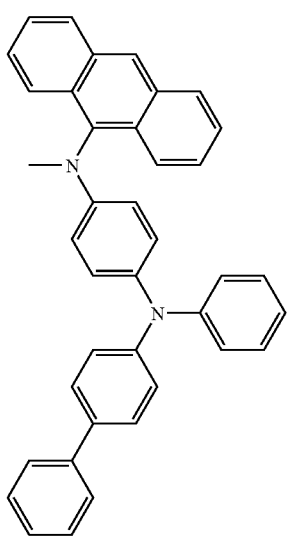

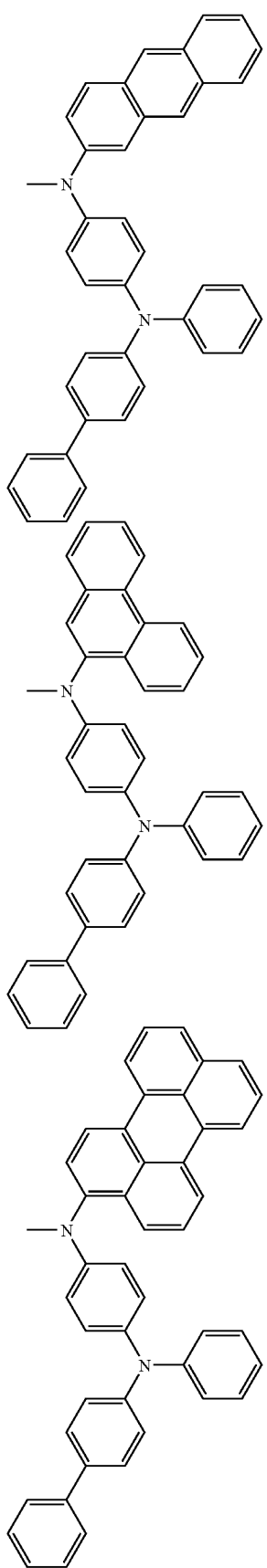
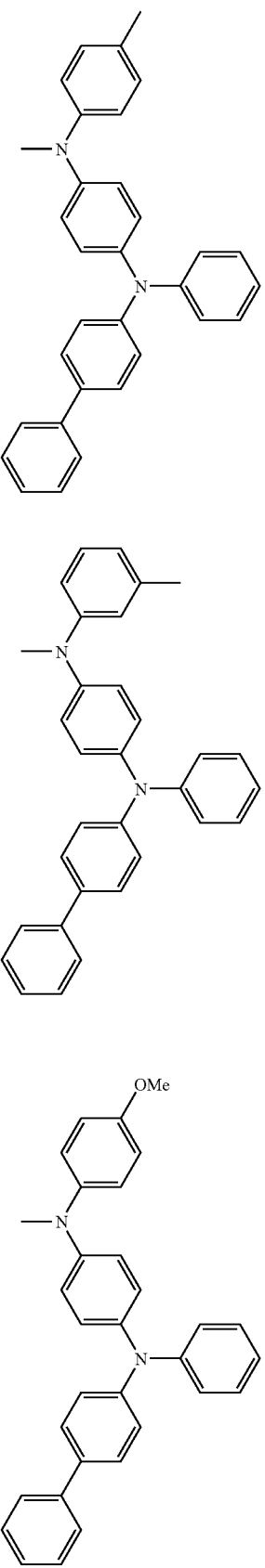

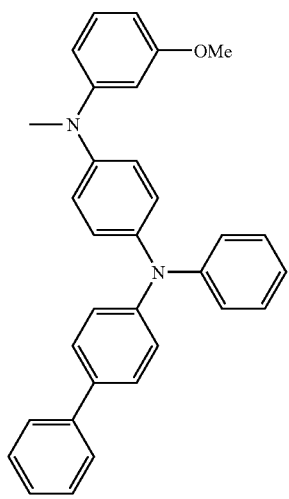
64
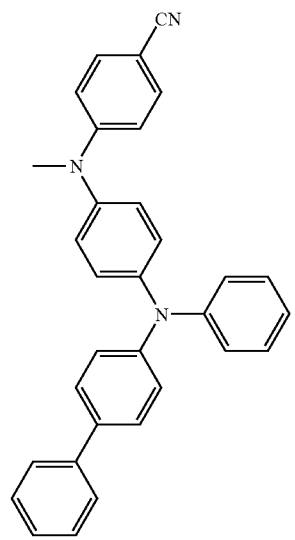
67
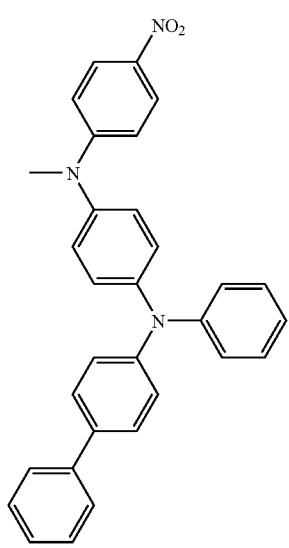
65
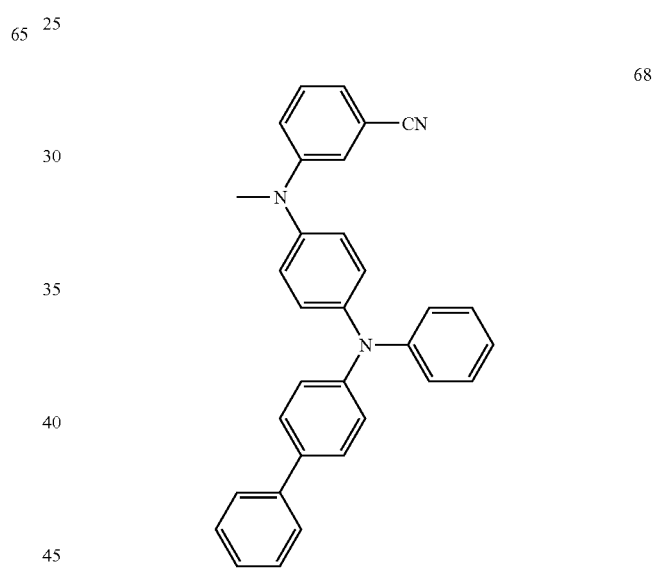
68
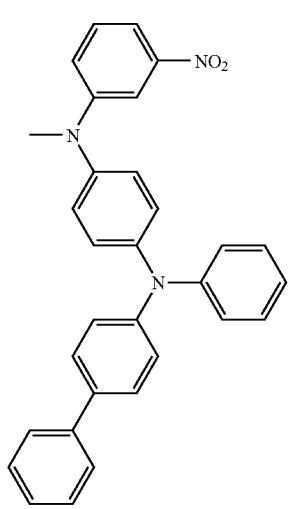
66
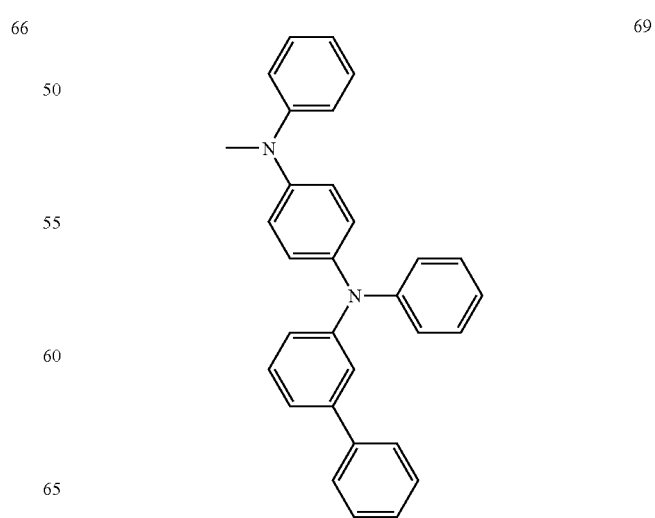
69

70
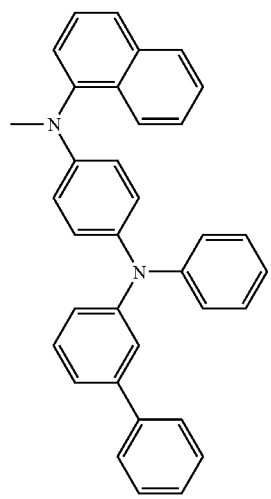
71
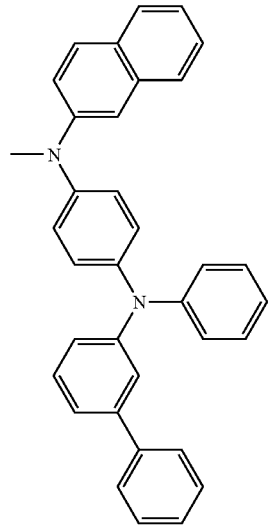
72
73
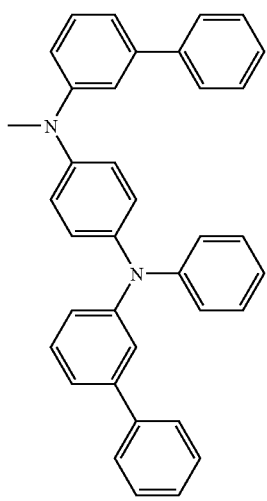
74
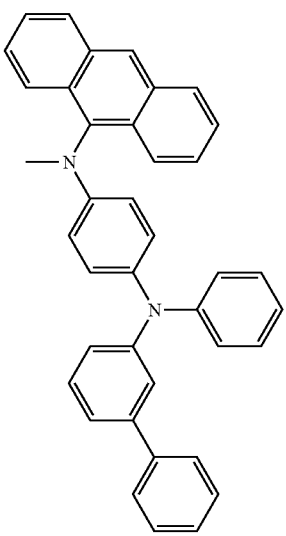
75
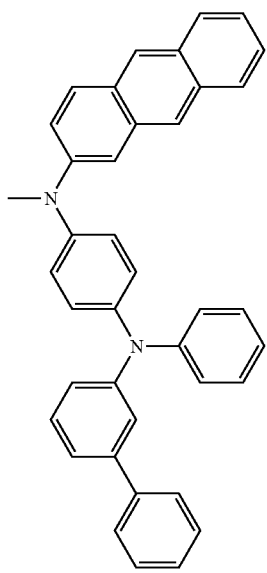

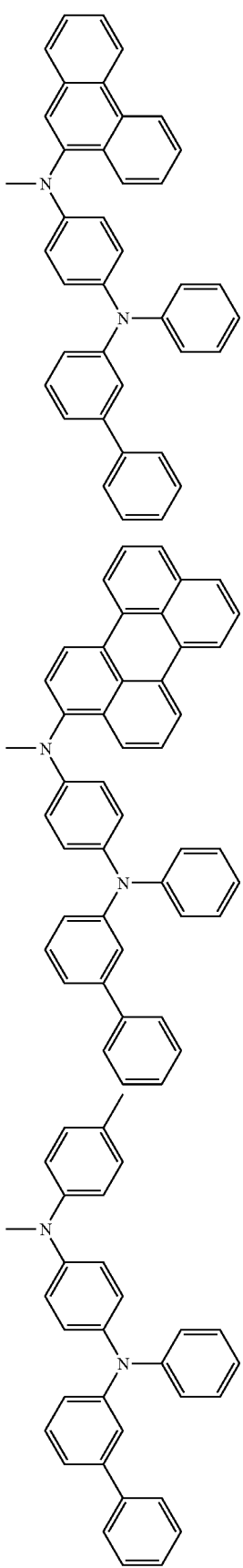
76
77
78
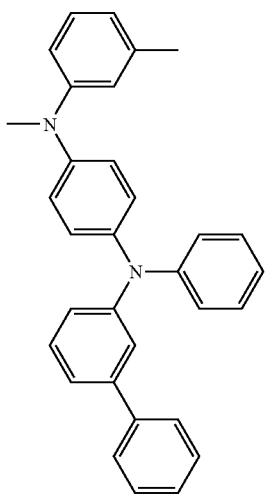
79
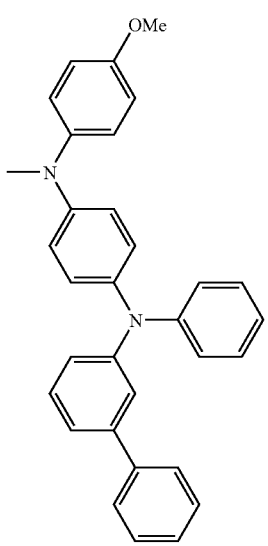
80
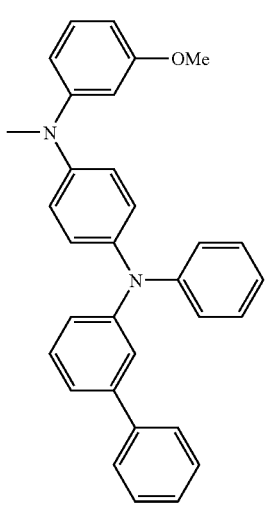
81

82
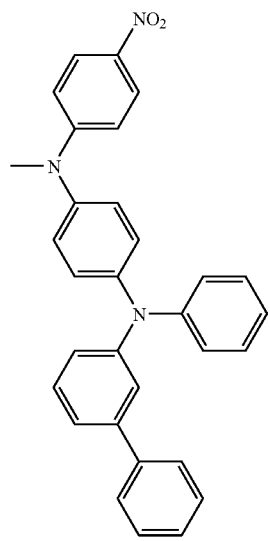
83
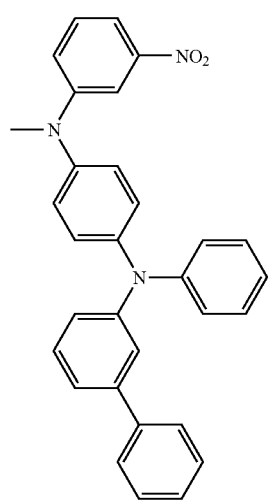
84
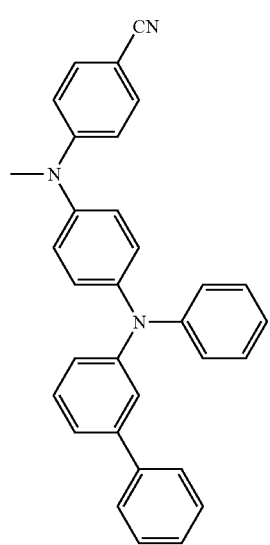
85
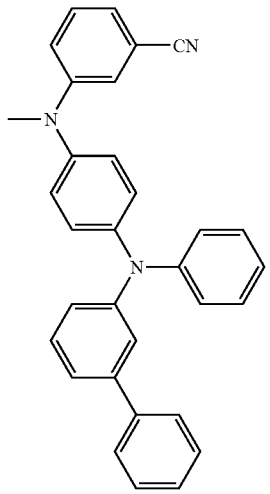
86
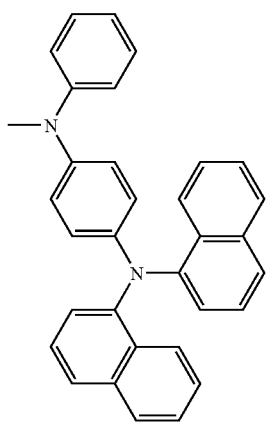
87
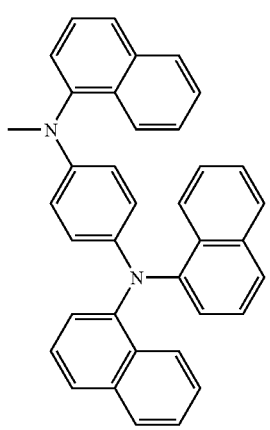

88
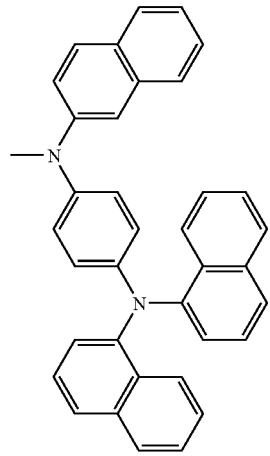
89
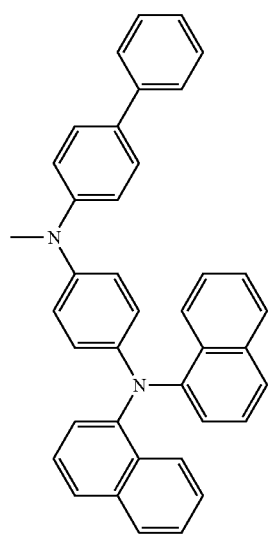
90
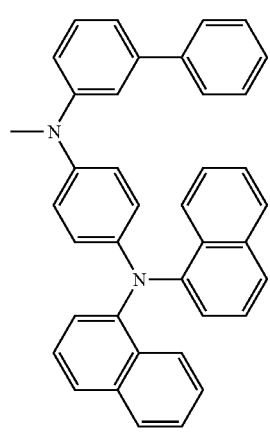
91
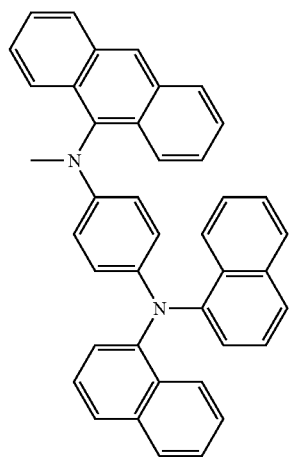
92
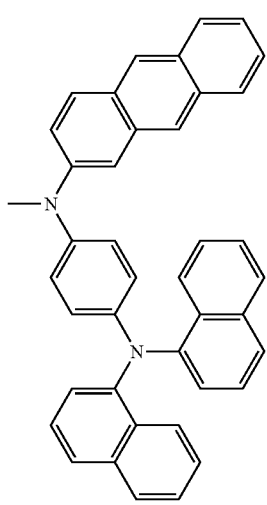
93
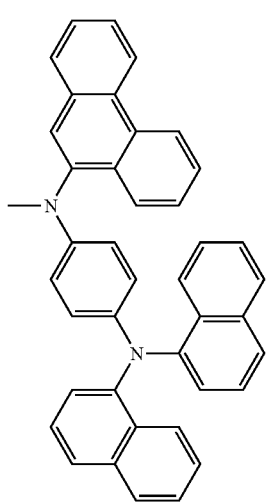

94
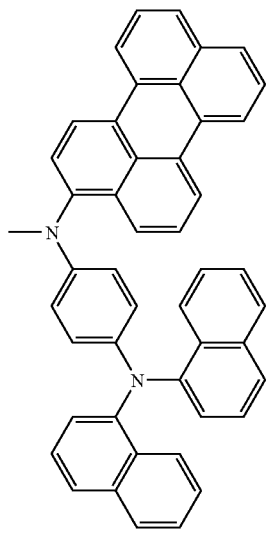
95
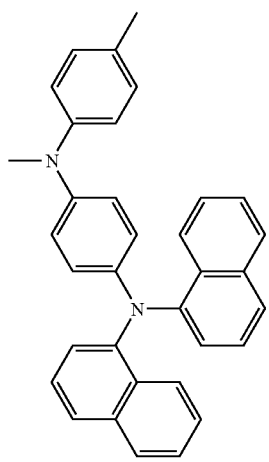
96
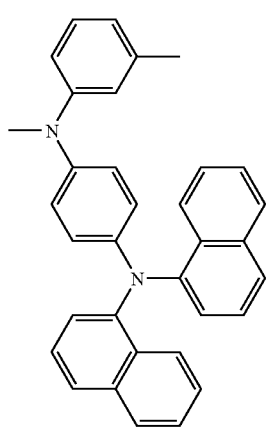
97
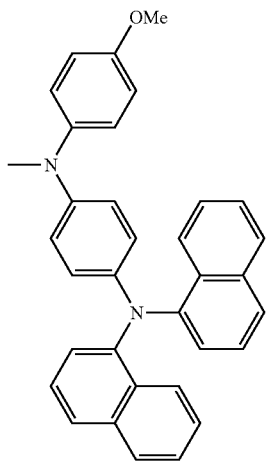
98
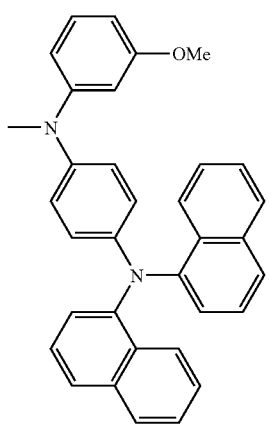
99
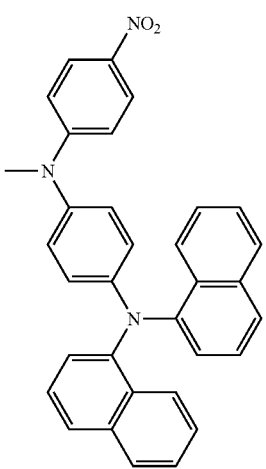

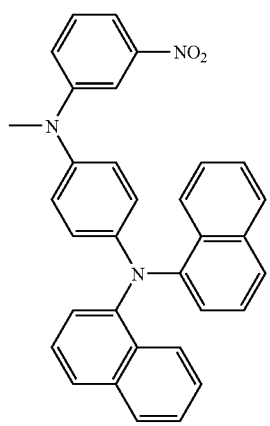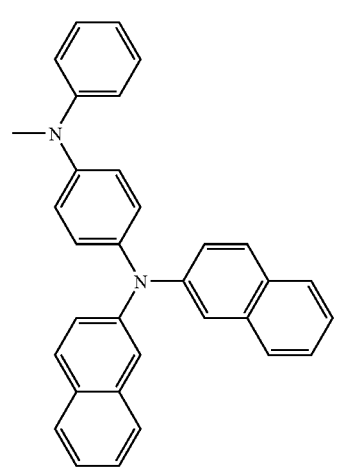

106
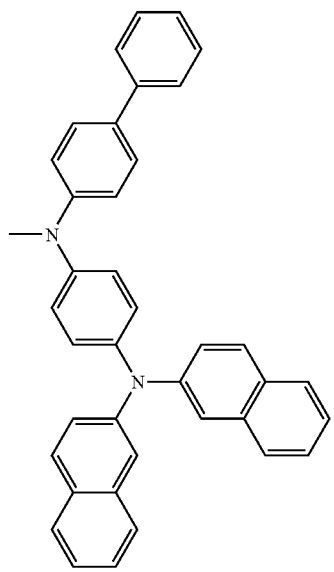
107
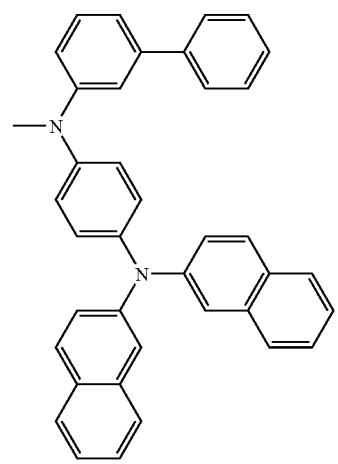
108
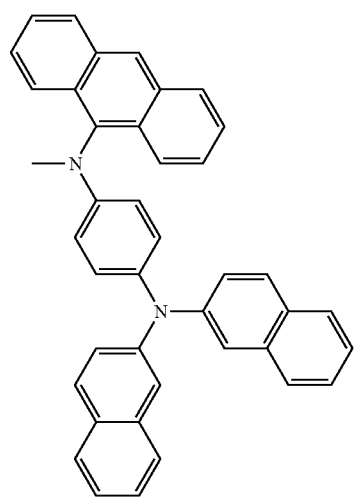
109
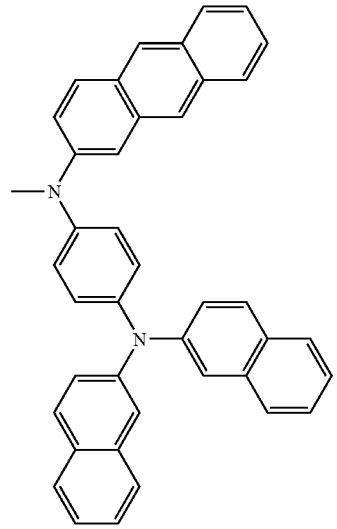
110
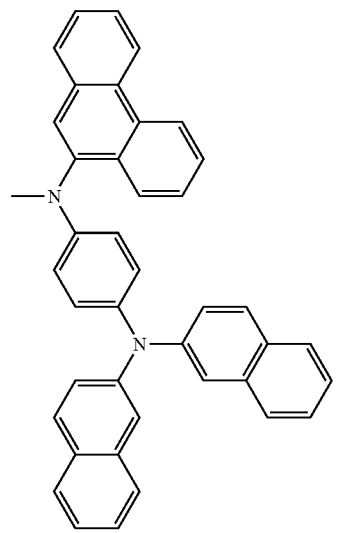
111
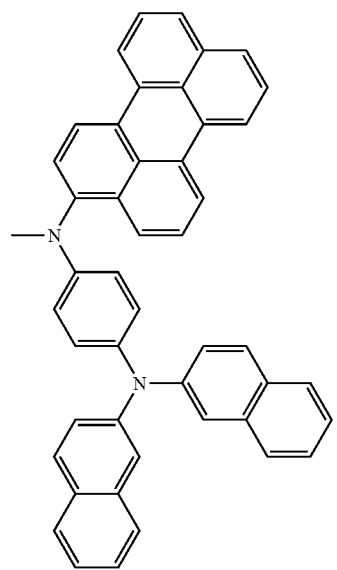

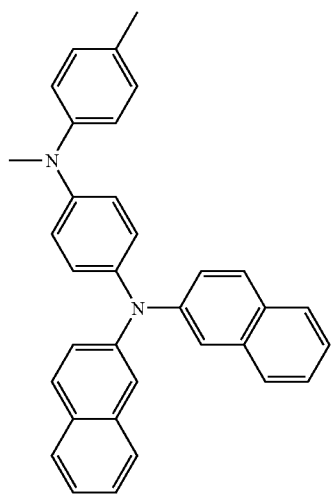
112
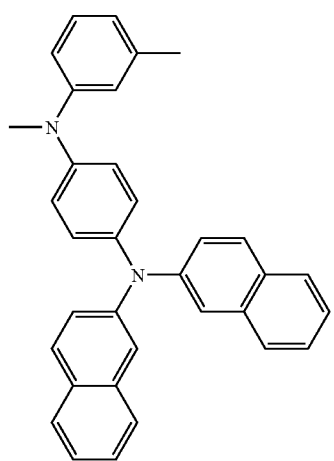
113
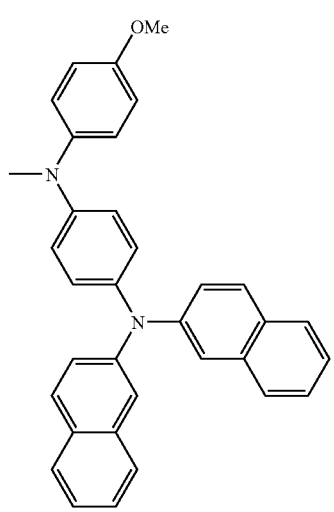
114
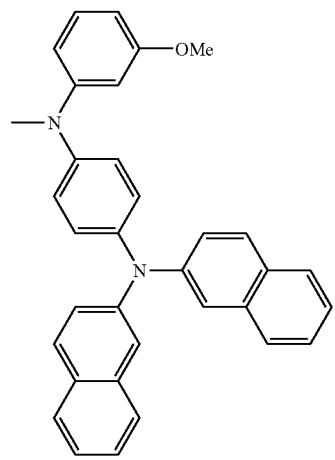
115
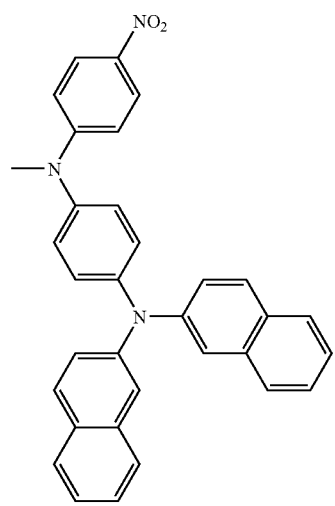
116
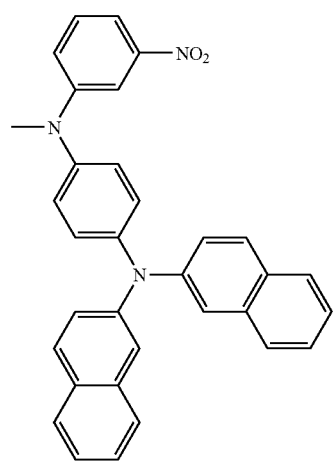
117

118 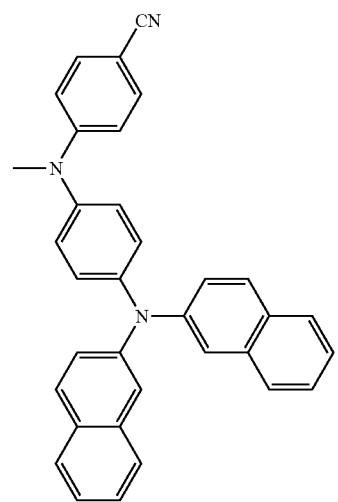
119 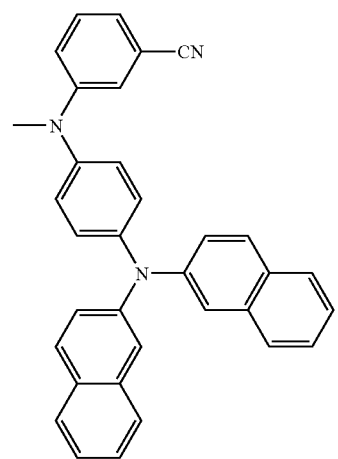
120 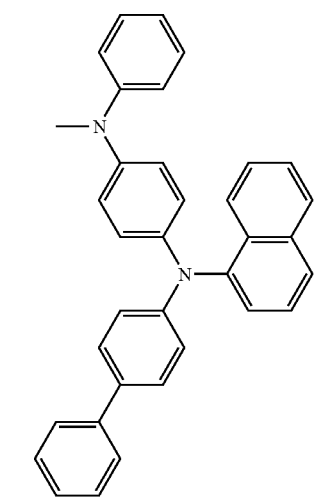
121 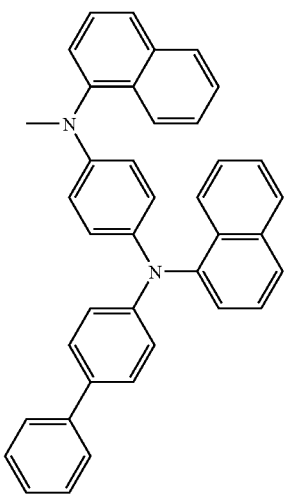
122 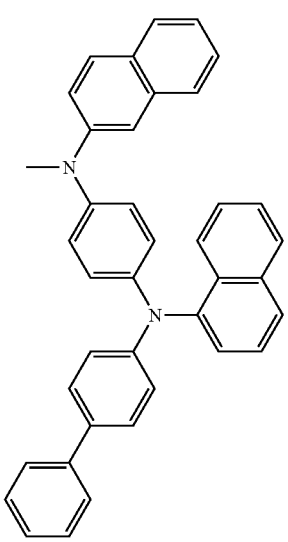
123 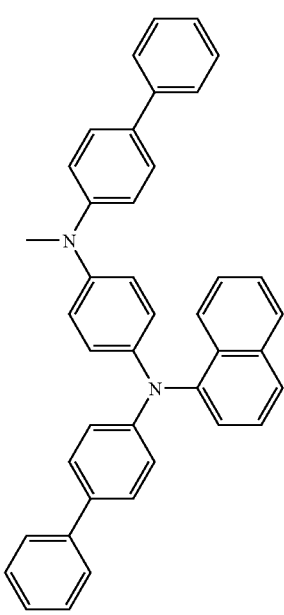

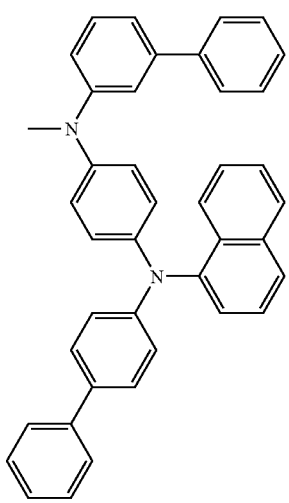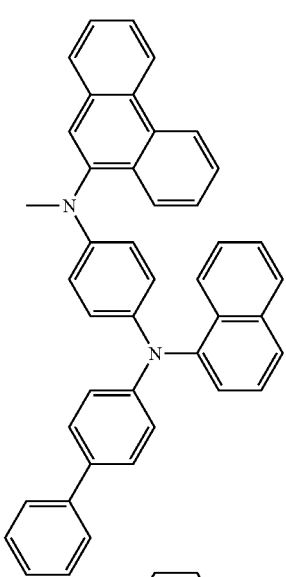

130
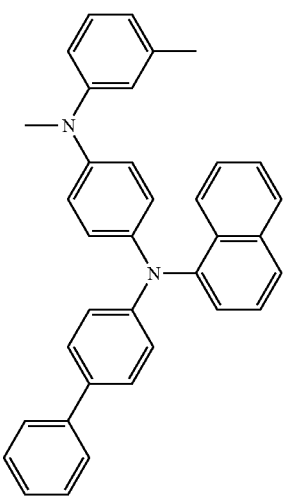
131
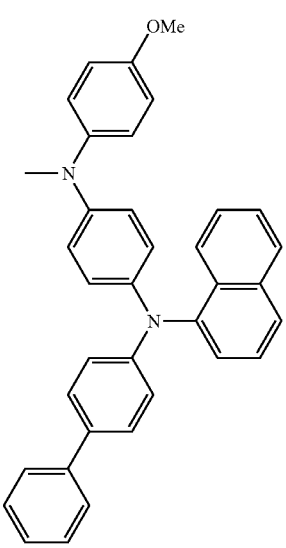
132
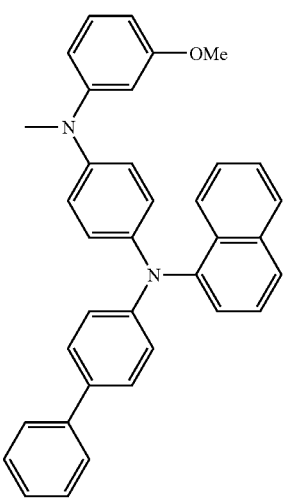
133
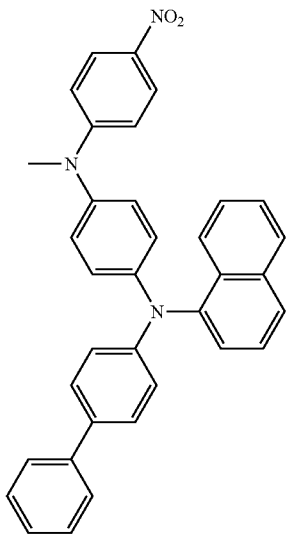
134
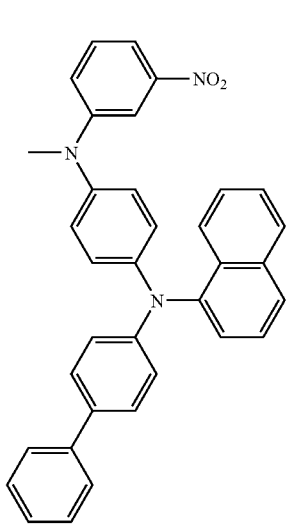
135
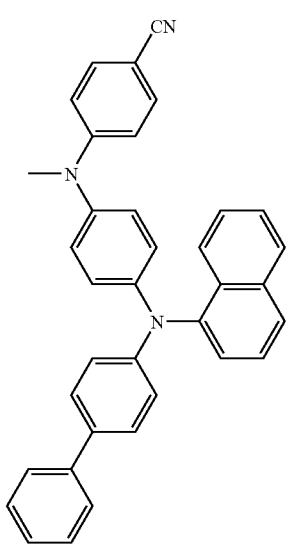

136
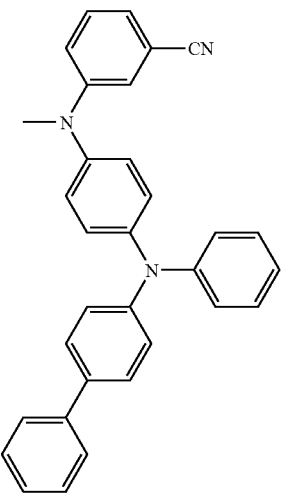
137
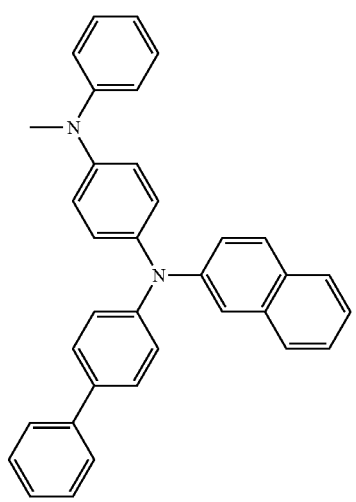
138
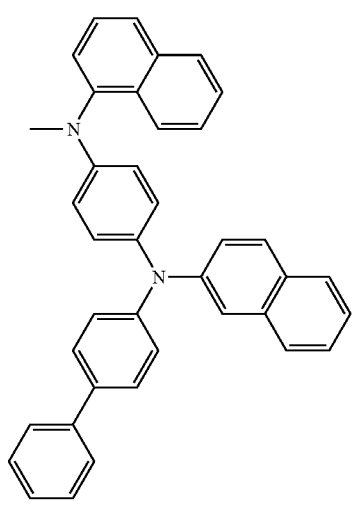
139
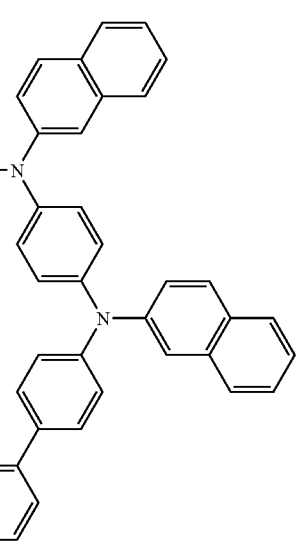
140
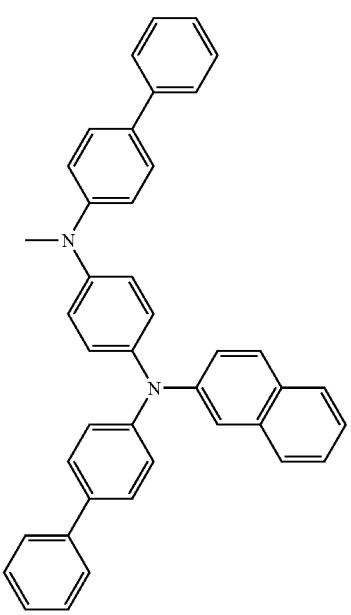
141
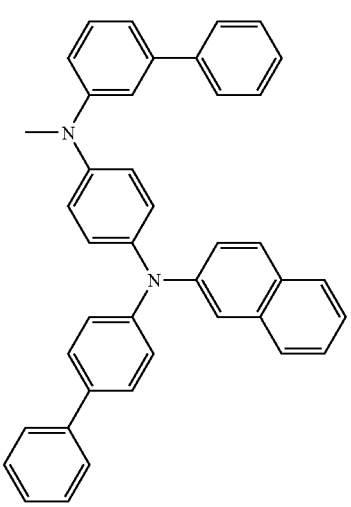

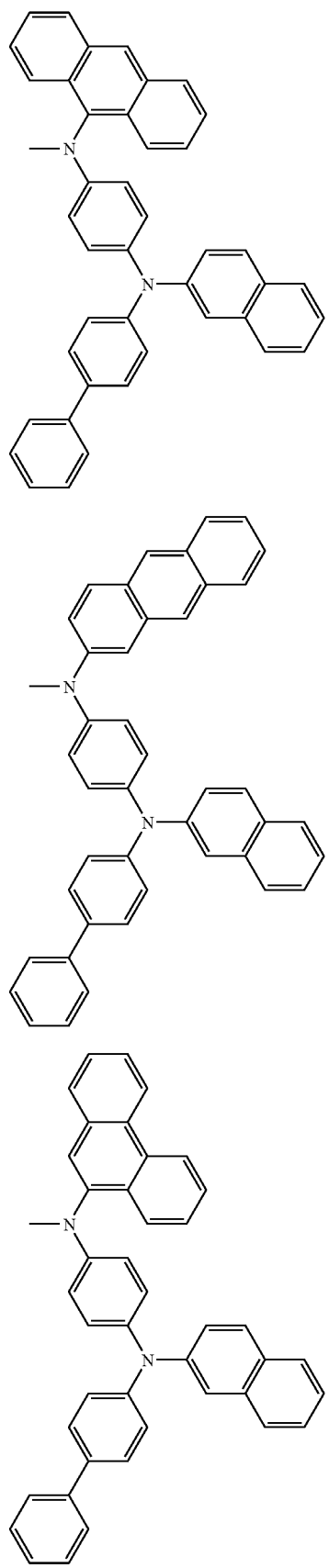
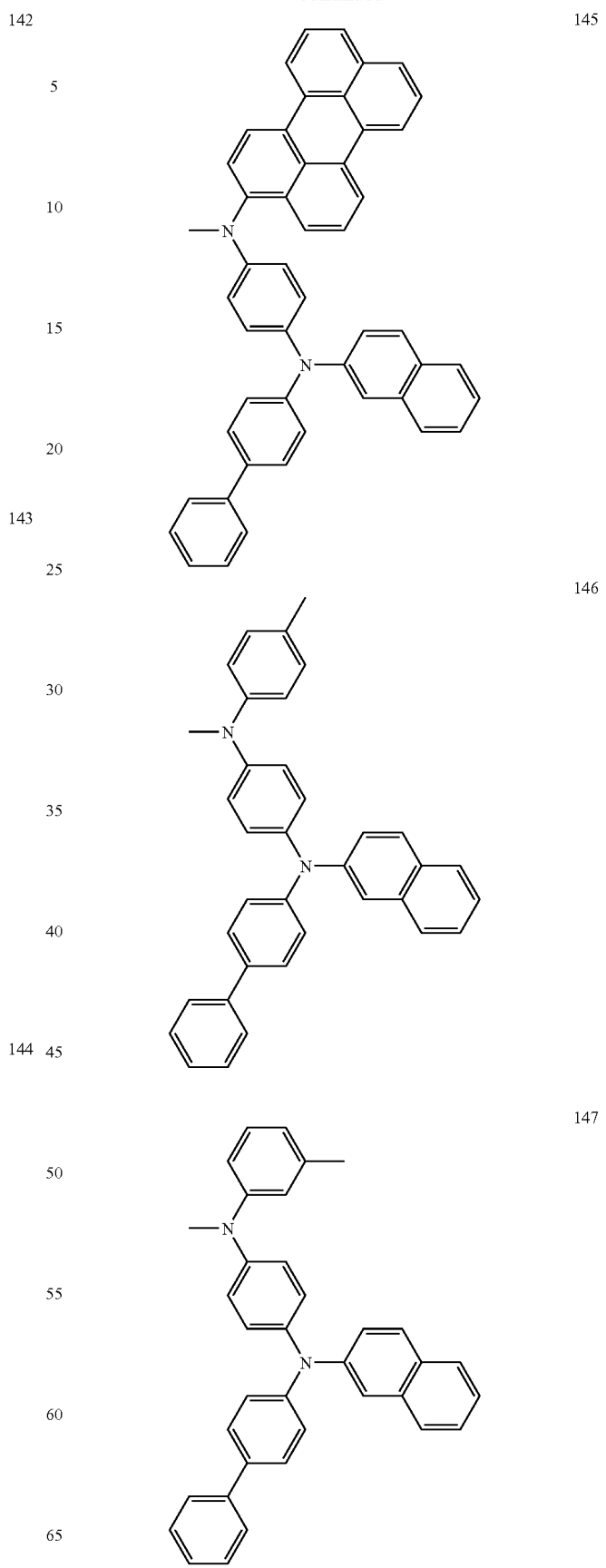

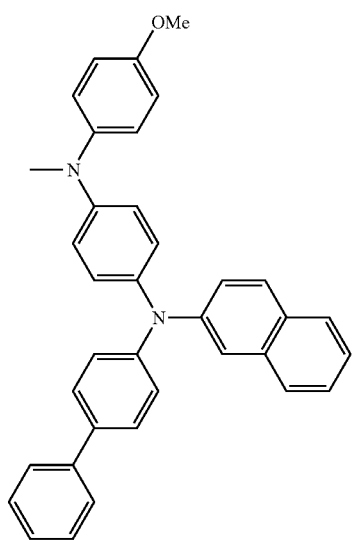
148
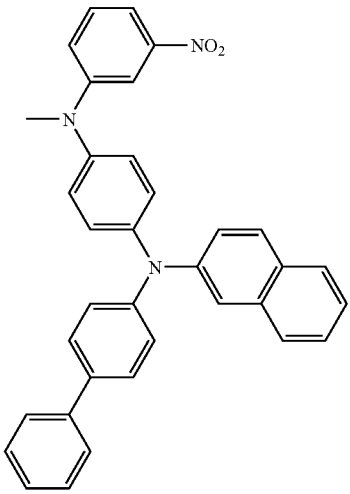
151
149
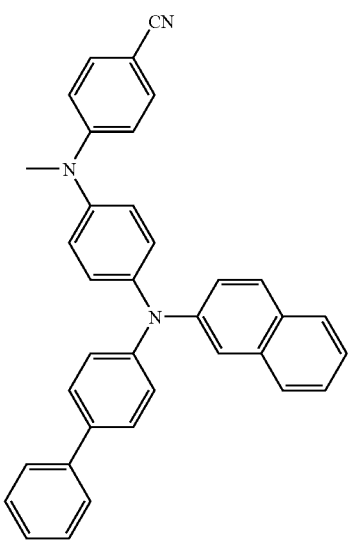
152
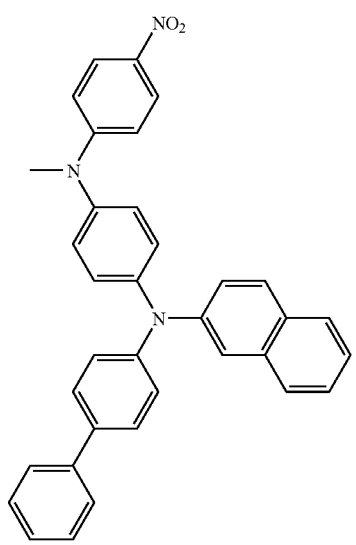
150
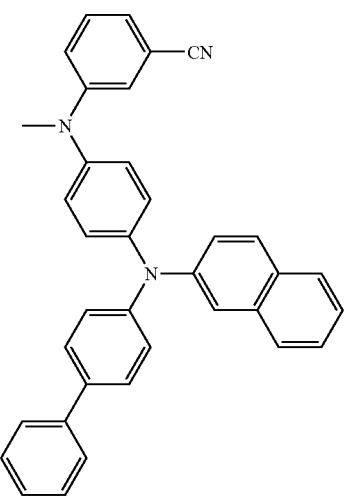
153

154
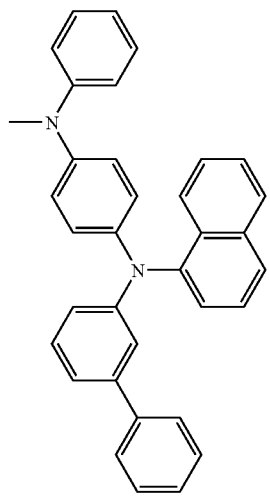
155
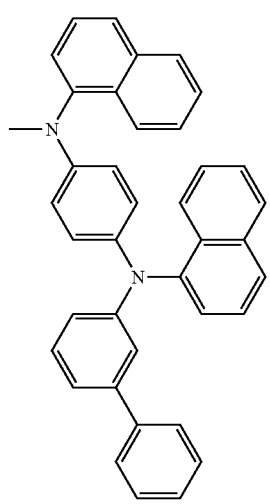
156
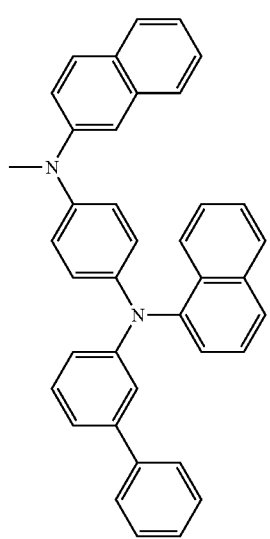
157
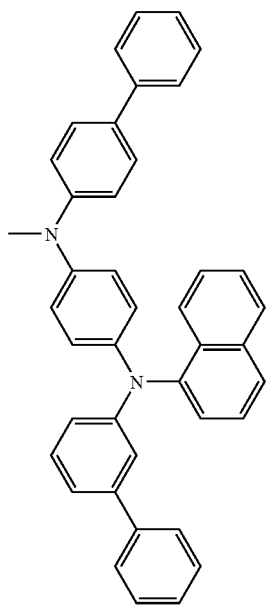
158
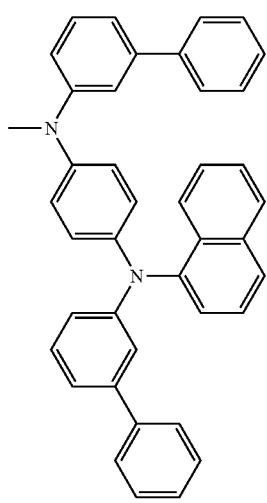
159
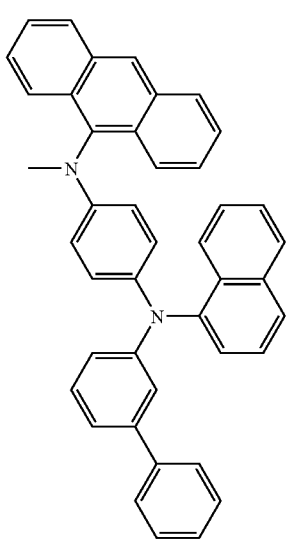

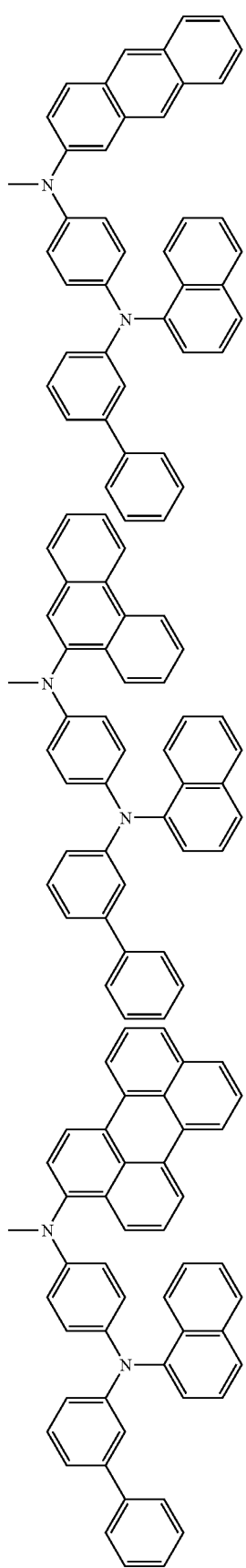
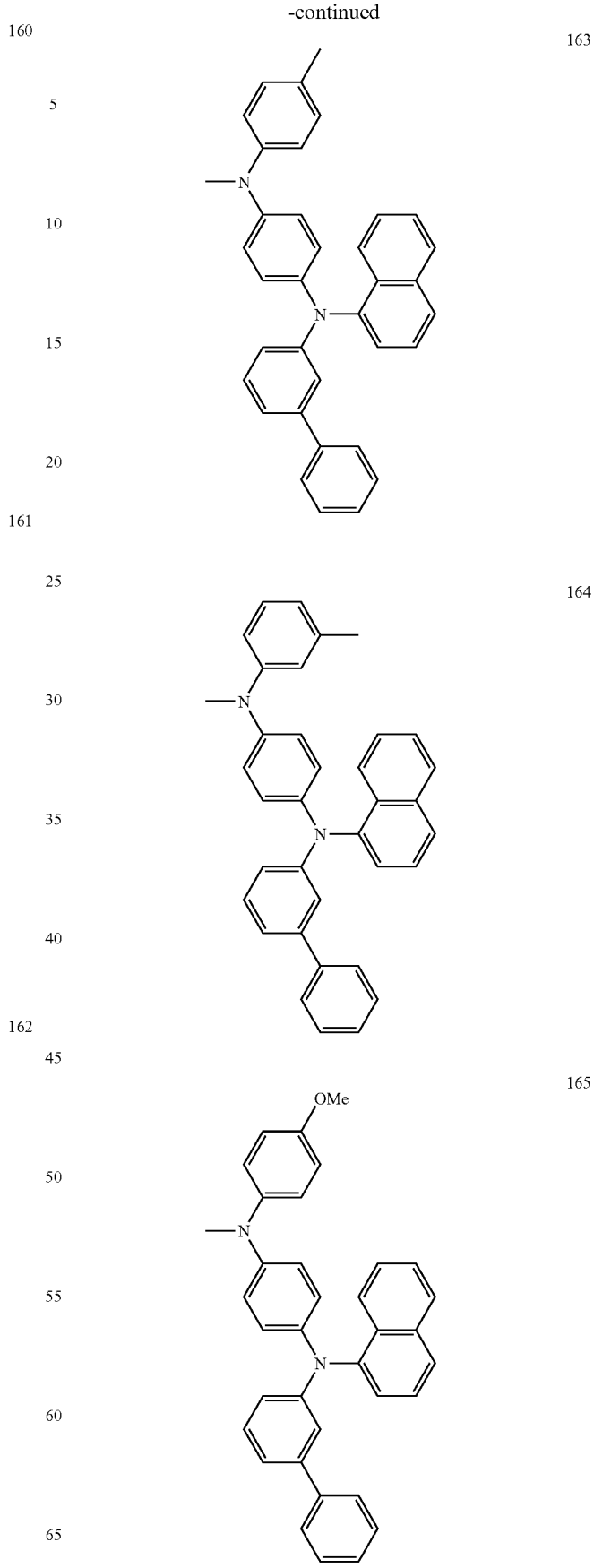

63
-continued
166
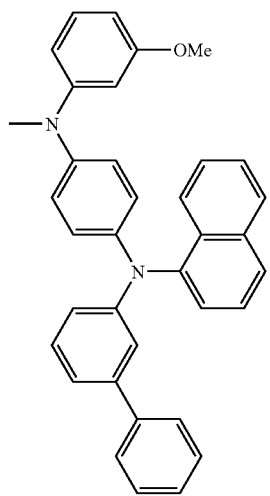
167
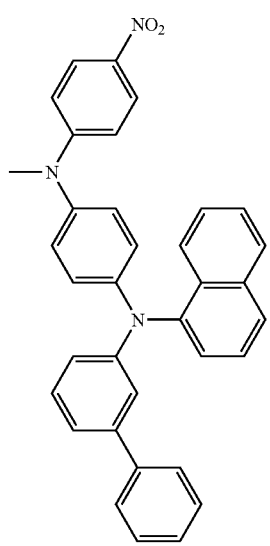
168
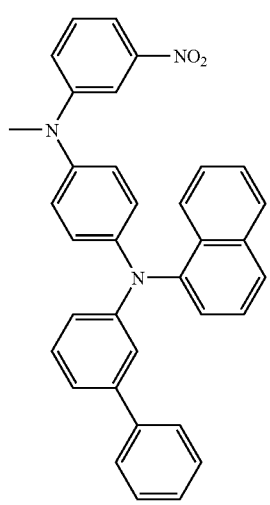
64
-continued
169
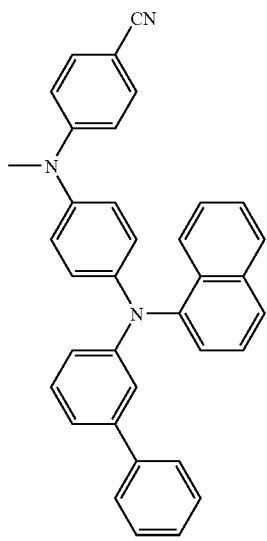
170
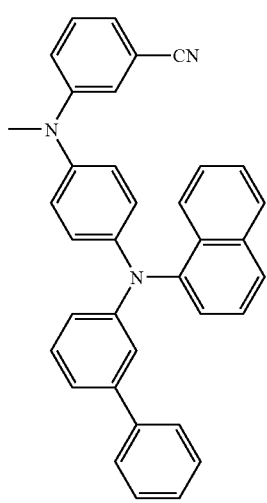
171
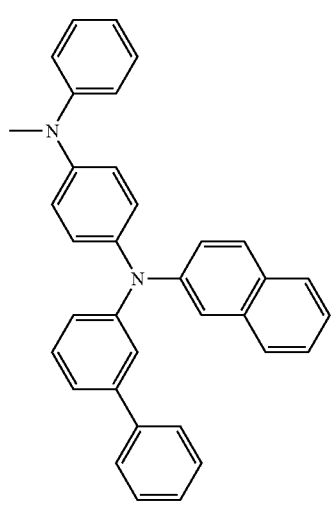

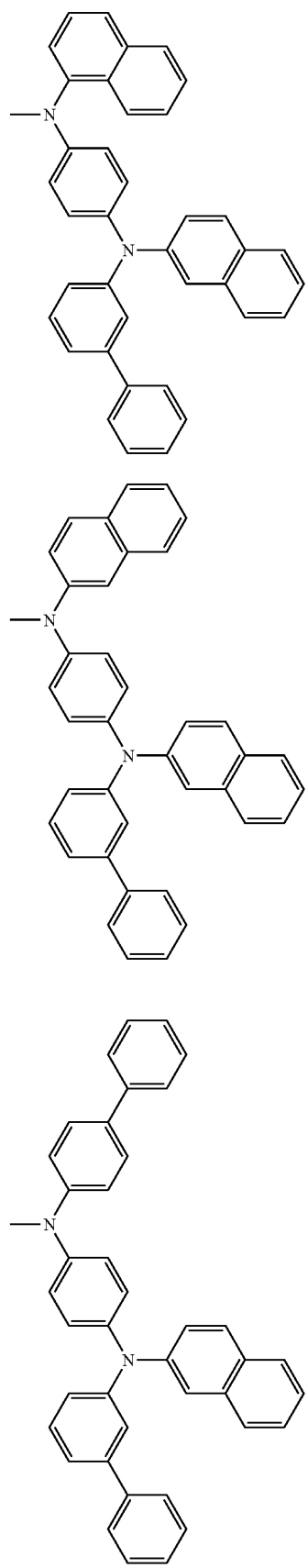
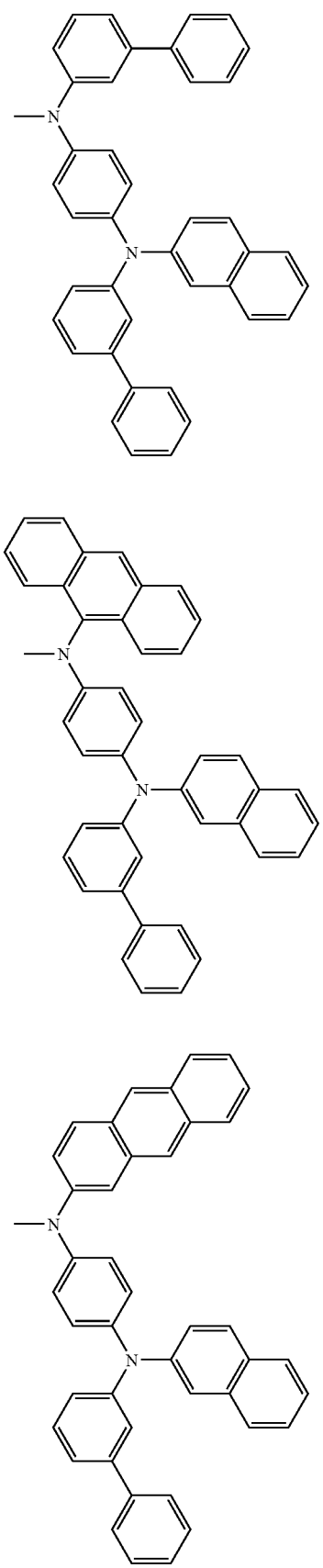

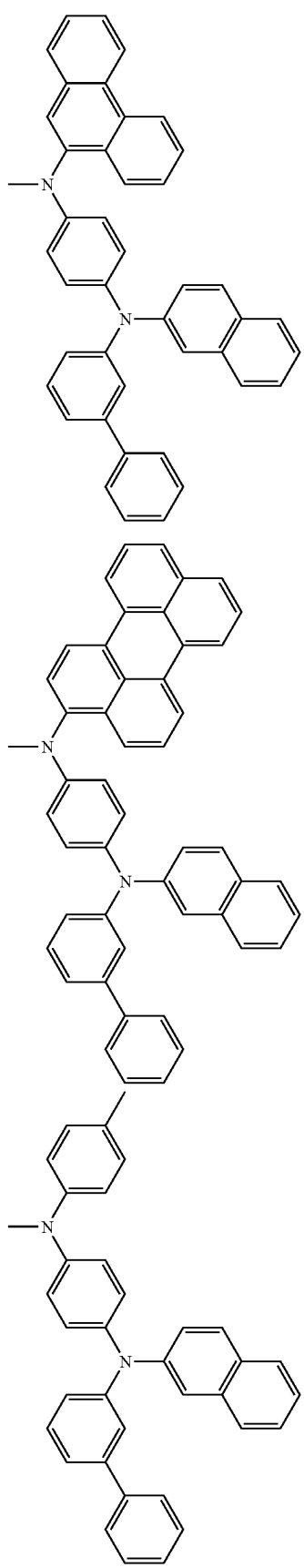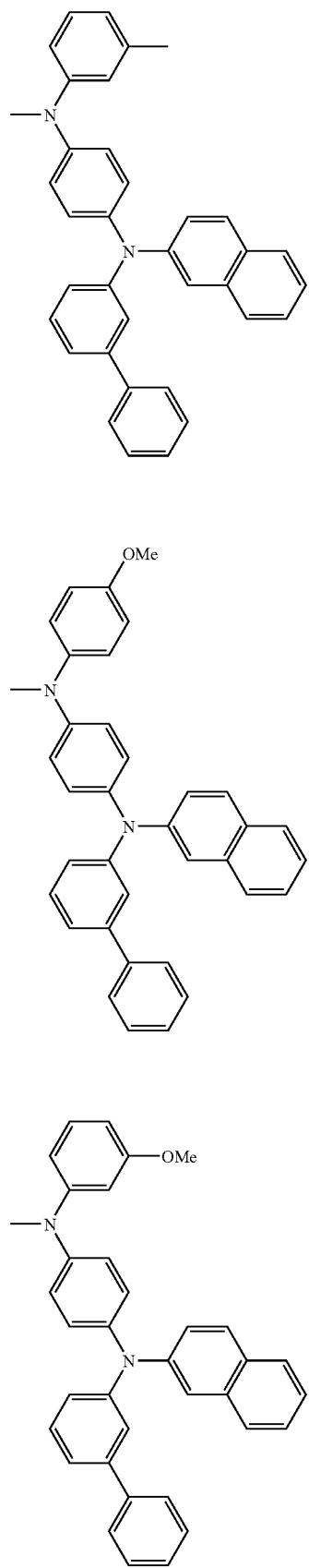

184
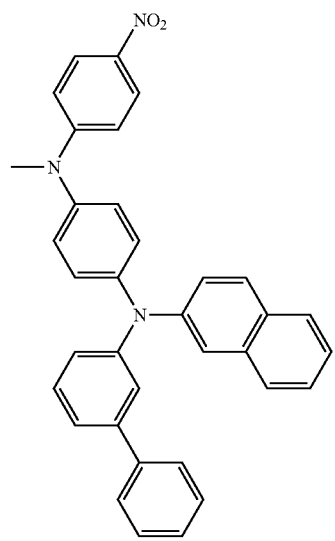
187
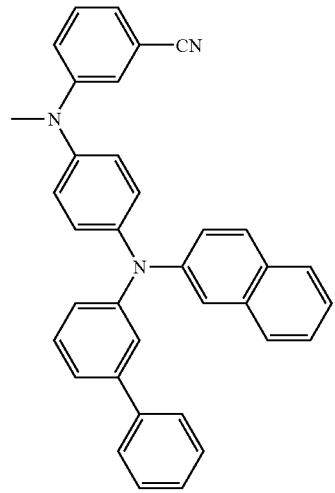
185
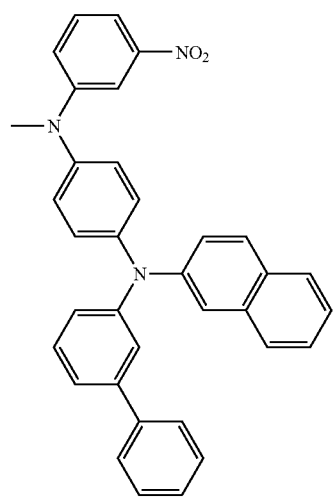
188
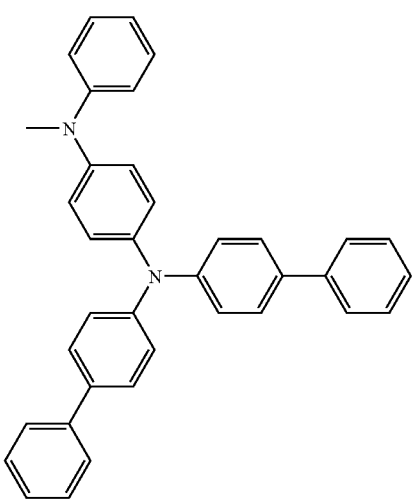
186
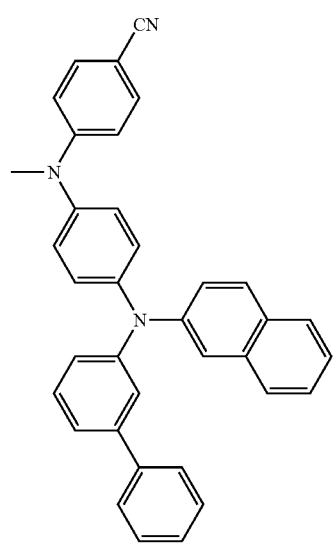
189
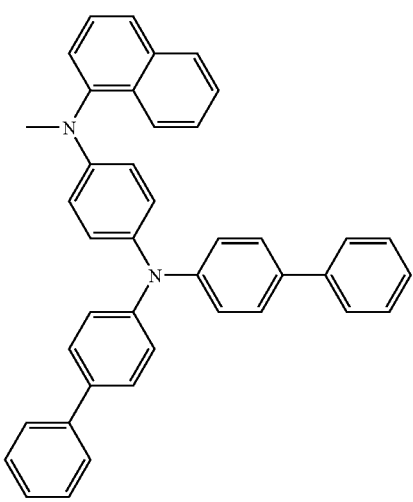

71
-continued
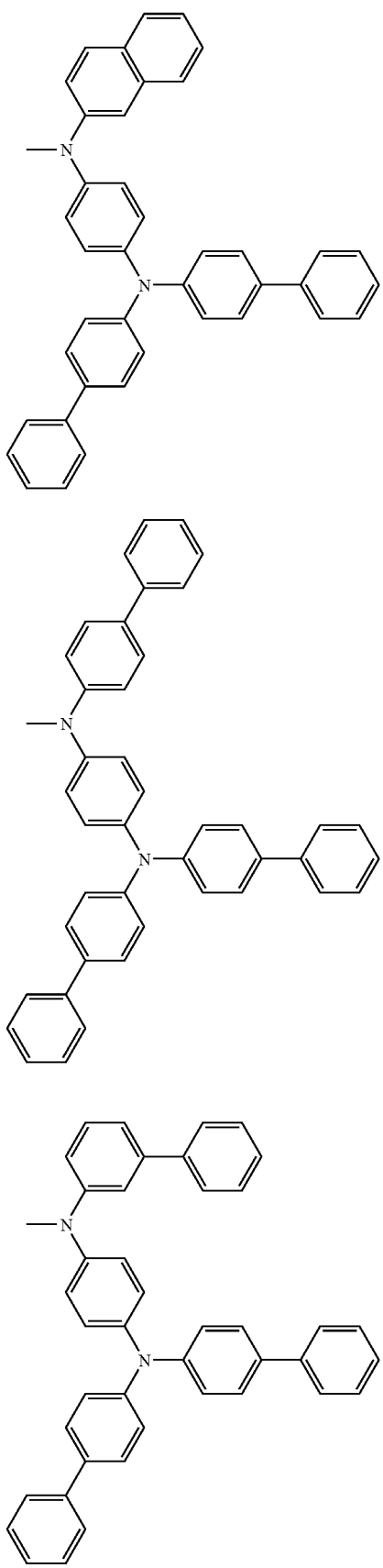
72
-continued
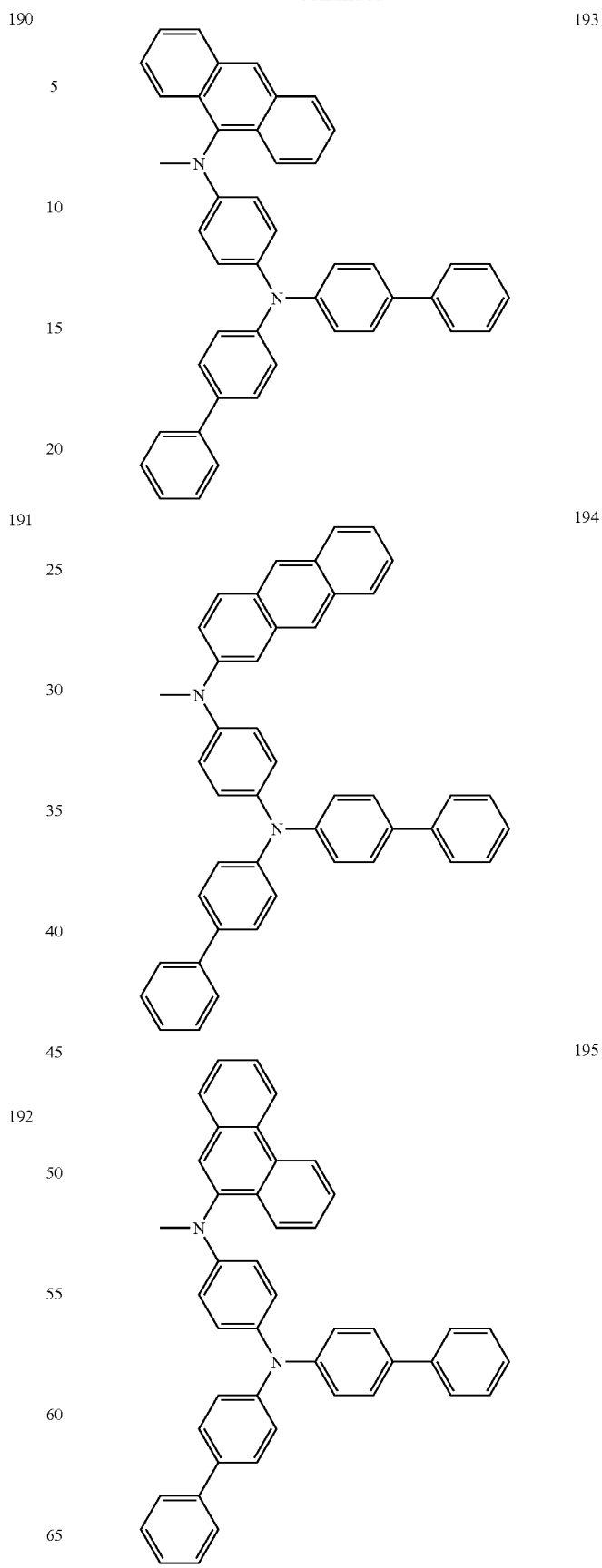

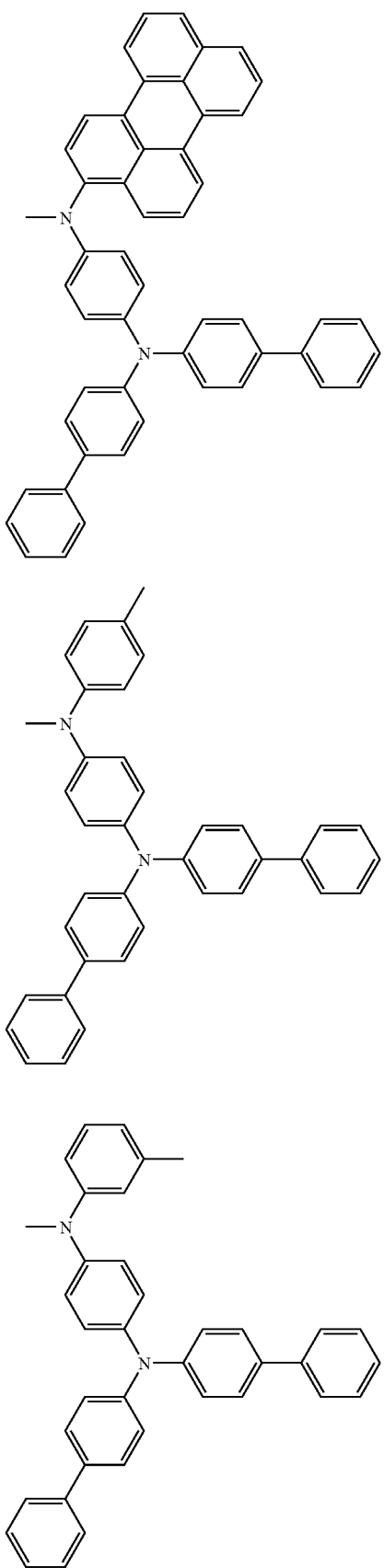
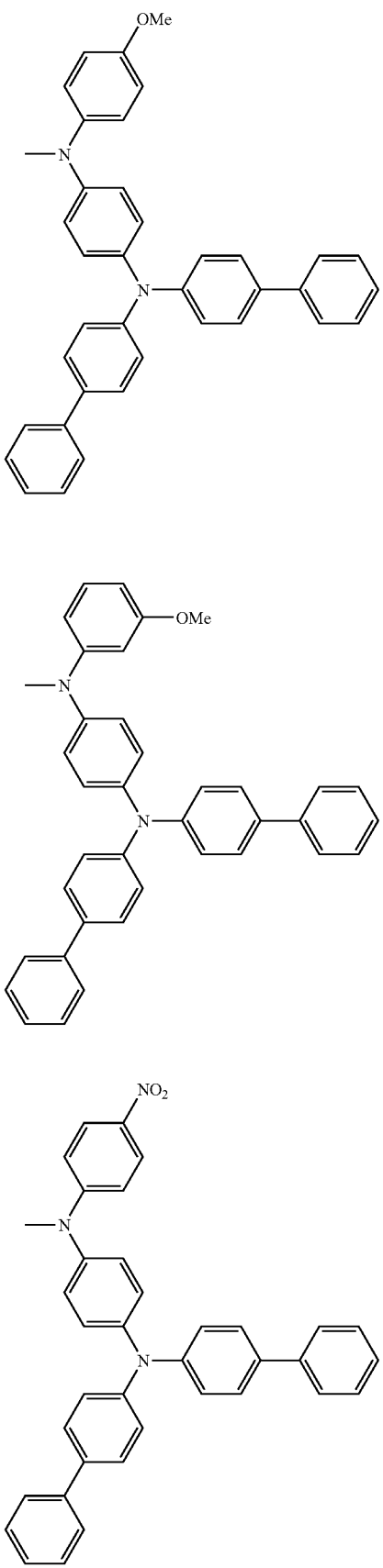

202
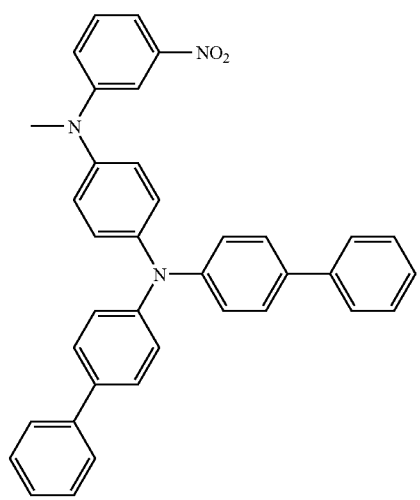
203
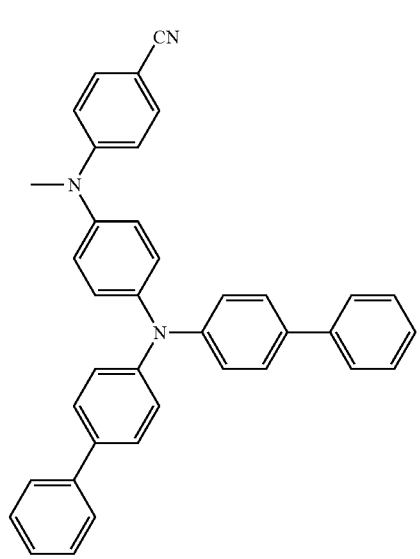
204
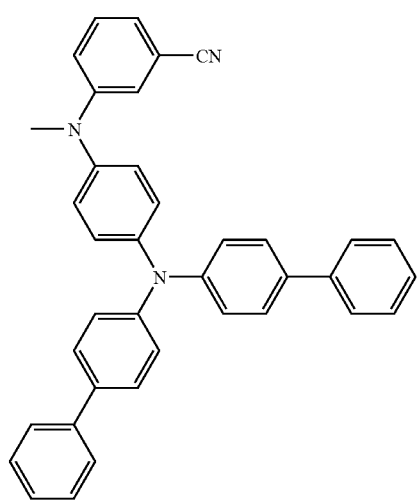
205
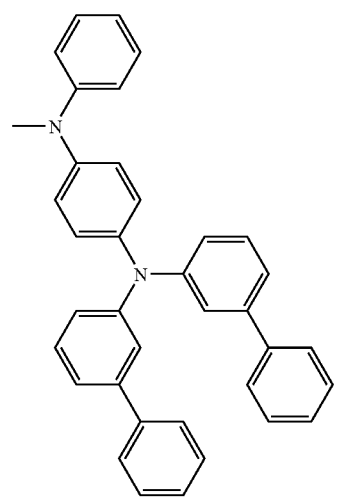
206
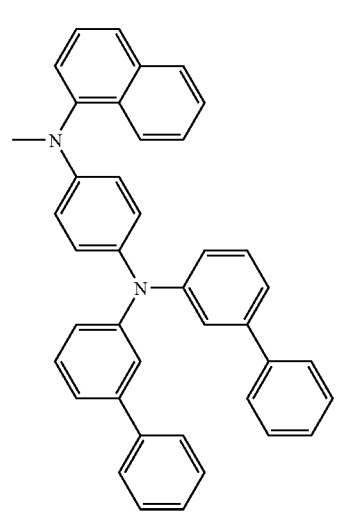
207
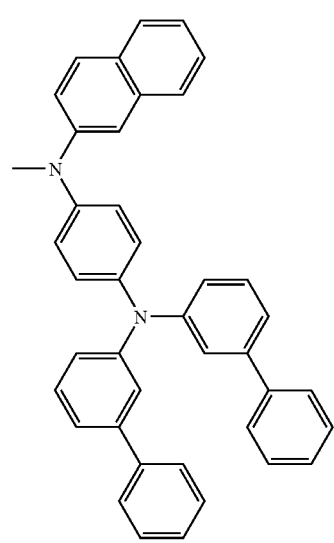

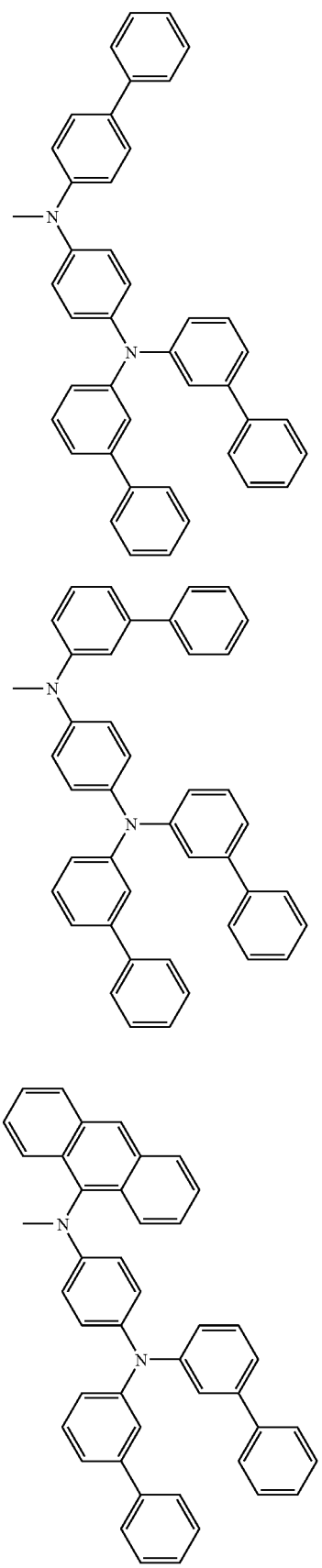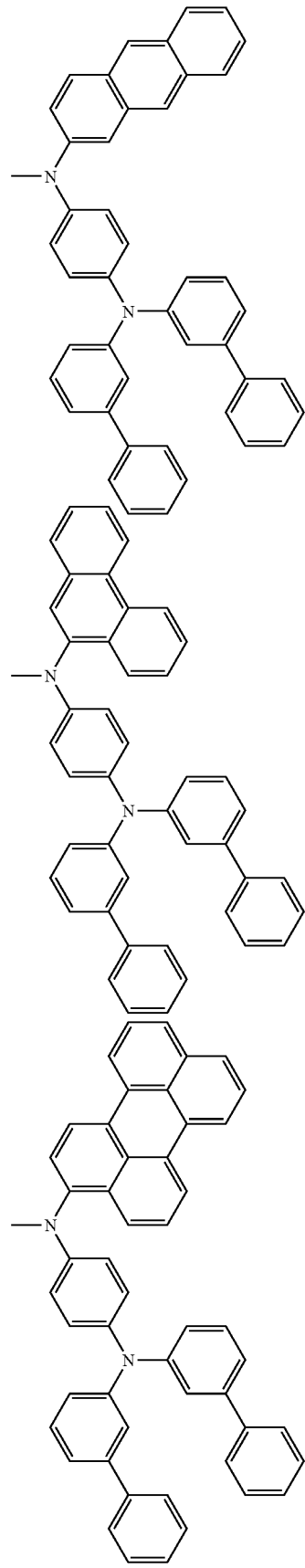

214
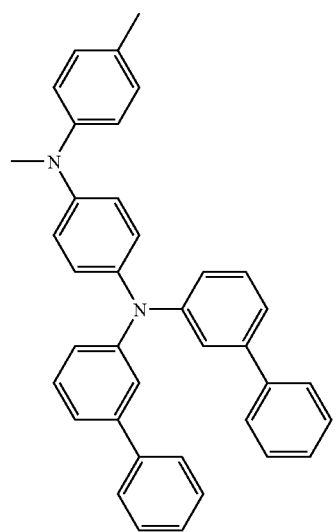
215
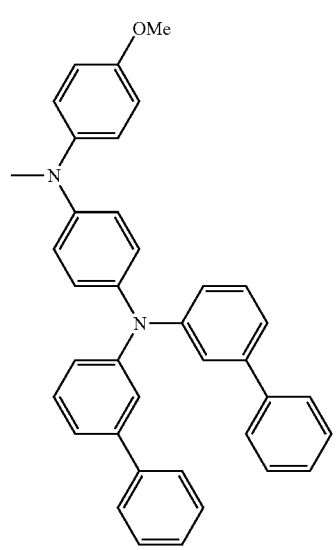
216
217
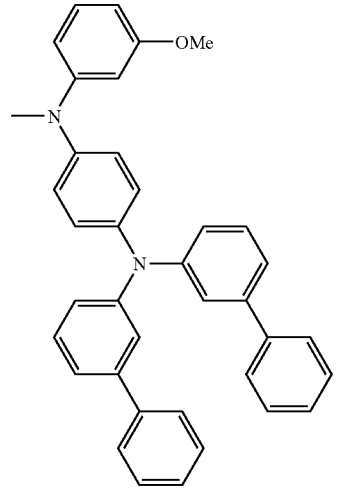
218
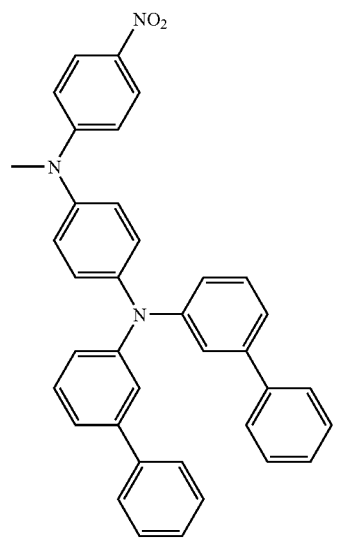
219

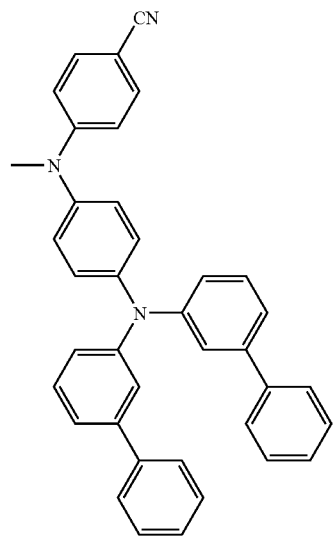
220
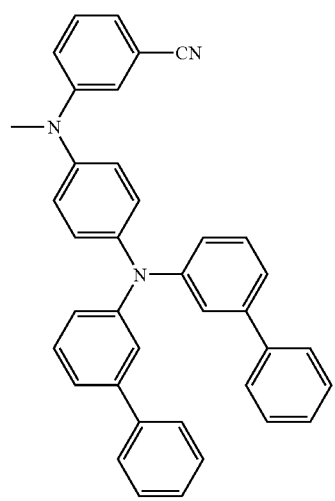
221
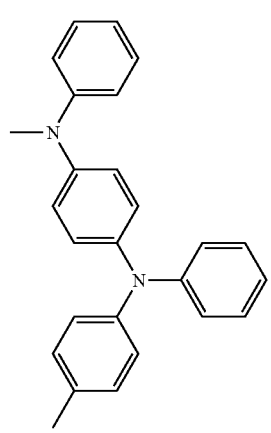
222
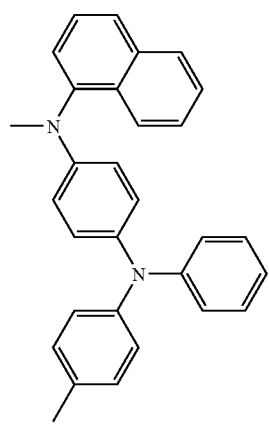
223
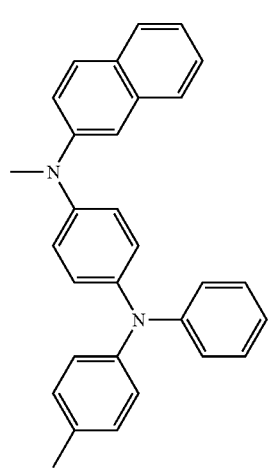
224
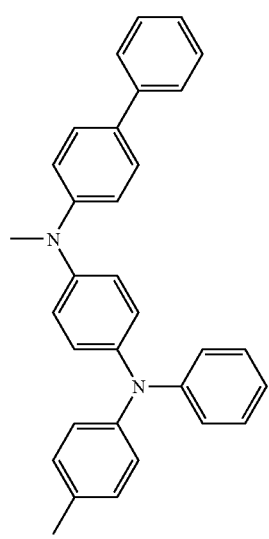
225

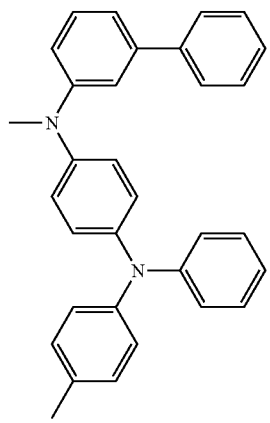 226
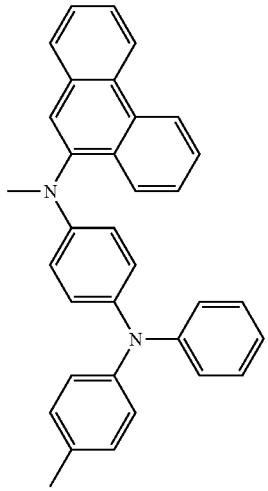 229
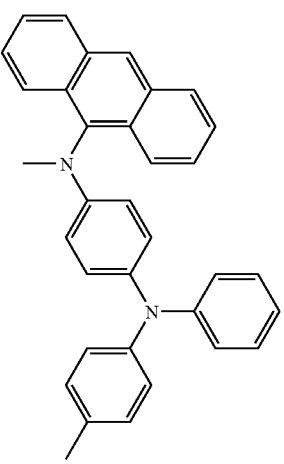 227
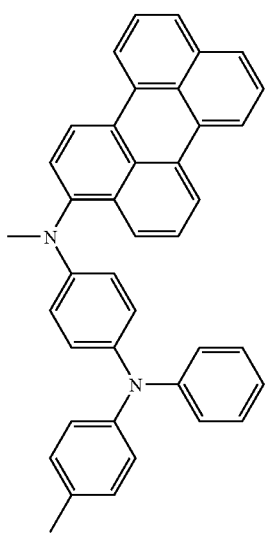 230
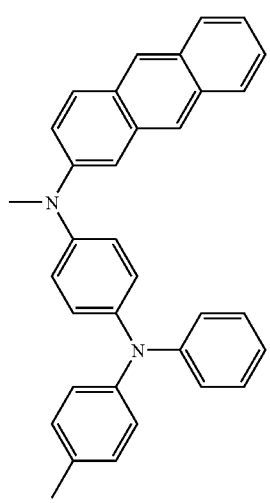 228
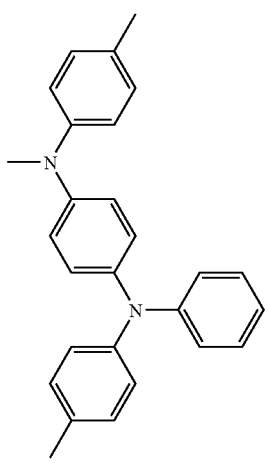 231

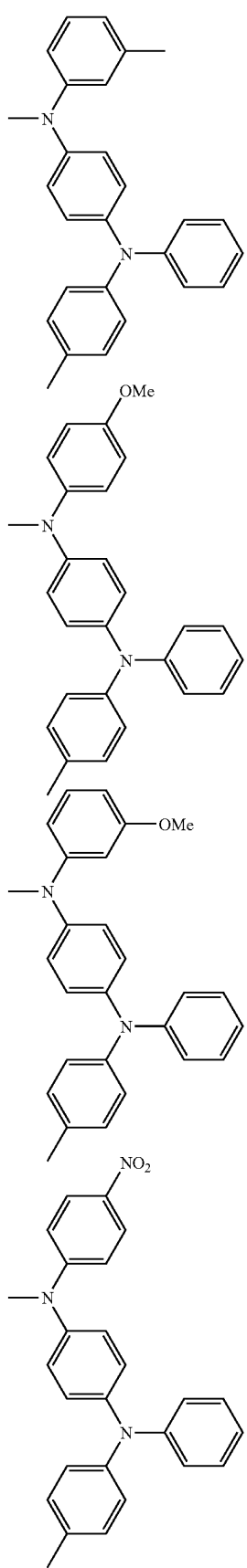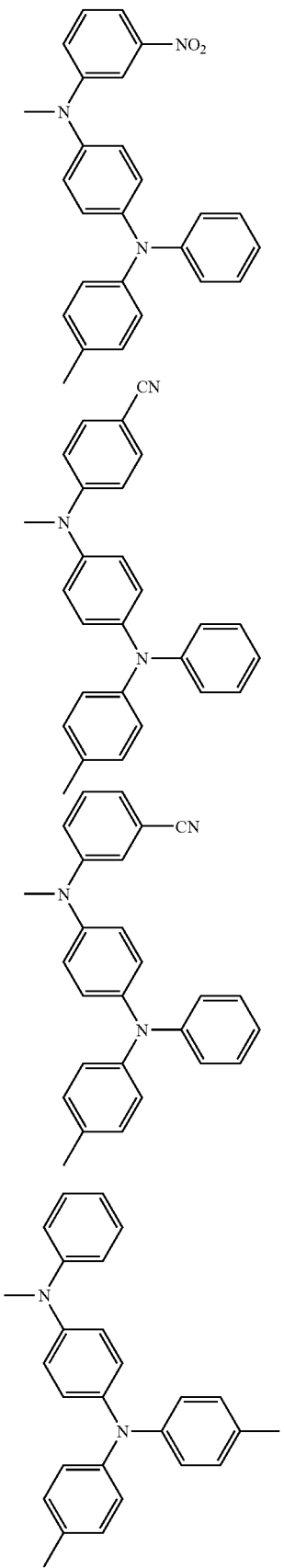

240 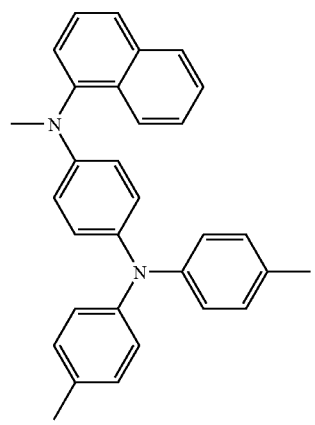
241 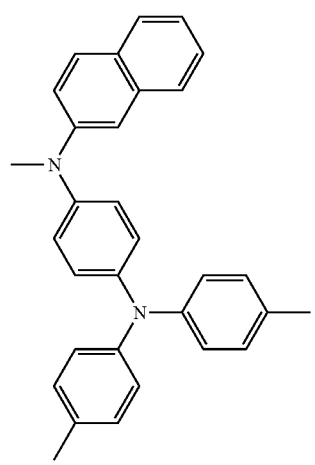
242 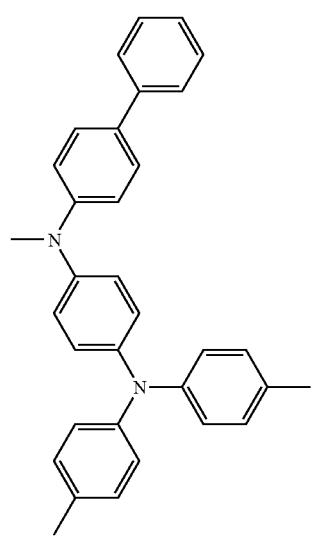
243 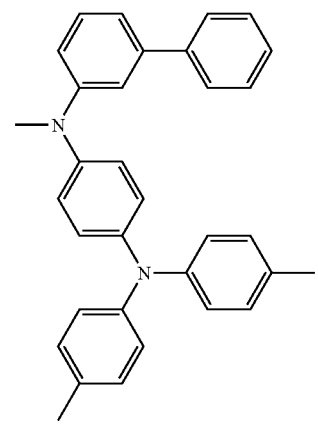
244 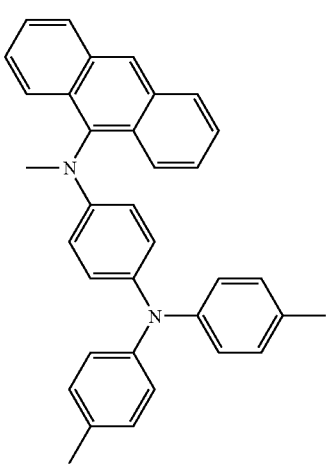
245 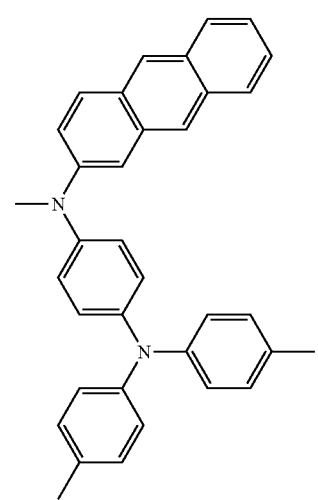

246
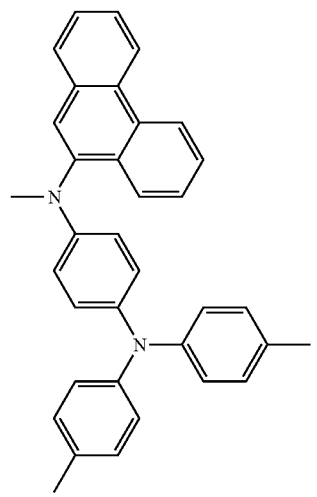
247
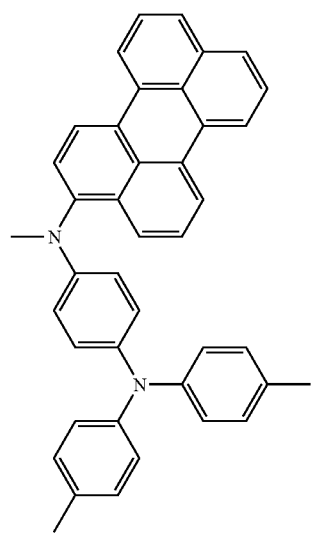
248
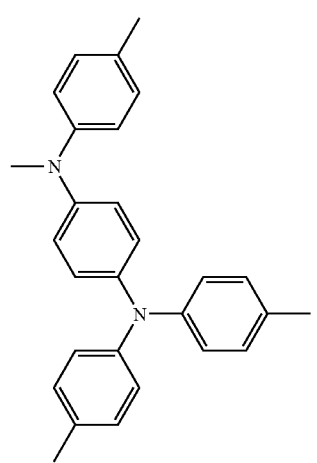
249
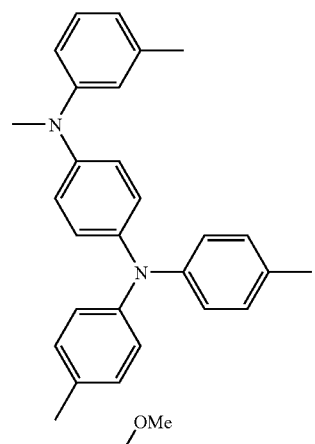
250
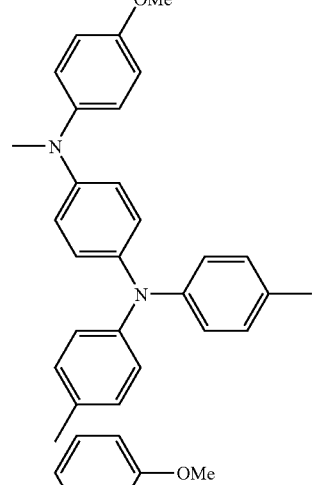
251
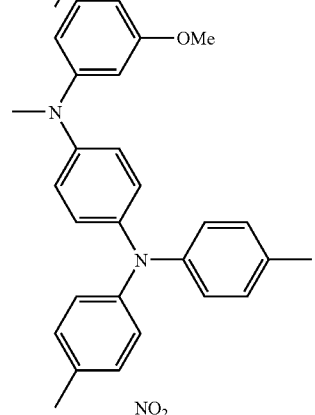
252
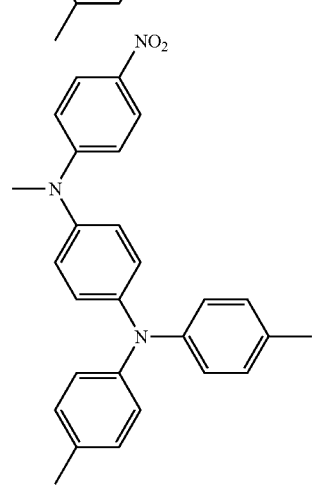

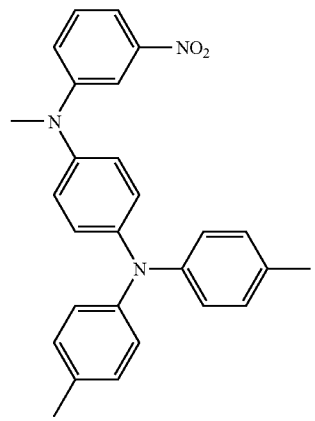
253
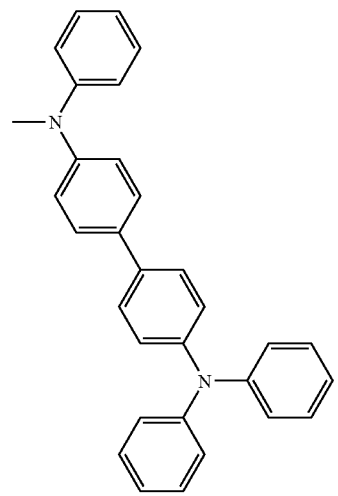
256
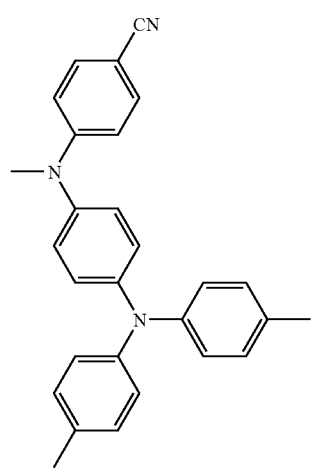
254
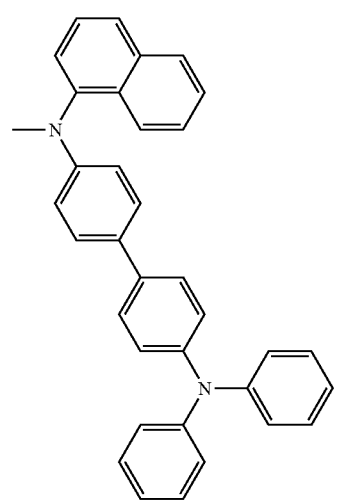
257
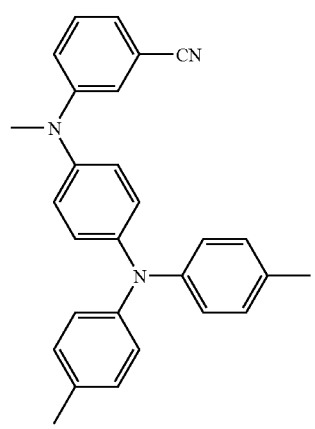
255
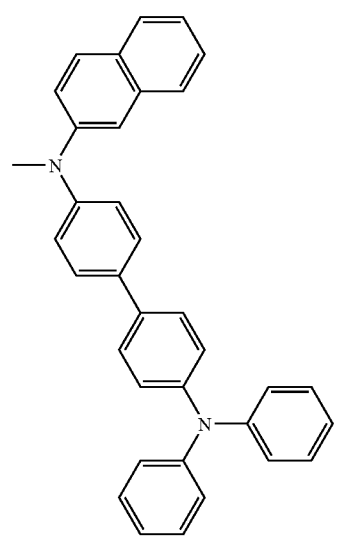
258

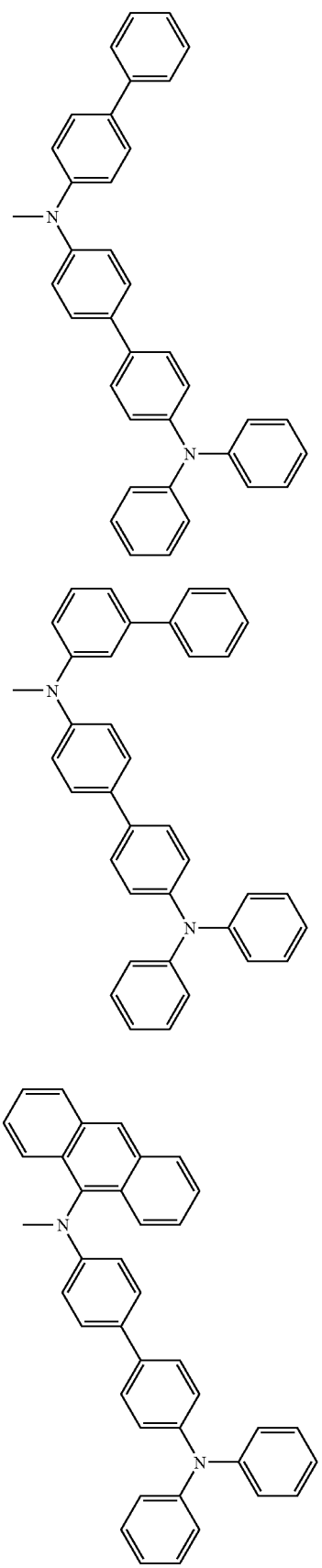
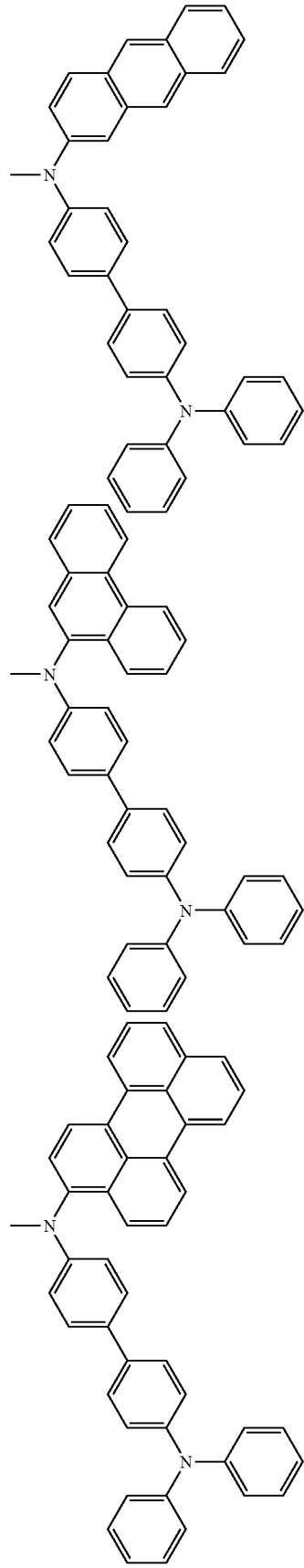

265
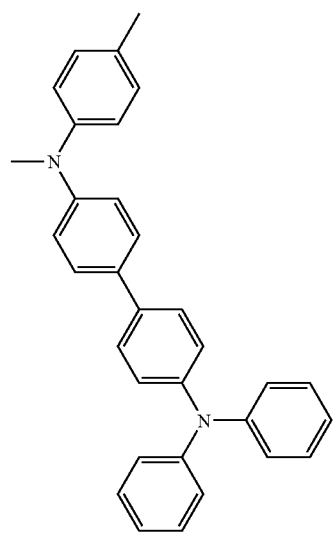
266
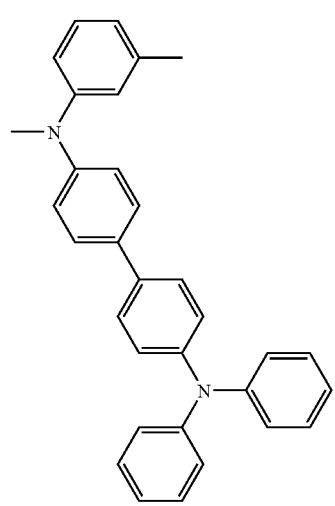
267
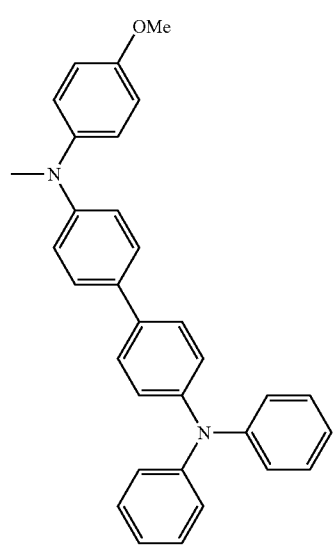
268
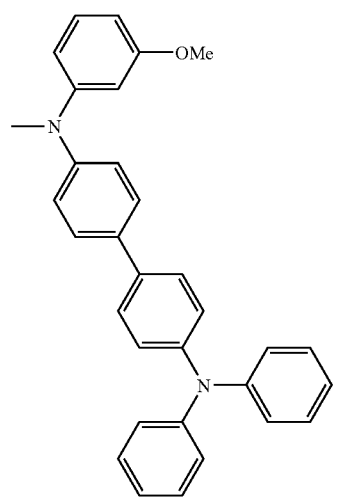
269
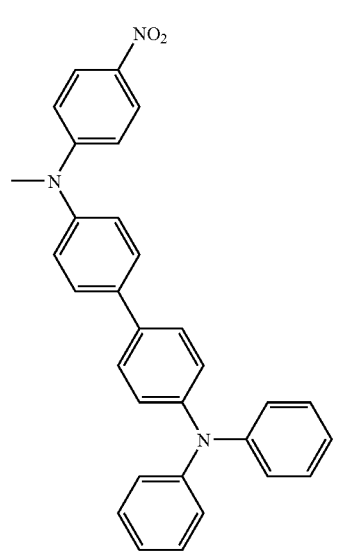
270
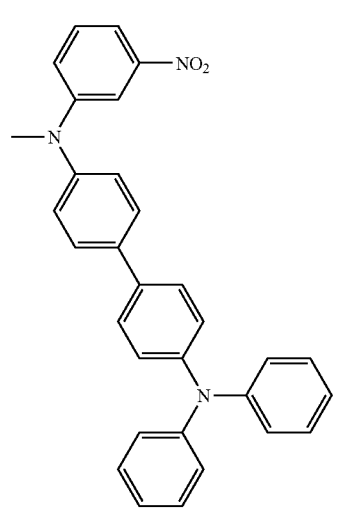

271
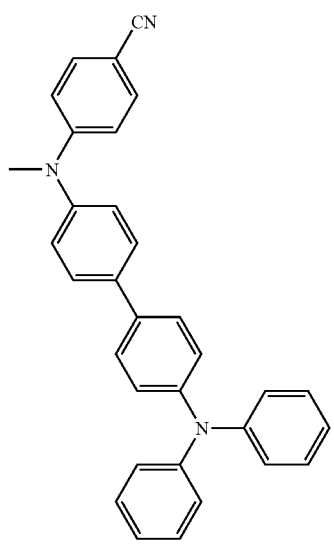
272
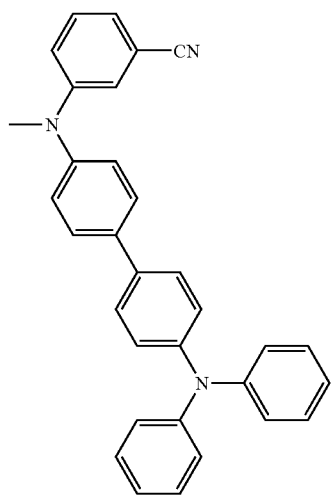
273
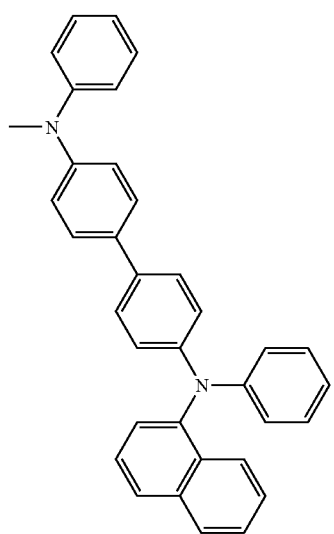
274
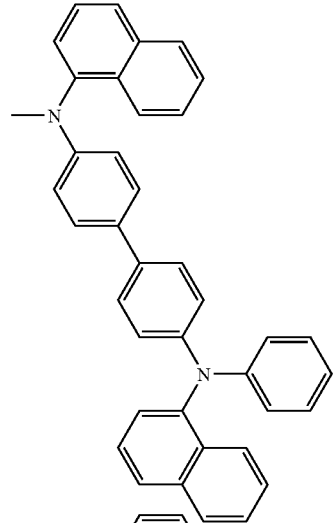
275
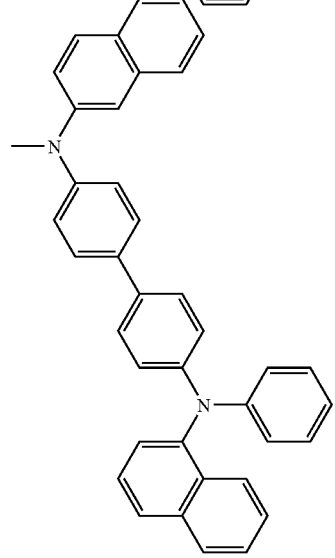
276
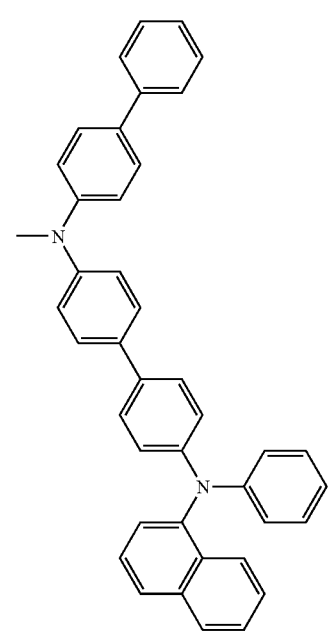

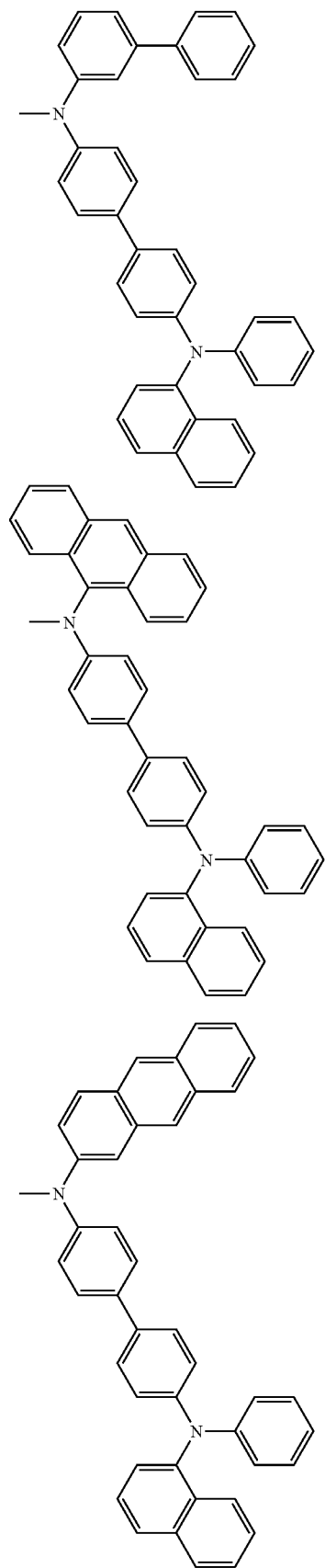

-continued
282
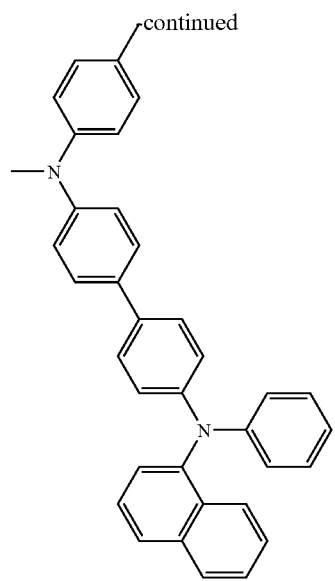
283
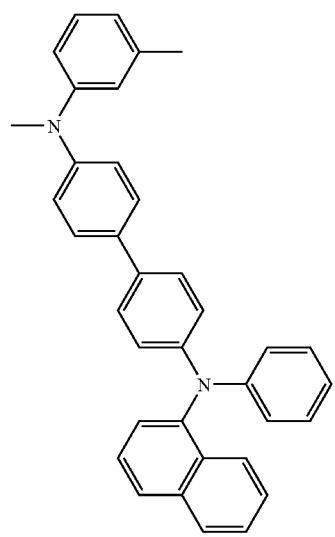
284
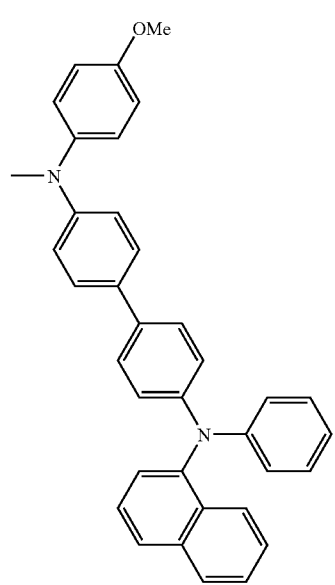
-continued
285
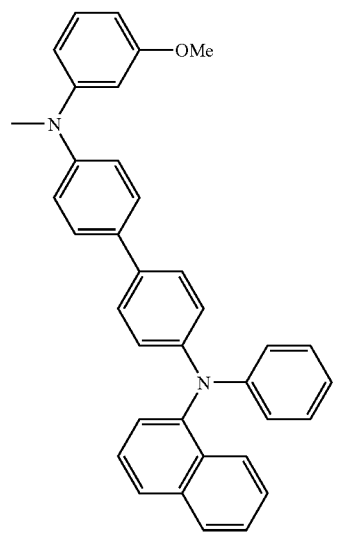
286
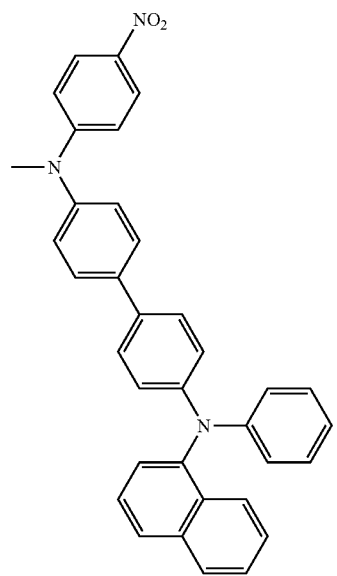
287
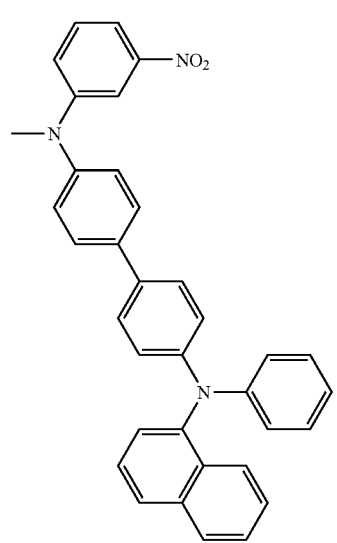

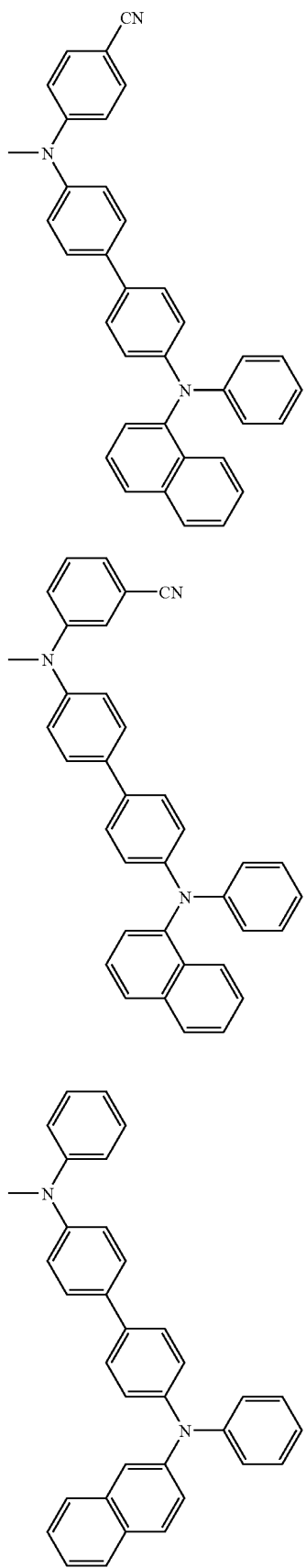
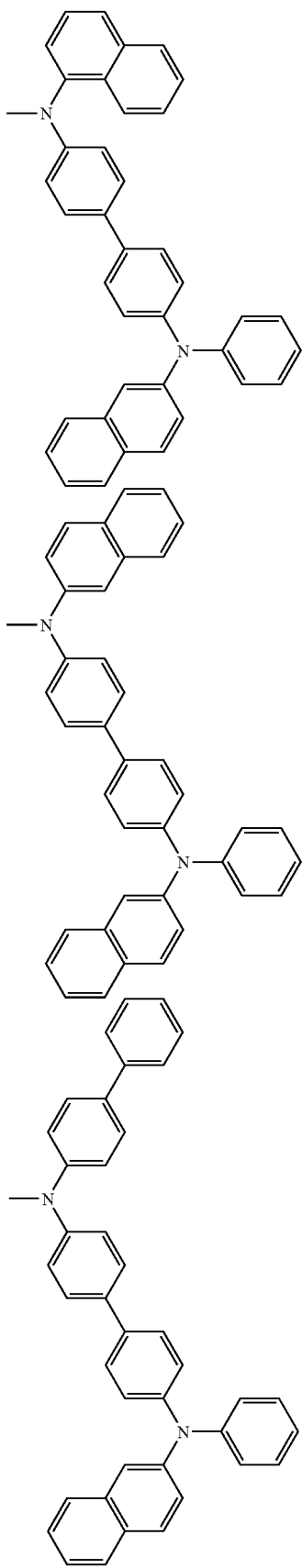

105
-continued
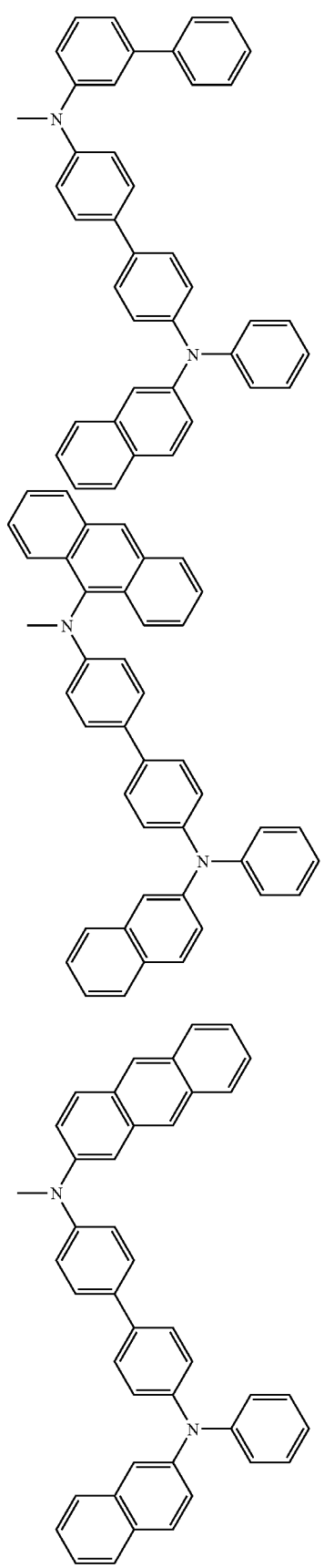
106
-continued
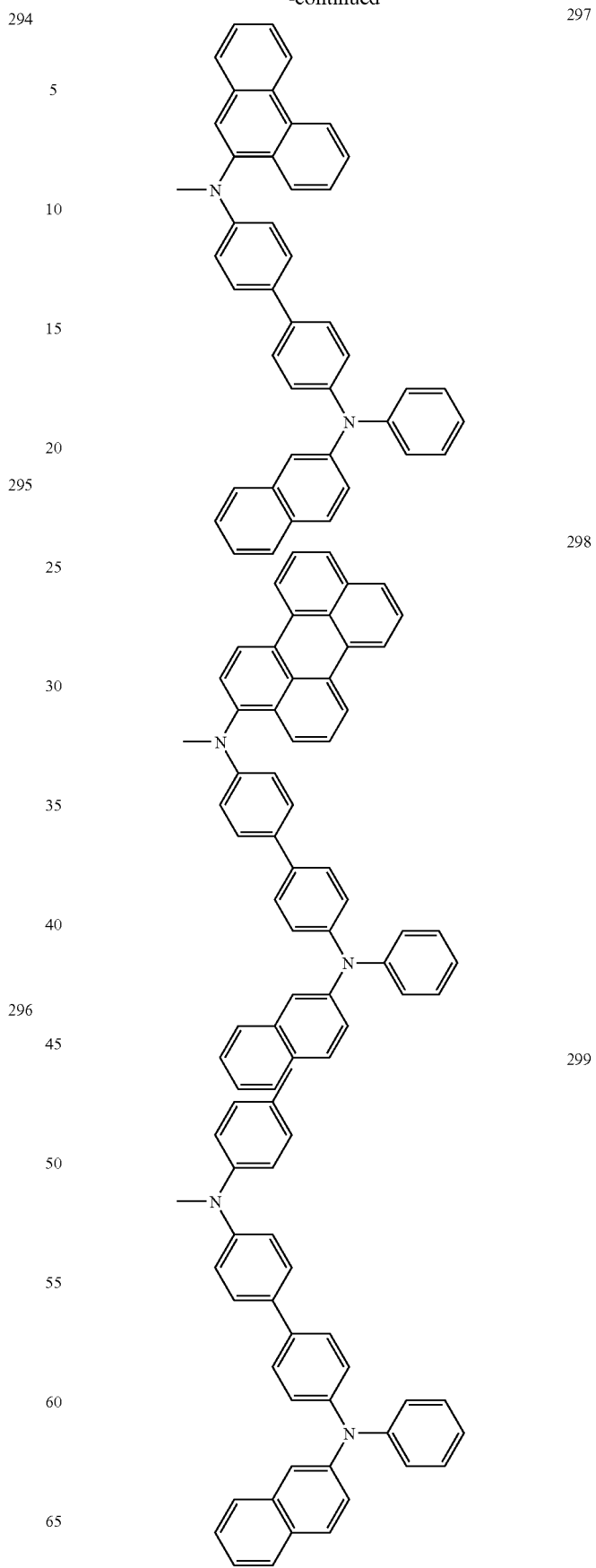

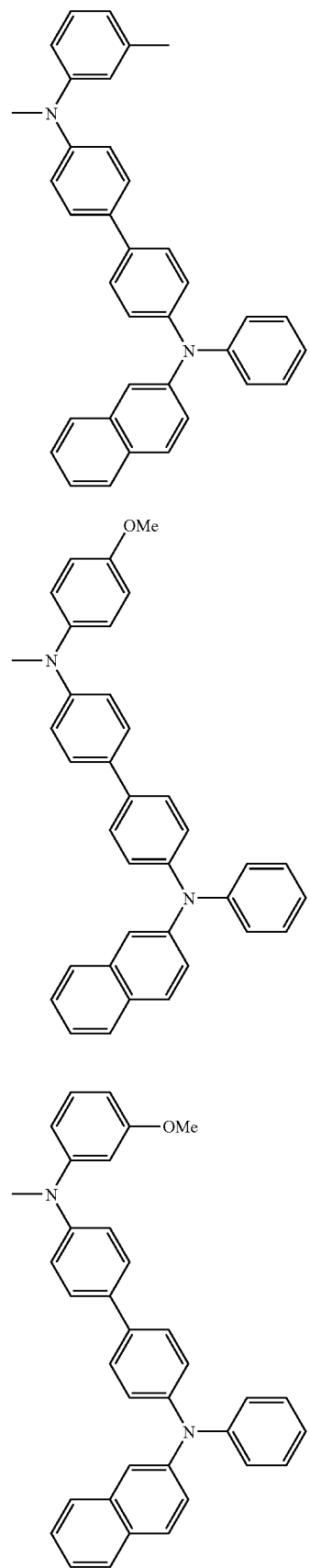
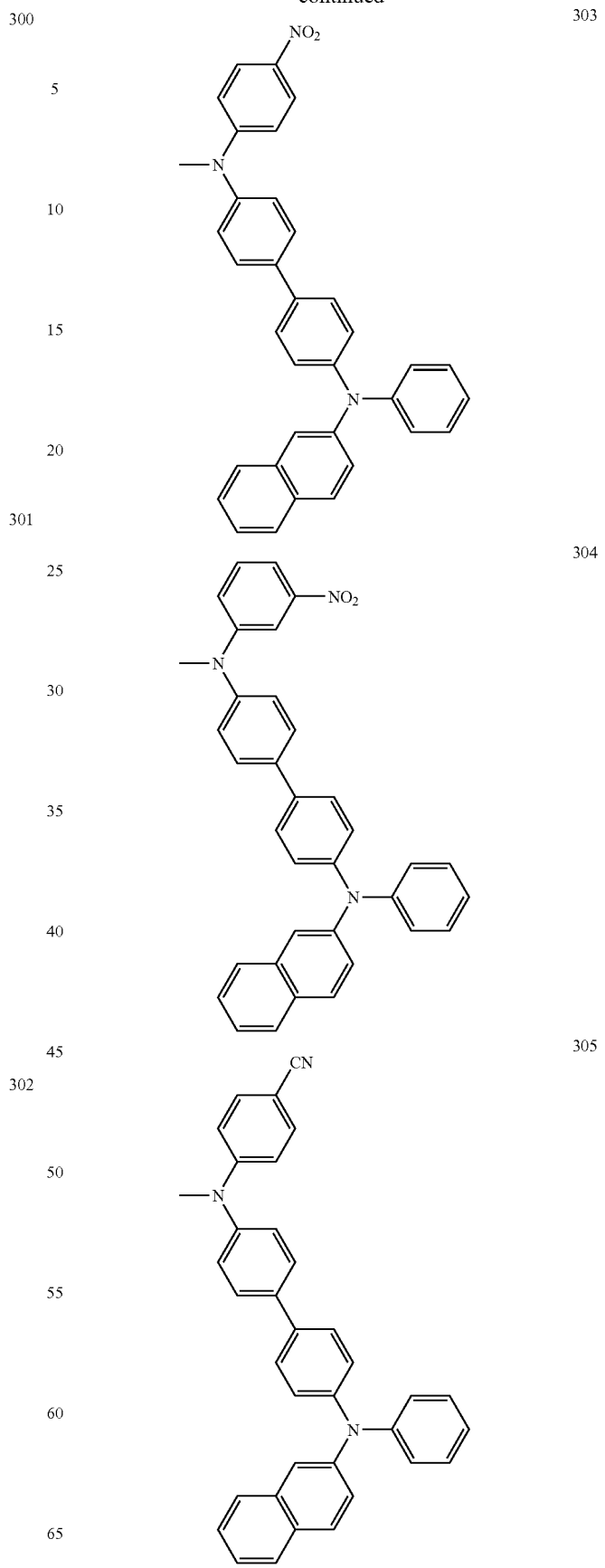

109
-continued
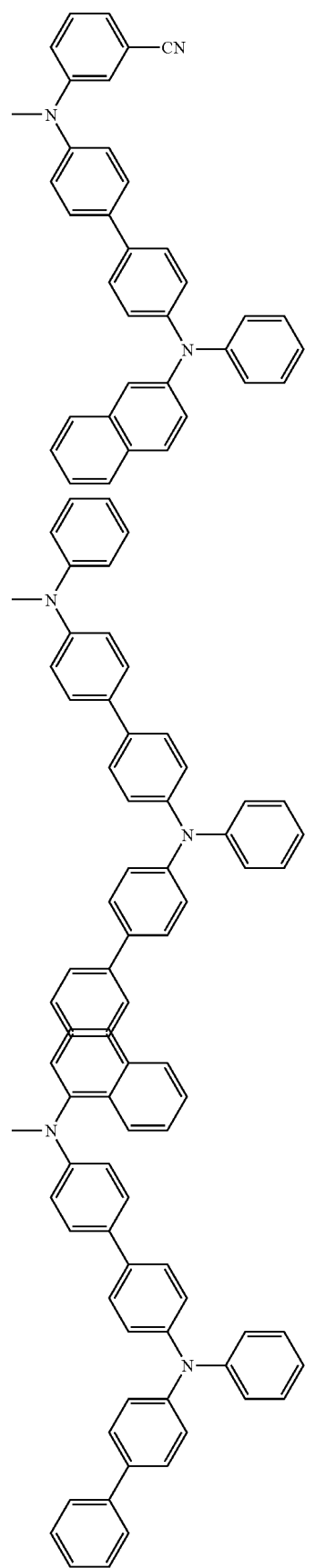
306
307
308
110
-continued
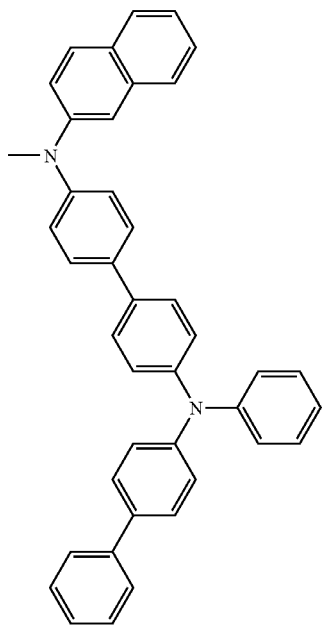
309
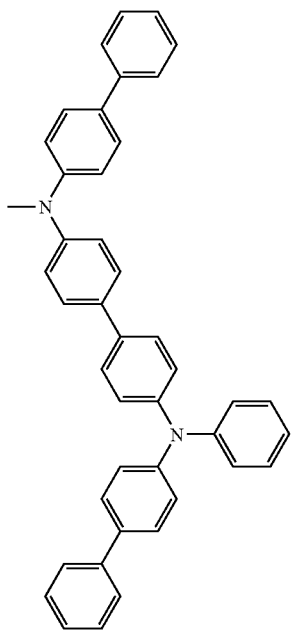
310

311
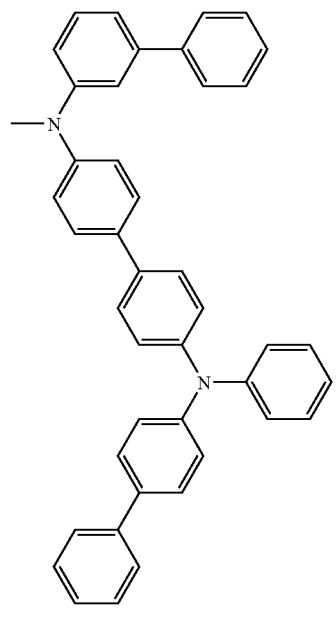
312
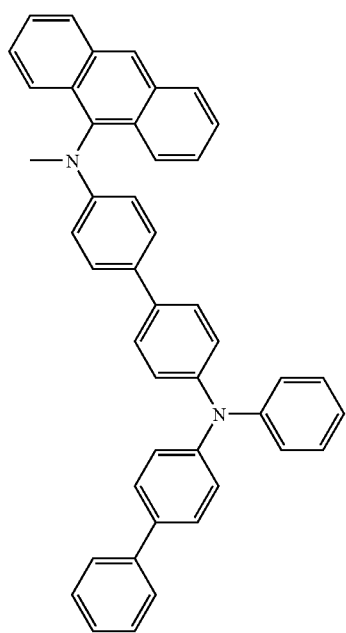
313
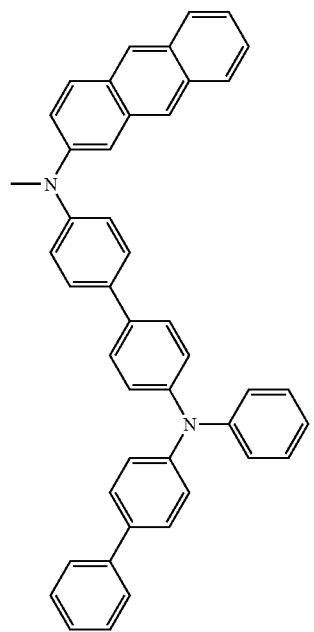
314
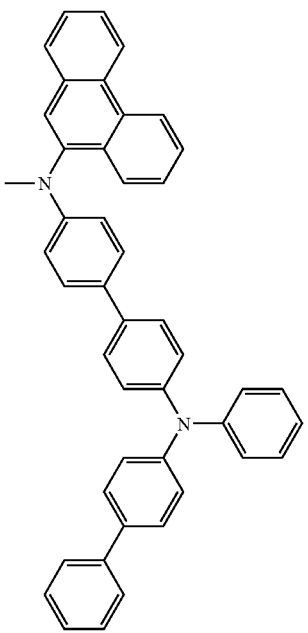

113
-continued
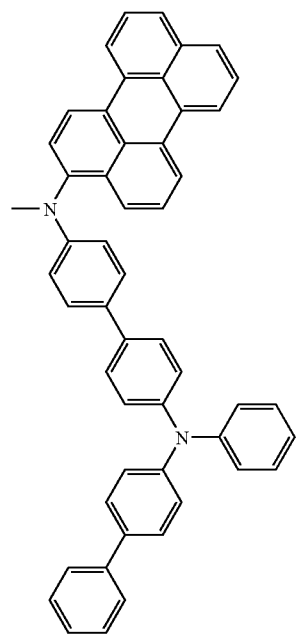
315
114
-continued
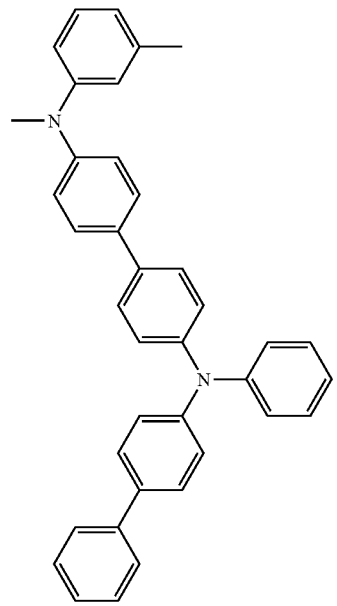
317
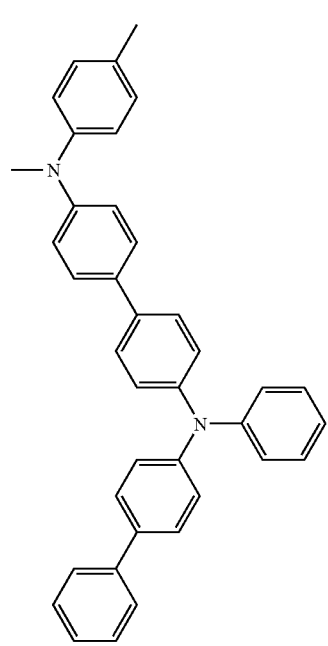
316
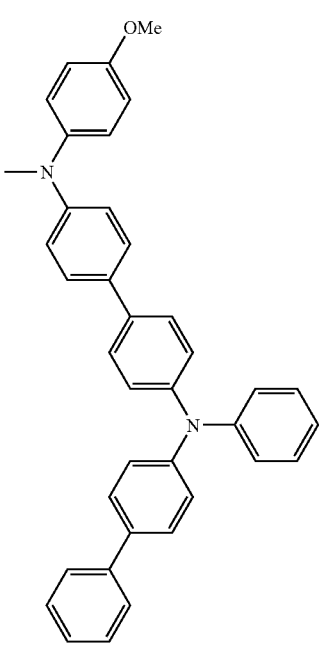
318

115
-continued
116
-continued
319
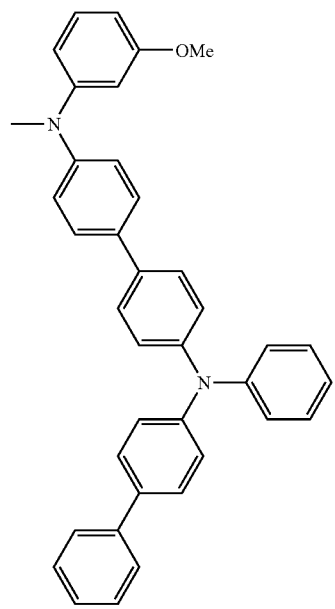
321
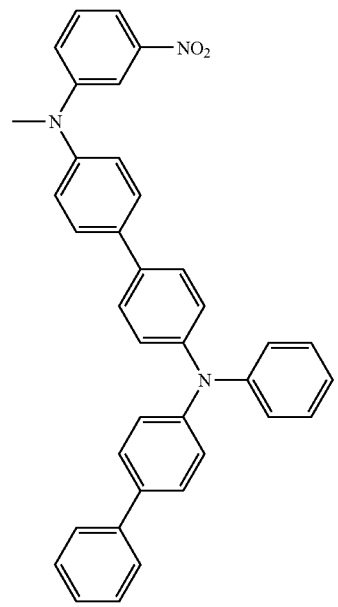
320
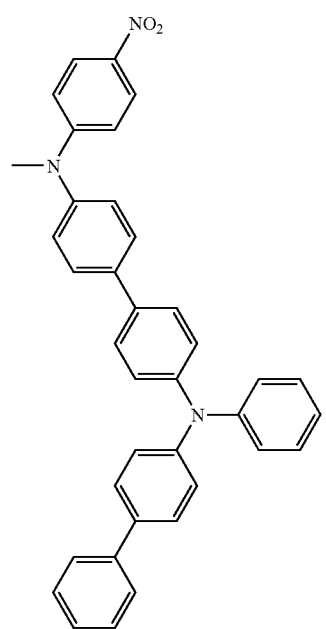
322
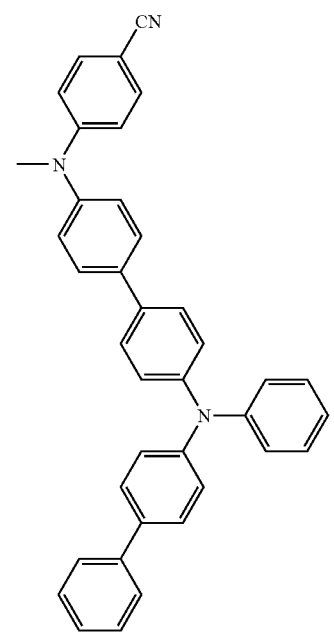

117
-continued
323
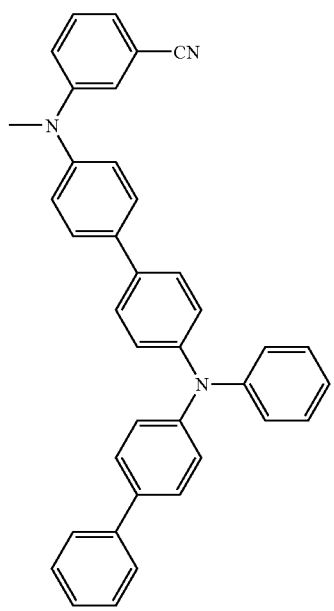
324
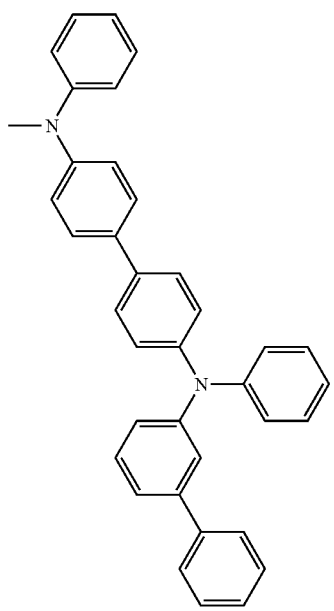
118
-continued
325
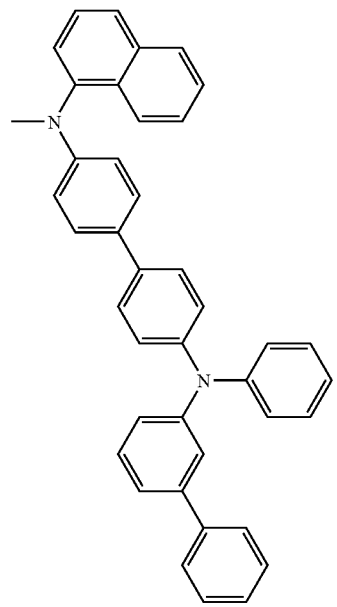
326
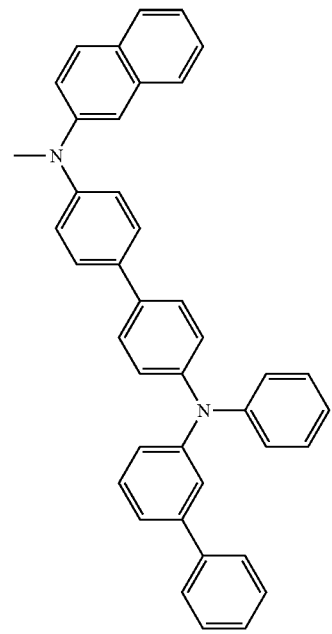

327
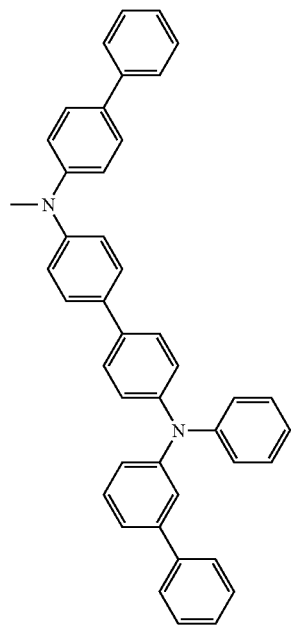
328
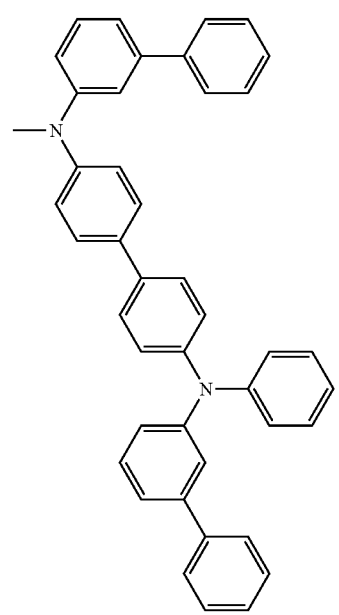
329
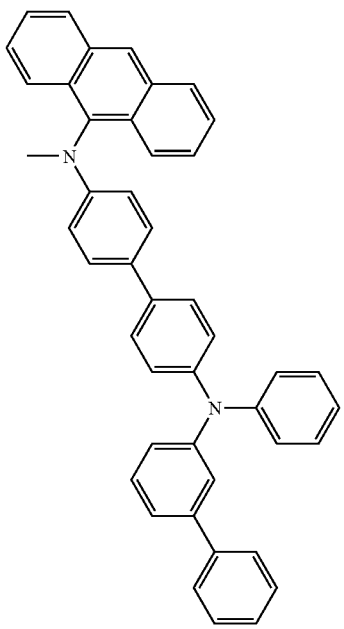
330
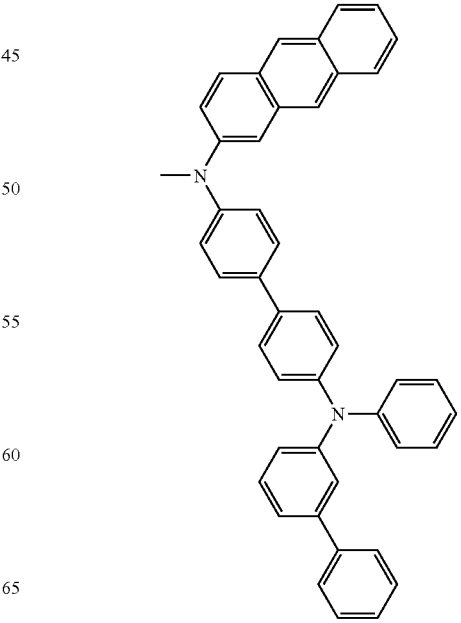

121
-continued
331
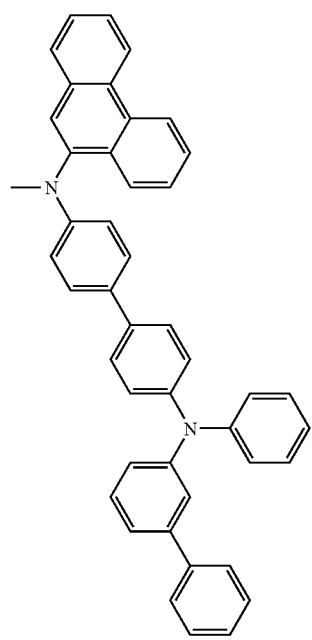
332
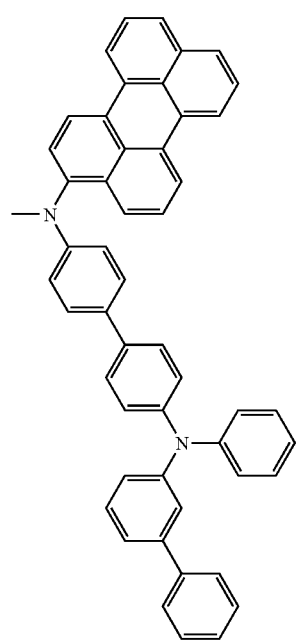
122
-continued
333
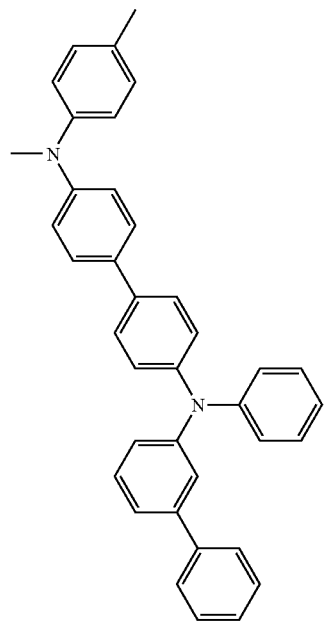
334
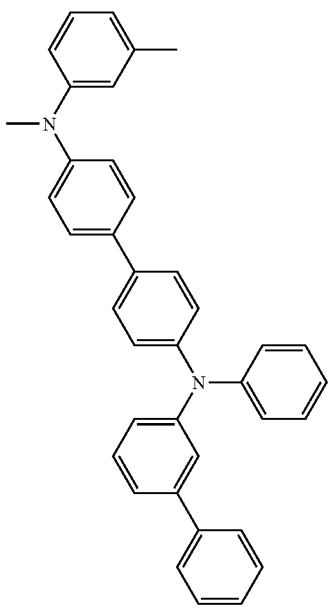

123
-continued
124
-continued
335
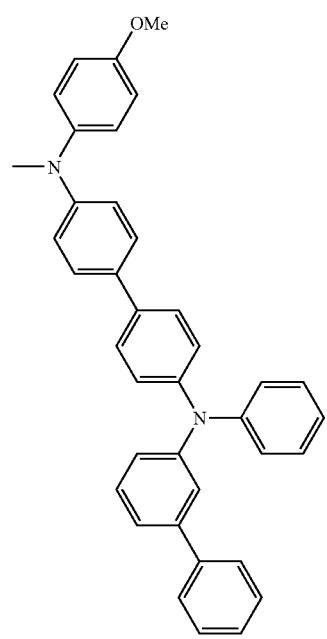
337
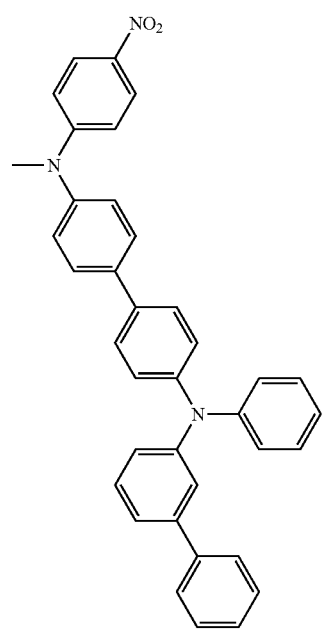
336
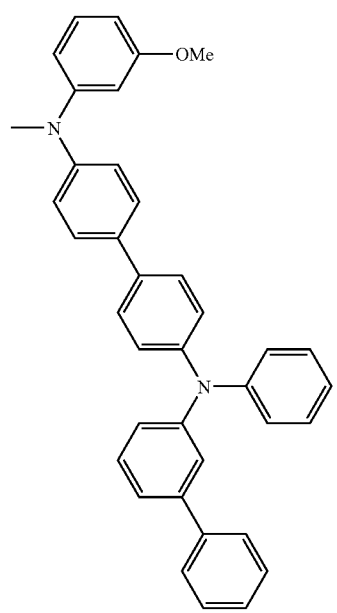
338
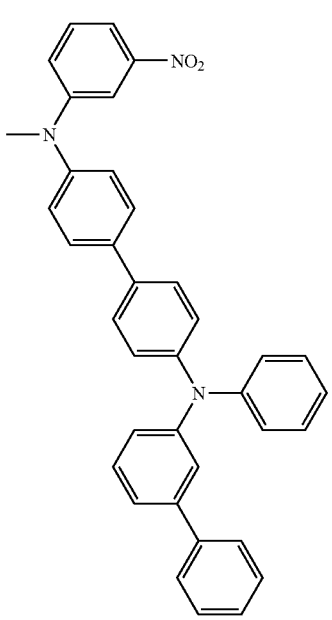

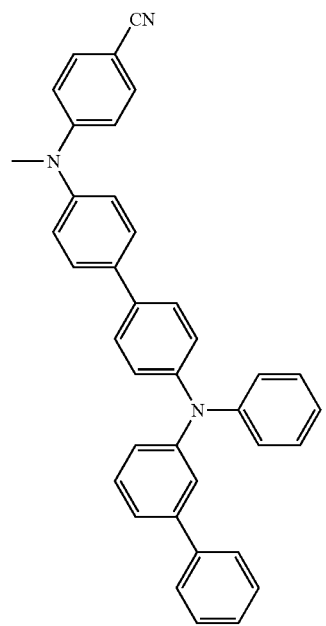
339
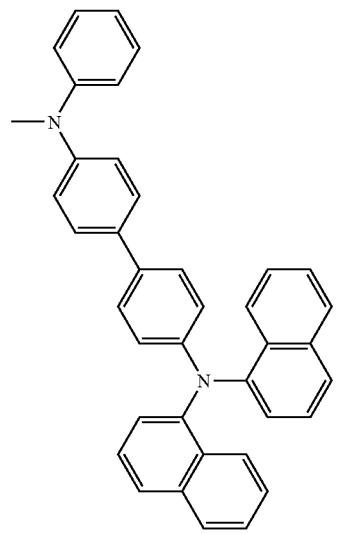
341
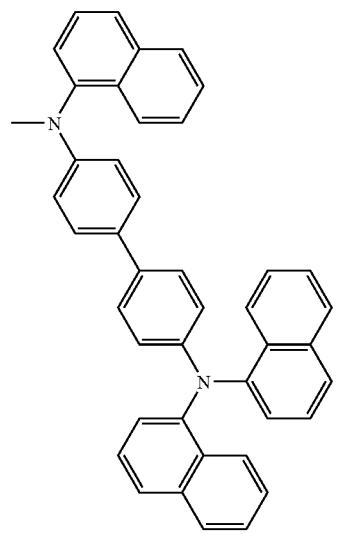
342
340
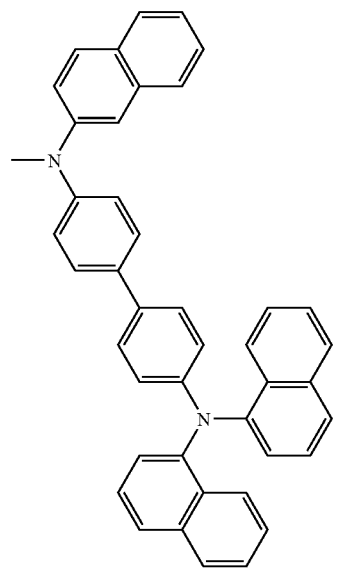
343

344
345
346
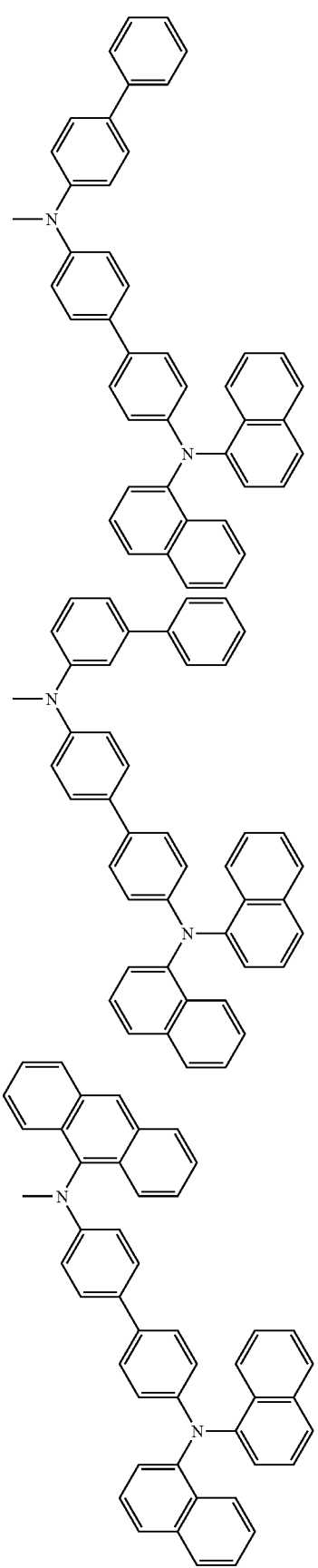
347
348
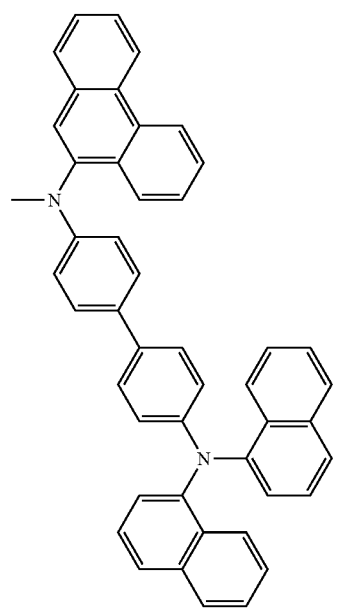

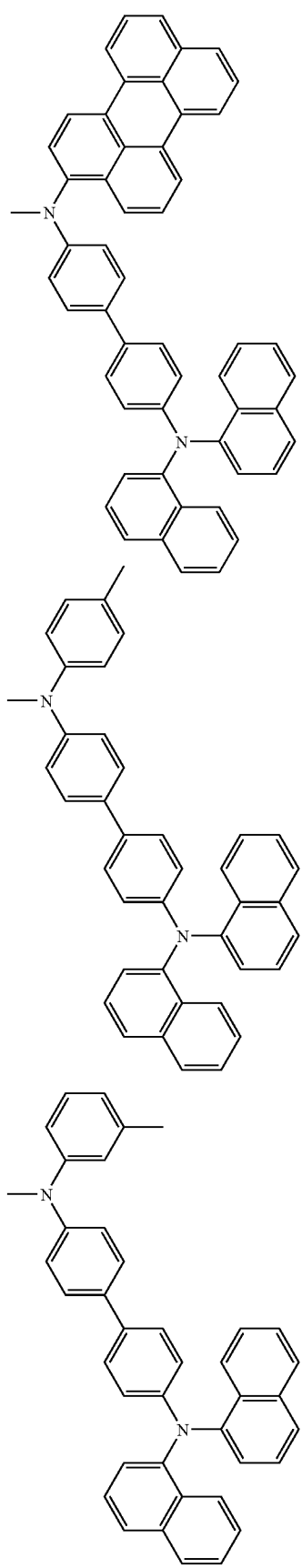
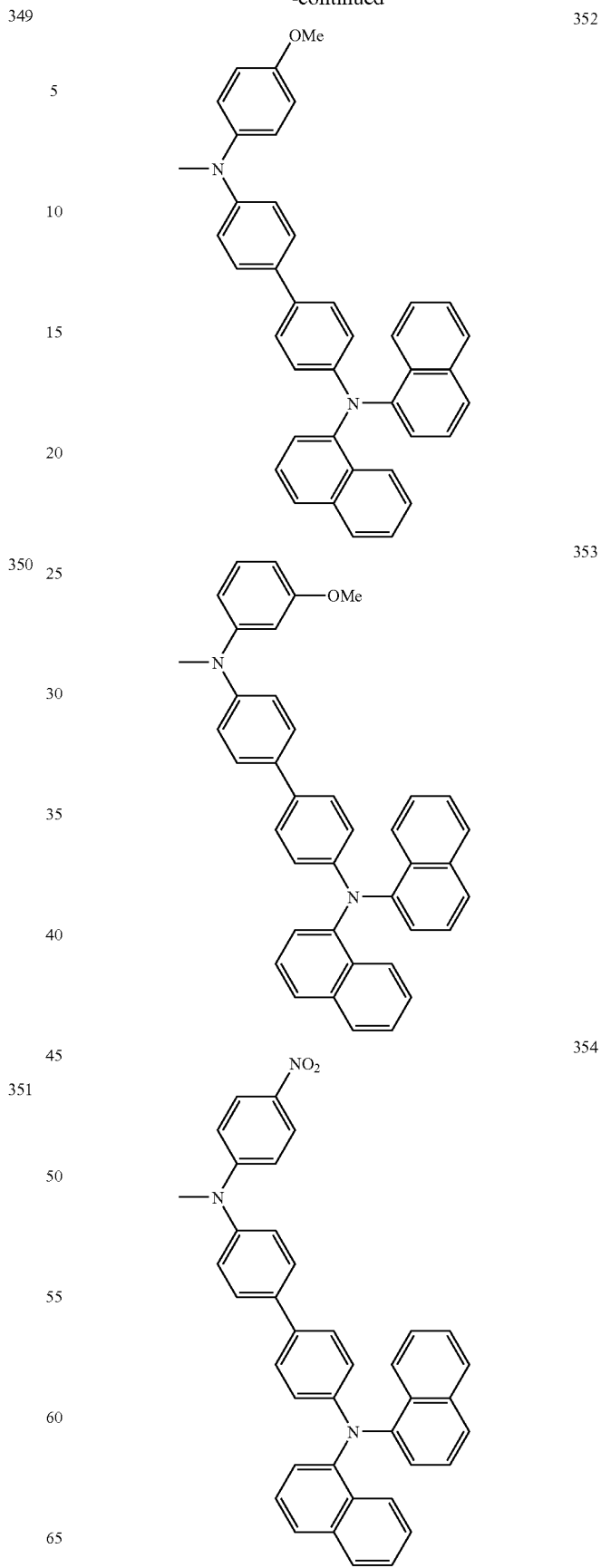

355
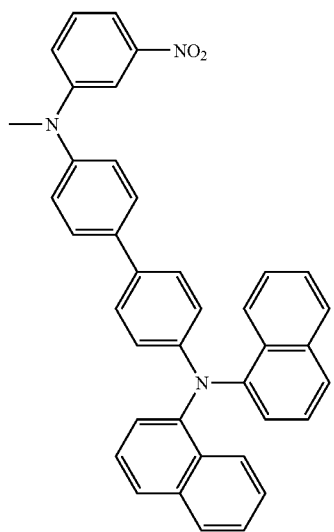
356
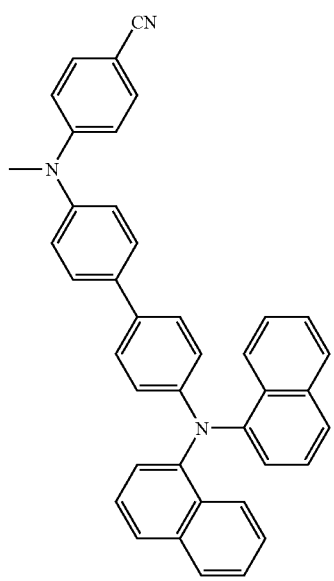
357
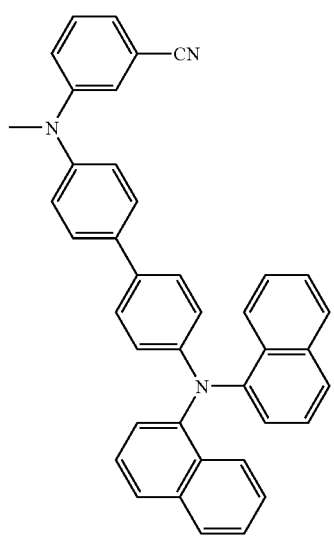
358
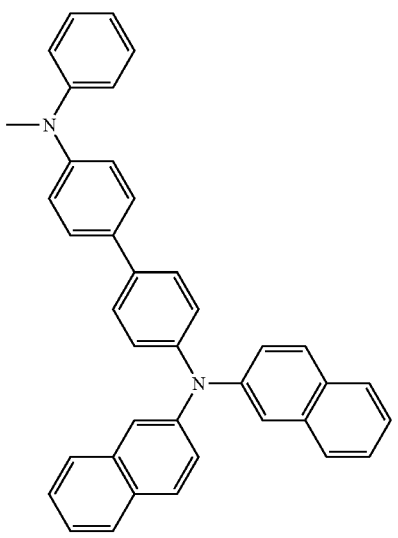
359
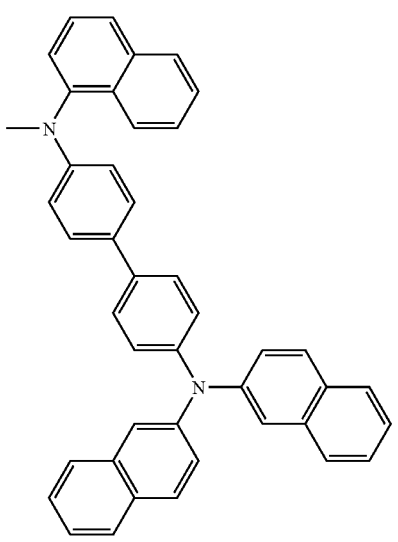
360
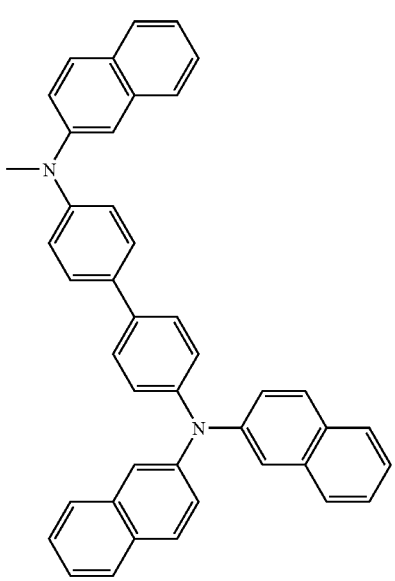

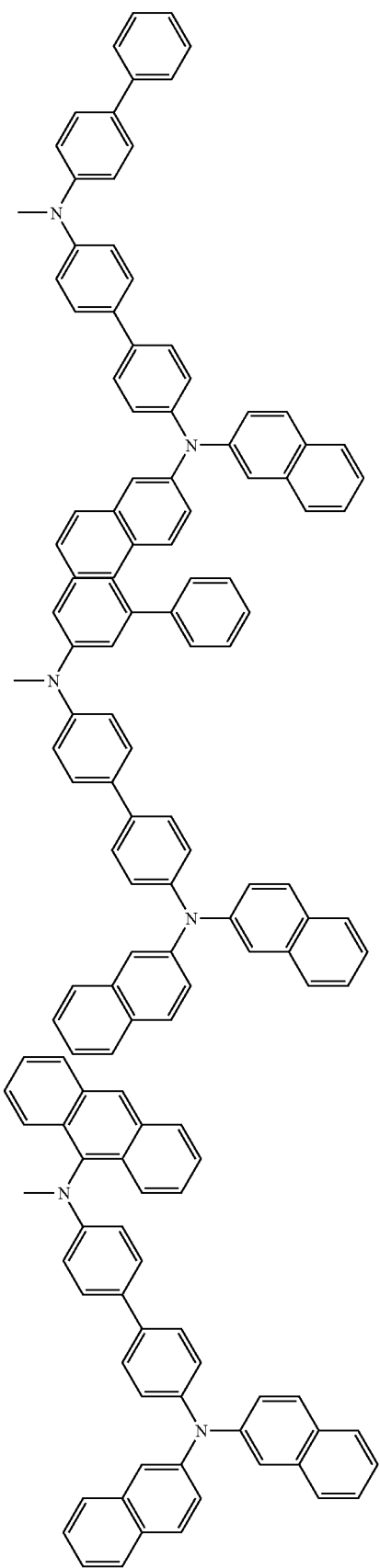
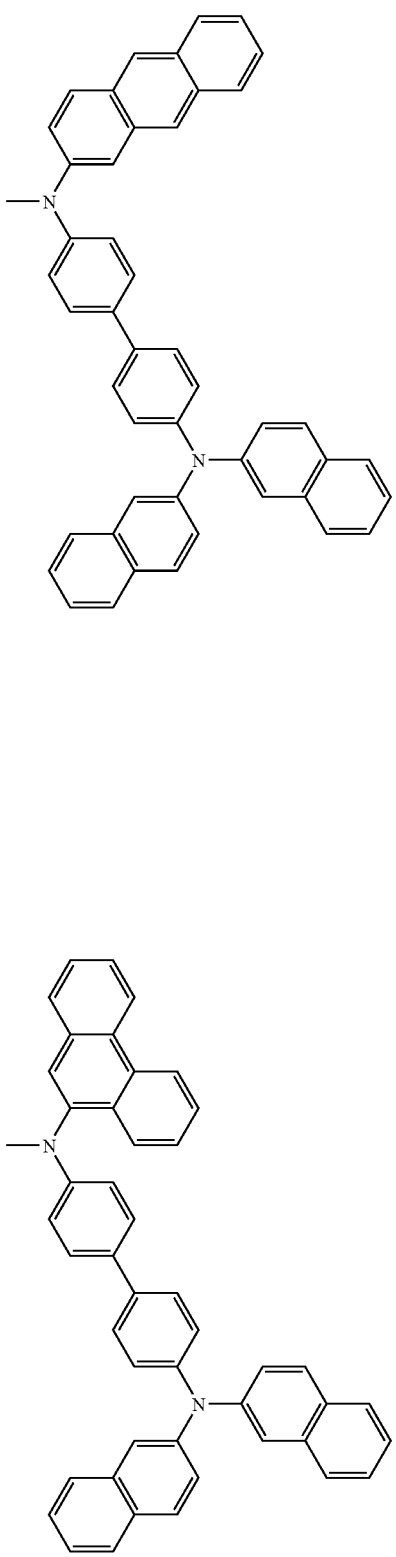

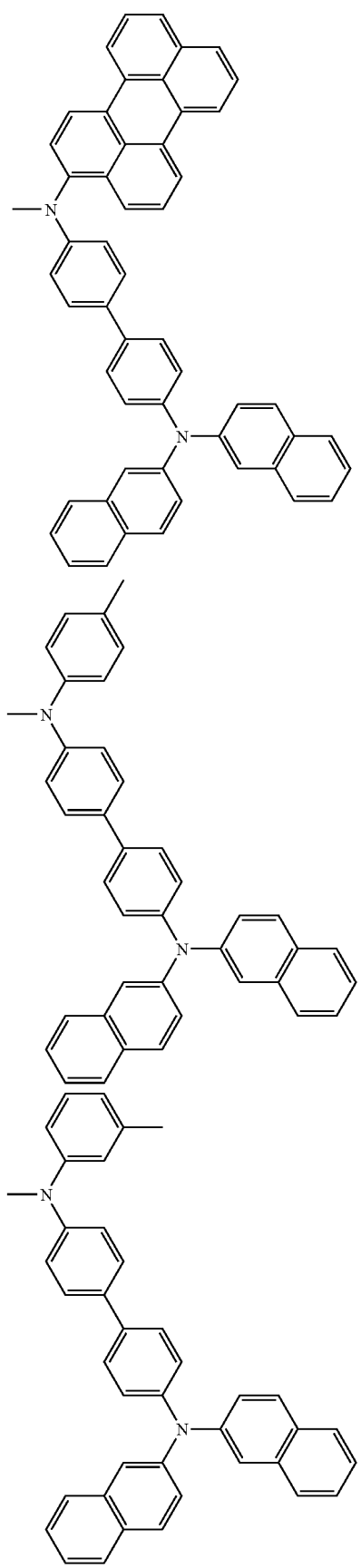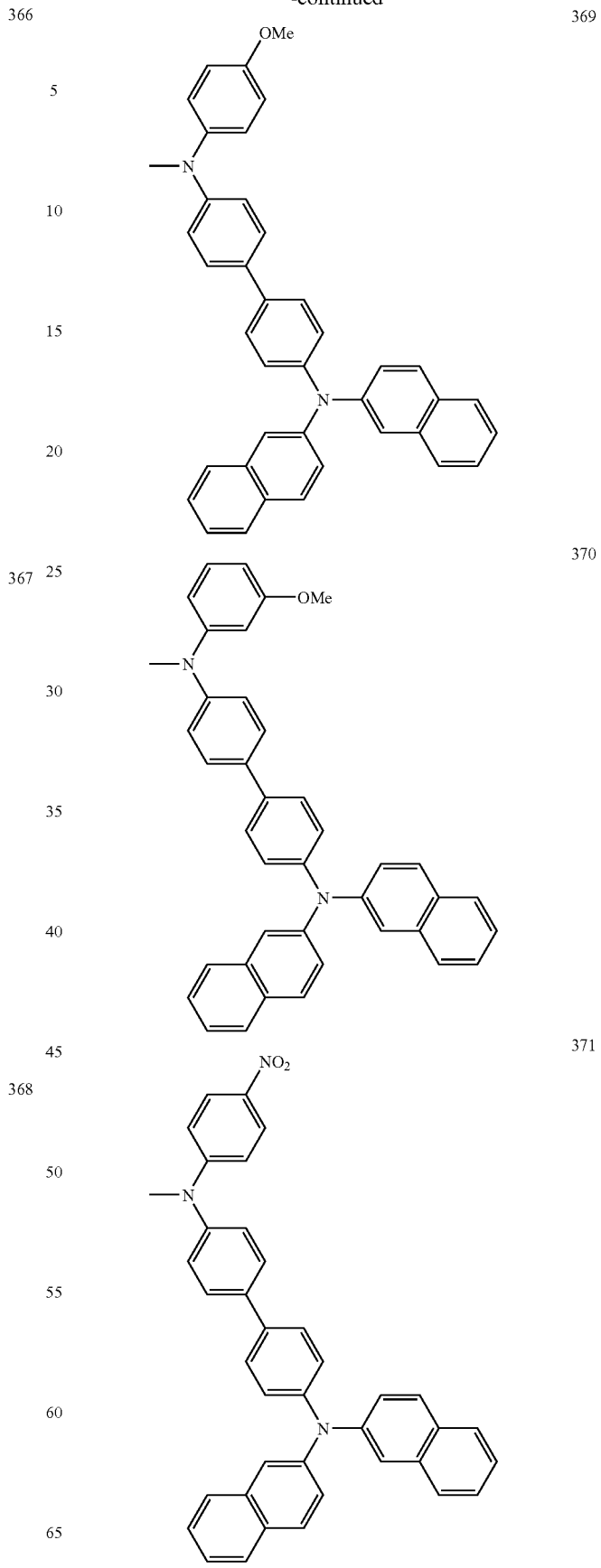

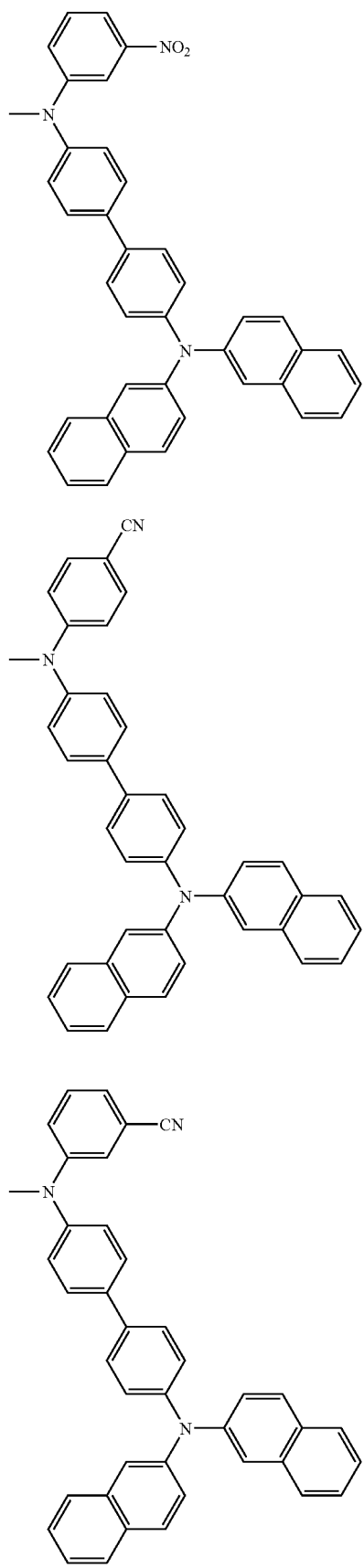
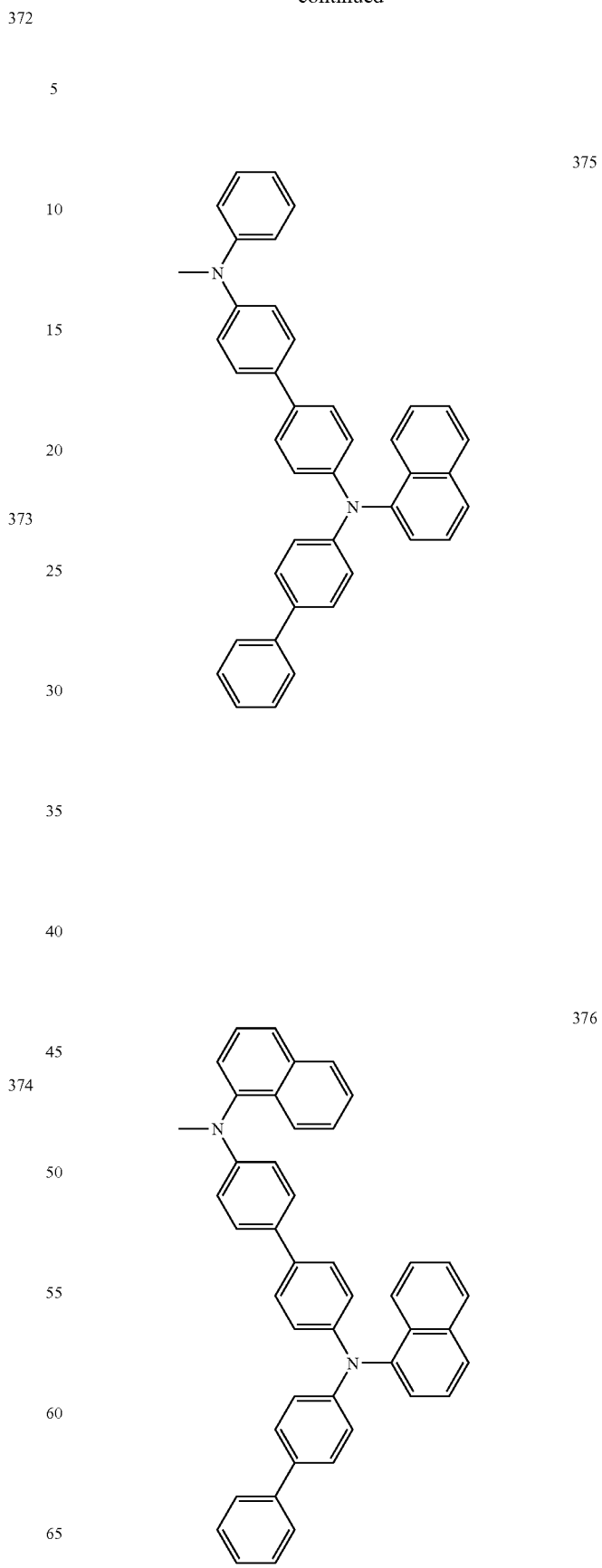

377
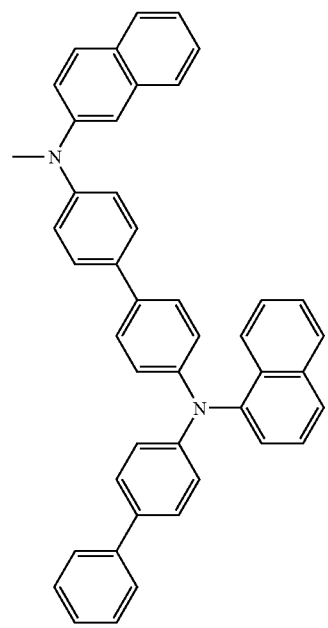
379
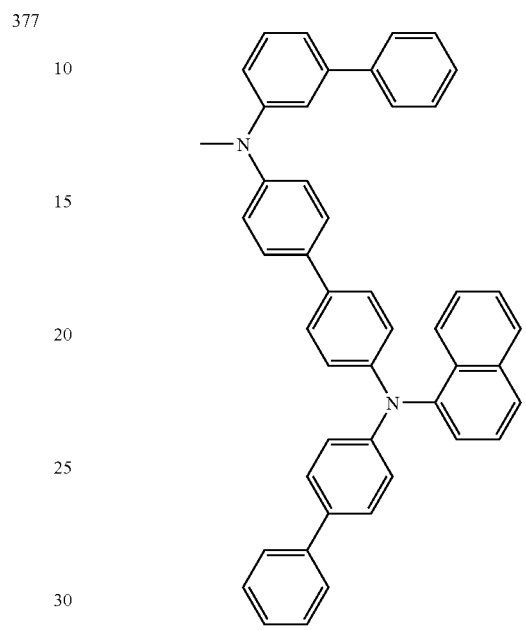
378
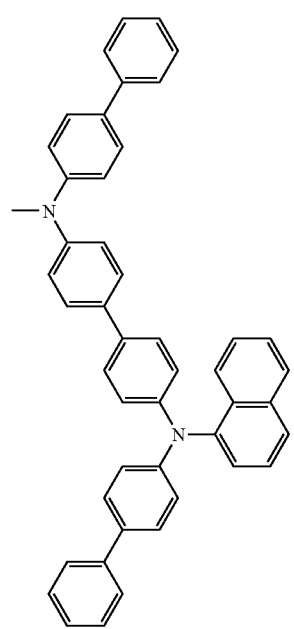
380
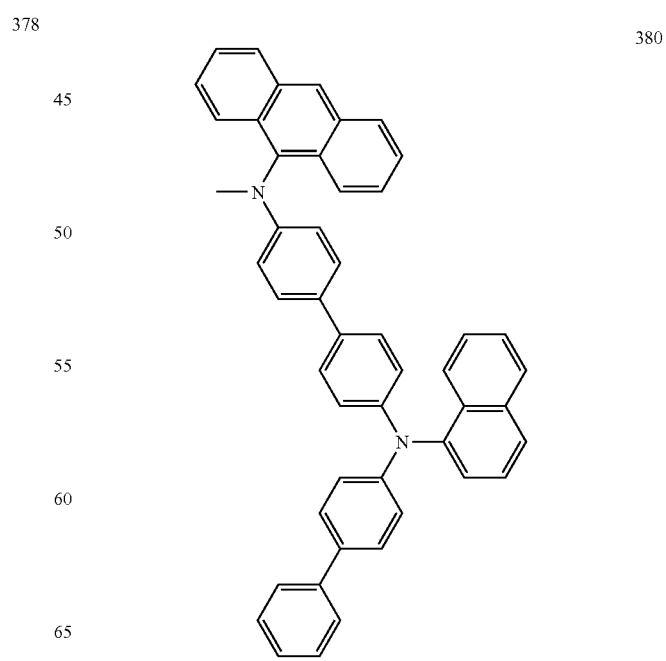

141
-continued
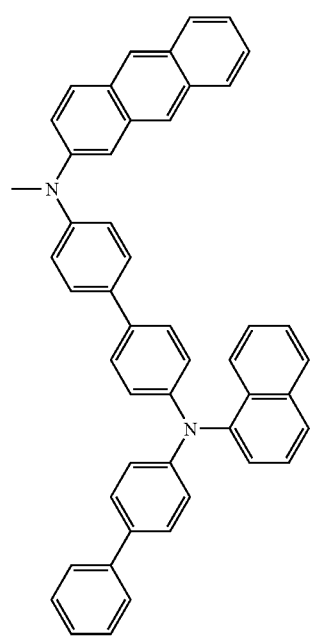
382
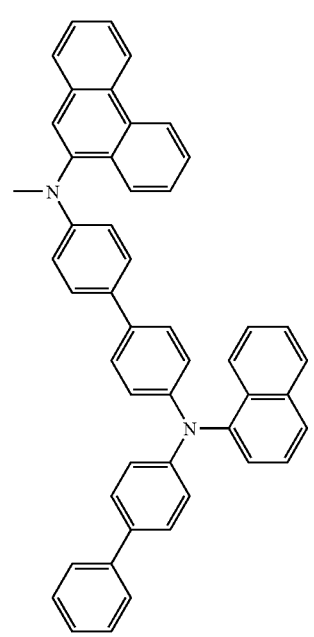
142
-continued
381
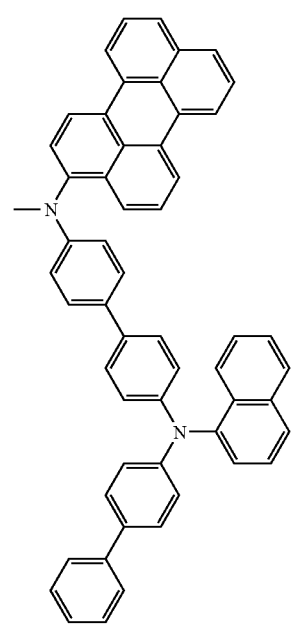
384
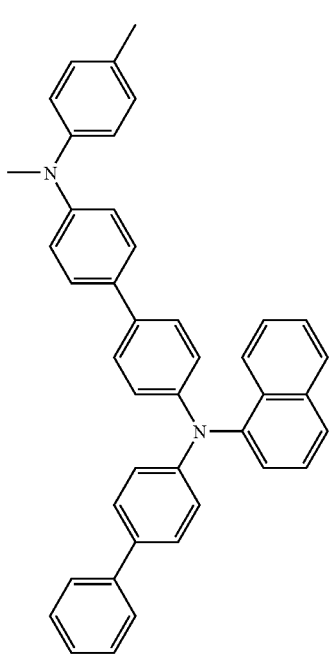

385
386
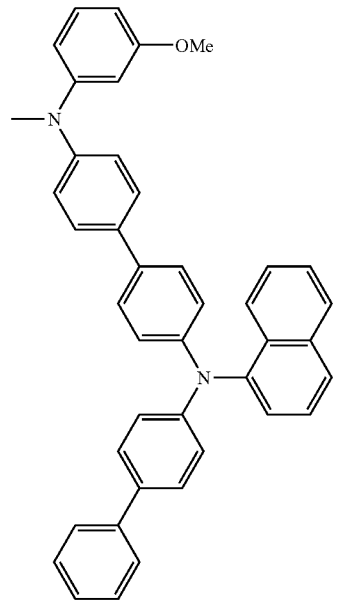
387
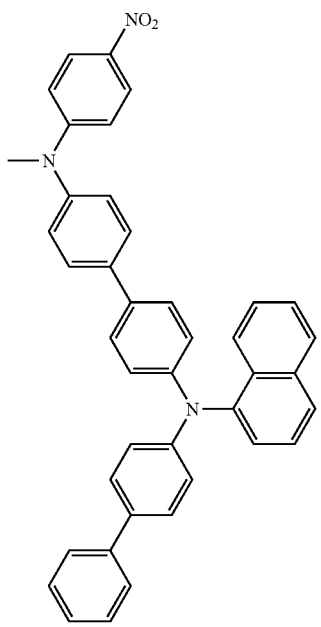
388

145
-continued
146
-continued
389
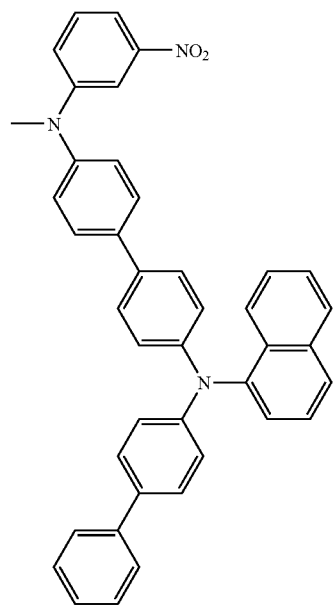
391
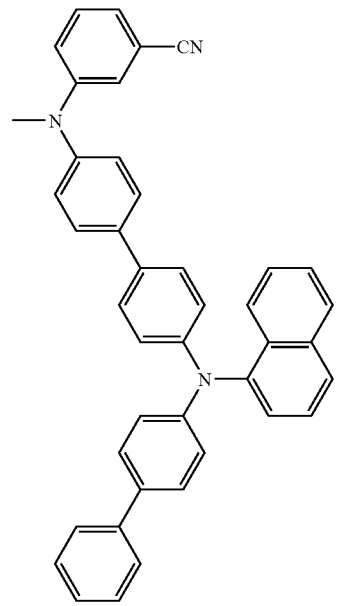
390
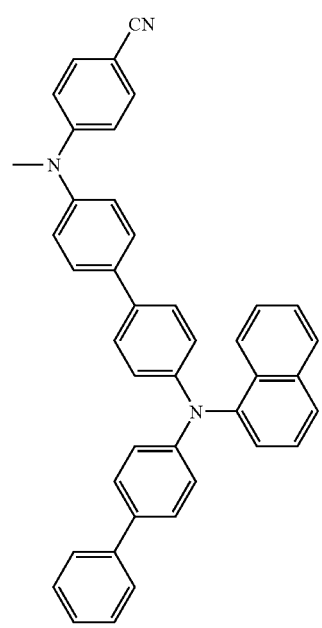
392
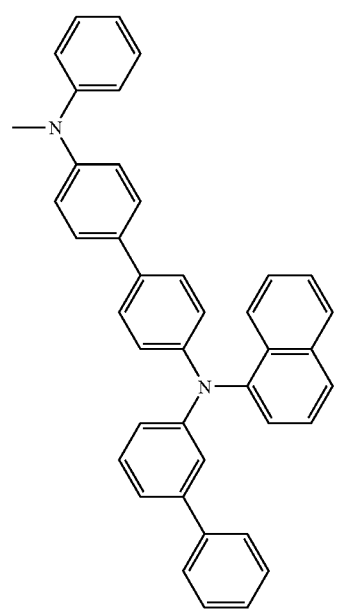

147
-continued
148
-continued
393
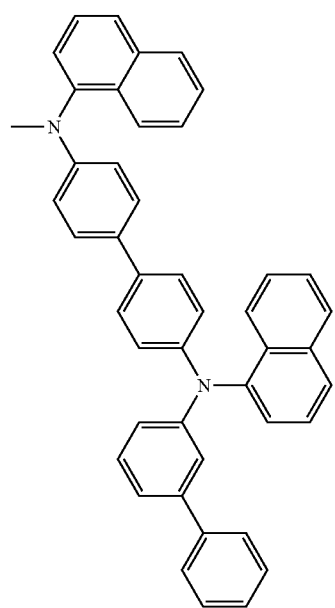
395
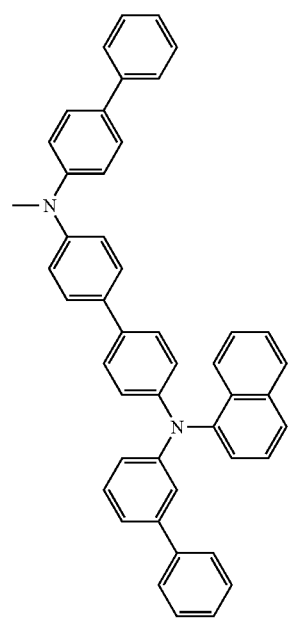
394
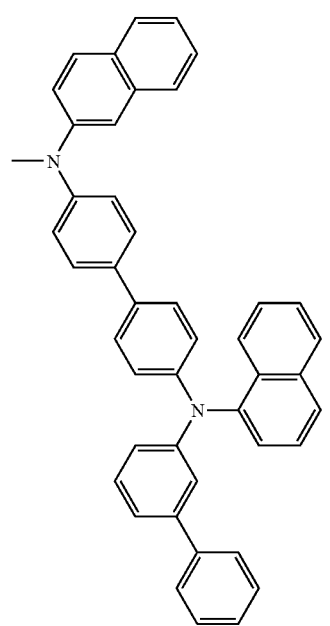
396
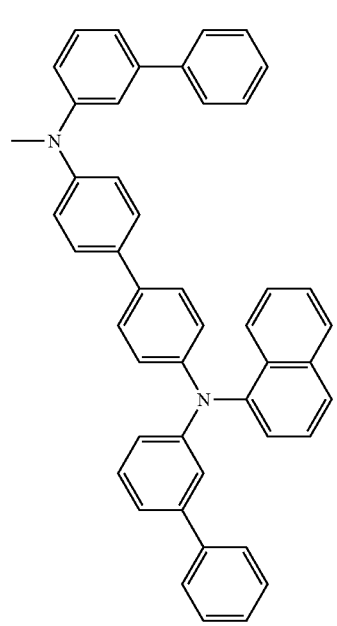

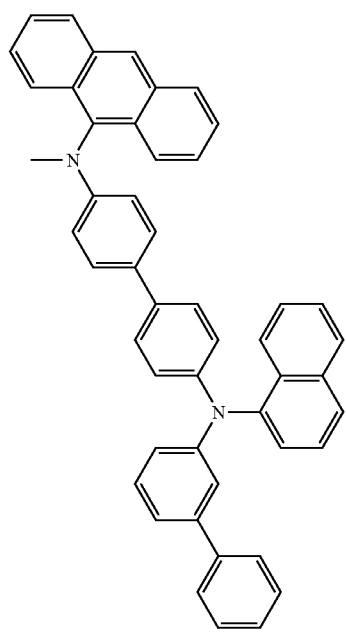
397
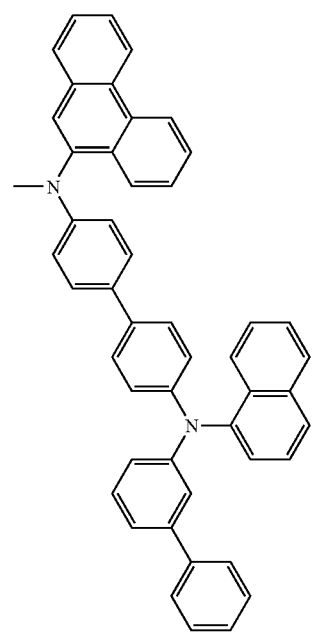
399
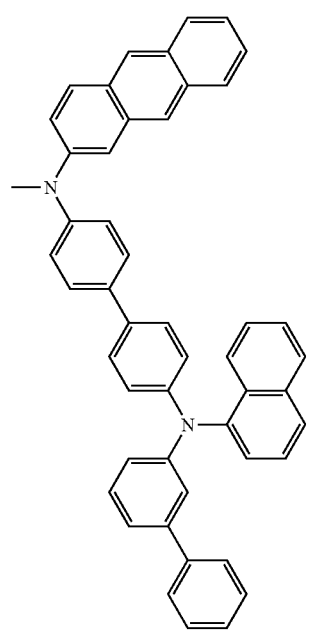
398
400

401
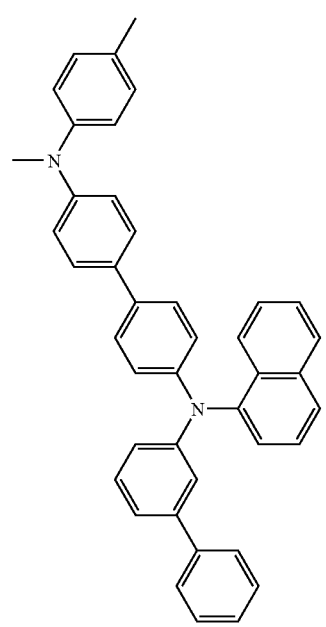
403
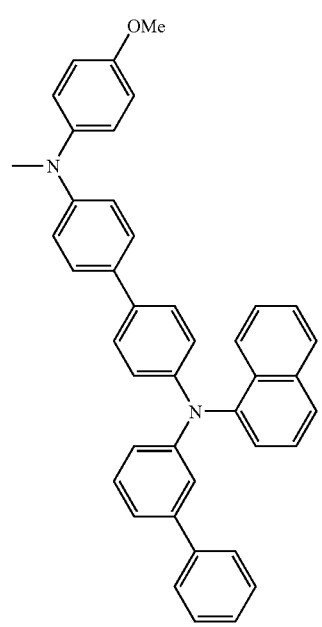
402
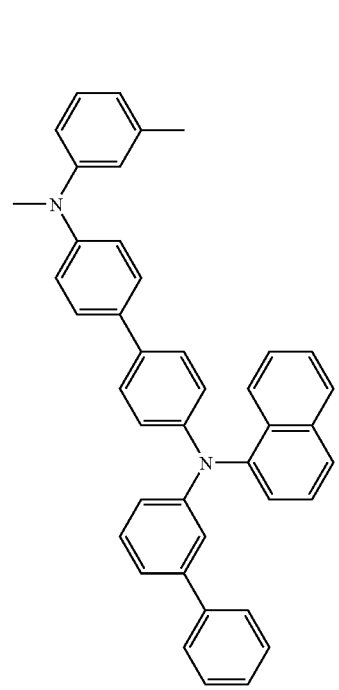
404
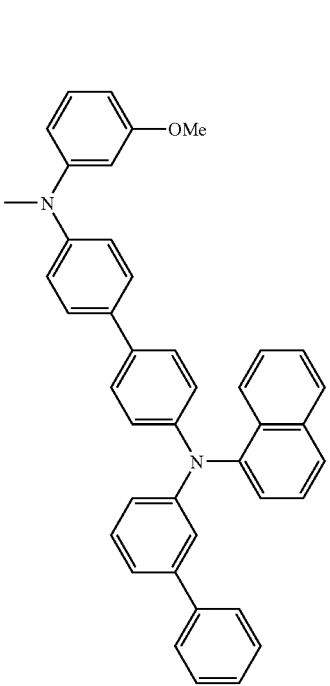

153
-continued
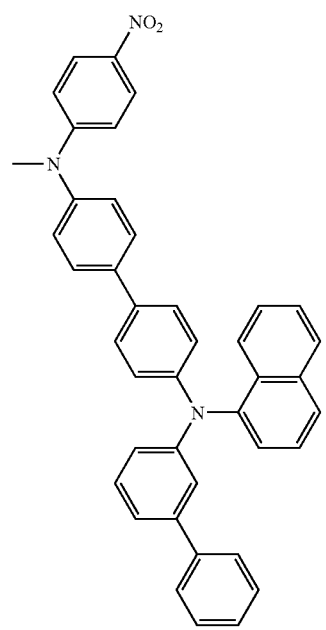
405
154
-continued
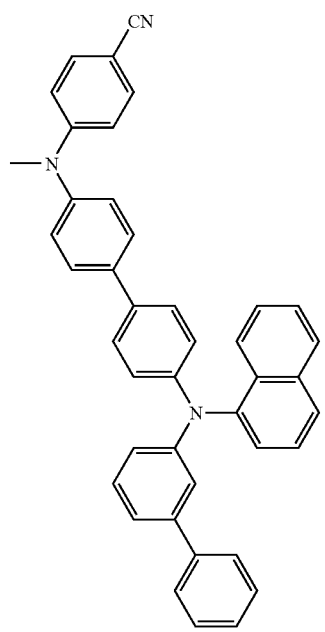
407
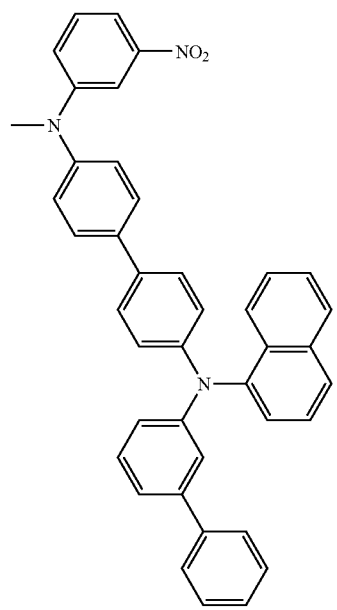
406
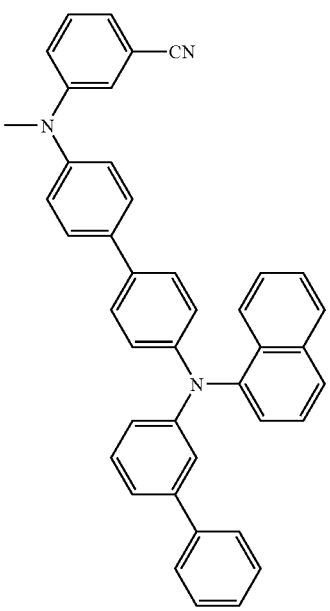
408

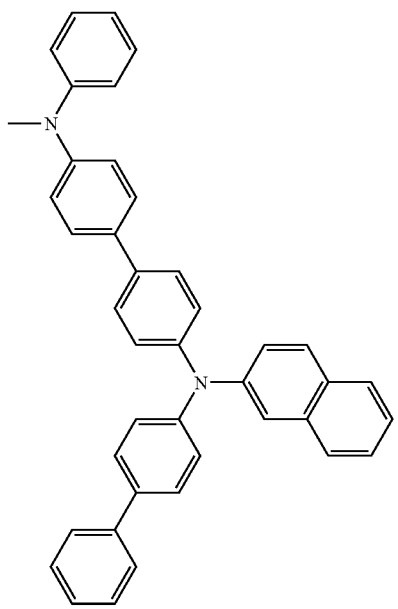
409
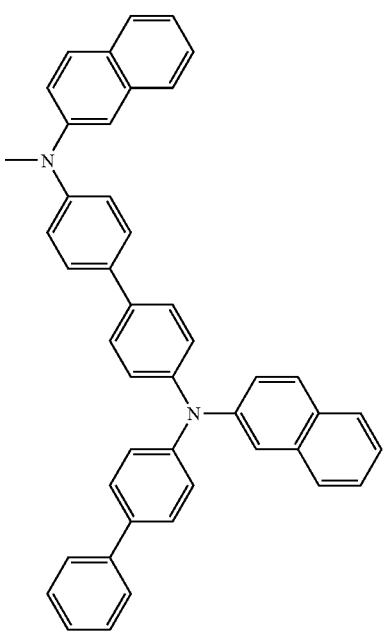
411
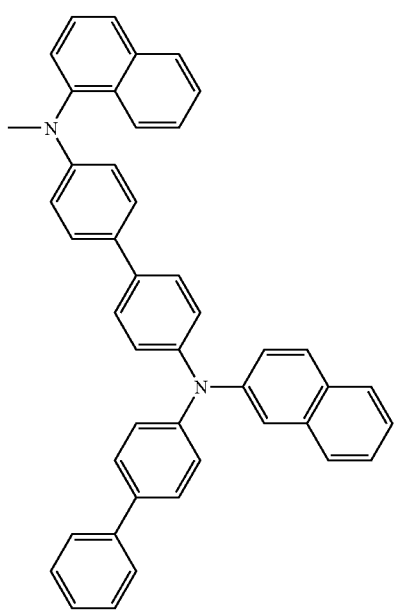
410
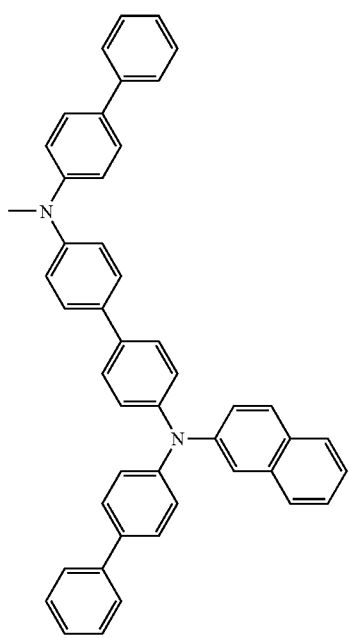
412

413
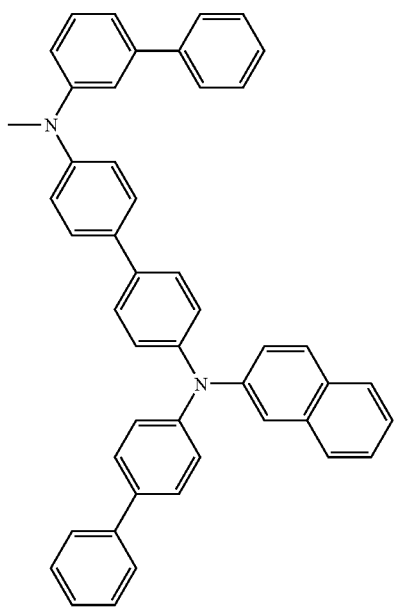
415
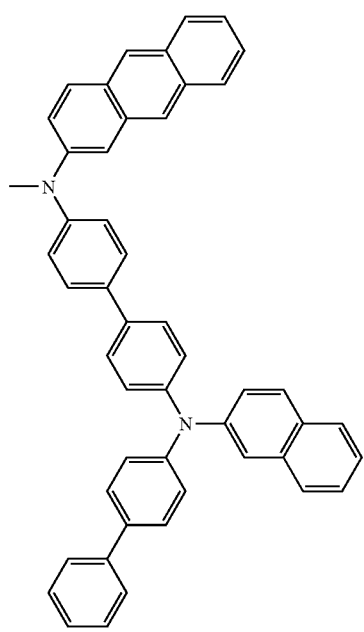
414
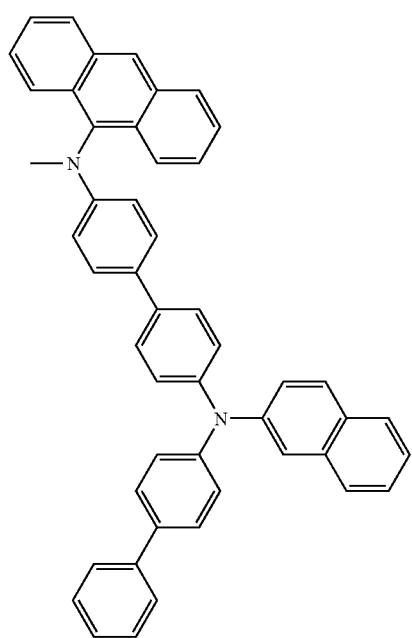
416
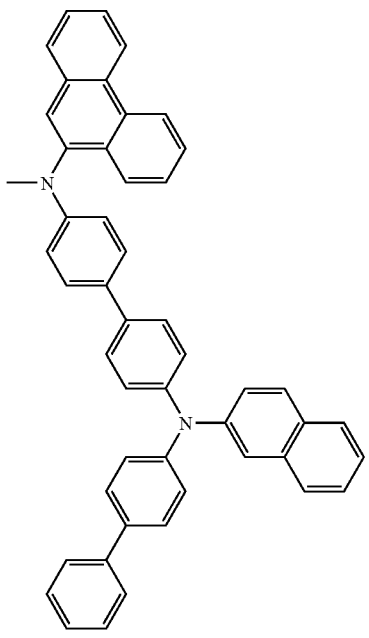

417
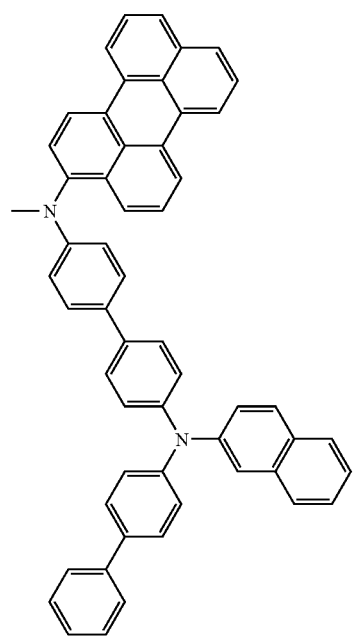
419
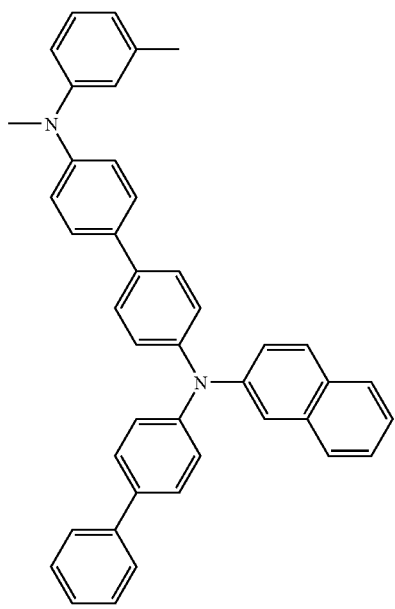
418
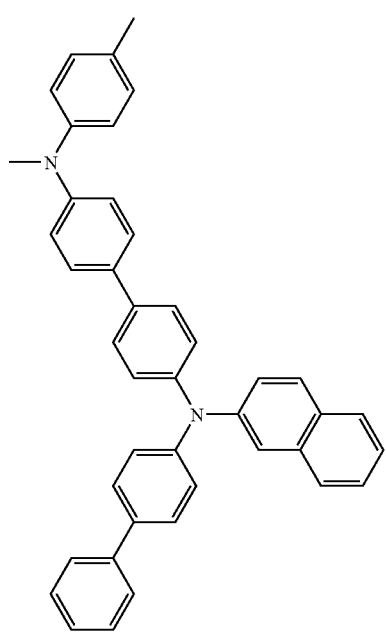
420
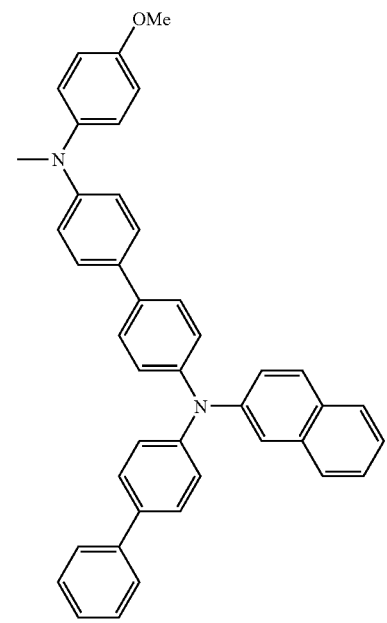

421
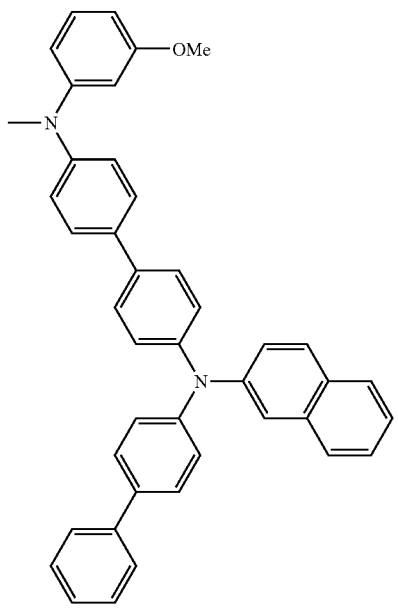
422
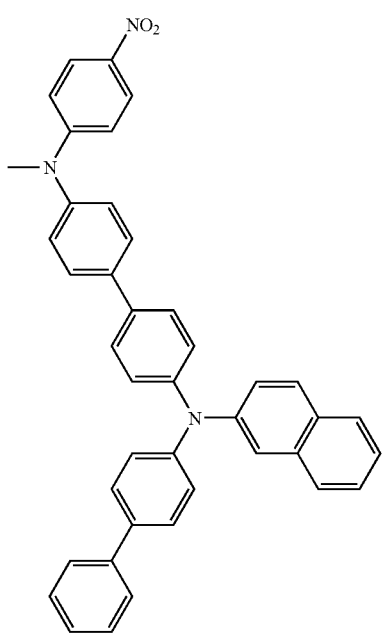
423
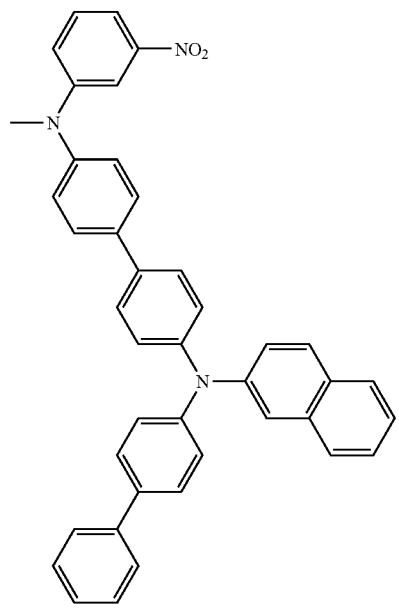
424
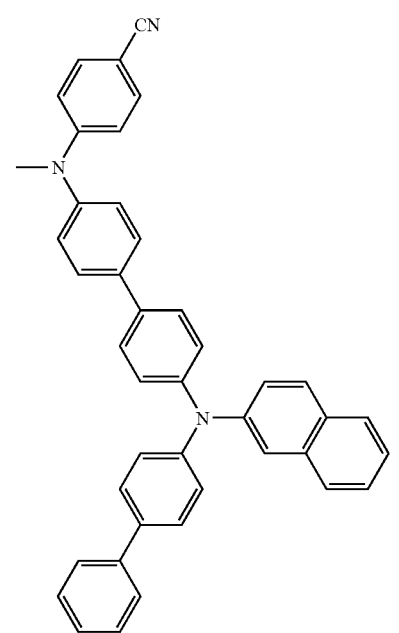

163
-continued
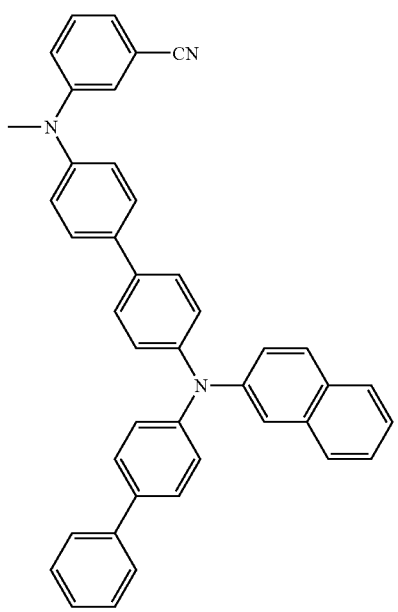
425
164
-continued
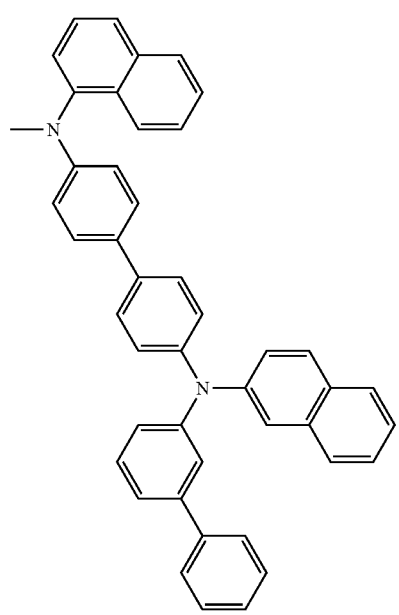
427
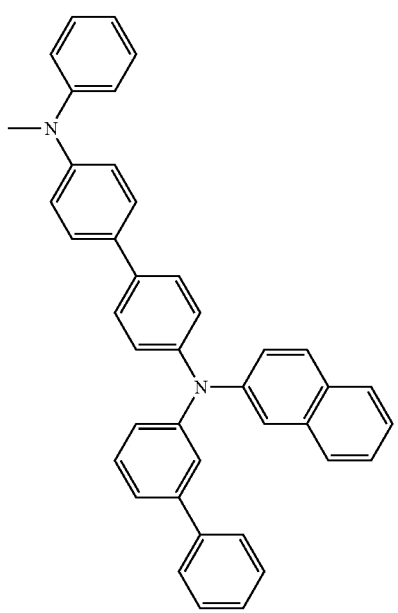
426
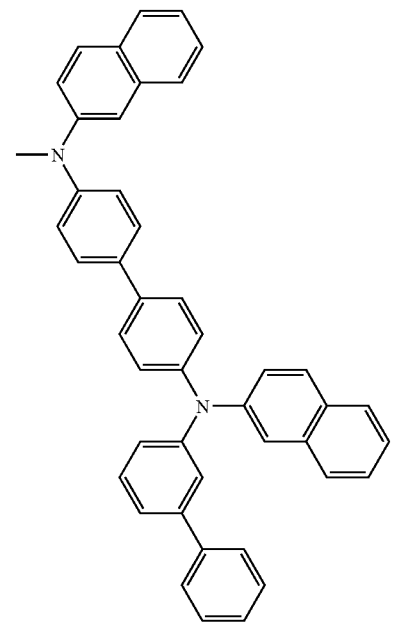
428

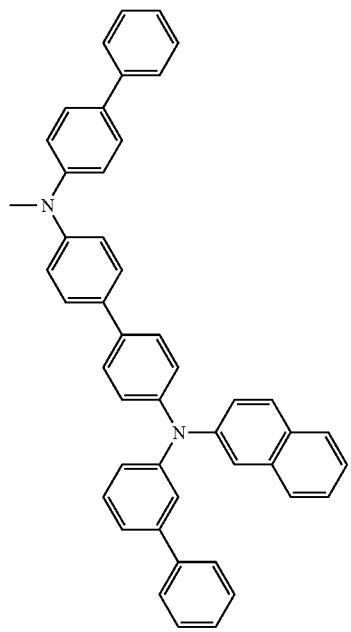
429
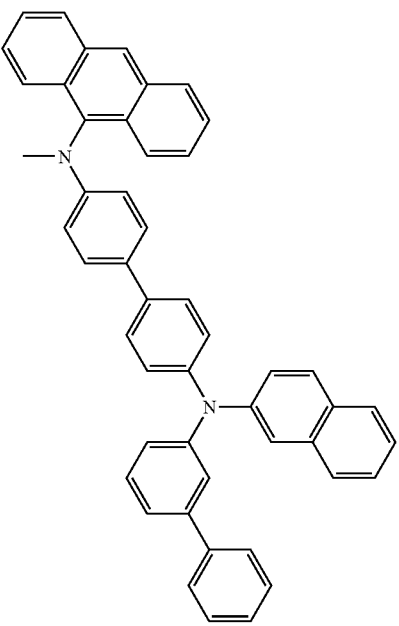
431
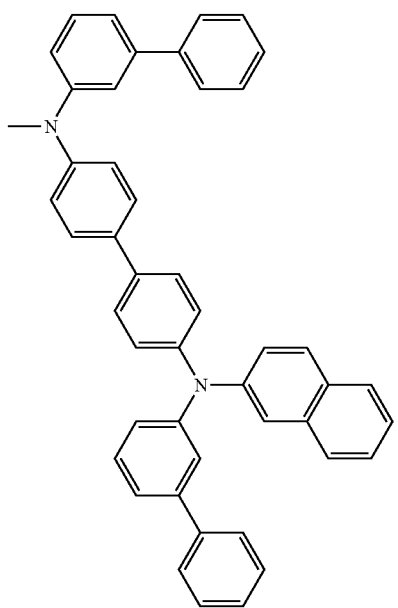
430
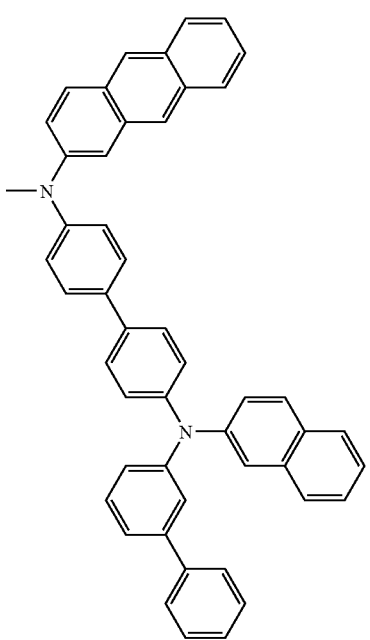
432

433
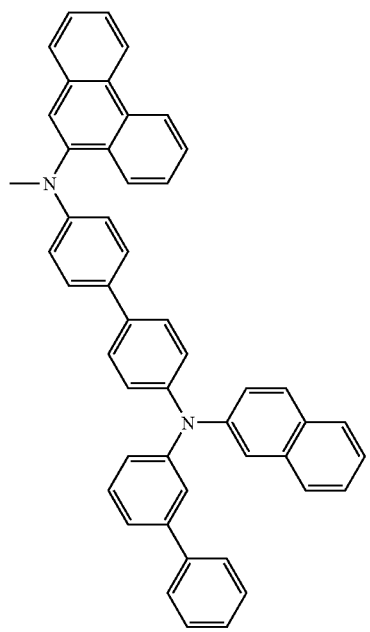
434
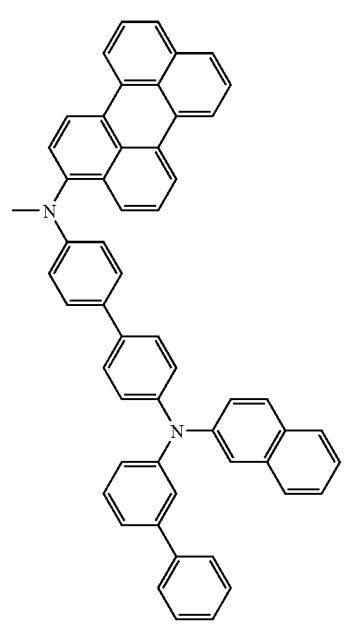
435
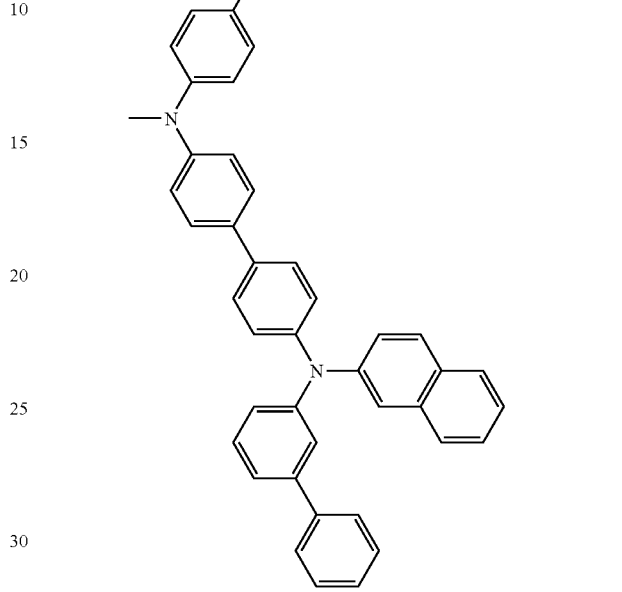
436
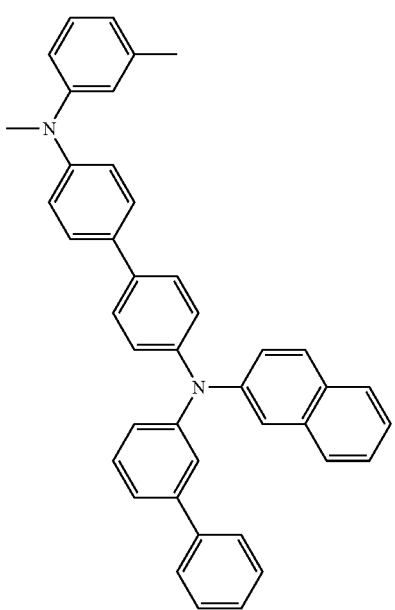

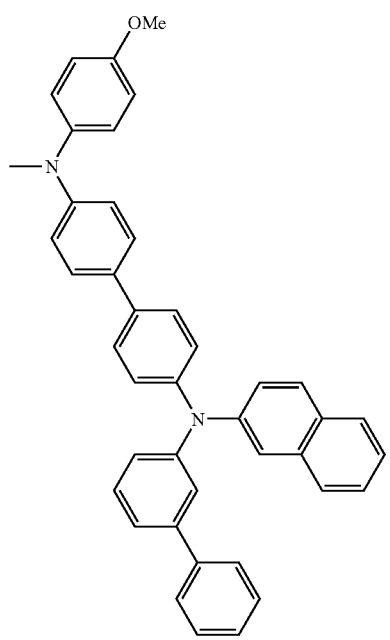
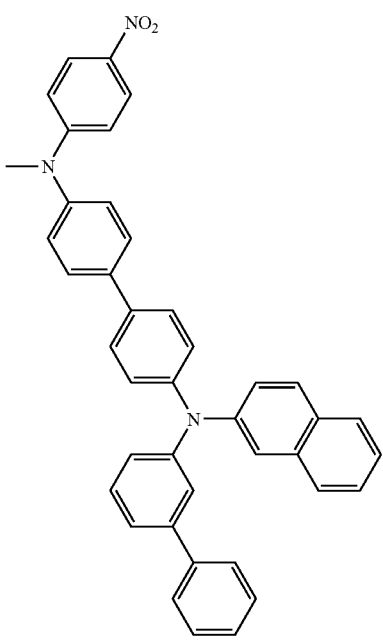

441
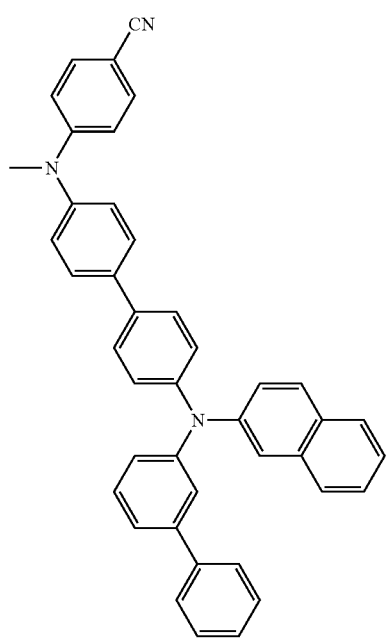
442
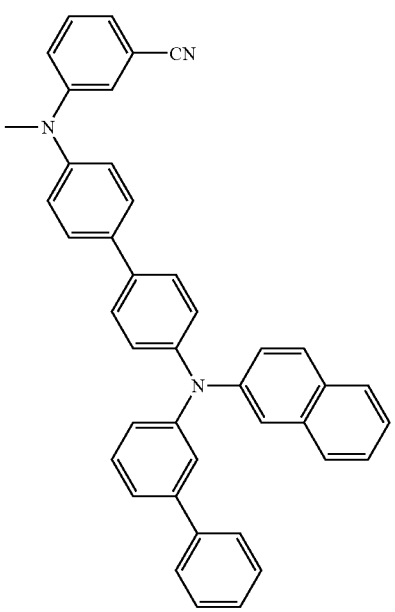
443
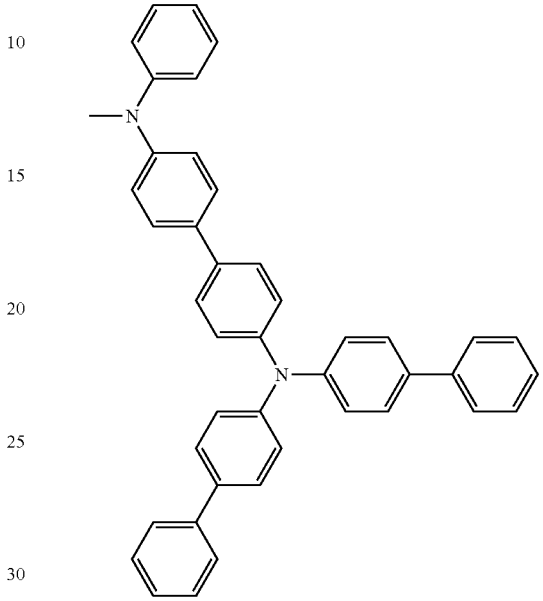
444
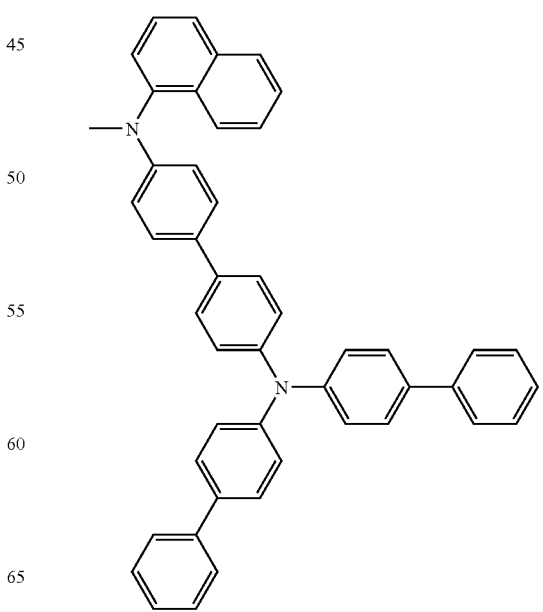

173
-continued
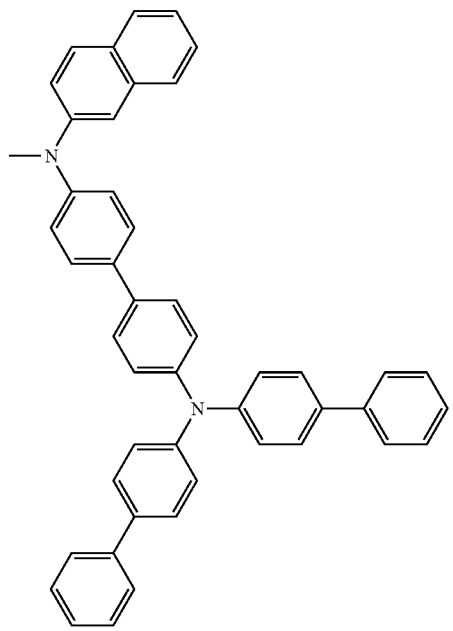
174
-continued
445
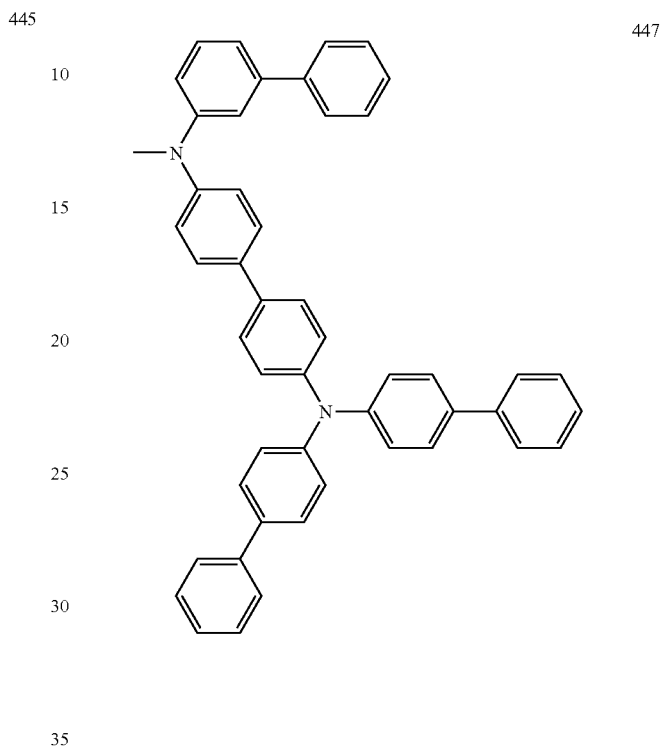
447
446
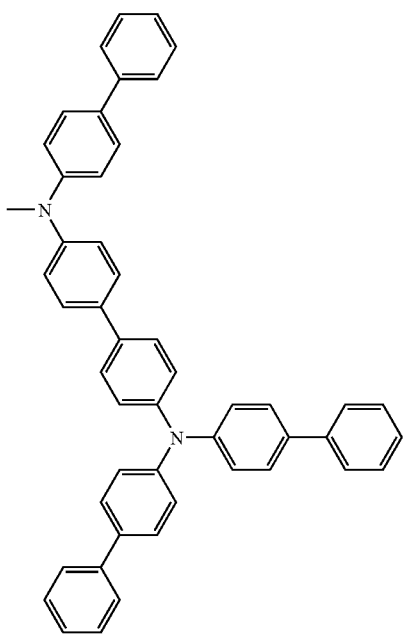
448
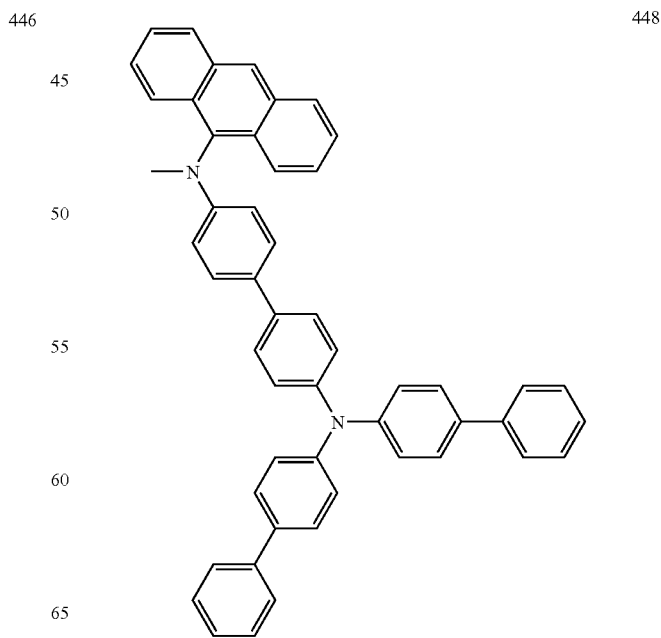

-continued
449
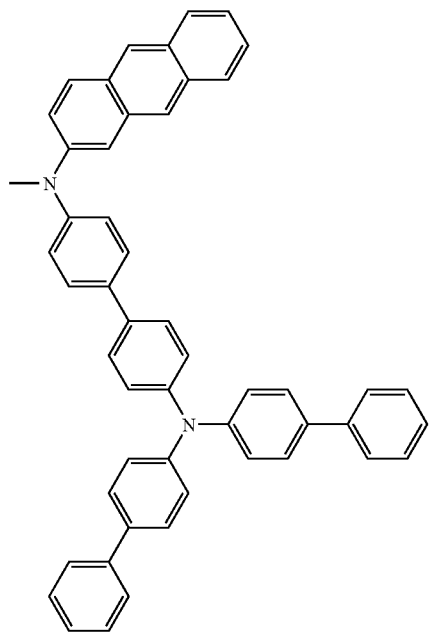
450
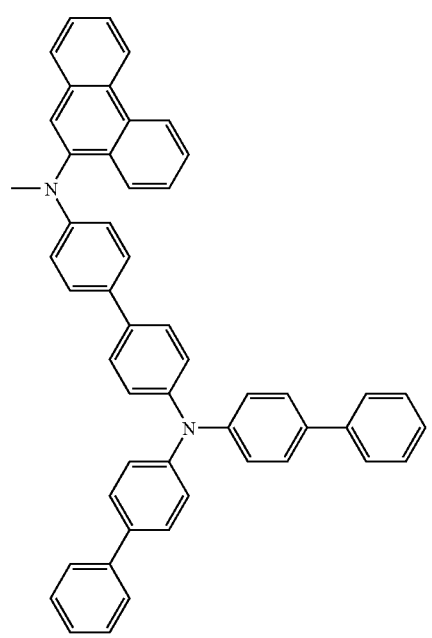
-continued
451
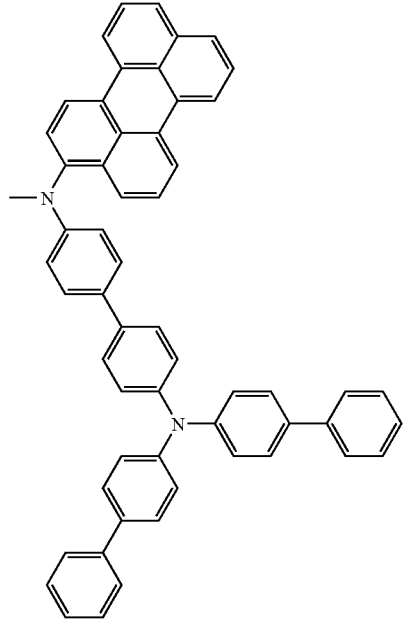
452

177
-continued
178
-continued
453
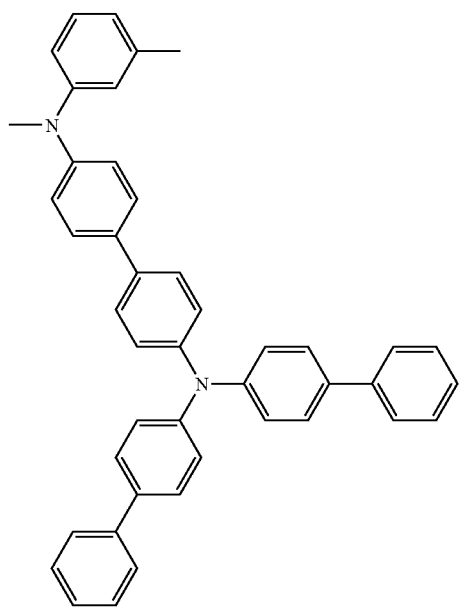
455
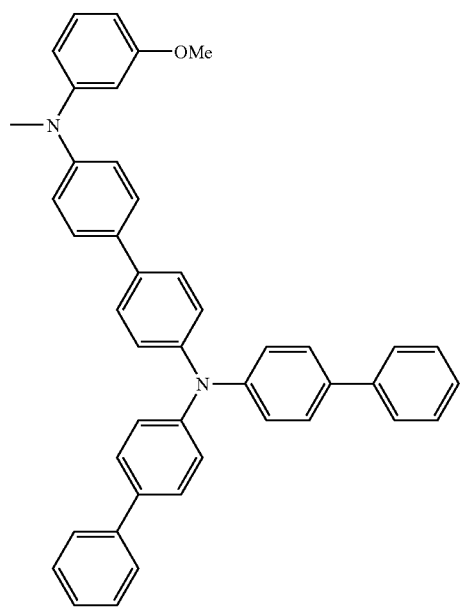
454
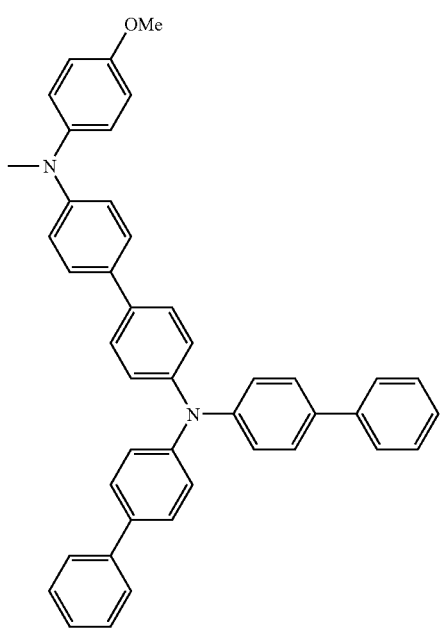
456
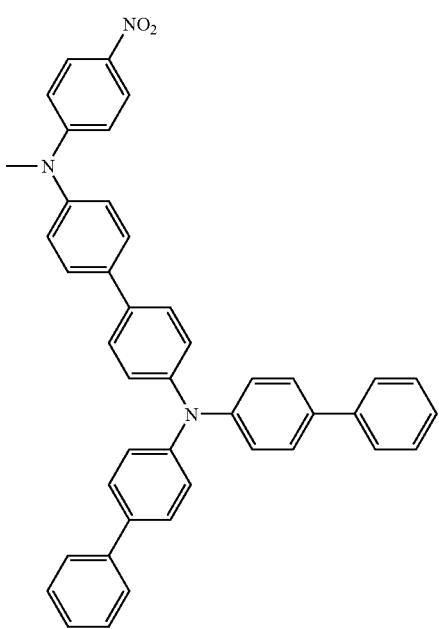

455
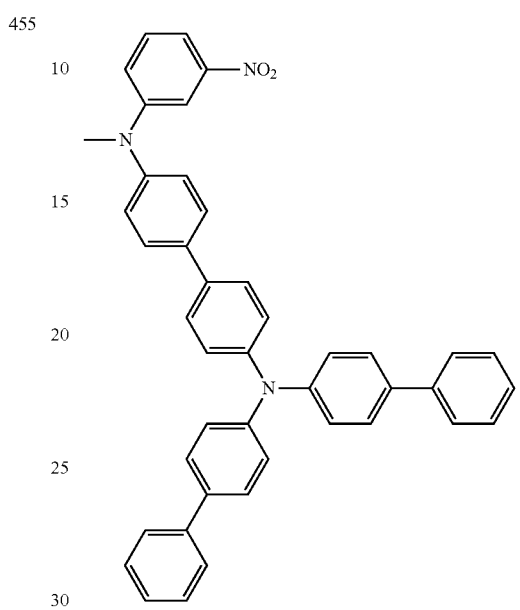
457
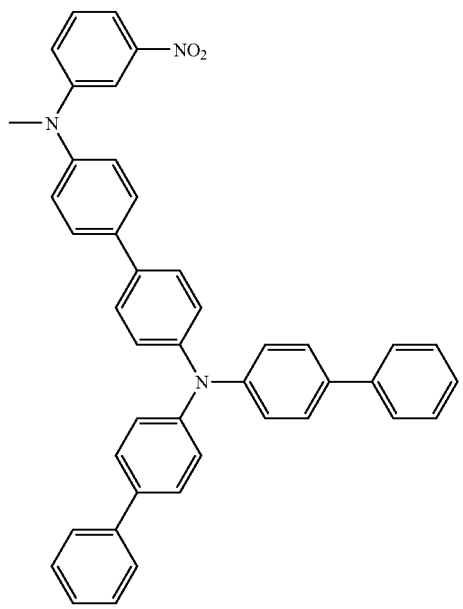
456
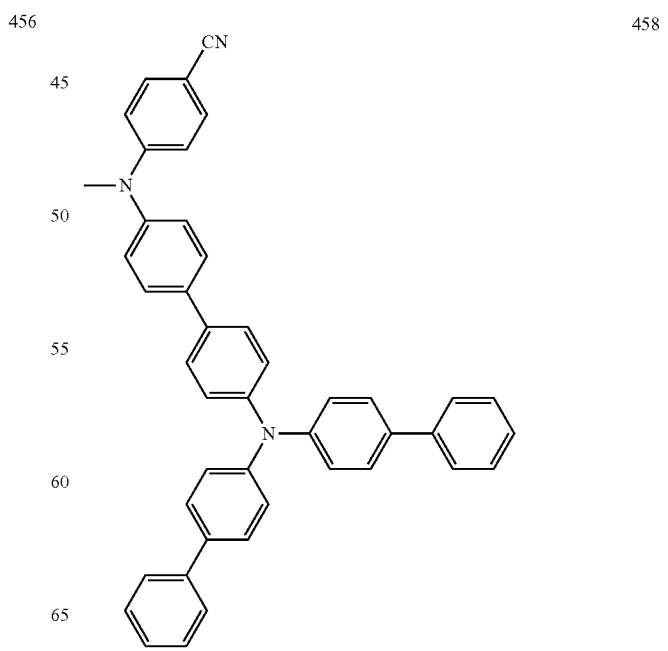
458
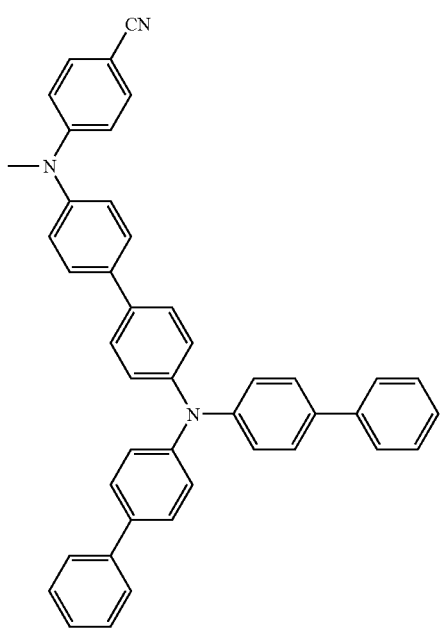

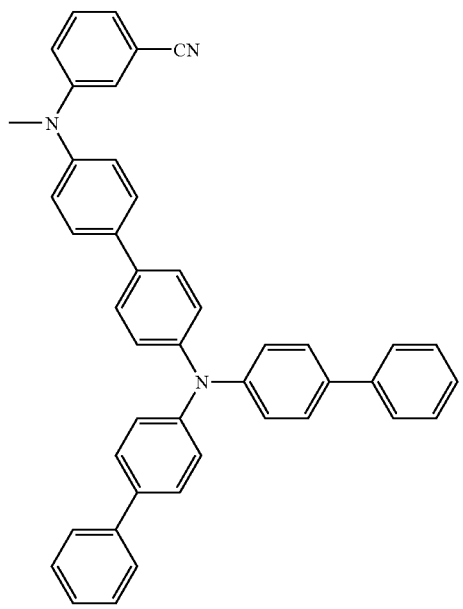
459
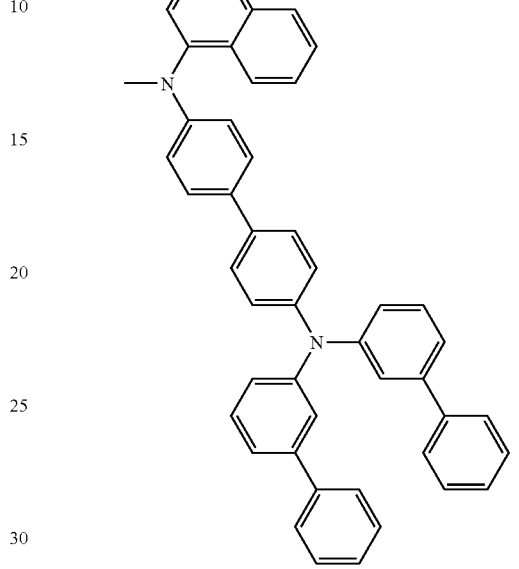
461
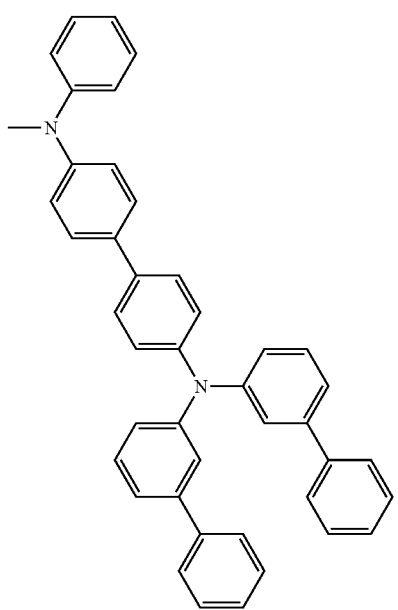
460
462

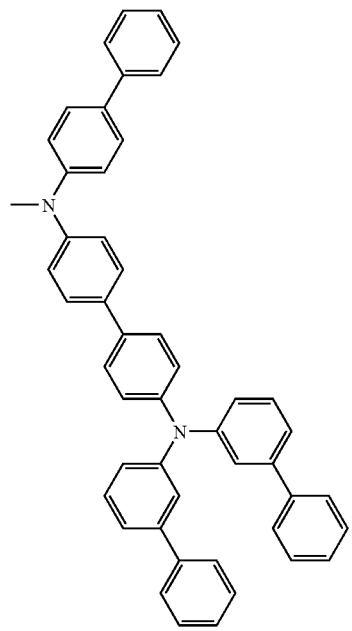
463
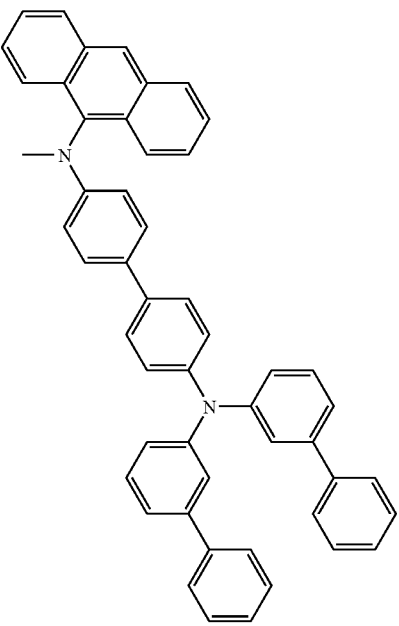
465
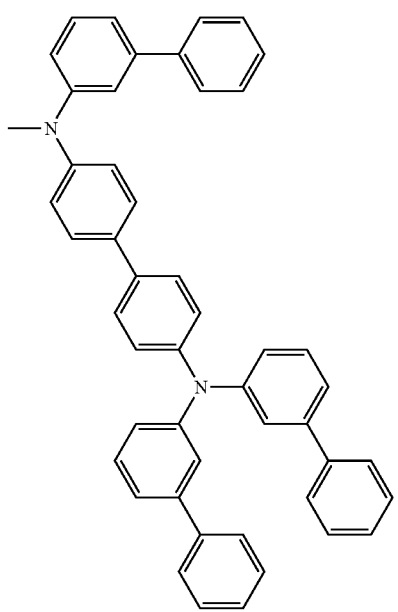
464
466

467
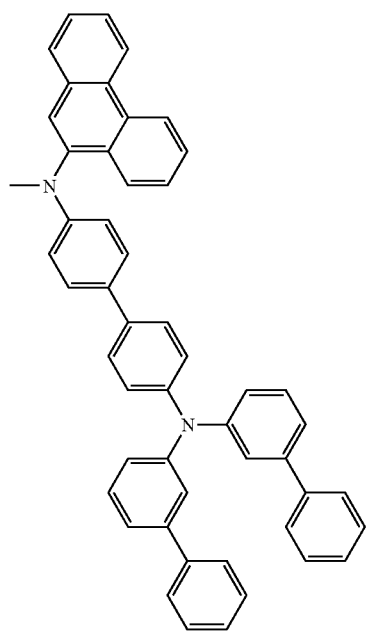
468
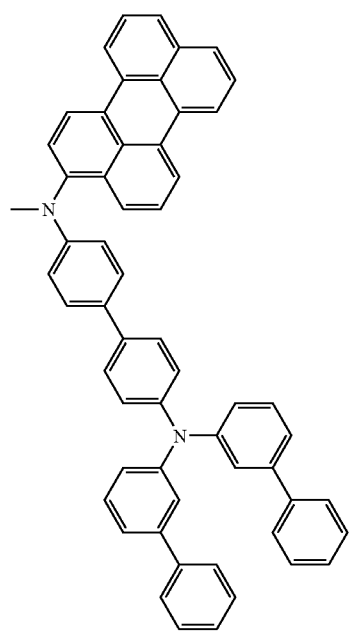
469
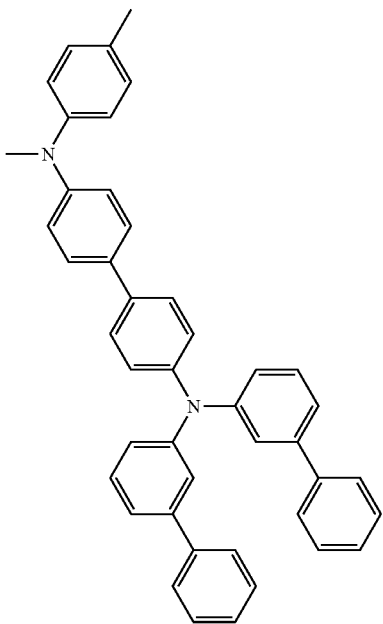
470
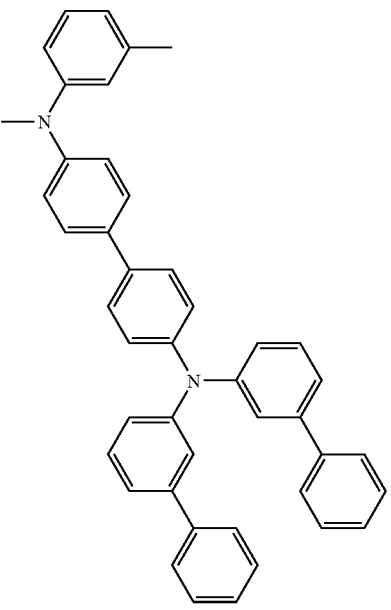

471
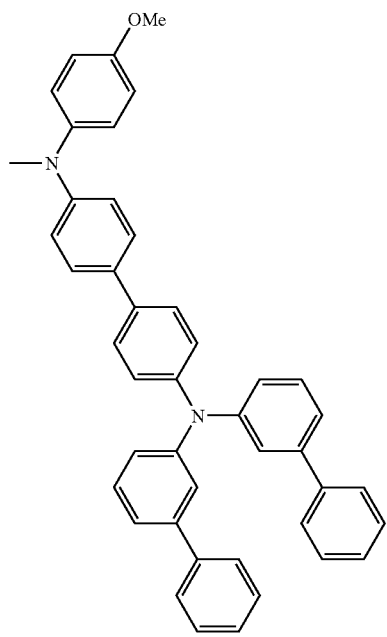
473
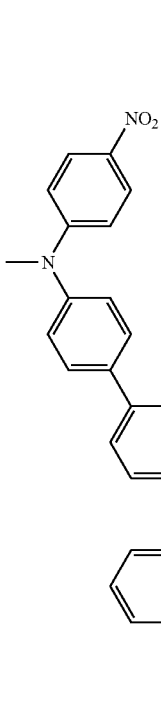
472
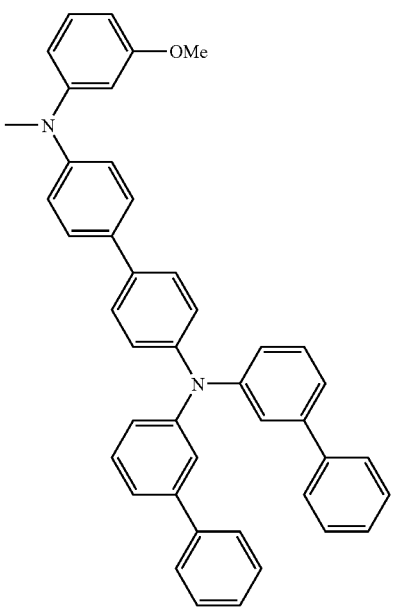
474
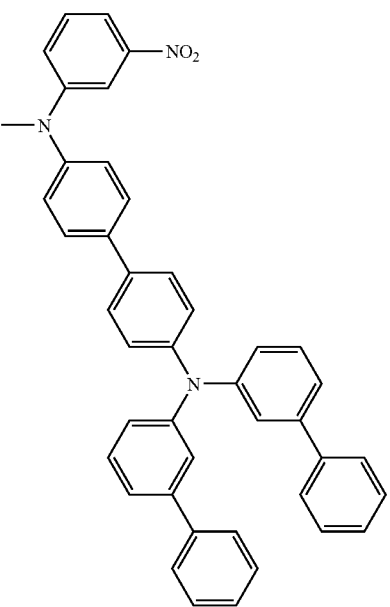

475 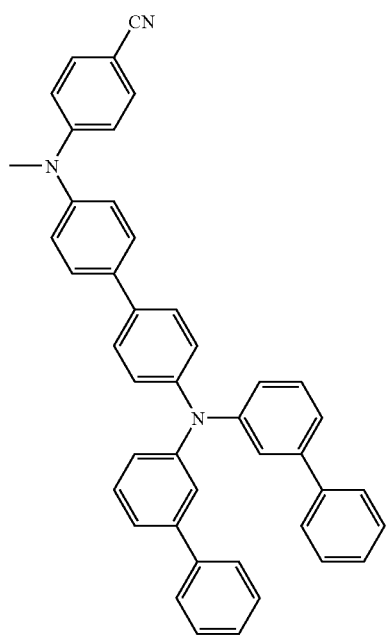
476 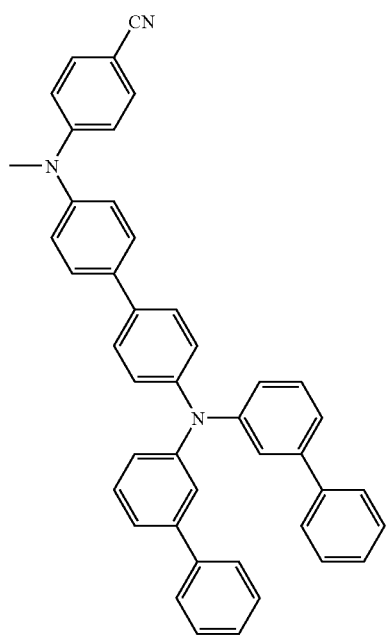
477 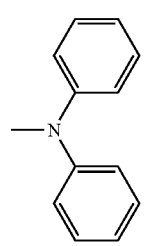
478 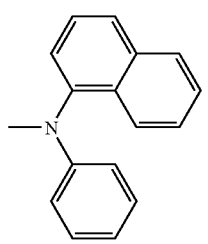
479 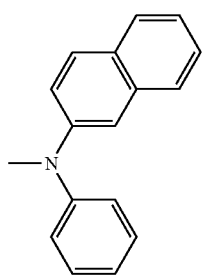
480 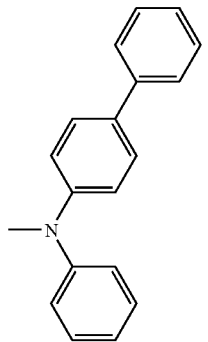
481 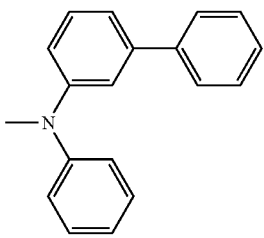
482 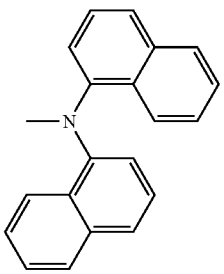

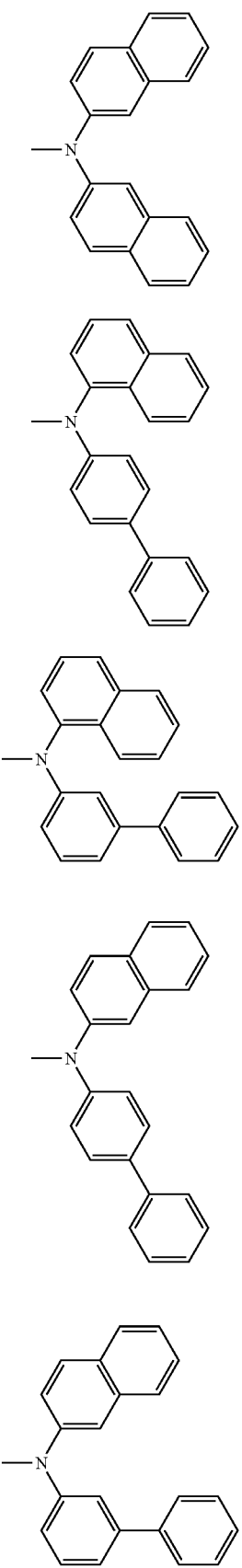
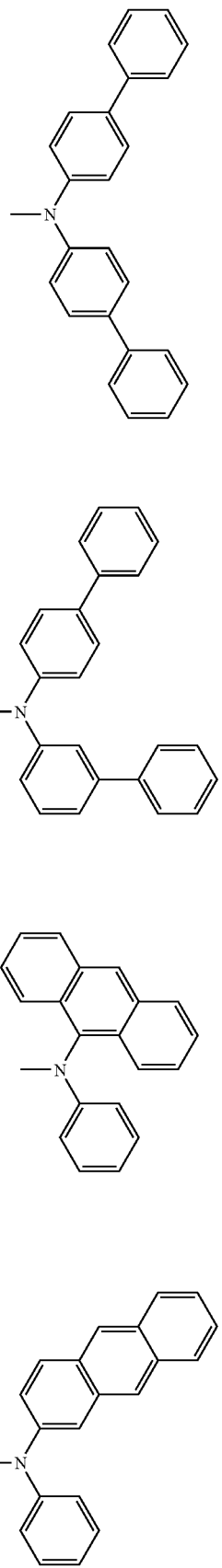

| 193 -continued | | 194 -continued | |
|---|---|---|---|
| 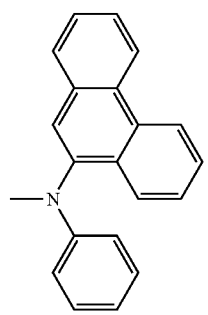 | 492 | 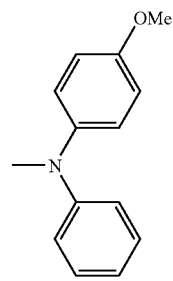 | 497 |
| 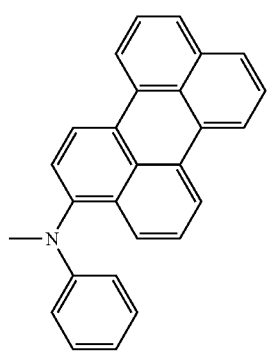 | 493 | 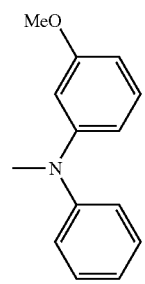 | 498 |
| 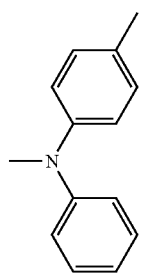 | 494 | 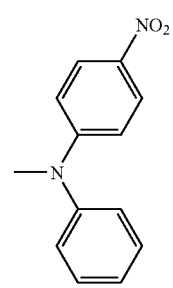 | 499 |
| 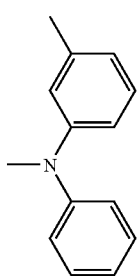 | 495 | 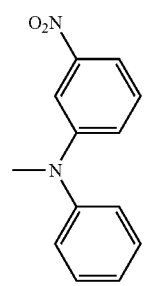 | 500 |
| 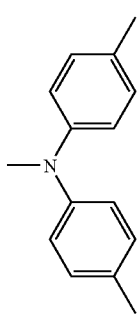 | 496 | 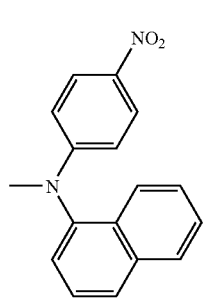 | 501 |

| | | |
|---|---|---|
| 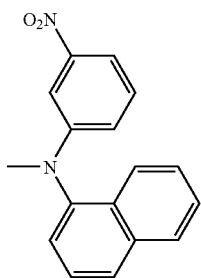 502 | 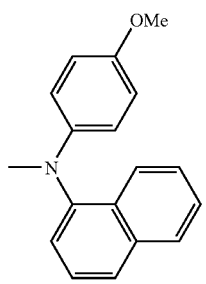 | 507 |
| 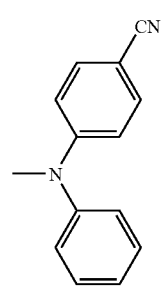 503 | 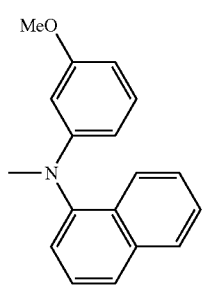 | 508 |
| 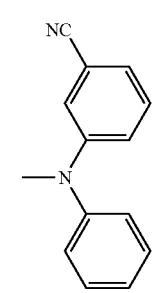 504 | 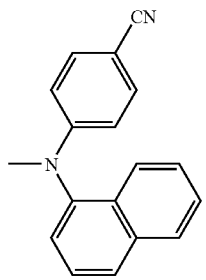 | 509 |
| 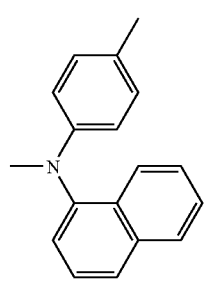 505 | 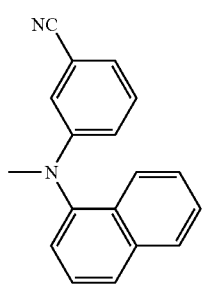 | 510 |
| 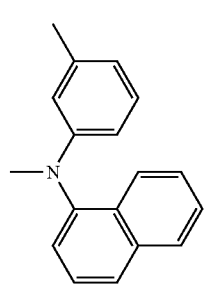 506 | 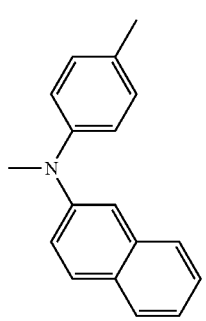 | 511 |

197
-continued
512
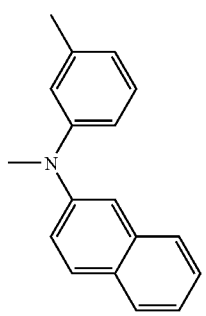
513
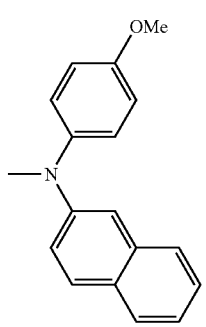
514
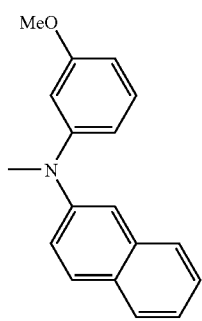
515
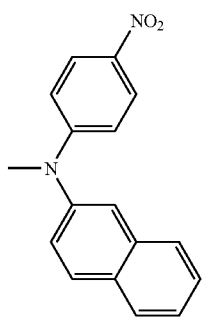
516
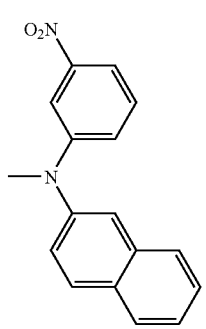
198
-continued
517
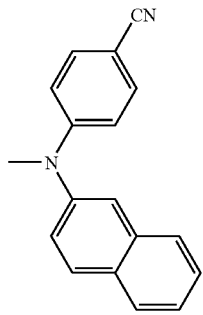
518
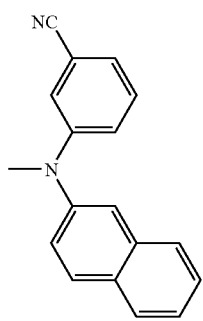
519
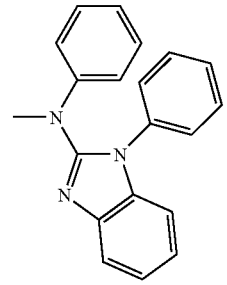
520
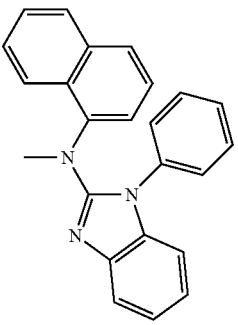
521
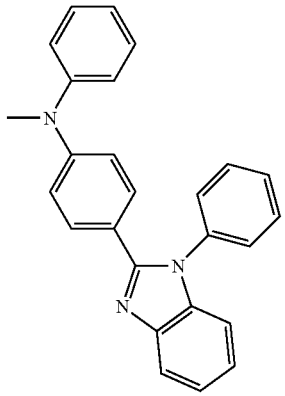

-continued
522
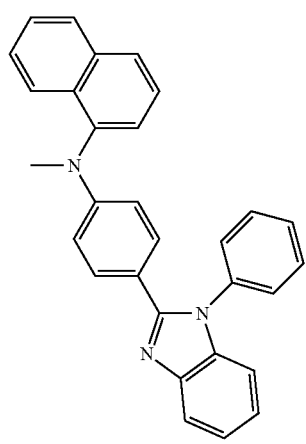
523
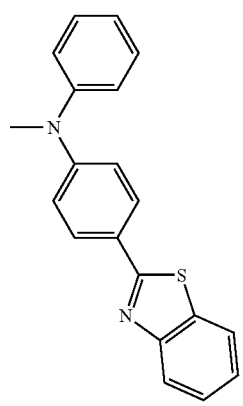
524
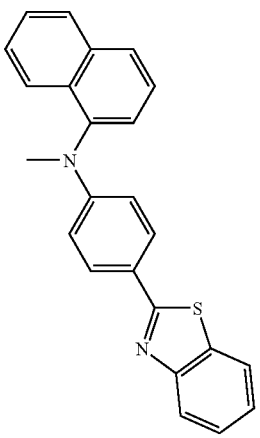
525
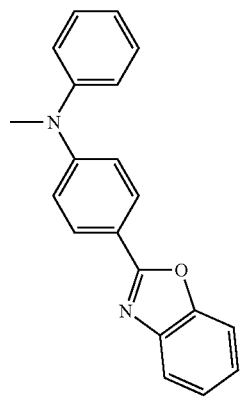
-continued
526
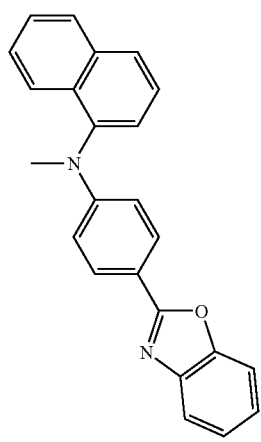
527
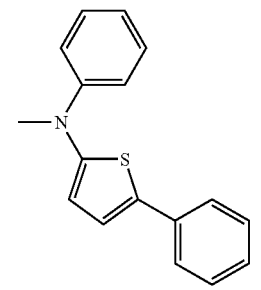
528
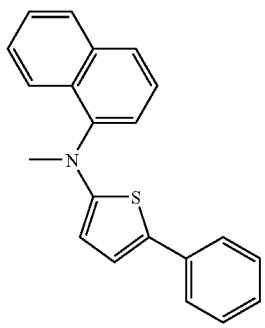
529
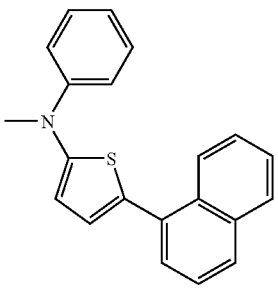
530
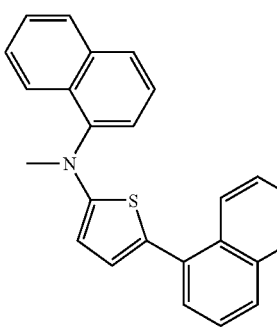

201
-continued

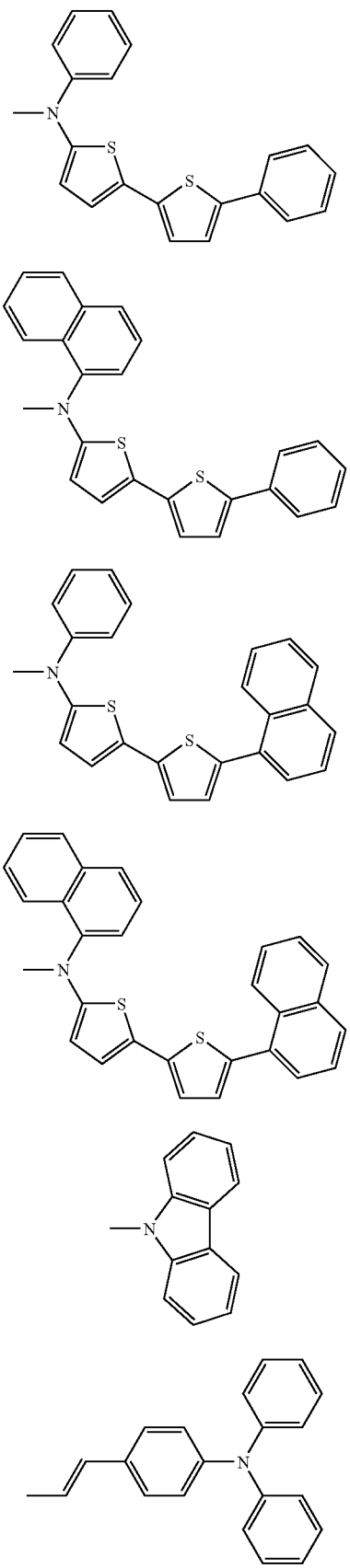

531
532
533
544
545
546

202
-continued

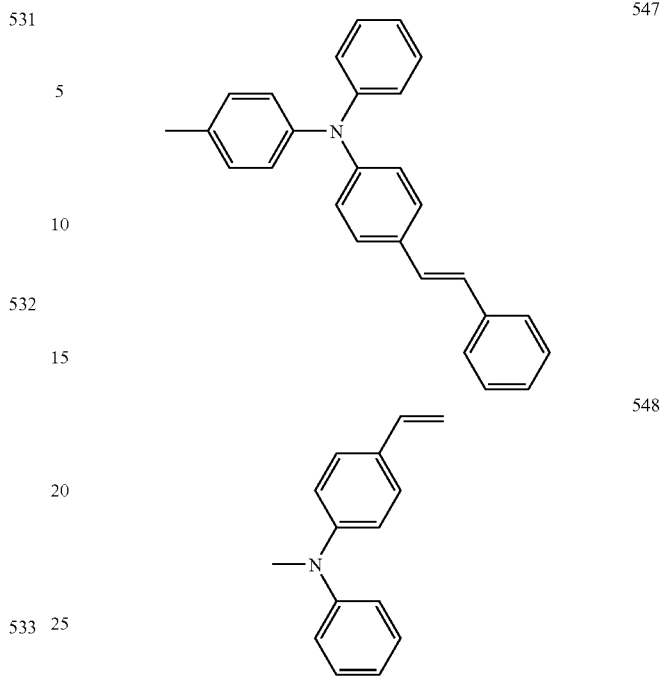

547
548

Various substituent groups are introduced into a core structure shown in Formula 1, in detail, the core structure in which a benzophenone group is bonded to a combination of an acridine group and a carbazole group to form an open spiro structure, thereby the compound of Formula 1 has characteristics suitable for application to an organic material layer used in an organic light emitting diode. This will be described in detail, below.

The steric core structure of the compound of Formula 1 can be divided into two portions, I and II as shown in the following Formula.

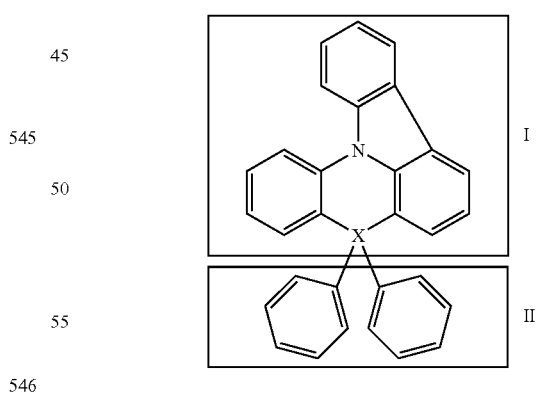

The compound of Formula 1 has the steric core structure, in which a plane I meets a plane II at a more planar angle being close to a right angle, unlike the closed spiro structure, in which a plane I is at a complete right angle with a plane II around X, and conjugation does not occur between the I and II portions around X. Furthermore, since one nitrogen atom is positioned among three aryl groups in the plane I, conjugation is limited in the plane I.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R13 positions and Z1 to Z8 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R13 and Z1 to Z8 positions of the core structure.

Additionally, by introducing various substituent groups into the core structure, compounds having intrinsic characteristics of the substituent groups can be obtained. For example, substituent groups, which are frequently applied to hole injection layer material, hole transport layer material, light emitting layer material, and electron transport layer materials during the production of the organic light emitting diode, are introduced into the core structure so as to produce substances capable of satisfying the requirements of each organic material layer. Particularly, since the core structure of the compound of Formula 1 includes the arylamine structure, it has an energy level suitable for the hole injection and/or hole transport materials in the organic light emitting diode. In the present invention, the compound having the proper energy level is selected depending on the substituent group among the compounds of Formula 1 to be used in the organic light emitting diode, whereby it is possible to realize a device having a low actuating voltage and a high light efficiency.

Furthermore, various substituent groups are symmetrically introduced into the core structure (the A and B portions are located at both sides of the core structure) so as to precisely control the energy band gap, improve interfacial characteristics with organic materials, and apply the compound to various fields.

In addition, if the numbers of amine contained in the substituent groups A and B are set to 2 or more (the numbers of amine contained in the substituent groups A and B are each set to 1 or more), it is possible to precisely control the HOMO or LUMO energy levels and the energy band gap, on the other hand, to improve interfacial characteristics with the organic materials, and apply the compound to various fields.

Additionally, various substituent groups are introduced into the steric structure of the compound of Formula 1 using open spiro bonding to control the three-dimensional structure of the organic material, so as to minimize $\pi$-$\pi$ interaction in the organic material, thereby preventing formation of excimers.

With respect to the energy band gap and the energy level, for example, since the compound of Formula 2-1-1 of Example 1 of the present invention, in which arylamine is introduced into the hole transport material or the hole injection material of the structure of Formula 1, has HOMO of 5.22 eV, it has an energy level suitable for the hole injection layer or the hole transport layer. Meanwhile, the compound of Formula 2-1-1 of Example 1 has the band gap of 2.89 eV, which is still larger than that of NPB, typically used as the hole transport layer material, thus it has a LUMO value of about 2.33 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting diode so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2-1-1 of Example 1, oxidation repeatedly occurs at the same voltage and the current amount is constant. This means that the compound has excellent stability to oxidation.

Meanwhile, since the compound of Formula 1 has a high glass transition temperature (Tg), it has excellent thermal stability. For example, the compound of Formula 2-1-1 of Example 1 of the present invention has a glass transition temperature of 172° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting diode. In connection with this, examples of the solution coating process include a spin coating process, a dip coating process, an inkjet printing process, a screen printing process, a spray process, and a roll coating process, but are not limited thereto.

Tertiary alcohol, which is produced by a reaction of a lithiated aryl and keto group, is heated in the presence of an acid catalyst to form a hexagonal cyclic structure while water is removed, thereby producing the compound of the present invention. The above-mentioned procedure for producing the compound is well known in the art, and those skilled in the art can change the production conditions during the production of the compound of Formula 1. The production will be described in detail in the preparation examples later.

Further, the present invention provides an organic light emitting diode which comprises a first electrode, at least one organic material layer, and a second electrode, wherein the first electrode, the organic material layer(s), and the second electrode form a layered structure and at least one layer of the organic material layers includes a compound represented by Formula 1 of the present invention.

The organic light emitting diode of the present invention can be produced using known materials through a known process, modified only in that at least one layers of organic material layer(s) include the compound of the present invention, that is, the compound of Formula 1.

The organic material layer(s) of the organic light emitting diode according to the present invention may have a single layer structure, or alternatively, a multilayered structure in which two or more organic material layers are layered. For example, the organic light emitting diode of the present invention may comprise a hole injection layer, a hole transport layer, a light emitting layer, an electron transport layer, and an electron injection layer as the organic material layers. However, the structure of the organic light emitting diode is not limited to this, but may comprise a smaller number of organic material layers.

If the organic light emitting diode according to the present invention has a multilayered structure of organic material layer, the compound of Formula 1 can be contained in a hole injection layer, a hole transport layer, a hole injection and transport layer, a light emitting layer, and a hole transport layer. In the present invention, the compound of Formula 1 is preferably contained in a hole injection layer, a hole transport layer, or a hole injection and transport layer.

The organic light emitting diode of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

MODE FOR THE INVENTION

A better understanding of a method of producing a compound of Formula 1 and the production of an organic light emitting diode using the same may be obtained in light of the following preparation examples and examples which are set forth to illustrate, but are not to be construed to limit the present invention.

In order to produce the compound represented by Formula 1, any one of the compounds of the following Formulae a to b may be used as a starting material.

[Formula a]

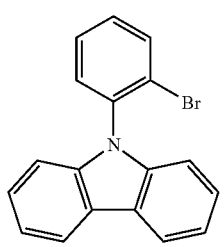

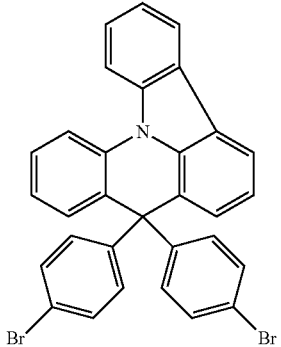

[Formula b]

Preparation Example 1

Preparation of Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature was conducted, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the resulting white solid compound of Formula a (800 mg, yield 25%).

MS: $[M+H]^+$=323.

Preparation Example 2

Preparation of Starting Material Represented by Formula b

The starting material represented by Formula a (6.96 g, 21.6 mmol) was dissolved in 300 ml of purified THF (tetrahydrofuran) and cooled to −78° C., and n-BuLi (2.5 M in hexane, 8.64 ml, 21.6 mmol) was slowly dropped thereon. Stirring was conducted at the same temperature for 30 min, and 4,4'-dibromobenzophenone (6.12 g, 18.0 mmol) was added thereto. After stirring was conducted at the same temperature for 40 min, the temperature was raised to normal temperature and stirring was carried out for an additional 3 hours. The reaction was completed in an ammonium chloride ($NH_4Cl$) aqueous solution, and extraction was conducted with ethyl ether. Water was removed from an organic material layer using anhydrous magnesium sulfate ($MgSO_4$), and an organic solvent was then removed therefrom. The produced solid was dispersed in ethanol, stirred for one day, filtered, and vacuum dried to produce 10.12 g of intermediate material (96.4% yield). The intermediate solid was dispersed in 10 ml of acetic acid, ten drops of concentrated sulfuric acid were added thereto, and reflux was conducted for 4 hours. The resulting solid was filtered, washed with ethanol, and vacuum dried to produce 9.49 g of compound of Formula b (yield 96.8%).

MS: $[M+H]^+$=565.

Example 1

Preparation of Compound Represented by Following Formula 2-1-1

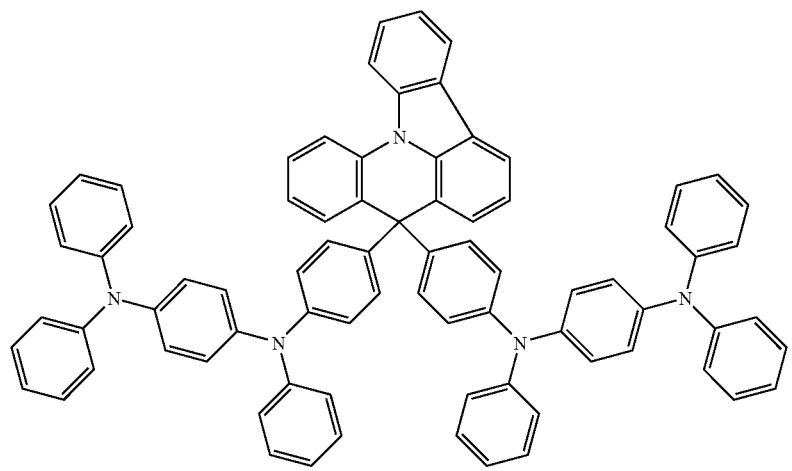

[Formula 2-1-1]

1) Production of arylamine (4-(N-phenyl-N-phenylamino)phenyl-1-phenylamine) to produce the compound represented by Formula 2-1-1

4-bromophenyl-N-phenyl-N-phenylamine (13.5 g, 41.6 mmol) and aniline (3.98 ml, 43.7 mmol) were dissolved in 120 ml of toluene, sodium-tertiary-butoxide (10.00 g, 104.1 mmol), bisdibenzylidene acetone palladium (0) (0.48 g, 0.83 mmol), and 50 wt % tri-tertiary-butylphosphine toluene solution (0.58 ml, 1.25 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (9.6 g, yield 69%).

MS: $[M+H]^+$=336.

2) The compound of Formula b (3.0 g, 5.3 mmol) and 4-(N-phenyl-N-phenylamino)phenyl-1-phenylamine (4.12 g, 12.3 mmol) were dissolved in 80 ml of toluene, and sodium-tertiary-butoxide (1.54 g, 16.0 mmol), bis-dibenzylidene acetone palladium(0) (0.06 g, 0.11 mmol), and 50 wt % tri-tertiary-butylphosphine toluene solution (0.06 ml, 0.16 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 2-1-1 (2.7 g, yield 47%).

MS: $[M+H]^+$=1076.

Example 2

Preparation of Compound Represented by Following Formula 2-2-2

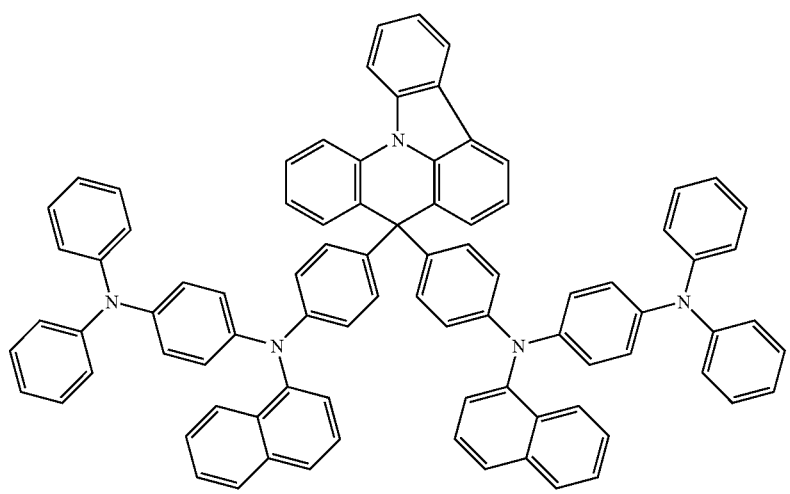

[Formula 2-2-2]

1) Production of arylamine (4-(N-phenyl-N-phenylamino)phenyl-1-naphthylamine) to produce the compound represented by Formula 2-2-2

4-bromophenyl-N-phenyl-N-phenylamine (15.0 g, 46.3 mmol) and 1-naphthylamine (7.29 g, 50.9 mmol) were dissolved in 200 ml of toluene, sodium-tertiary-butoxide (13.34 g, 138.8 mmol), bisdibenzylidene acetone palladium (0) (0.53 g, 0.93 mmol), and 50 wt % tri-tertiary-butylphosphine toluene solution (0.56 ml, 1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (13 g, yield 73%).

MS: [M+H]$^+$=386.

2) The compound of Formula b (5.00 g, 8.88 mmol) and 4-(N-phenyl-N-phenylamino)phenyl-1-naphthylamine (7.90 g, 20.4 mmol) were dissolved in 120 ml of toluene, and sodium-tertiary-butoxide (5.89 g, 61.3 mmol), tris-dibenzylidene acetone palladium(0) (0.24 g, 0.41 mmol), and 50 wt % tri-tertiary-butylphosphine toluene solution (0.25 ml, 0.61 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 2-2-2 (5.2 g, yield 50%).

MS: [M+H]$^+$=1176.

Example 3

Preparation of Compound Represented by Following Formula 2-4-4

1) Production of arylamine (4-(N-phenyl-N-phenylamino)phenyl-1-biphenylamine) to produce the compound represented by Formula 2-4-4

4-bromophenyl-N-phenyl-N-phenylamine (17.4 g, 53.7 mmol) and 4-aminobiphenyl (9.99 g, 59.0 mmol) were dissolved in 250 ml of toluene, sodium-tertiary-butoxide (17.02 g, 177.1 mmol), bisdibenzylidene acetone palladium (0) (0.68 g, 1.2 mmol), and 50 wt % tri-tertiary-butylphosphine toluene solution (0.72 ml, 1.8 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (16 g, yield 73%).

MS: [M+H]$^+$=412.

2) The Compound of Formula b (4.7 g, 8.3 mmol) and 4-(N-phenyl-N-phenylamino)phenyl-1-biphenylamine (7.9 g, 19.2 mmol) were dissolved in 150 ml of toluene, and sodium-tertiary-butoxide (5.53 g, 57.5 mmol), bis-dibenzylidene acetone palladium(0) (0.22 g, 0.38 mmol), and 50 wt % tri-tertiary-butylphosphine toluene solution (0.23 ml, 0.58 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 2-4-4 (4.9 g, yield 48%).

MS: [M+H]$^+$=1227.

[Formula 2-4-4]

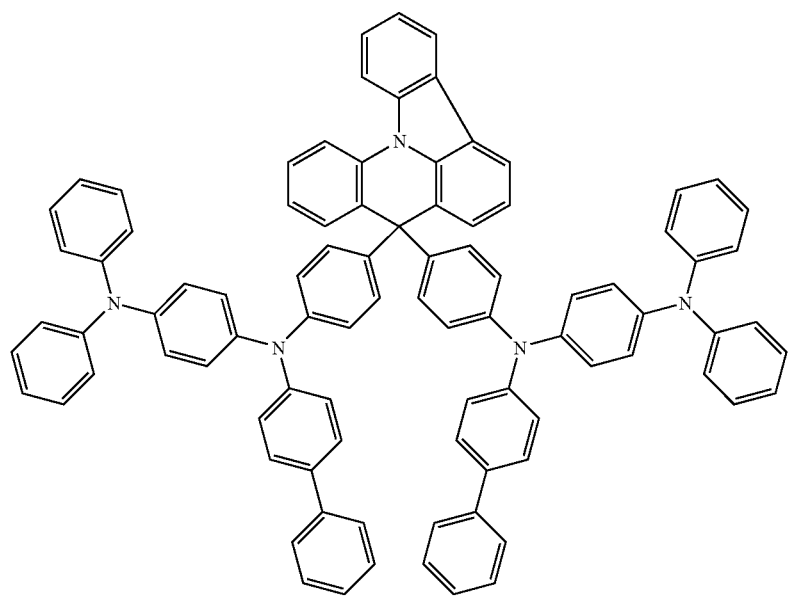

Example 4

Preparation of Compound Represented by Following Formula 2-18-18

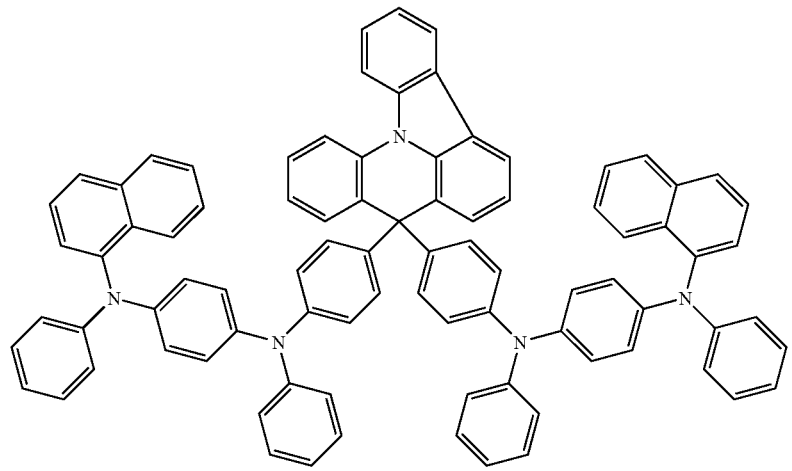

[Formula 2-18-18]

1) Production of arylamine (4-(N-phenyl-N-naphthylamino)phenyl-1-phenylamine) to produce the compound represented by Formula 2-18-18

4-bromophenyl-N-phenyl-N-naphthylamine (7.00 g, 18.7 mmol) and aniline (2.56 ml, 28.1 mmol) were dissolved in 100 ml of toluene, sodium-tertiary-butoxide (5.40 g, 56.1 mmol), bisdibenzylidene acetone palladium (0) (0.22 g, 0.37 mmol), and 50 wt % tri-tertiary-butylphosphine toluene solution (0.28 ml, 0.37 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (5.1 g, yield 70%).

MS: $[M+H]^+=386$.

2) The Compound of Formula b (2.5 g, 4.4 mmol) and 4-(N-phenyl-N-naphthylamino)phenyl-1-phenylamine (3.86 g, 10.0 mmol) were dissolved in 50 ml of toluene, and sodium-tertiary-butoxide (1.26 g, 13.2 mmol), tris-dibenzylidene acetone palladium(0) (0.08 g, 0.08 mmol), and 50 wt % tri-tertiary-butylphosphine toluene solution (0.04 ml, 0.13 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 2-18-18 (2.5 g, yield 49%).

MS: $[M+H]^+=1175$.

Example 5

Preparation of Compound Represented by Following Formula 2-19-19

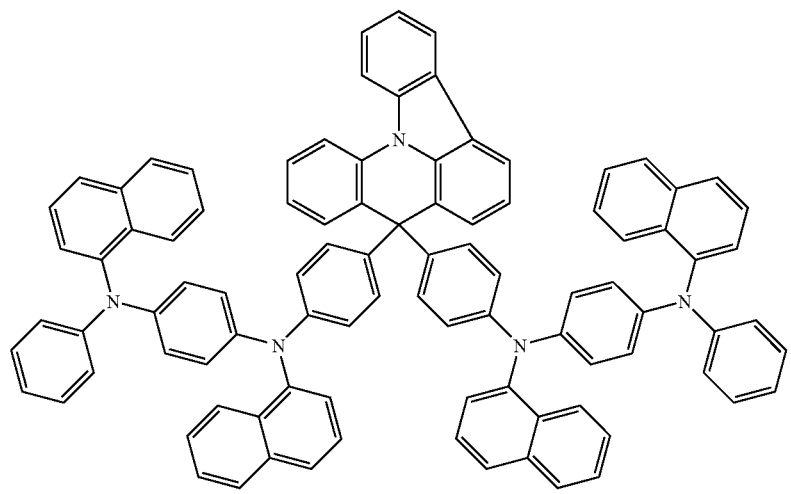

[Formula 2-19-19]

1) Production of arylamine (4-(N-phenyl-N-naphthylamino)phenyl-1-naphthylamine) to produce the compound represented by Formula 2-19-19

4-bromophenyl-N-phenyl-N-naphthylamine (14.0 g, 37.4 mmol) and 1-naphthylamine (6.43 g, 44.9 mmol) were dissolved in 200 ml of toluene, bis-dibenzylidene acetone palladium (0) (0.645 g, 1.12 mmol), 50 wt % tri-tertiary-butylphosphine toluene solution (0.74 ml, 1.5 mmol), and sodium-tertiary-butoxide (8.99 g, 93.5 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (8.53 g, yield 52.2%).

MS: [M+H]$^+$=437.

2) The Compound of Formula b (5.00 g, 8.88 mmol) and 4-(N-phenyl-N-naphthylamino)phenyl-1-naphthylamine (8.53 g, 19.5 mmol) were dissolved in 50 ml of toluene, and bisdibenzylidene acetone palladium(0) (0.204 g, 0.360 mmol), 50 wt % tri-tertiary-butylphosphine toluene solution (0.31 ml, 0.62 mmol) and sodium-tertiary-butoxide (4.69 g, 48.8 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-19-19 (5.60 g, yield 49.5%).

MS: [M+H]$^+$=1229.

Example 6

Preparation of Compound Represented by Following Formula 2-21-21

1) Production of arylamine (4-(N-phenyl-N-naphthylamino)phenyl-1-biphenylamine) to produce the compound represented by Formula 2-21-21

4-bromophenyl-N-phenyl-N-naphthylamine (14.0 g, 37.4 mmol) and 4-aminobiphenyl (6.96 g, 41.2 mmol) were dissolved in 200 ml of toluene, bis-dibenzylidene acetone palladium (0) (0.47 g, 0.82 mmol), 50 wt % tri-tertiary-butylphosphine toluene solution (0.50 ml, 1.2 mmol), and sodium-tertiary-butoxide (11.86 g, 123.4 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (7.5 g, yield 43%).

MS: [M+H]$^+$=462.

2) The Compound of Formula b (3.3 g, 5.8 mmol) and 4-(N-phenyl-N-naphthylamino)phenyl-1-biphenylamine (5.90 g, 12.8 mmol) were dissolved in 70 ml of toluene, and bisdibenzylidene acetone palladium(0) (0.15 g, 0.26 mmol), 50 wt % tri-tertiary-butylphosphine toluene solution (0.16 ml, 0.38 mmol) and sodium-tertiary-butoxide (3.68 g, 38.3 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-21-21 (3.9 g, yield 51%).

MS: [M+H]$^+$=1229.

[Formula 2-21-21]

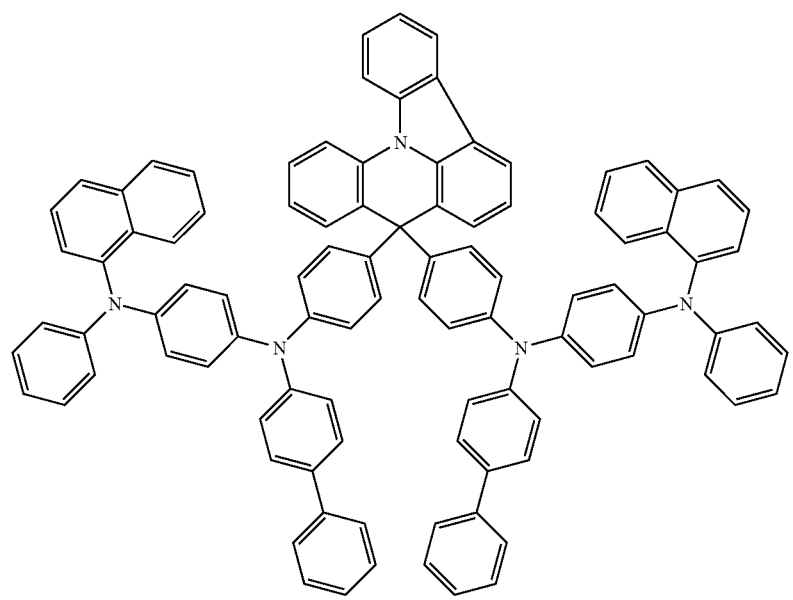

Example 7

Preparation of Compound Represented by Following Formula 2-256-256

[Formula 2-256-256]

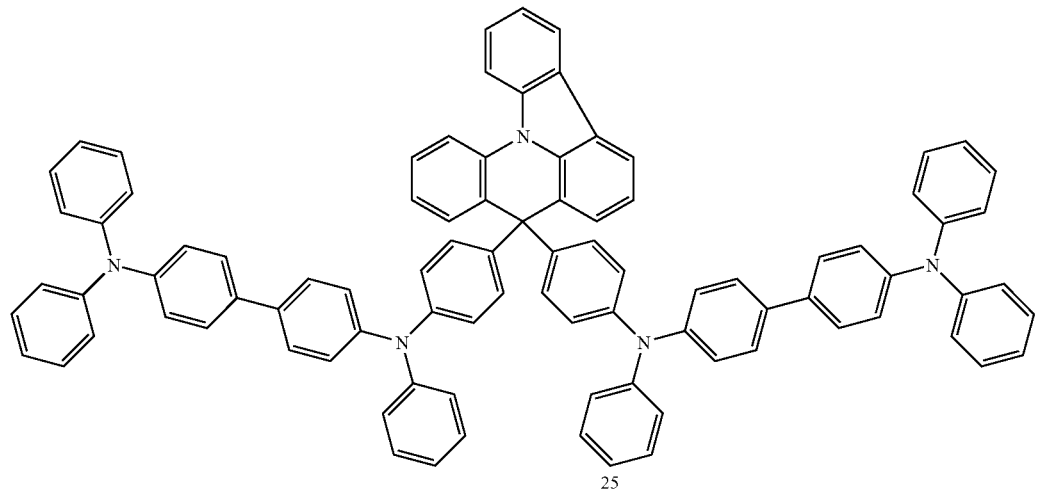

1) Production of arylamine (4-(N,N-diphenylamino)-biphenyl-aniline) to produce the compound represented by Formula 2-256-256

4-chlorobiphenyl-N,N-diphenylamine (4.00 g, 11.2 mmol) and aniline (1.13 ml, 12.4 mmol) were dissolved in 100 ml of toluene, bisdibenzylidene acetone palladium(0) (0.129 g, 0.225 mmol), 50 wt % tri-tertiary-butylphosphine toluene solution (0.17 ml, 0.34 mmol), and sodium-tertiary-butoxide (2.70 g, 28.1 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group as an amine derivative (3.77 g, yield 81.3%).

MS: $[M+H]^+=413$.

2) The Compound of Formula b (2.30 g, 4.08 mmol) and 4-(N,N-diphenylamino)-biphenyl-aniline (3.70 g, 8.97 mmol) were dissolved in 30 ml of toluene, and bisdibenzylidene acetone palladium(0) (0.094 g, 0.16 mmol), 50 wt % tri-tertiary-butylphosphine toluene solution (0.14 ml, 0.29 mmol) and sodium-tertiary-butoxide (2.16 g, 22.4 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-256-256 (2.7 g, yield 54%).

MS: $[M+H]^+=1229$.

Example 8

Preparation of Compound Represented by Following Formula 3-2-2

[Formula 3-2-2]

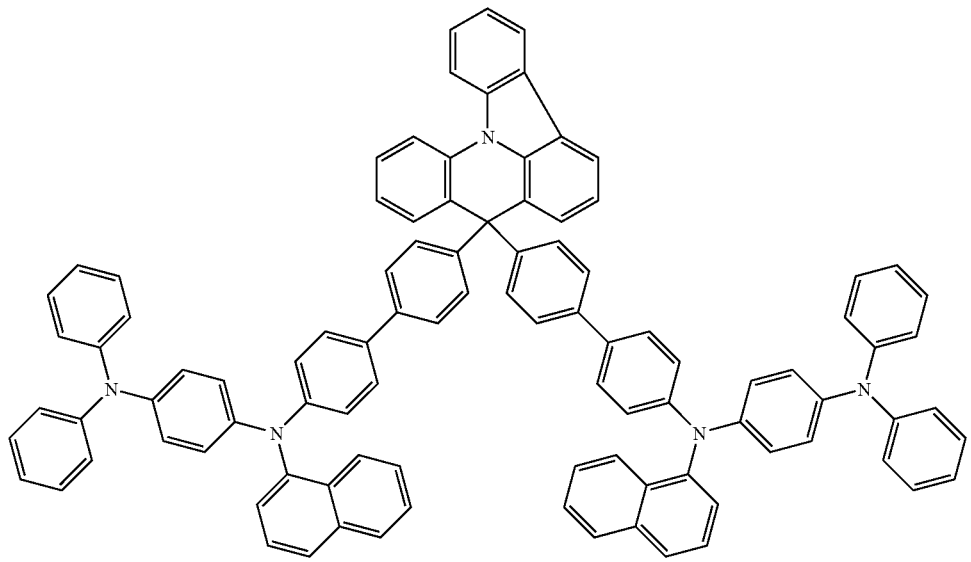

1) Production of arylamine (4-(N-phenyl-N-phenylamino)phenyl-1-naphthylamine) to produce the compound represented by Formula 3-2-2

Synthesis was conducted through the same procedure as in synthesis of the arylamine connection group of the compound represented by Formula 2-2-2.

2) The starting material represented by Formula b (10.0 g, 17.8 mmol) was completely dissolved in 200 ml of THF, 4-chloro-phenylboronic acid (8.30 g, 53.3 mmol), 2 M potassium carbonate solution, tetrakis(triphenylphosphine)palladium(0) (0.62 g, 0.53 mmol), and 10 ml of ethanol were added thereto, and reflux was conducted for 24 hours. After the reaction was completed, cooling to normal temperature was conducted, and filtration was conducted. Washing was conducted with water and ethanol several times. Recrystallization was conducted with ethanol, and vacuum drying was conducted to produce a compound (9.5 g, 85% yield).

MS: $[M+H]^+$=627.

The compound obtained by the above reaction (5.00 g, 7.98 mmol) and 4-(N-phenyl-N-phenylamino)phenyl-1-naphthylamine (7.09 g, 18.4 mmol) were dissolved in 120 ml of toluene, and sodium-tertiary-butoxide (5.29 g, 55.0 mmol), bis-dibenzylidene acetone palladium(0) (0.21 g, 0.37 mmol), and 50 wt % tri-tertiary-butylphosphine toluene solution (0.22 ml, 0.55 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 3-2-2 (5.6 g, yield 53%).

MS: $[M+H]^+$=1327.

Experimental Example 1

Production of Organic Light Emitting Diode

A glass substrate (corning 7059 glass), on which ITO (indium tin oxide) was applied to a thickness of 1,000 to form a thin film, was put in distilled water, in which a detergent was dissolved, and washed using ultrasonic waves. In connection with this, a product manufactured by Fischer Co. was used as the detergent, and distilled water was produced by filtering twice using a filter manufactured by Millipore Co. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. Furthermore, the substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 80 by heating on a transparent ITO electrode, which was prepared through the above procedure, so as to form an anode including an ITO conductive layer and an N-type organic material. Interfacial characteristic between the substrate and hole injection layer can be improved by the anode. Subsequently, the compound of Formula 2-1-1 was deposited to a thickness of 800 on the thin film to form a hole injection layer.

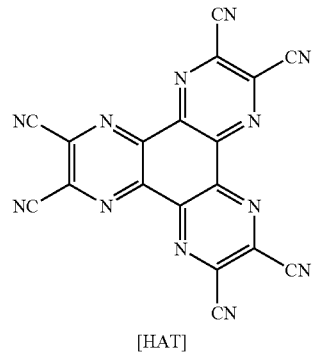

[HAT]

NPB was deposited to a thickness of 300 on the layer to form a hole transport layer. Then, $Alq_3$ was deposited to a thickness of 300 on the hole transport layer to form a light emitting layer. An electron transport layer material of the following Formula was deposited to a thickness of 200 on the light emitting layer to form an electron transport layer.

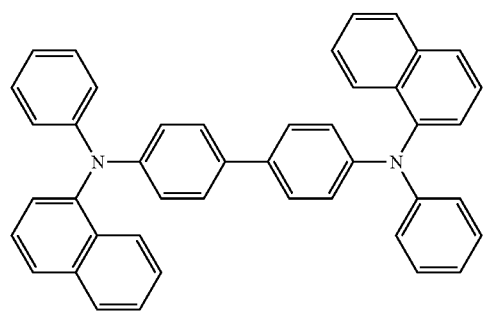

[NPB]

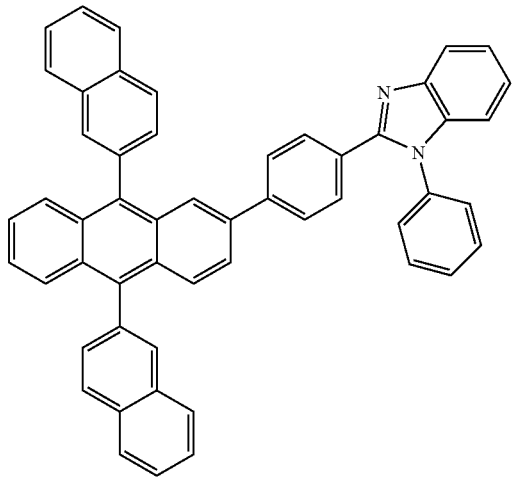

[Electron transport layer material]

Lithium fluoride (LiF) having a thickness of 12 and aluminum having a thickness of 2,000 were sequentially deposited on the electron transport layer to form a cathode.

In the above procedure, the deposition speed of an organic material was maintained at 0.3 to 0.8 Å/sec. Furthermore, lithium fluoride and aluminum were deposited at speeds of 0.3 Å/sec and 1.5 to 2.5 Å/sec, respectively, on the cathode. During the deposition, a vacuum was maintained at 1 to 3 $10^{-7}$.

The resulting device had an electric field of 8.78 V at a forward current density of 100 mA/cm², and a spectrum having a light efficiency of 2.01 lm/W. The operation and light emission of the device at the above-mentioned actuating voltage mean that the compound of Formula 2-1-1, which formed the layer between the thin film formed on the substrate and the hole transport layer, functions to inject holes.

Experimental Example 2

Production of Organic Light Emitting Diode

The procedure of Example 1 was repeated to produce a device except that the compound of Formula 2-1-1 used as a hole injection layer was substituted with the compound of Formula 2-2-2.

The resulting device had an electric field of 8.75 V at a forward current density of 100 mA/cm², and a spectrum having a light efficiency of 2.01 lm/W.

Experimental Example 3

Production of Organic Light Emitting Diode

The procedure of Experimental Example 1 was repeated to produce a device except that the compound of Formula 2-1-1 used as a hole injection layer was substituted with the compound of Formula 2-4-4.

The resulting device had an electric field of 7.36 V at a forward current density of 100 mA/cm², and a spectrum having a light efficiency of 2.12 μm/W.

Experimental Example 4

Production of Organic Light Emitting Diode

The procedure of Experimental Example 1 was repeated to produce a device except that the compound of Formula 2-1-1 used as a hole injection layer was substituted with the compound of Formula 2-18-18.

The resulting device had an electric field of 8.58 V at a forward current density of 100 mA/cm², and a spectrum having a light efficiency of 1.97 lm/W.

Experimental Example 5

Production of Organic Light Emitting Diode

The procedure of Experimental Example 1 was repeated to produce a device except that the compound of Formula 2-1-1 used as a hole injection layer was substituted with the compound of Formula 2-19-19.

The resulting device had an electric field of 9.20 V at a forward current density of 100 mA/cm², and a spectrum having a light efficiency of 2.36 lm/W.

Experimental Example 6

Production of Organic Light Emitting Diode

The procedure of Experimental Example 1 was repeated to produce a device except that the compound of Formula 2-1-1 used as a hole injection layer was substituted with the compound of Formula 2-21-21.

The resulting device had an electric field of 8.18 V at a forward current density of 100 mA/cm², and a spectrum having a light efficiency of 2.67 lm/W.

Experimental Example 7

Production of Organic Light Emitting Diode

The procedure of Experimental Example 1 was repeated to produce a device except that the compound of Formula 2-1-1 used as a hole injection layer was substituted with the compound of Formula 2-256-256.

The resulting device had an electric field of 6.79 V at a forward current density of 100 mA/cm², and a spectrum having a light efficiency of 1.83 lm/W.

Example 8

Production of Organic Light Emitting Diode

The procedure of Experimental Example 1 was repeated to produce a device except that the compound of Formula 2-1-1 used as a hole injection layer was substituted with the compound of Formula 3-2-2.

The resulting device had an electric field of 8.91 V at a forward current density of 100 mA/cm², and a spectrum having a light efficiency of 2.08 lm/W.

The invention claimed is:
1. A compound represented by the following Formula 1:

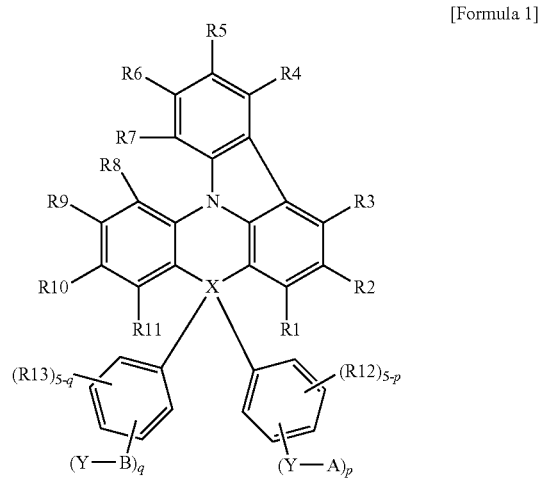

[Formula 1]

wherein, X is C or Si,
Ys are the same or different from each other, and each independently directly connected to each other; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups,
R1 to R11 are the same or different from each other, and each independently hydrogen, a substituted or unsubstituted alkyl group, a substituted or un-substituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R12 and R13 are the same or different from each other, and each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R7 and R8 are directly connected to each other, or form a condensation ring along with a group selected from the group consisting of O, S, NR, PR, C=O, CRR' and SiRR' in which R and R' are the same or different from each other, each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound, p and q are each independently an integer of 1 to 5, with the proviso that when p is an integer of 2 or more, q is 1, and when q is an integer of 2 or more, p is 1, A is

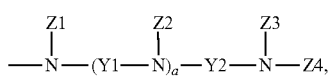

B is

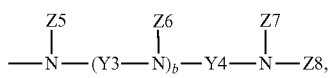

a and b are each independently an integer of 0 to 10,

Y1 to Y4 are the same or different from each other, and each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy and amino groups, and Z1 to Z8 are the same or different from each other, and each independently hydrogen; aliphatic hydrocarbons having 1 to 20 carbon atoms; aromatic hydrocarbons; aromatic hydrocarbons which are substituted with at least one substituent group selected from the group consisting of nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of nitro, nitrile, halogen, alkyl, alkoxy, amino, aromatic hydrocarbon, and heterocyclic groups; a thiophene group which is substituted with aliphatic hydrocarbons having 1 to 20 carbon atoms or aromatic hydrocarbons having 6 to 20 carbon atoms; or a boron group which is substituted with aromatic hydrocarbons.

2. The compound according to claim 1, wherein the bivalent aromatic hydrocarbon of Y and Y1 to Y4 of Formula 1 is selected from the group consisting of phenylene, biphenylene, terphenylene, naphthylene, anthracenylene, pyrenylene, and perylenylene.

3. The compound according to claim 1, wherein the bivalent heterocyclic group of Y and Y1 to Y4 of Formula 1 is selected from the group consisting of thio-phenylene, furylene, pyrrolylene, imidazolylene, thiazolylene, oxazolylene, oxa-diazolylene, thiadiazolylene, triazolylene, pyridylene, pyridazylene, pyrazinylene, quinolylene, and isoquinolylene.

4. The compound according to claim 1, wherein the aromatic hydrocarbon of Z1 to Z8 of Formula 1 is selected from the group consisting of phenyl, biphenyl, terphenyl, naphthyl, anthracenyl, pyrenyl, and perylenyl.

5. The compound according to claim 1, wherein the heterocyclic group of Z1 to Z8 of Formula 1 is selected from the group consisting of thiophene, furan, pyrrole, imidazole, thiazole, oxazole, oxadiazole, thiadiazole, triazole, pyridyl, pyridazyl, pyrazine, quinoline, and isoquinoline.

6. The compound according to claim 1, wherein the aliphatic hydrocarbon having 1 to 20 carbon atoms of Z1 to Z8 of Formula 1 is selected from the group consisting of a methyl group, an ethyl group, an n-propyl group, an iso-propyl group, an n-butyl group, a sec-butyl group, an iso-butyl group, a ter-butyl group, a pentyl group, a hexyl group, a styryl group, and an acetylene group.

7. The compound according to claim 1, wherein the aryl group of R1 to R13 of Formula 1 is selected from the group consisting of a phenyl group, a biphenyl group, a terphenyl group, a stilbene group, a naphthyl group, an anthracenyl group, a phenanthrene group, a pyrenyl group, and a perylenyl group.

8. The compound according to claim 1, wherein the arylamine group of R1 to R11 of Formula 1 is selected from the group consisting of a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

9. The compound according to claim 1, wherein the heterocyclic group of R1 to R13 of Formula 1 is selected from the group consisting of a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, and an acridyl group.

10. The compound according to claim 1, wherein the alkenyl, aryl, arylamine, and heterocyclic groups of R1 to R13 of Formula 1 are selected from the group consisting of the following Formulae:

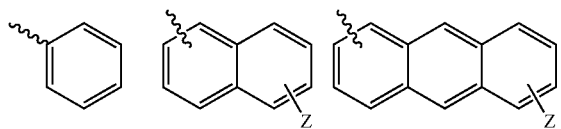

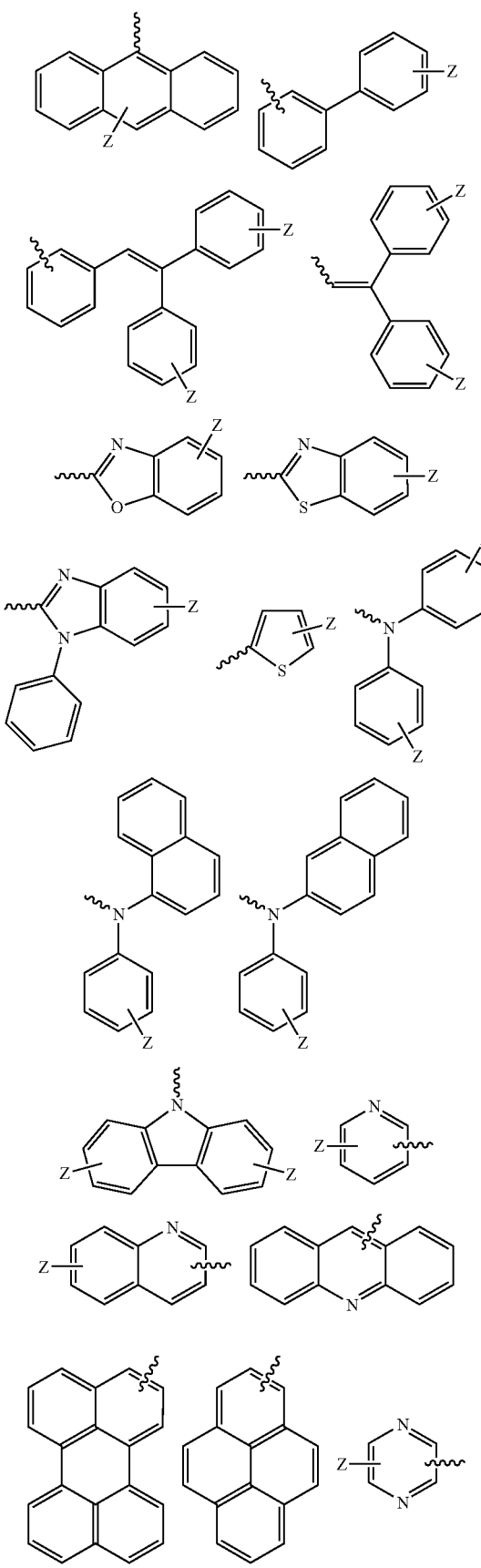
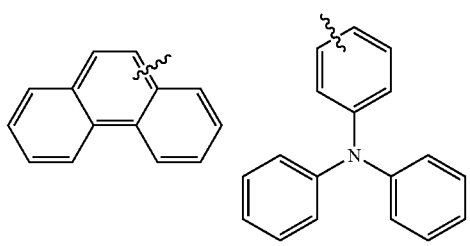
wherein Z is a group selected from the group consisting of hydrogen, aliphatic hydrocarbons having 1 to 20 carbon atoms, an alkoxy group, an arylamine group, an aryl group, a heterocyclic group, a nitrile group, and an acetylene group.
11. The compound according to claim 1, wherein Formula 1 is represented by any one of the following Formulae 2 to 7:
[Formula 2]
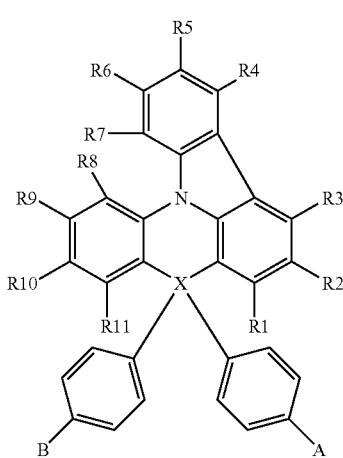
[Formula 3]
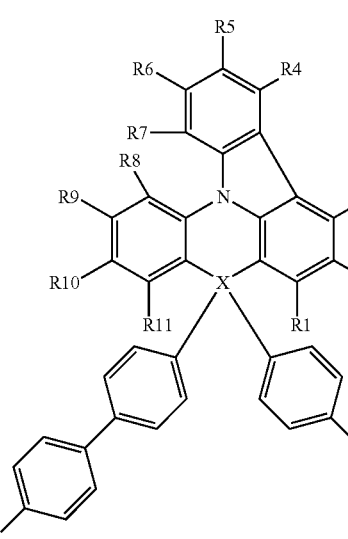

[Formula 4]
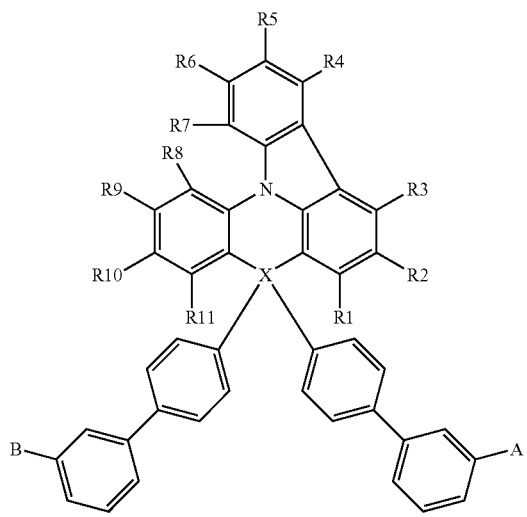
[Formula 5]
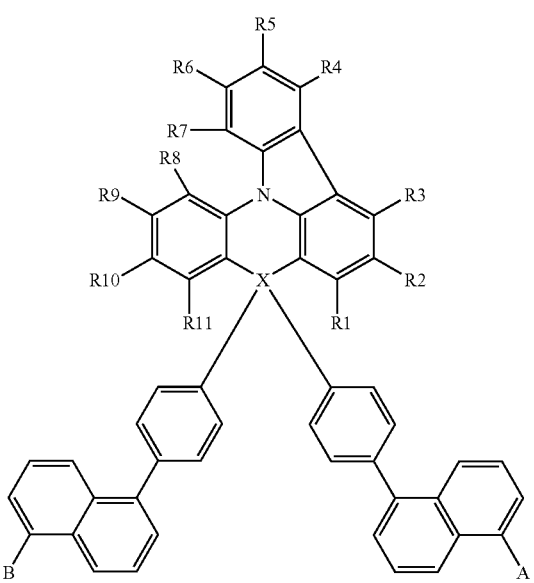
[Formula 6]
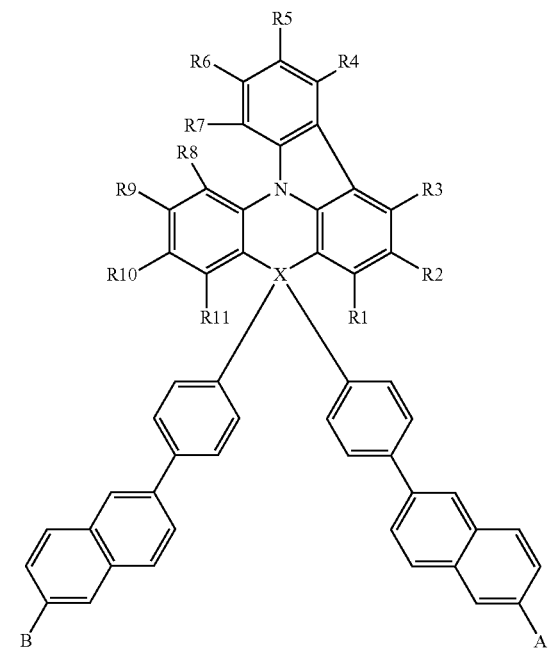
[Formula 7]
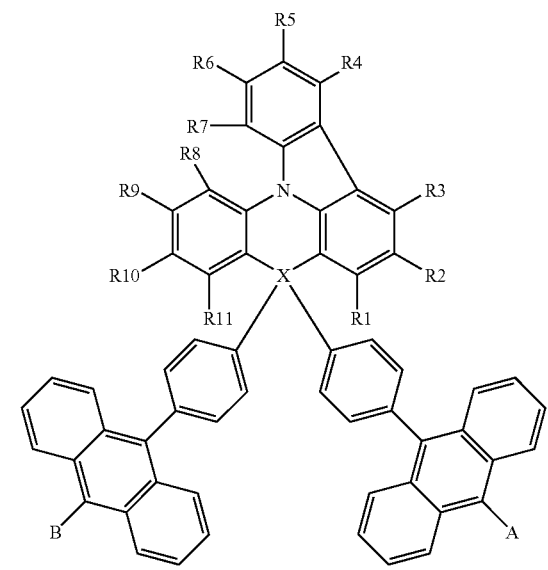
wherein X, R1 to R11, A, and B are as defined in Formula 1.
12. The compound according to claim 1, wherein A and B of Formula 1 are each independently selected from the group consisting of the following groups:

227
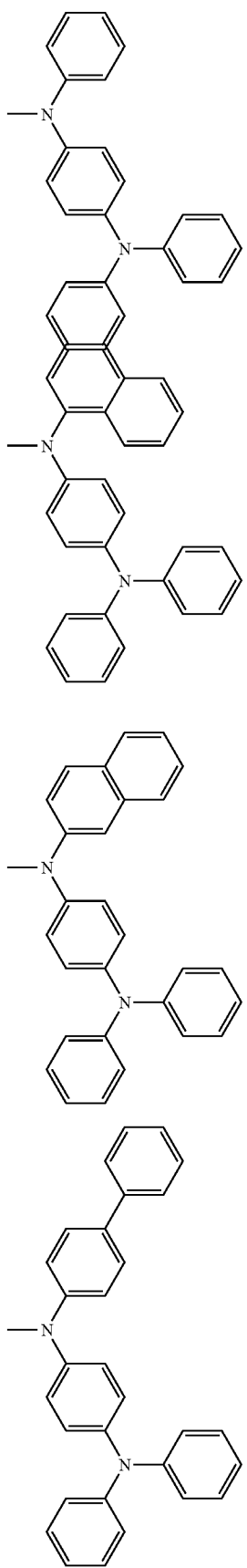
228
-continued
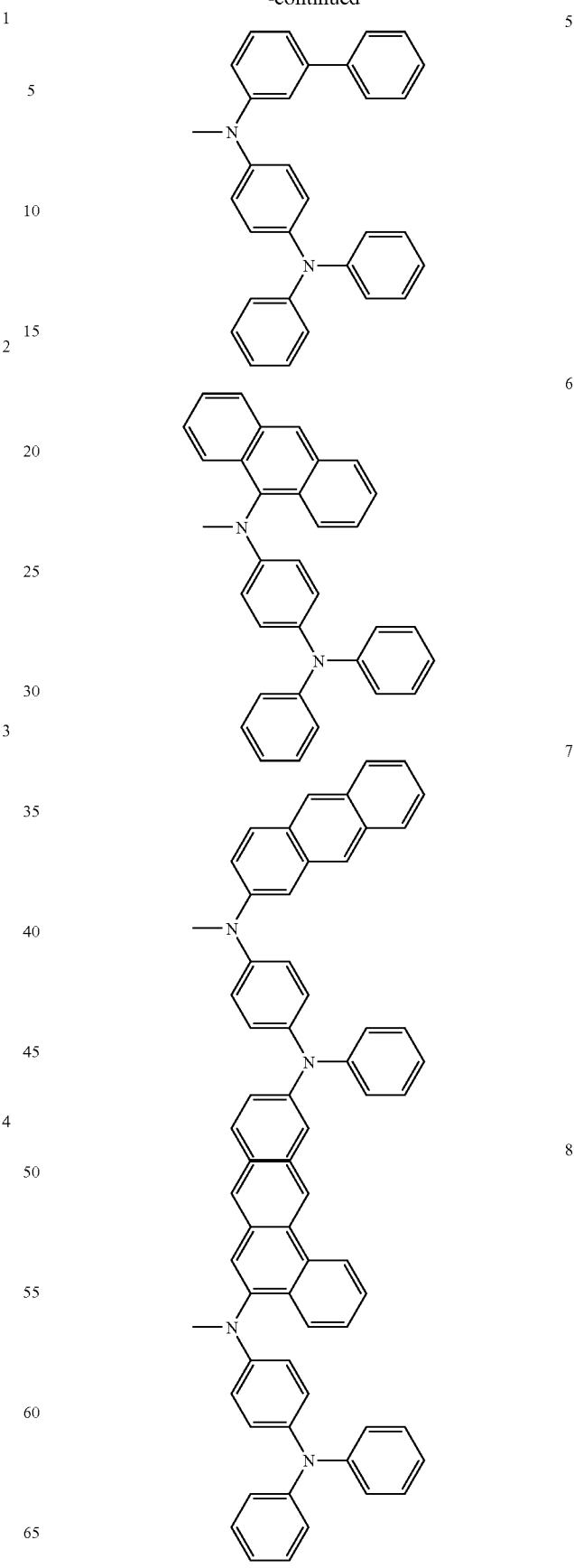

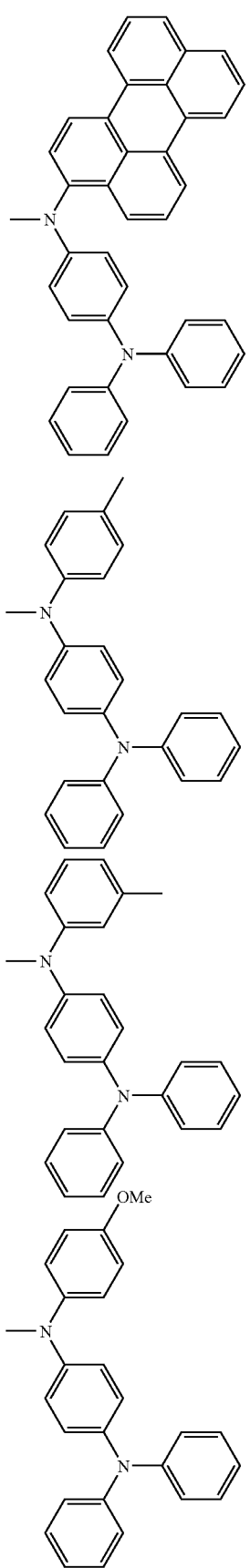
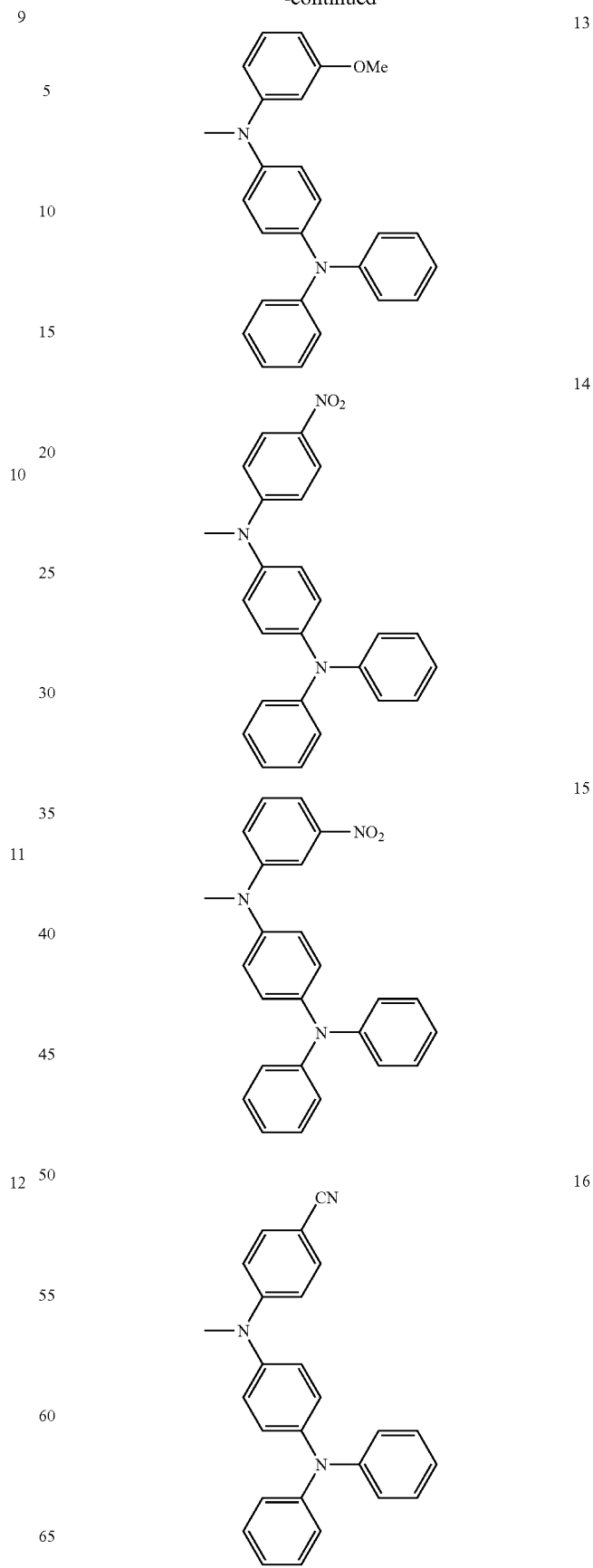

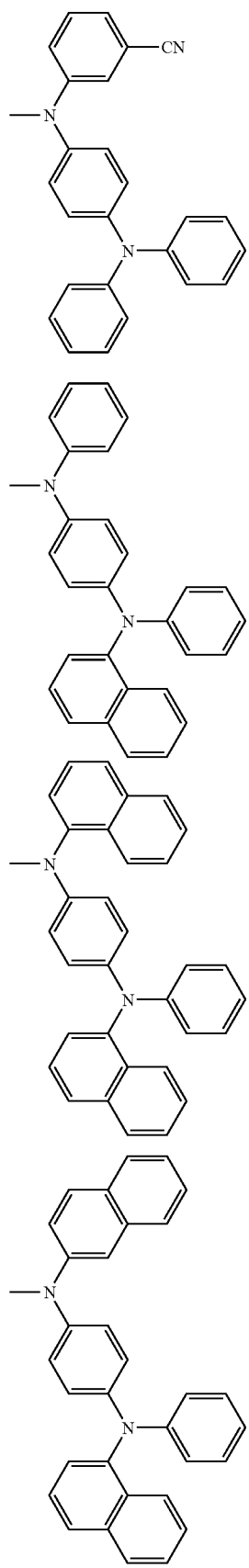
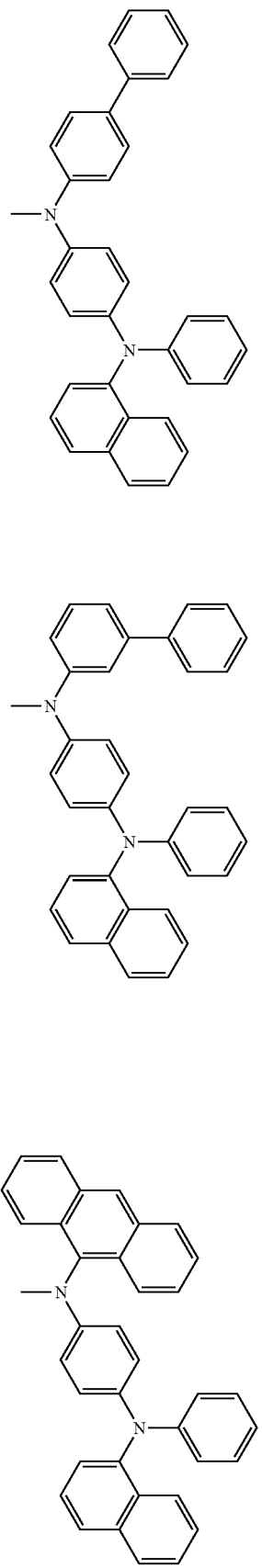

24
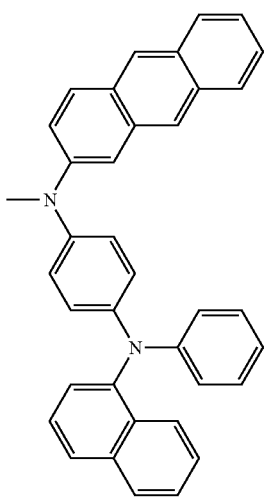
25
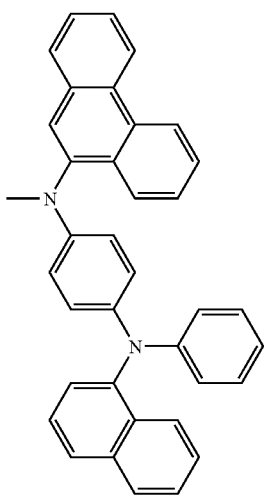
26
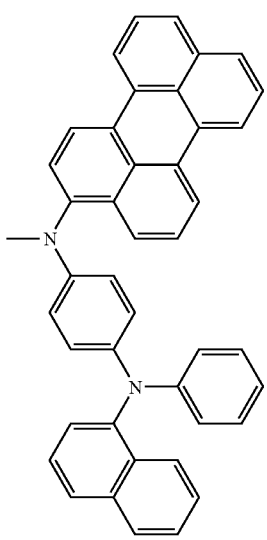
27
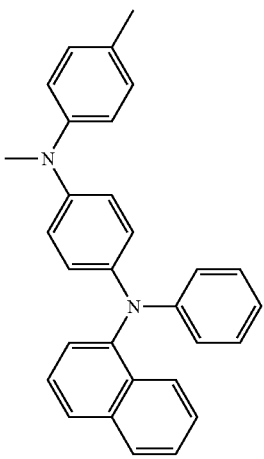
28
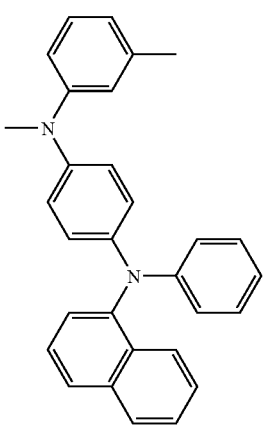
29
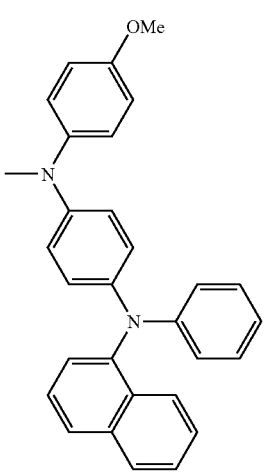

235
-continued
30
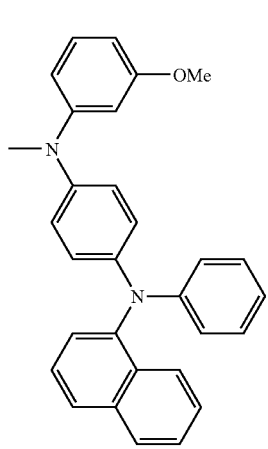
31
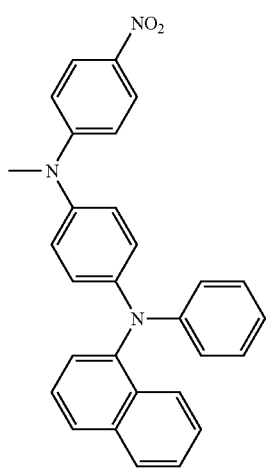
32
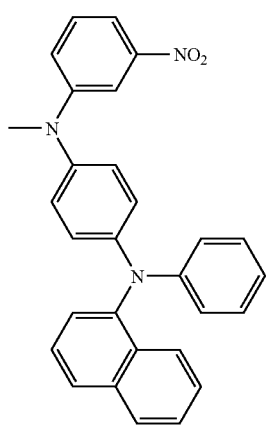
236
-continued
5
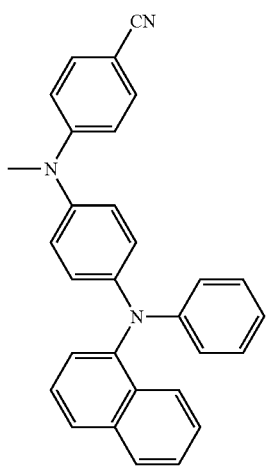
33
10
15
20
25
30
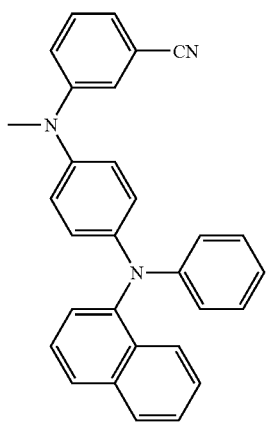
34
35
40
45
50
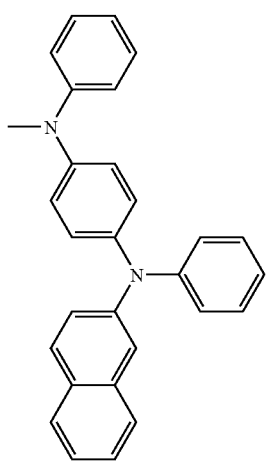
35
55
60
65

237
-continued
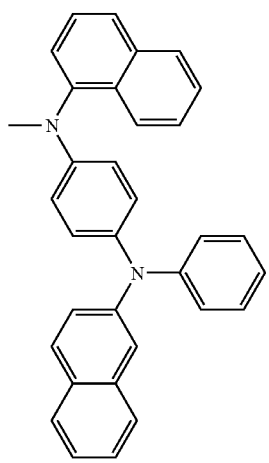
36
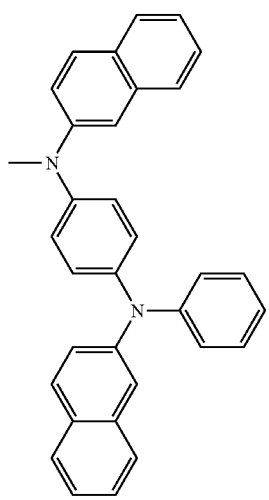
37
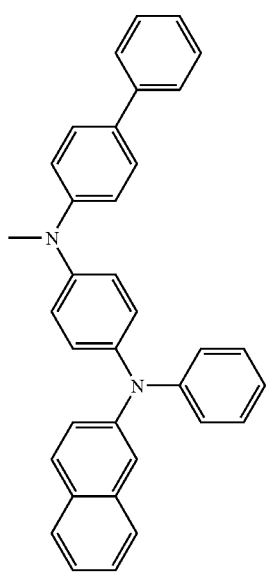
38
238
-continued
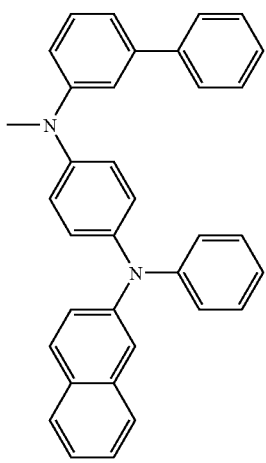
39
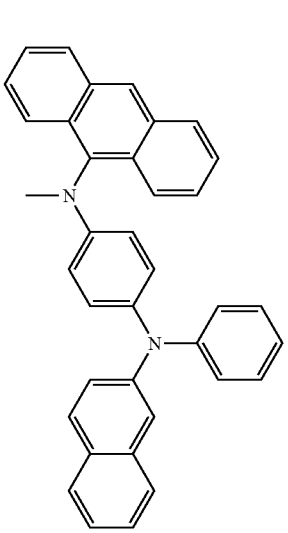
40
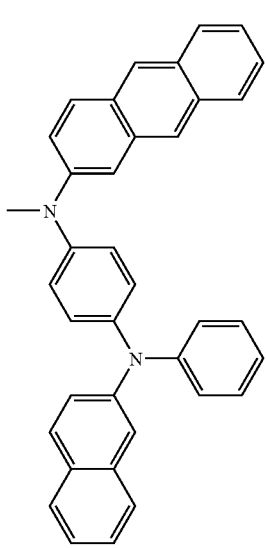
41

42
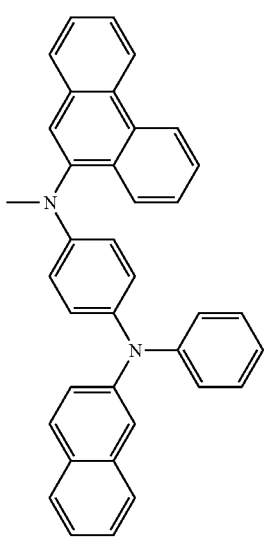
43
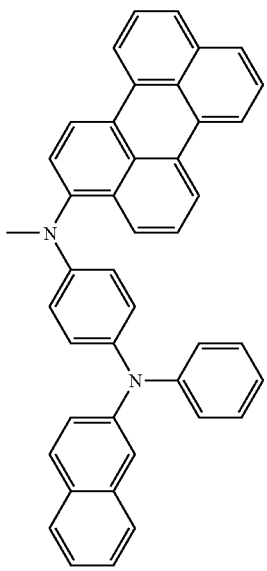
44
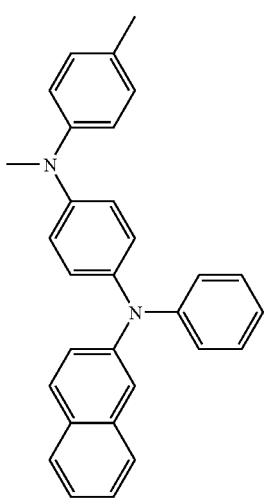
45
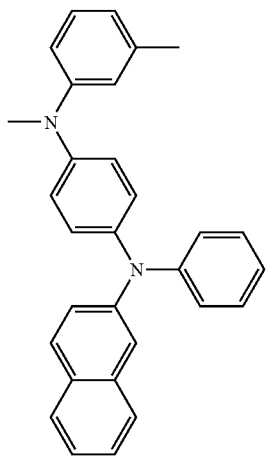
46
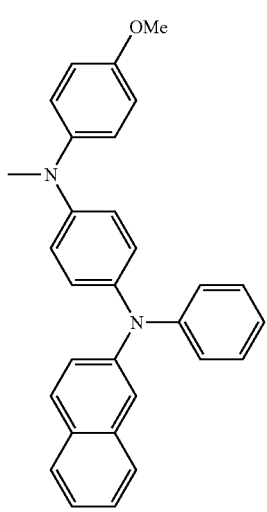
47
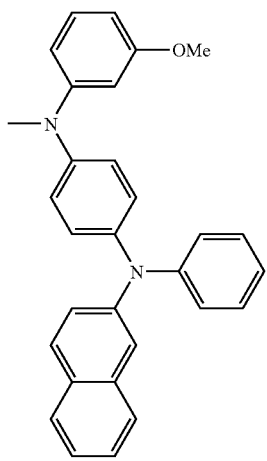

48
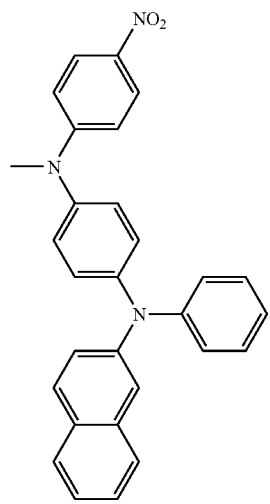
49
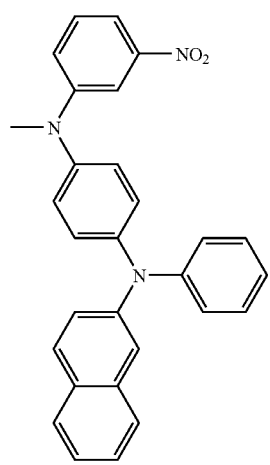
50
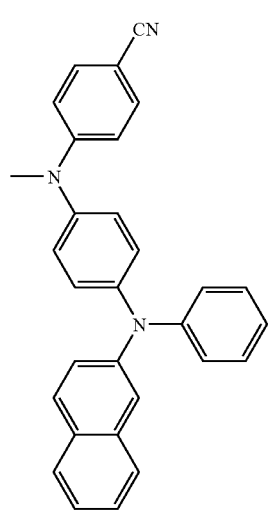
51
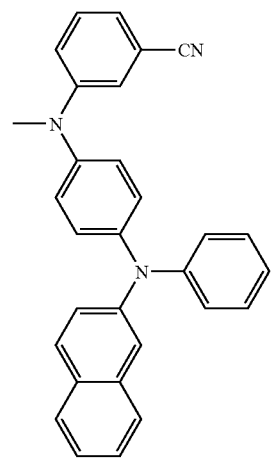
52
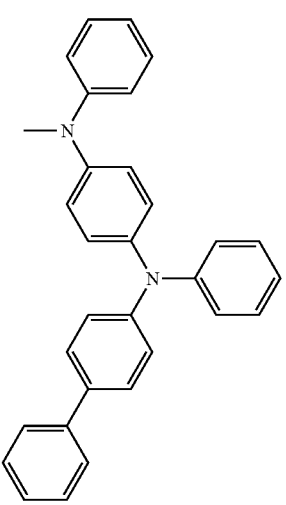
53
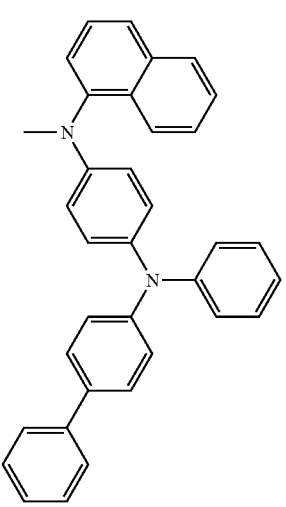

54
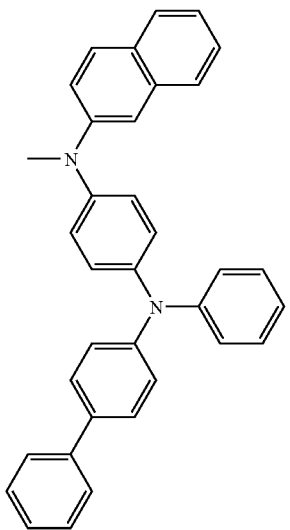
55
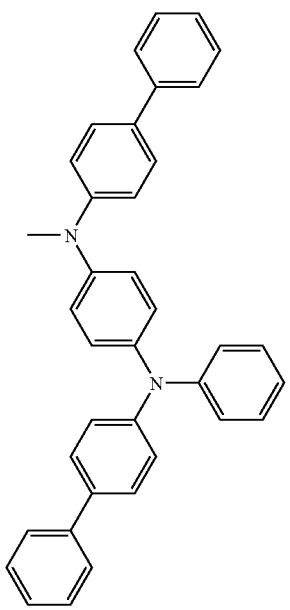
56
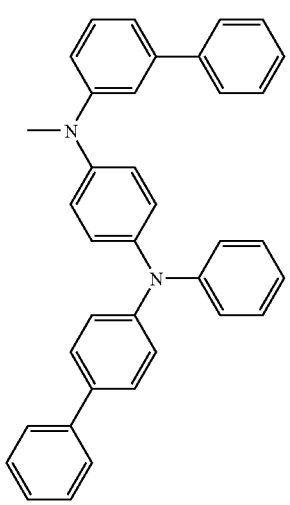
57
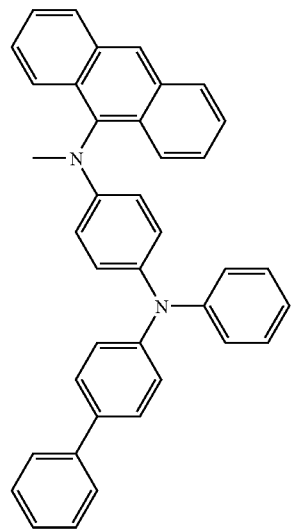
58
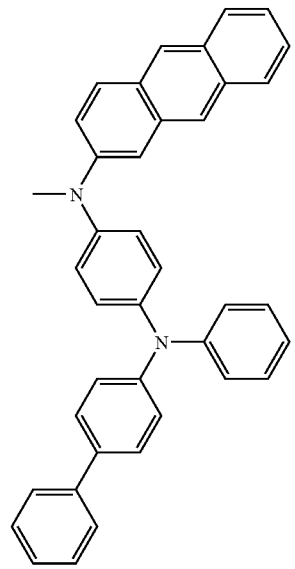
59
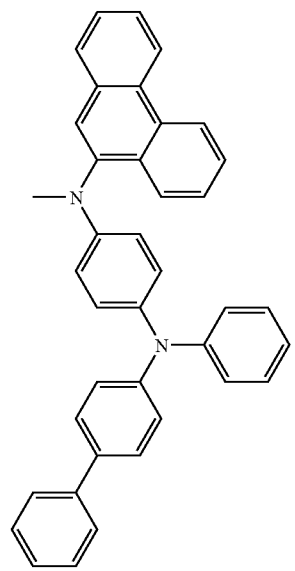

245
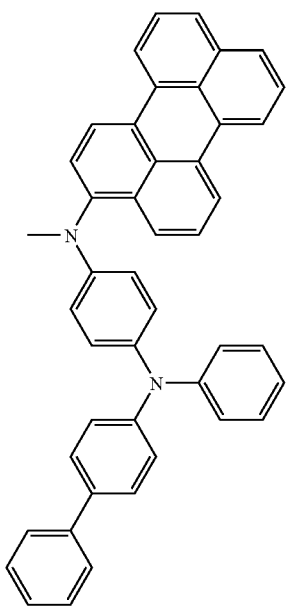
60
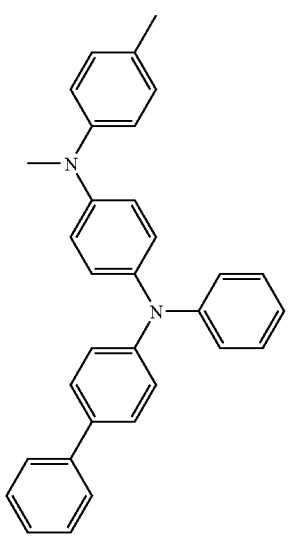
61
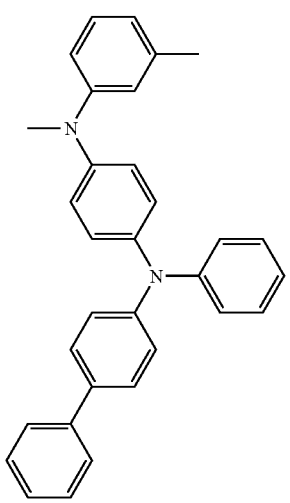
62
246
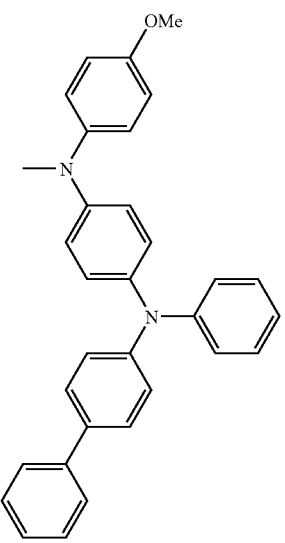
63
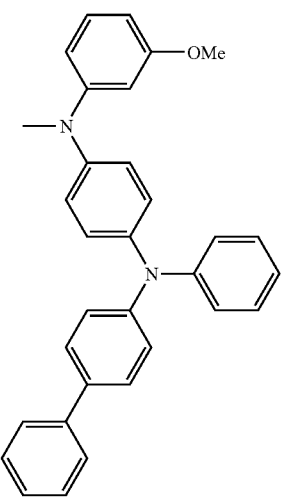
64
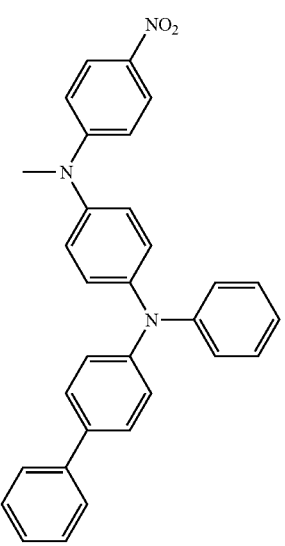
65

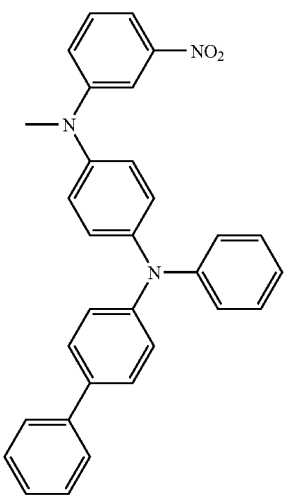
66
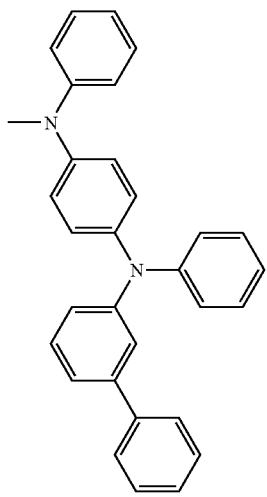
69
67
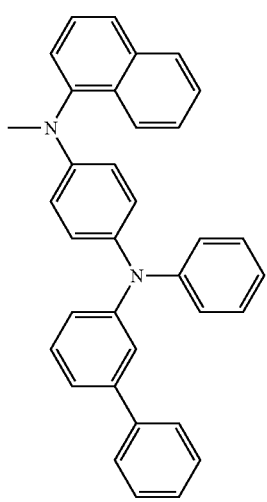
70
68
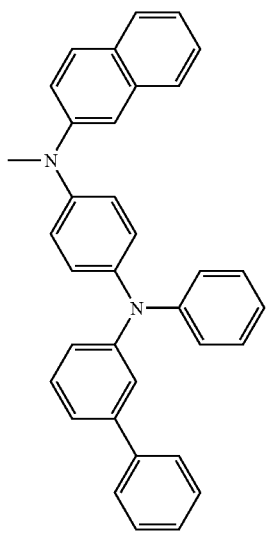
71

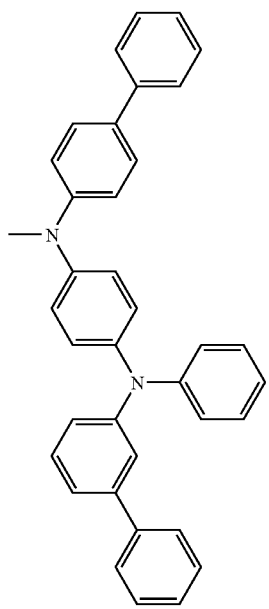
72
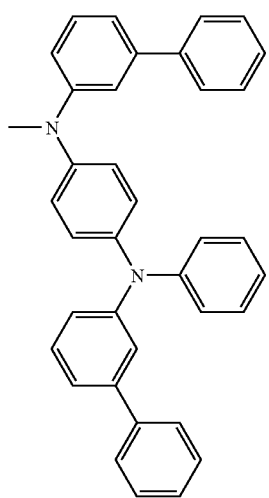
73
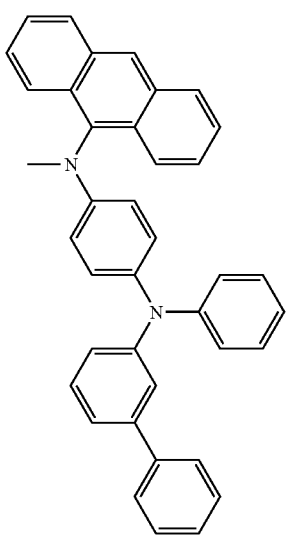
74
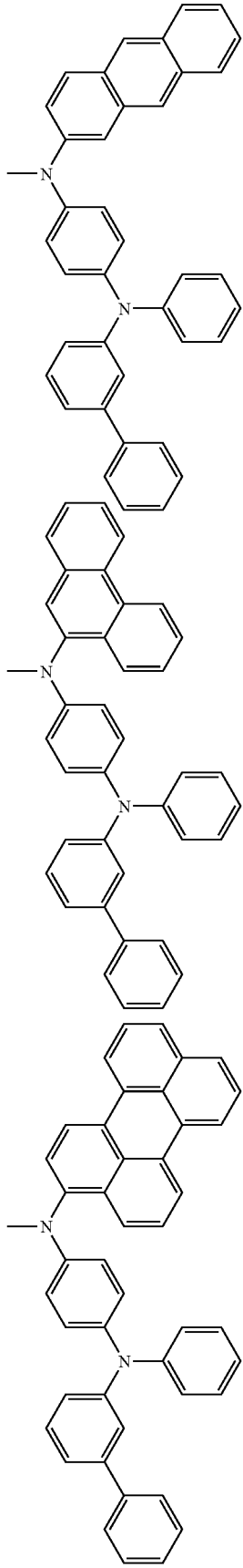

251
-continued
78
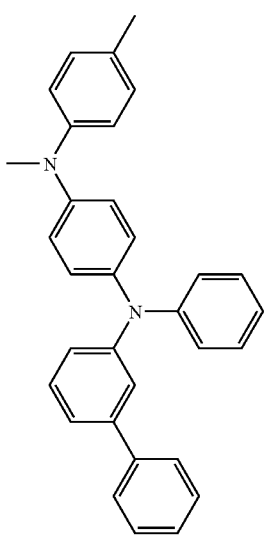
79
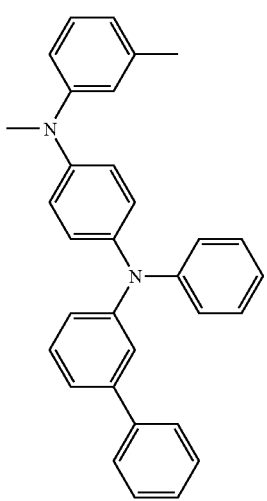
80
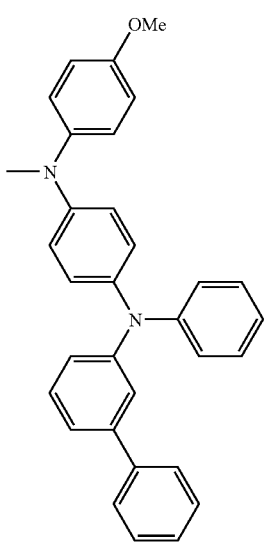
252
-continued
81
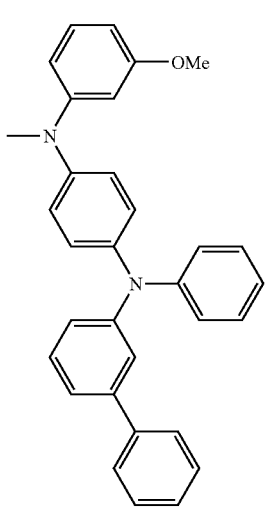
82
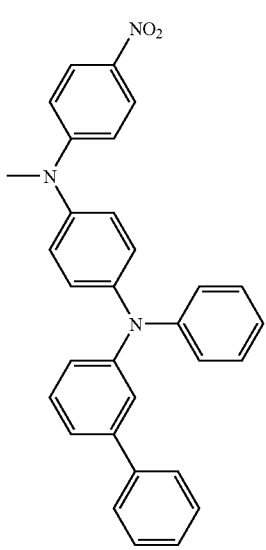
83
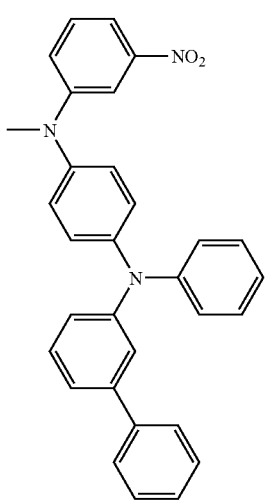

84
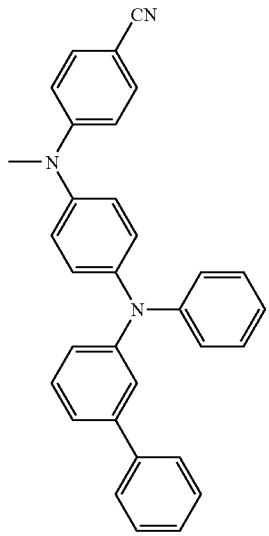
85
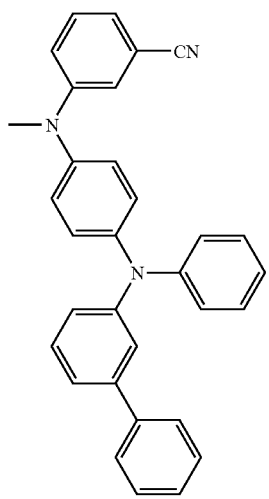
86
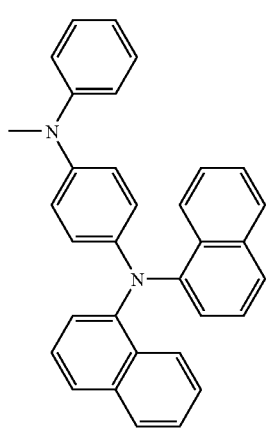
87
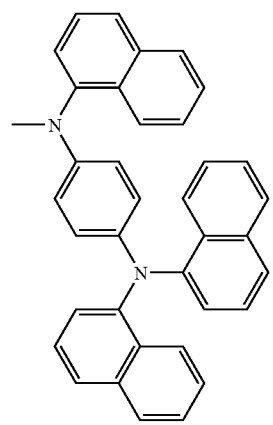
88
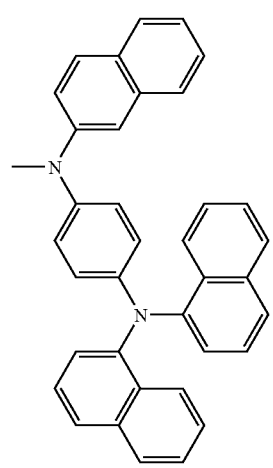
89
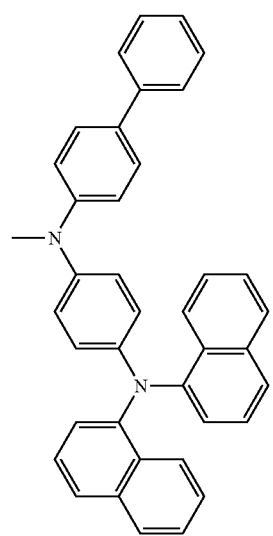

255
-continued
90
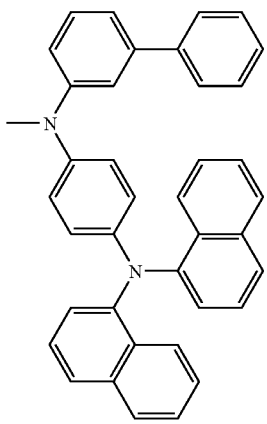
91
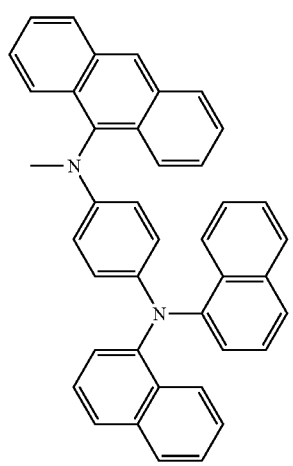
92
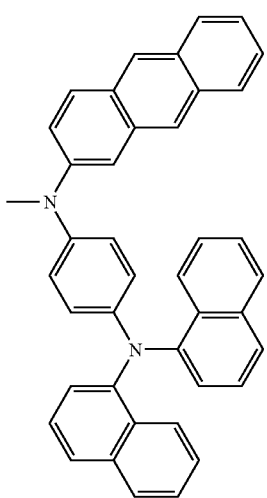
256
-continued
93
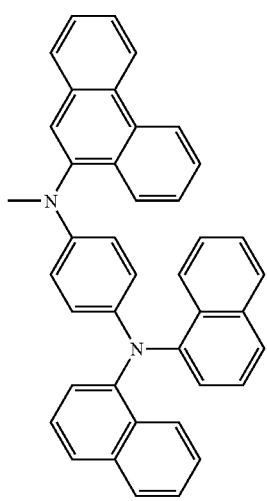
94
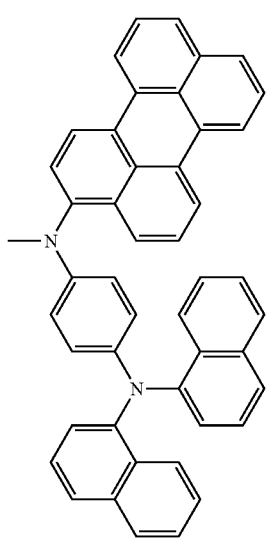
95
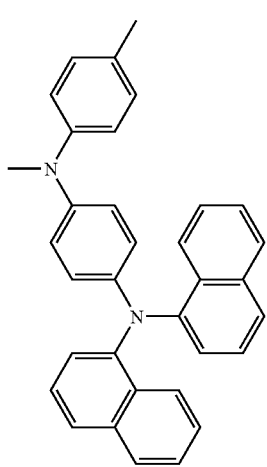

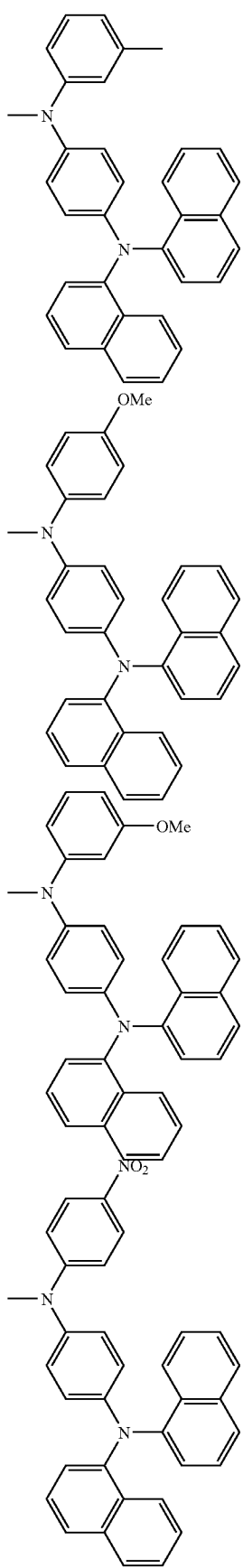
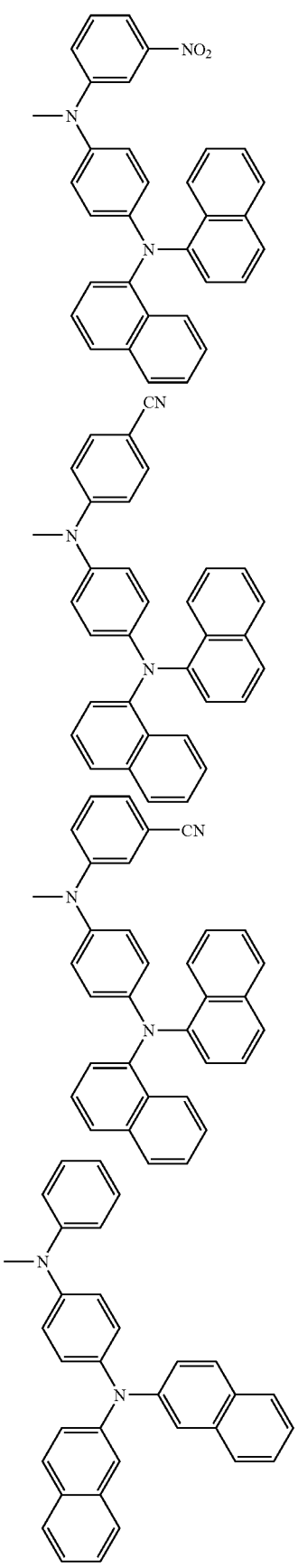

259
-continued
104
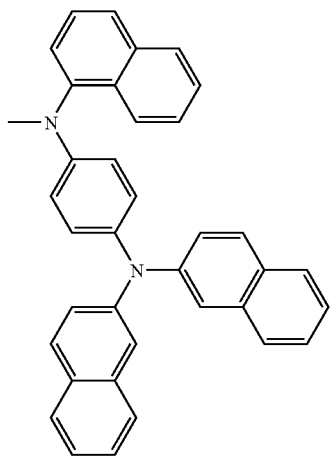
105
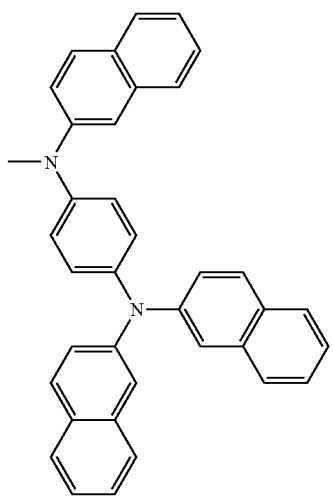
106
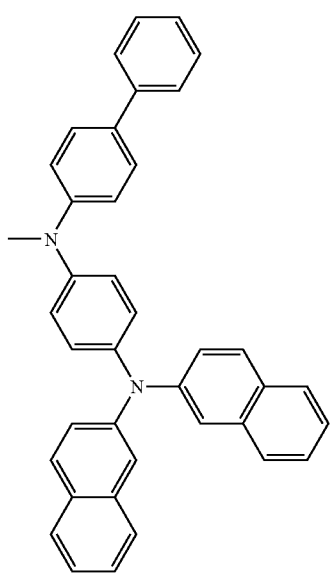
260
-continued
107
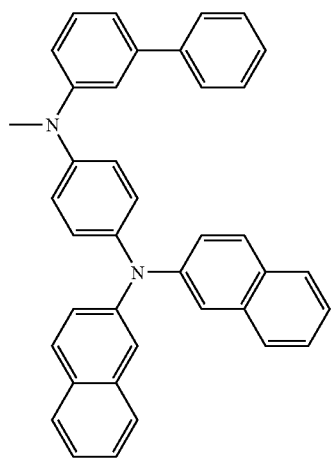
108
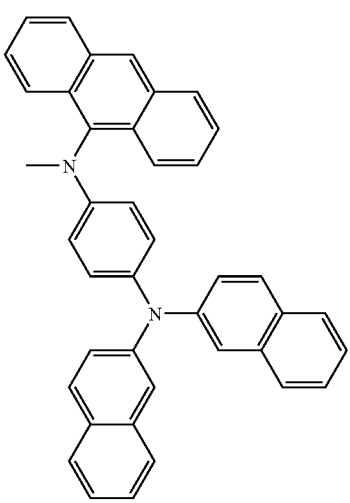
109
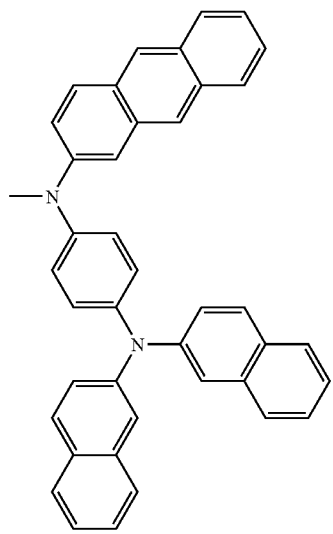

| 261 -continued | 262 -continued |
|---|---|
| 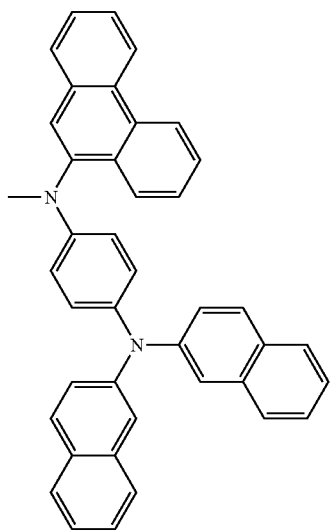 110 | 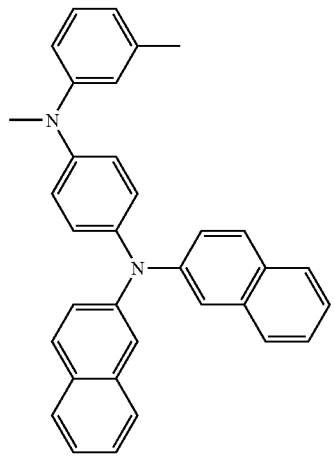 113 |
| 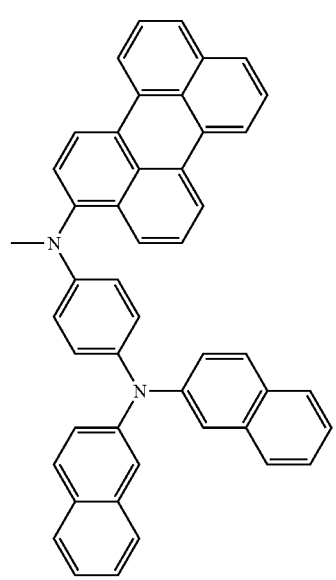 111 | 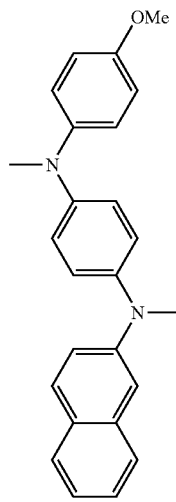 114 |
| 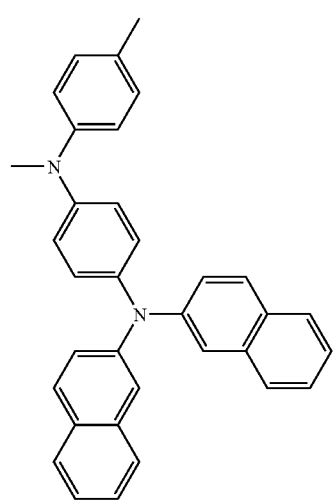 112 | 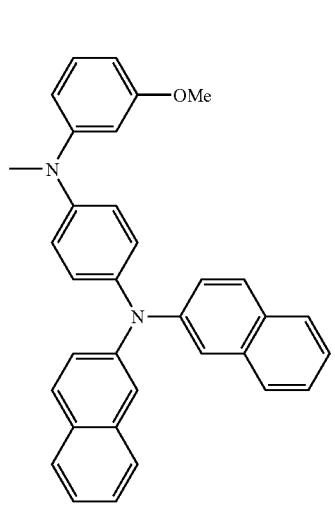 115 |

263
-continued
116
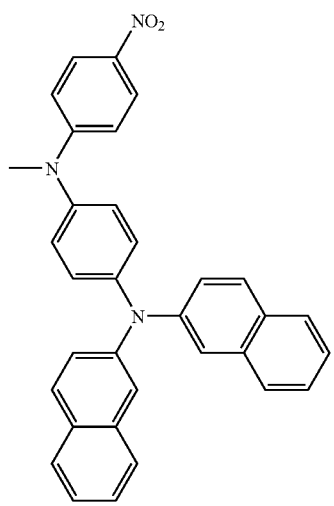
117
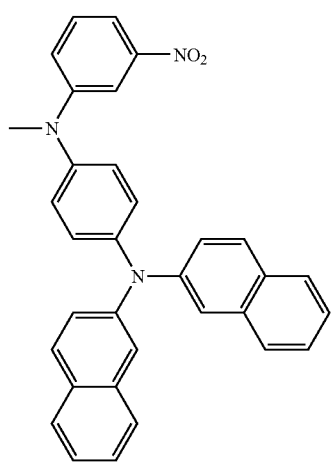
118
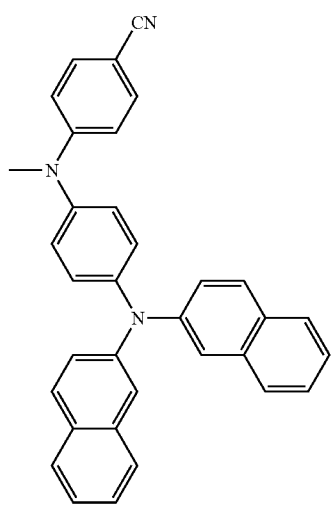
264
-continued
119
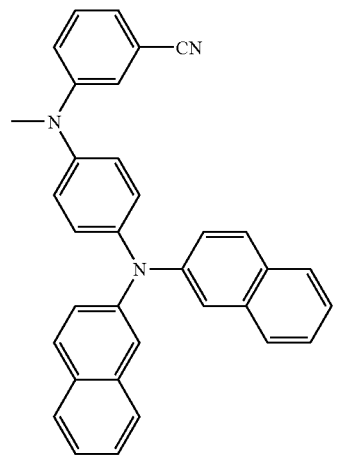
120
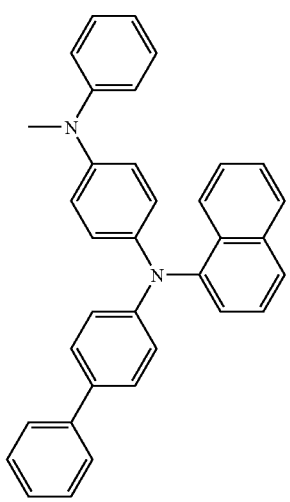
121
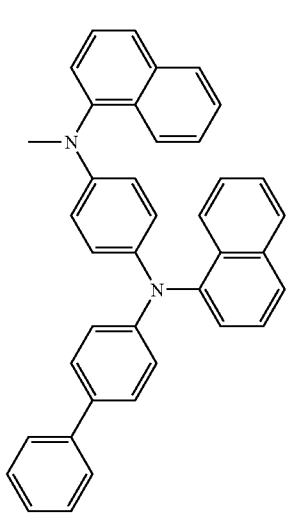

122
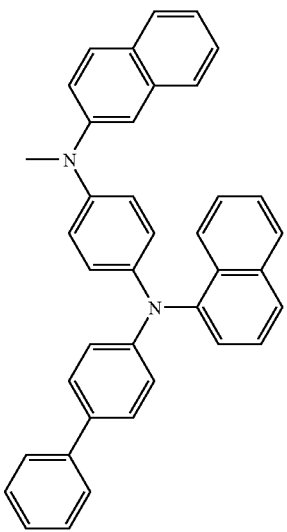
123
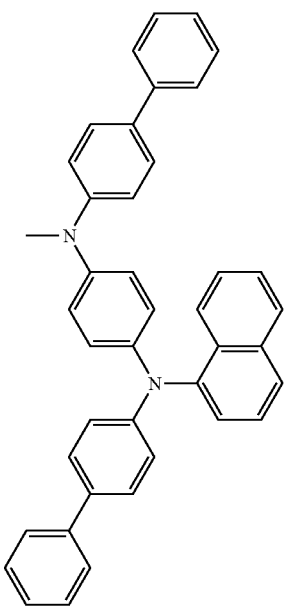
124
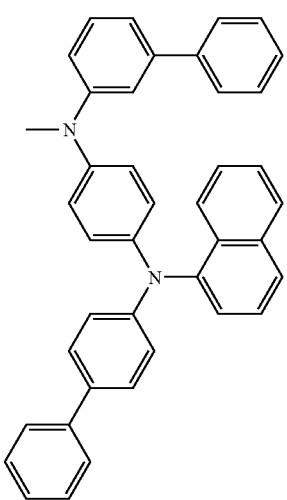
125
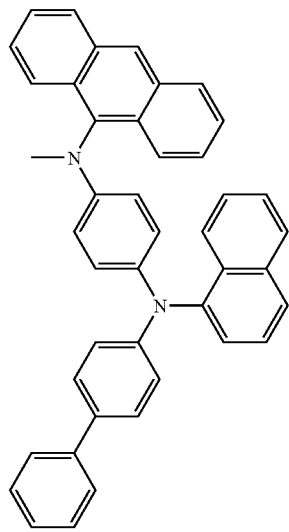
126
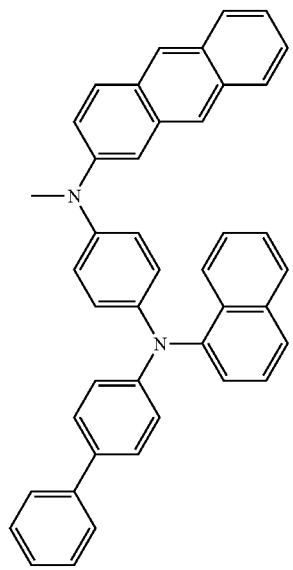
127
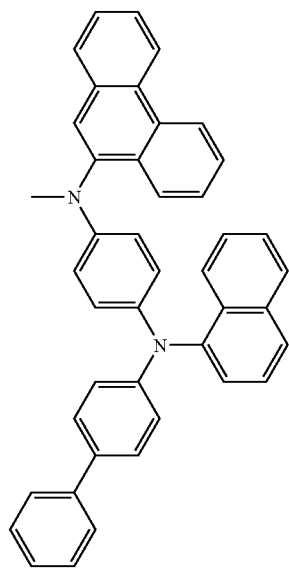

128
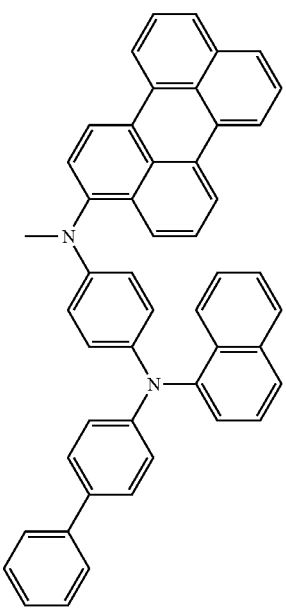
129
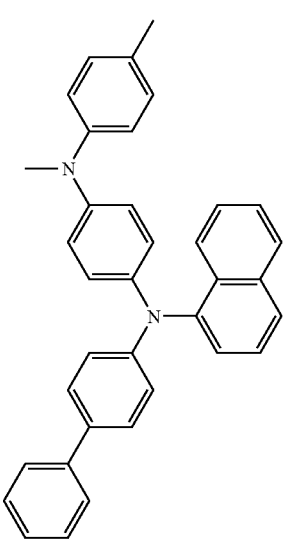
130
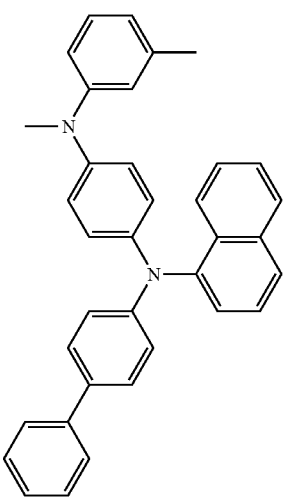
131
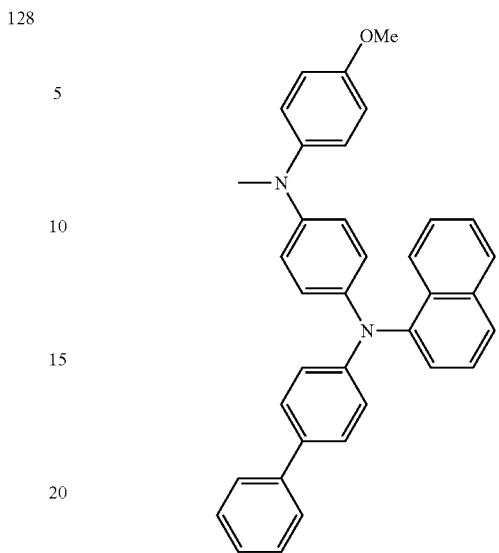
132
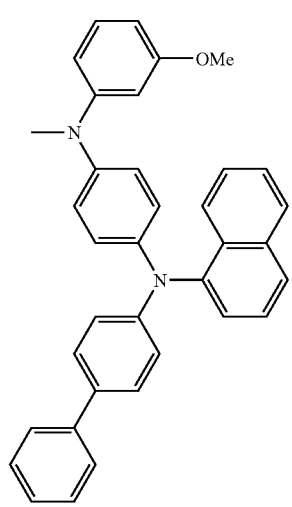
133
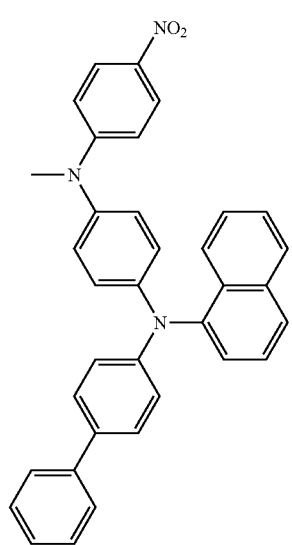

269
-continued
134
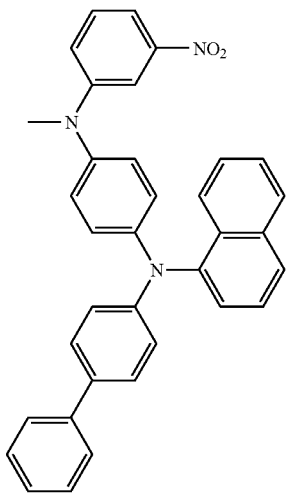
135
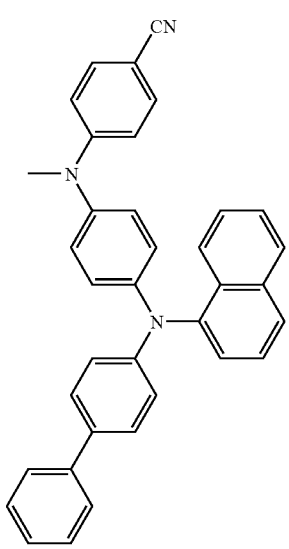
136
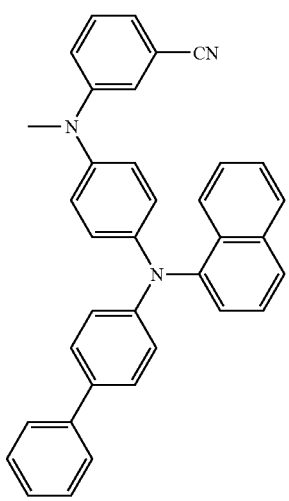
270
-continued
137
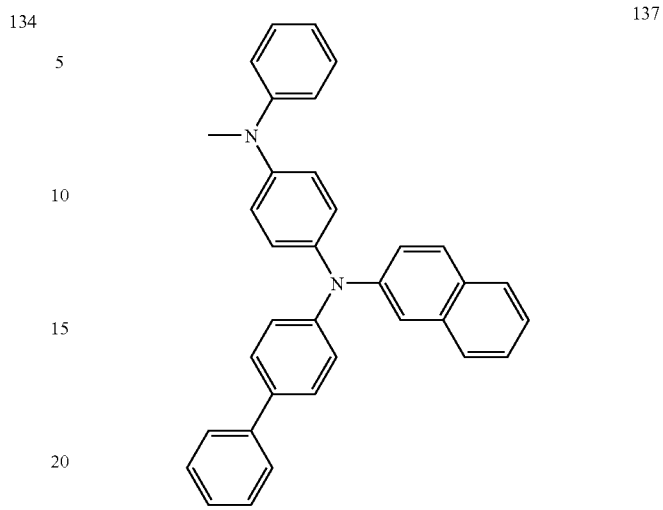
138
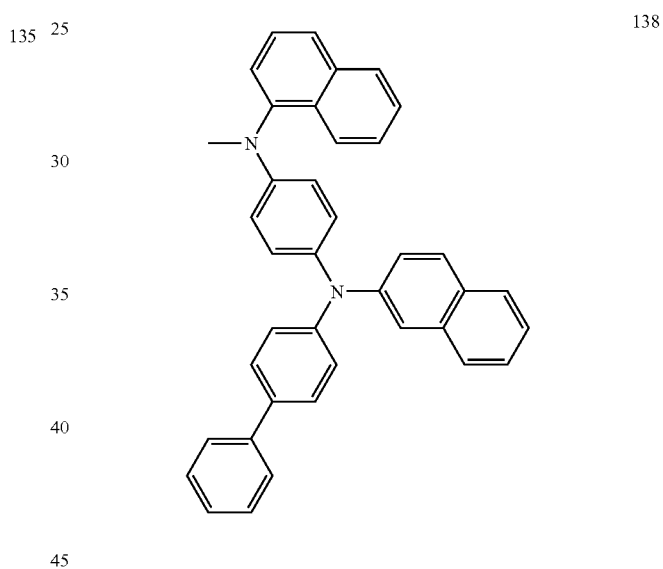
139
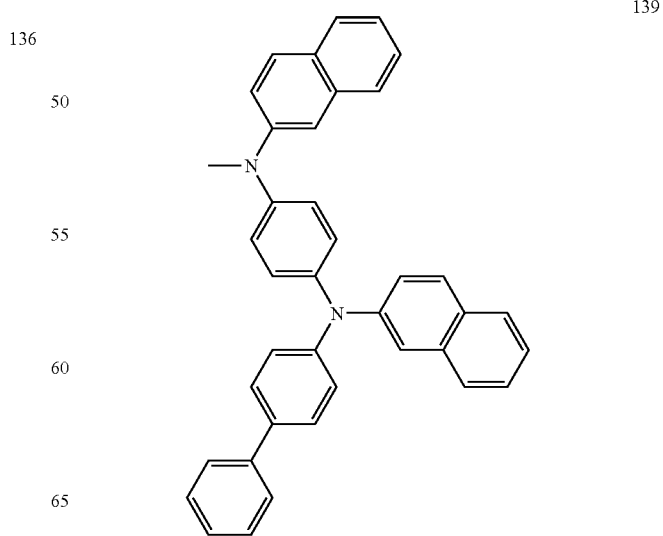

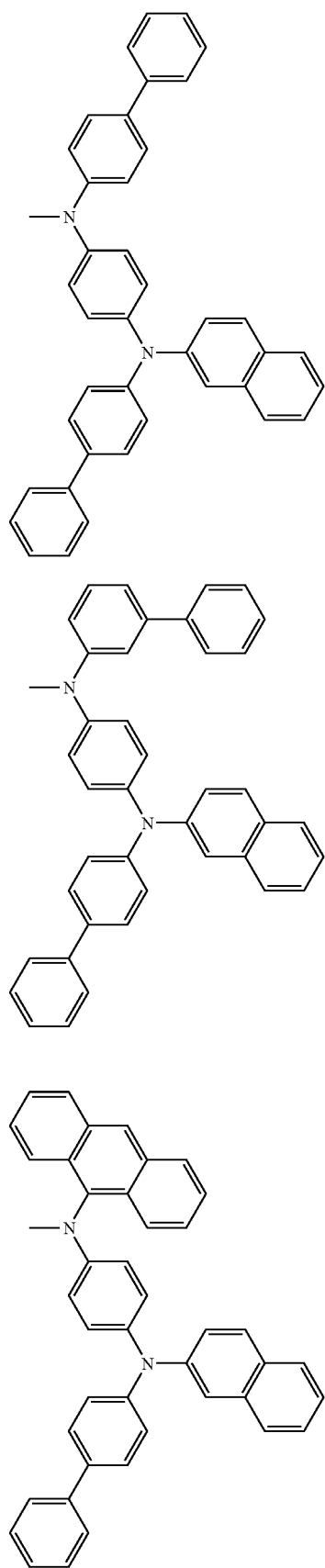
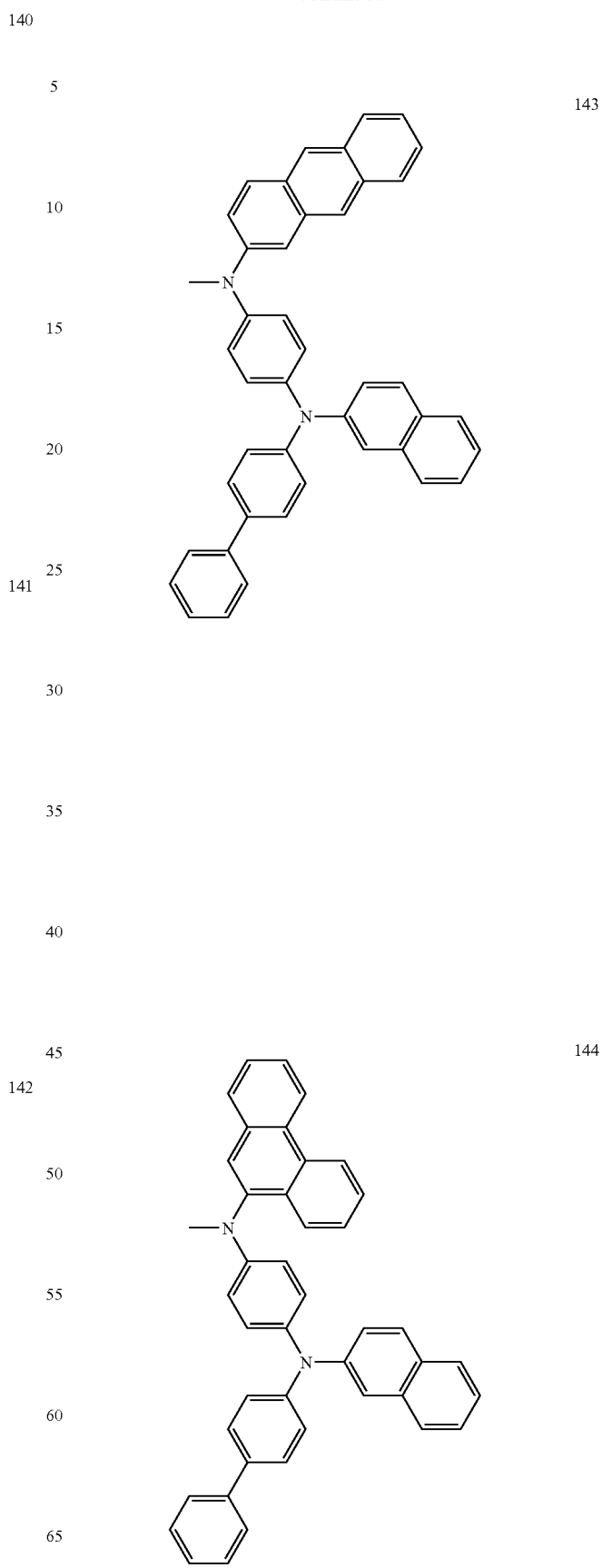

145 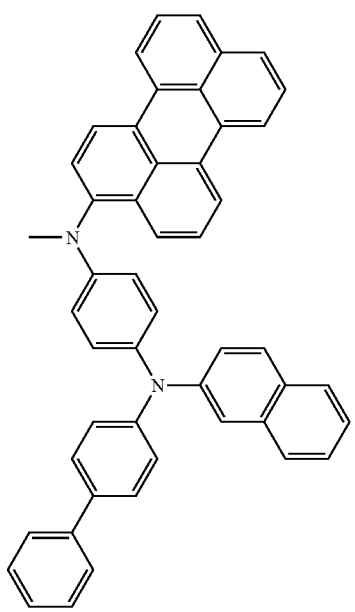
146 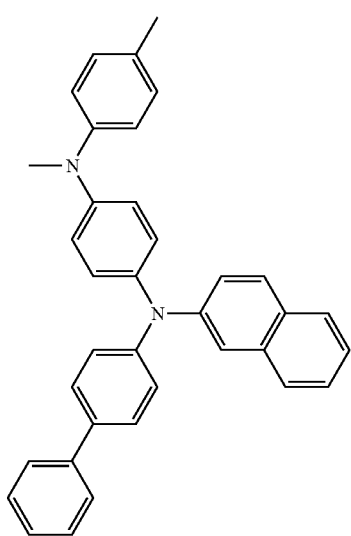
147 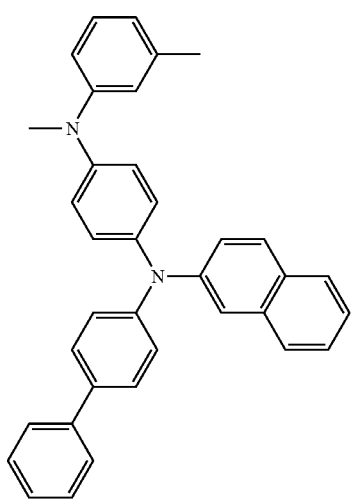
148 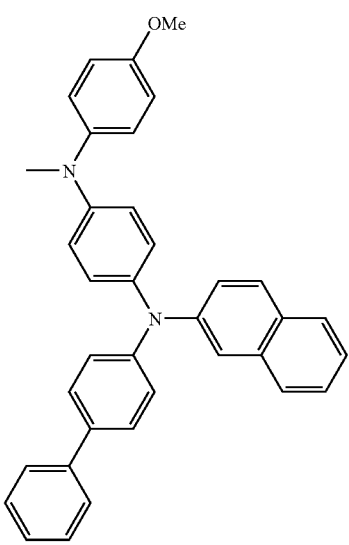
149 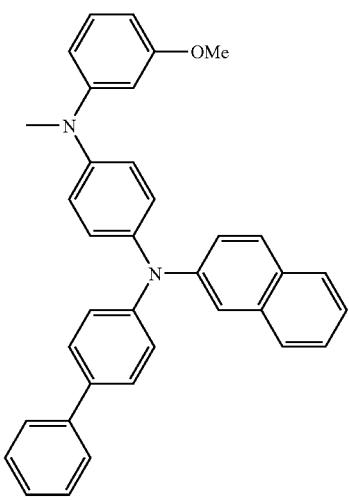
150 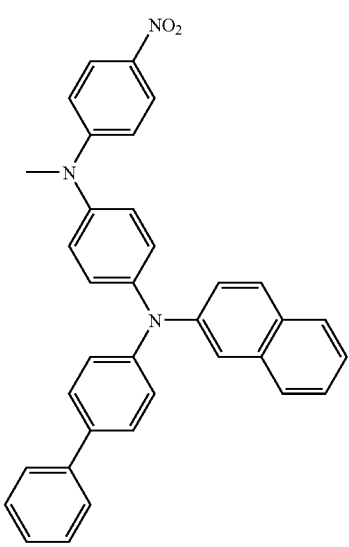

151
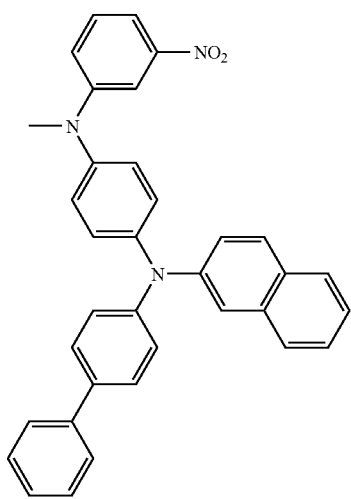
152
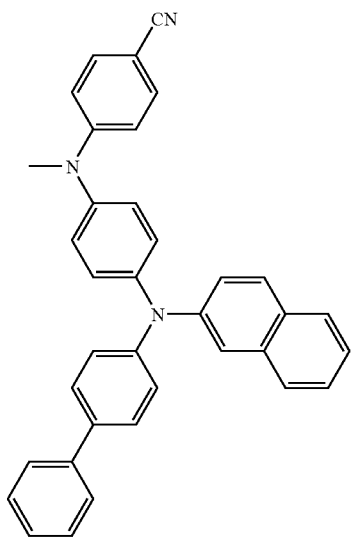
153
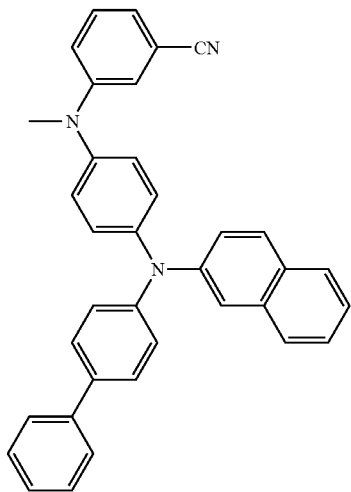
154
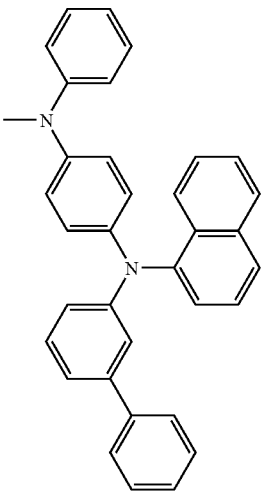
155
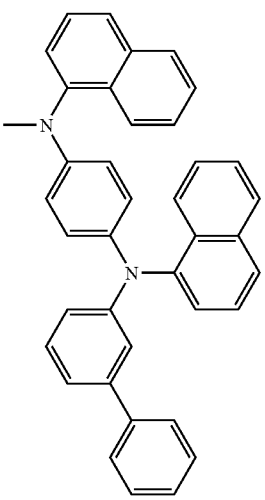
156
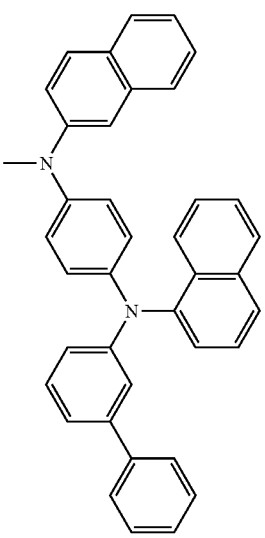

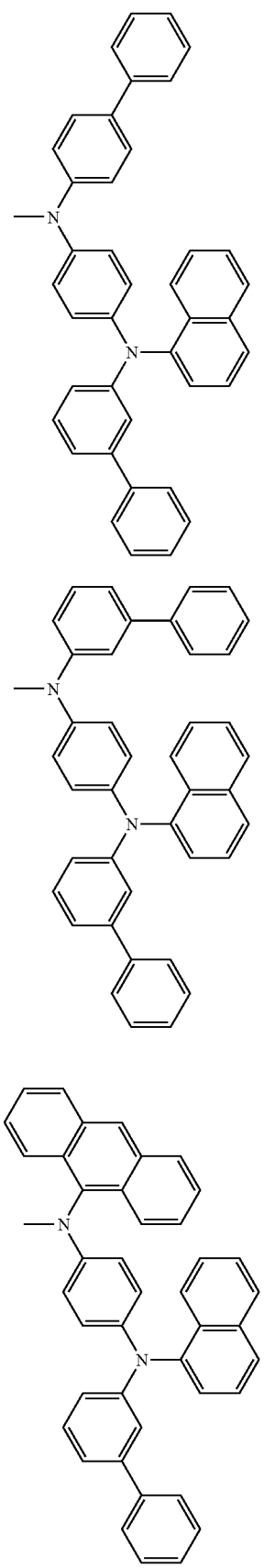
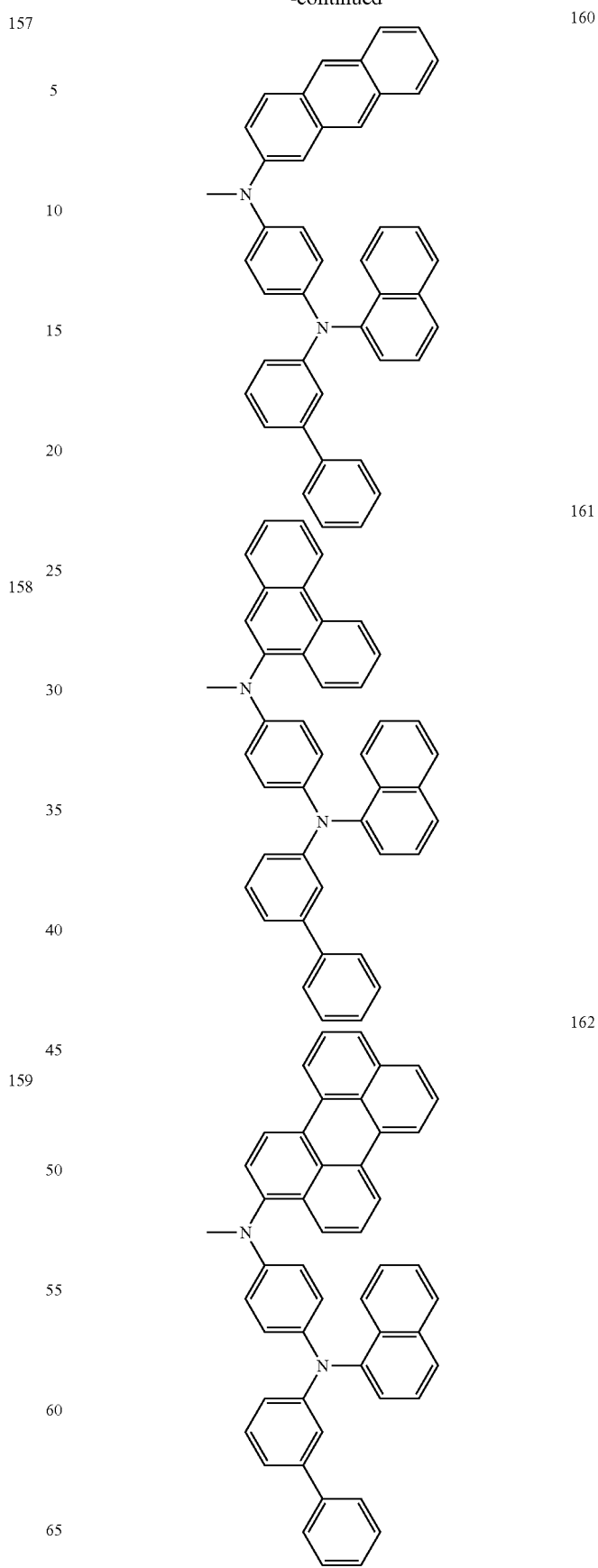

163 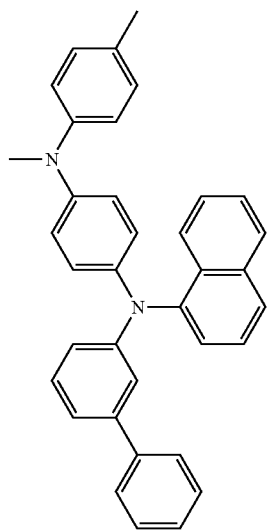
164 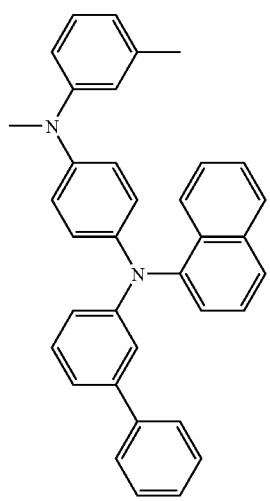
165 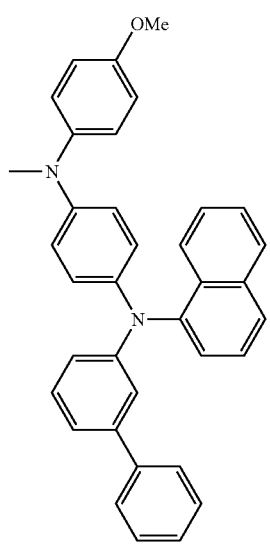
166 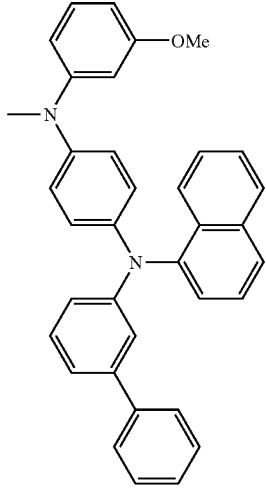
167 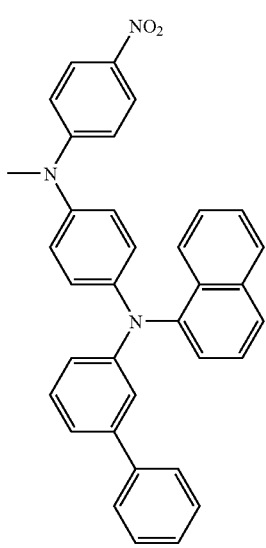
168 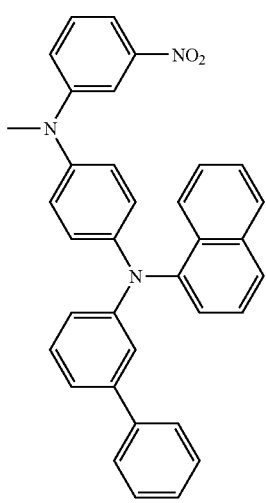

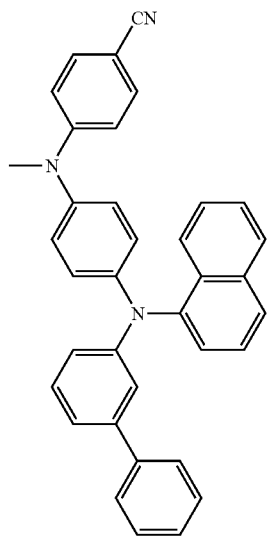
169
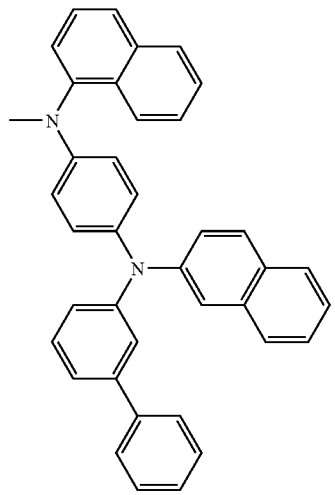
172
170
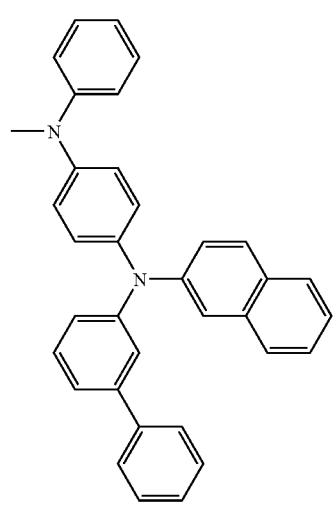
173
171
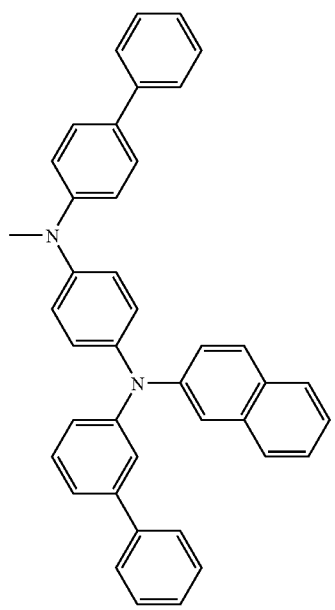
174

175
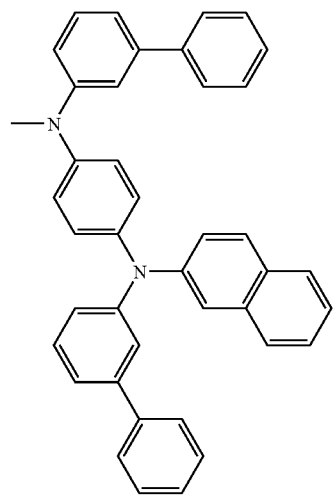
176
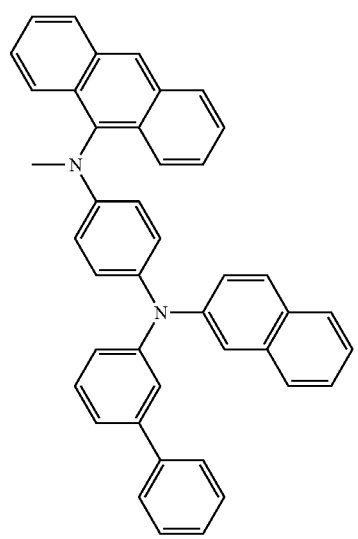
177
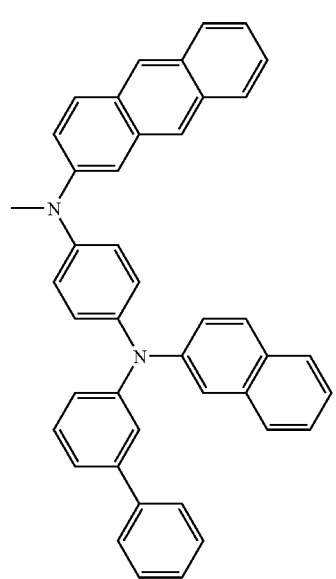
178
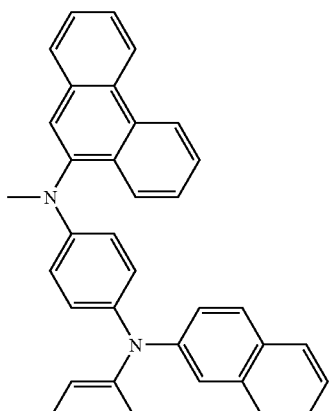
179
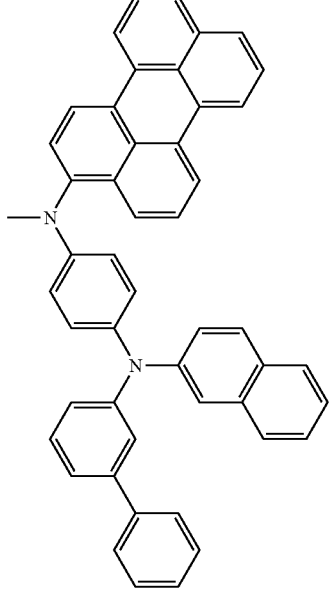
180
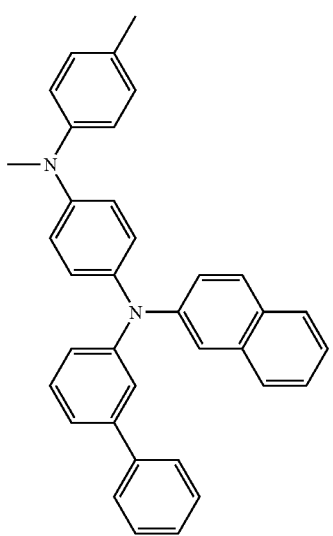

181
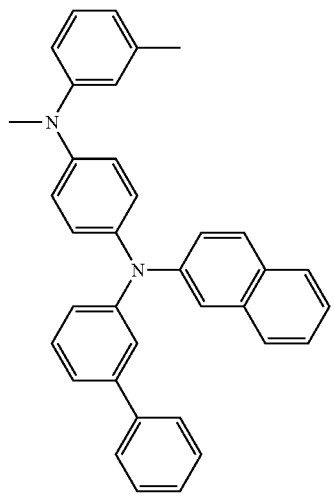
182
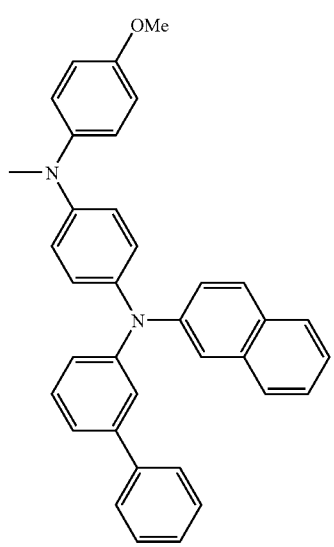
183
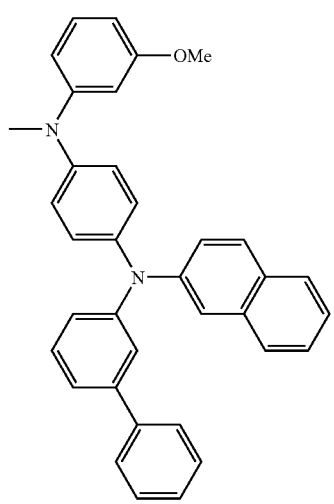
184
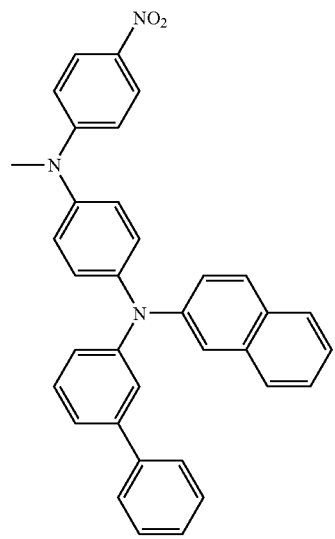
185
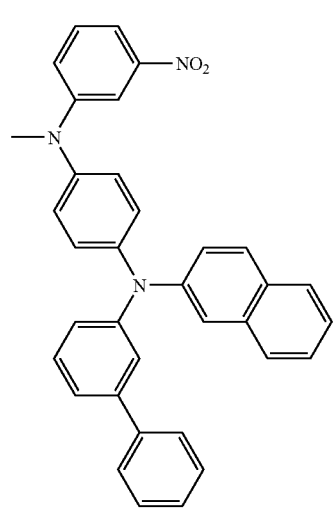
186
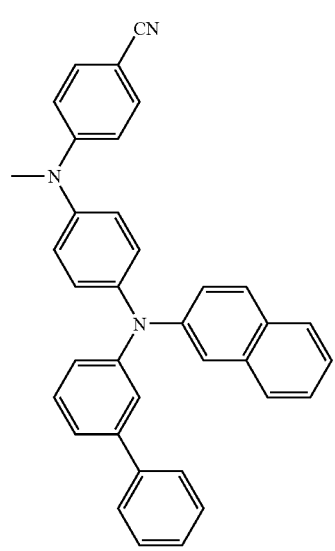

287
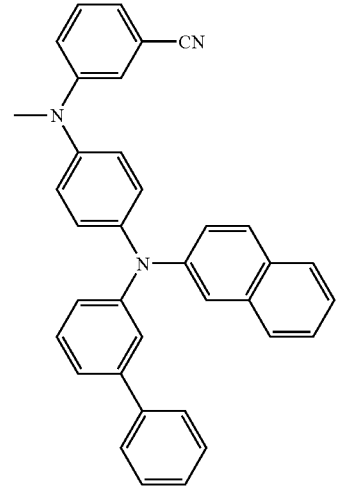
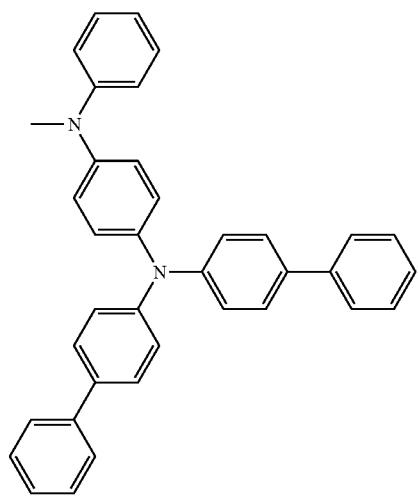
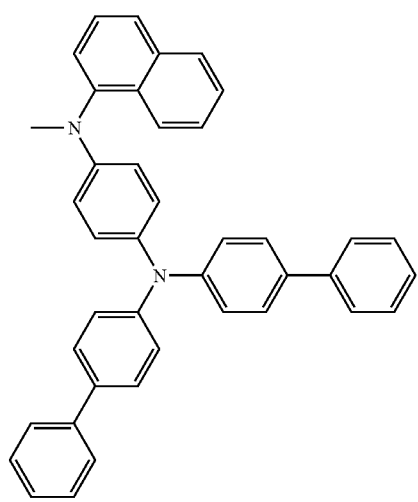
288
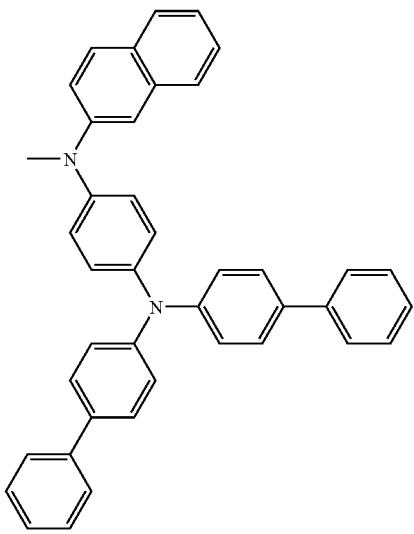
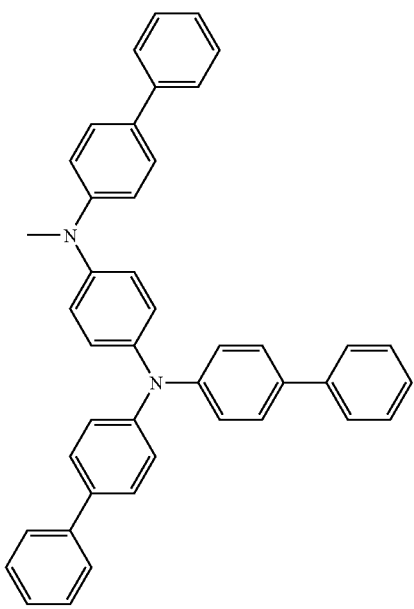
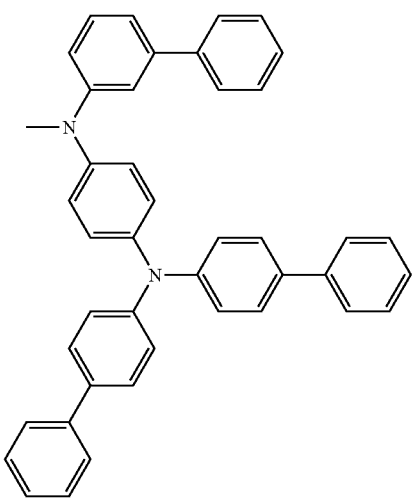

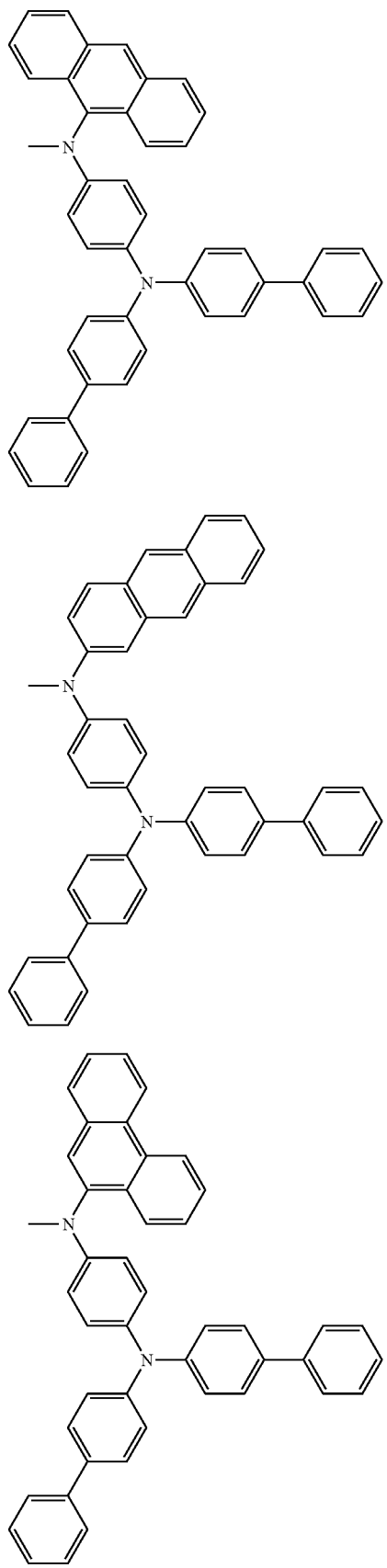
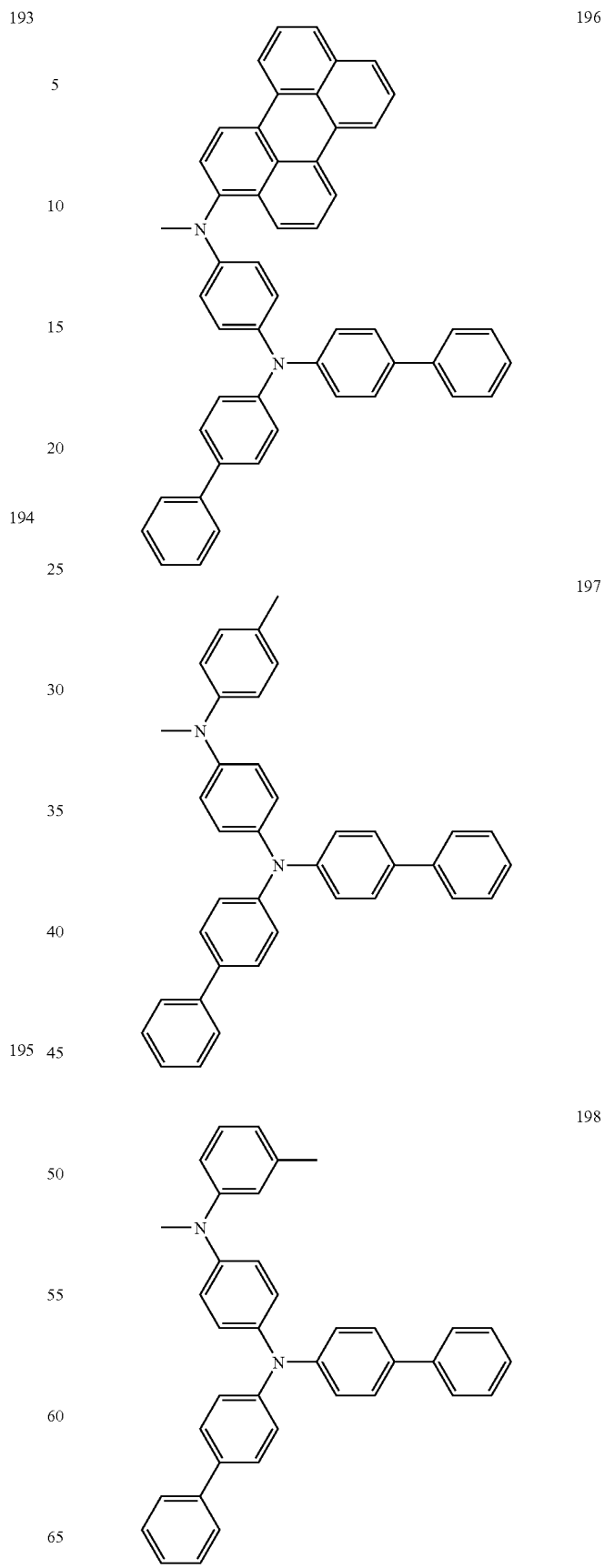

199
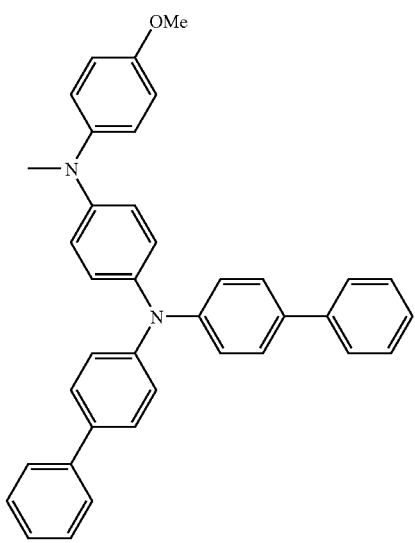
200
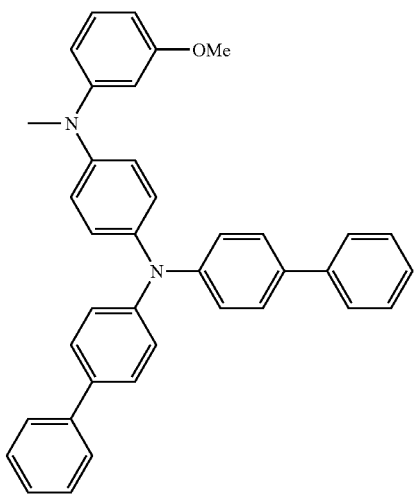
201
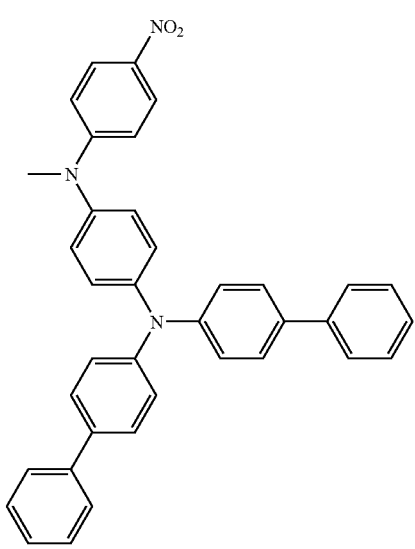
202
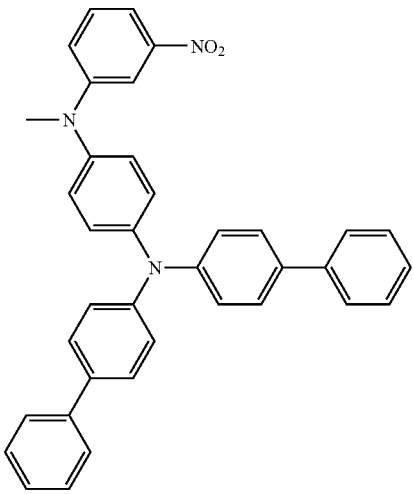
203
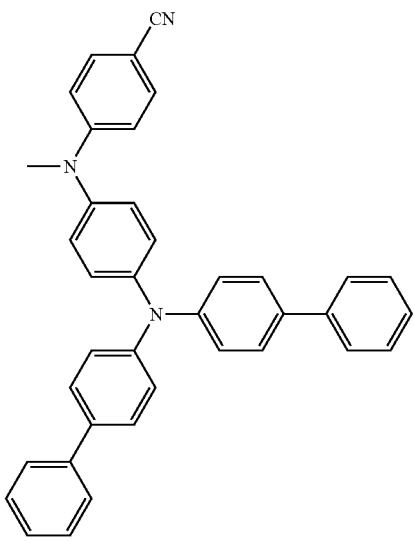
204
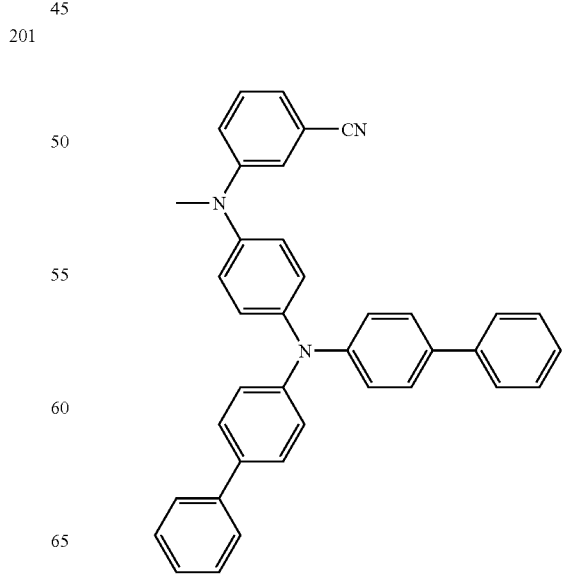

205
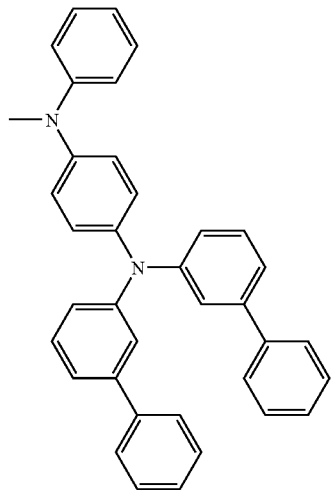
206
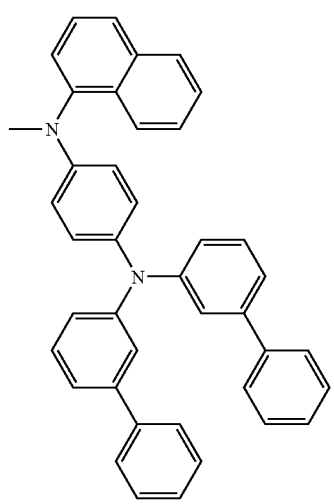
207
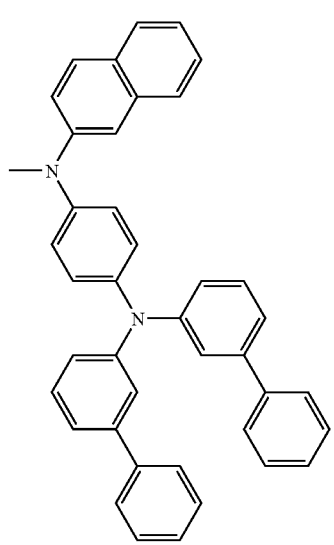
208
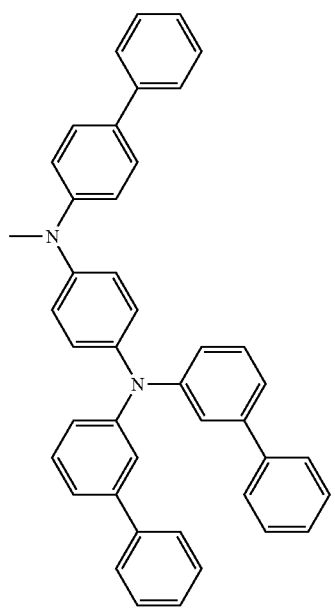
209
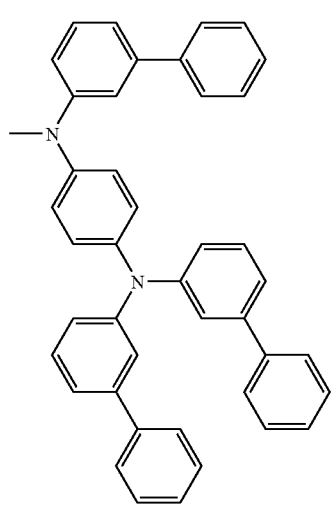
210
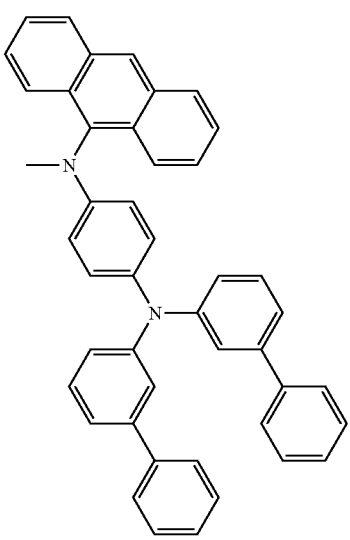

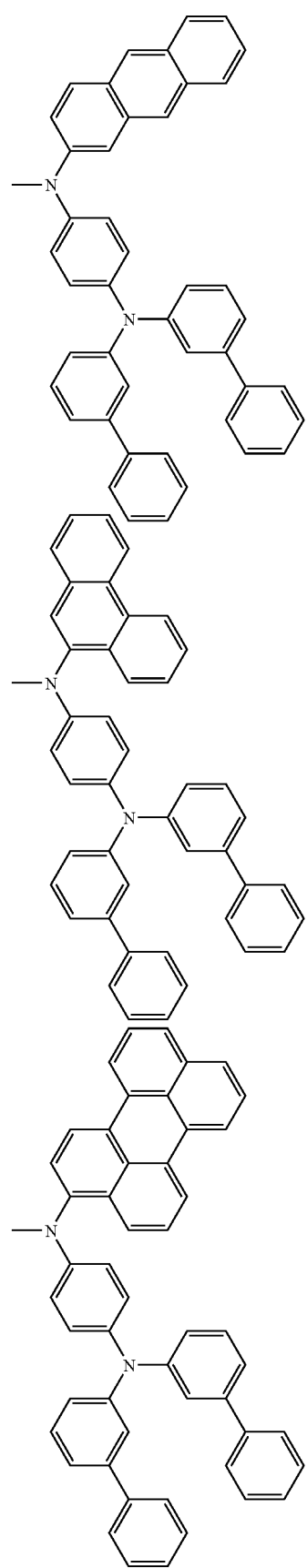
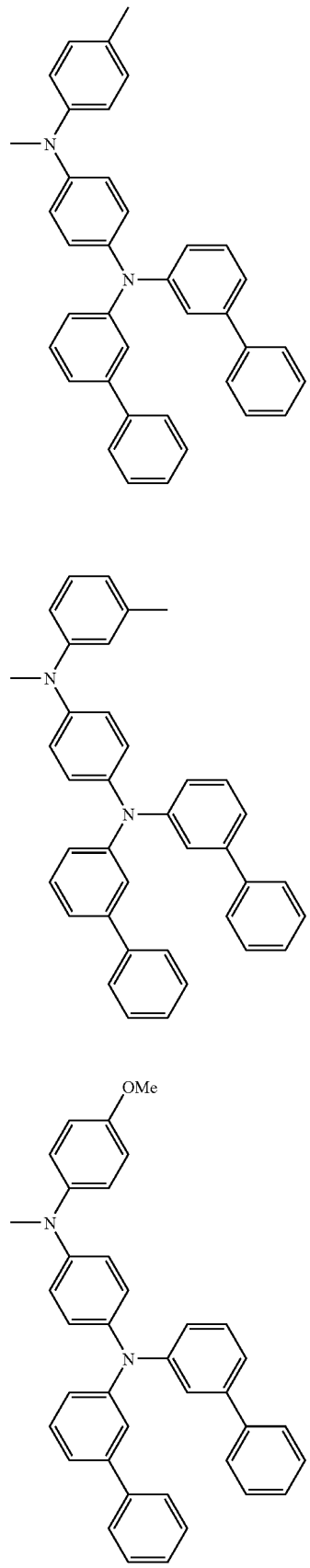

217
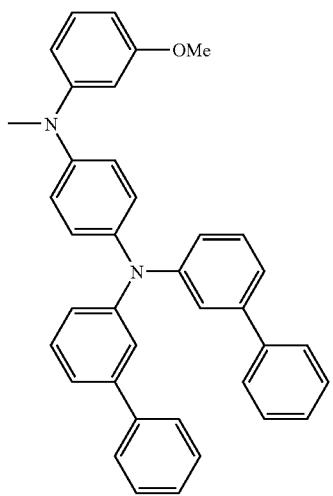
218
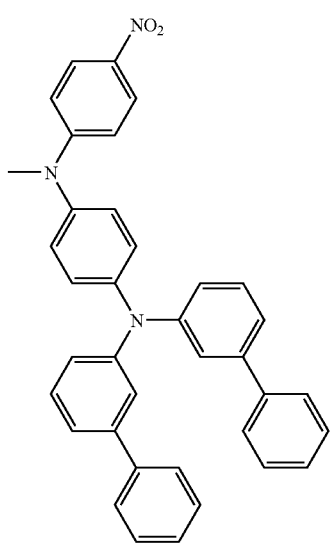
219
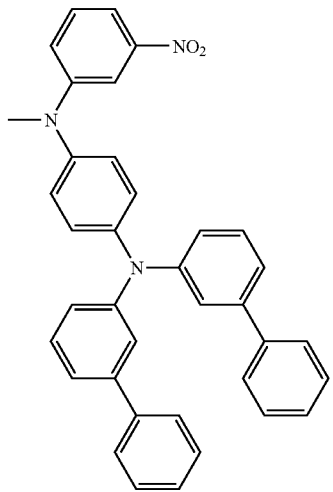
220
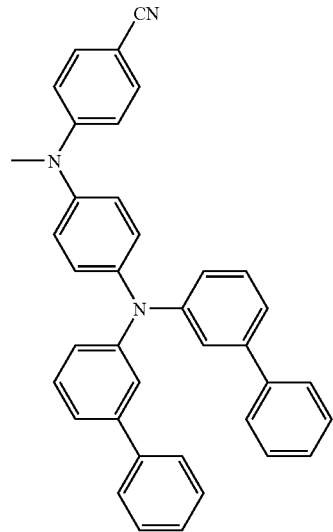
221
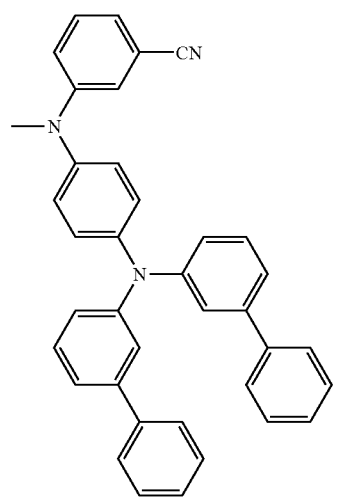
222
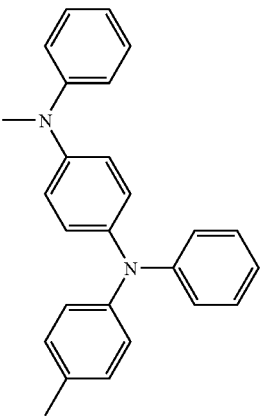

299
-continued
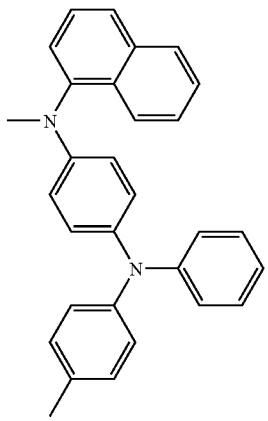
223
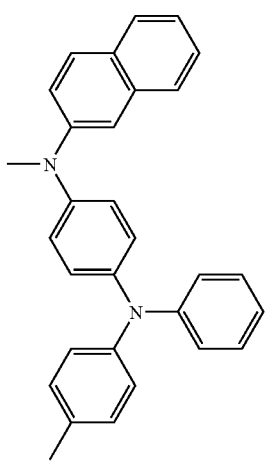
224
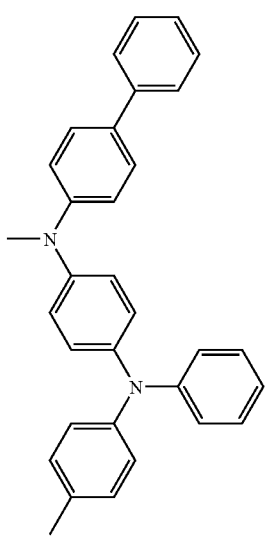
225
300
-continued
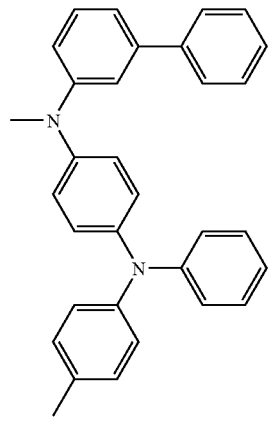
226
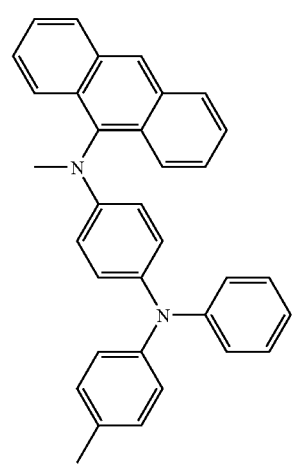
227
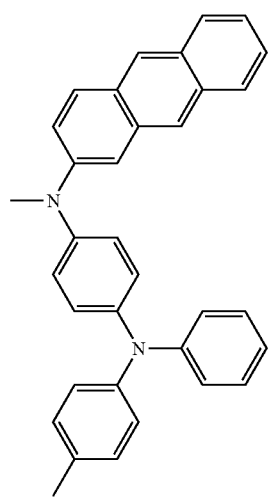
228

301
-continued
229
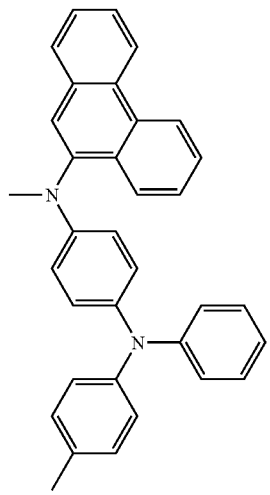
230
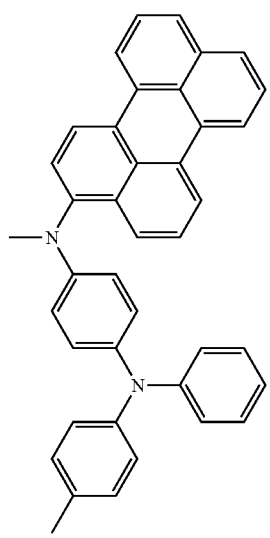
231
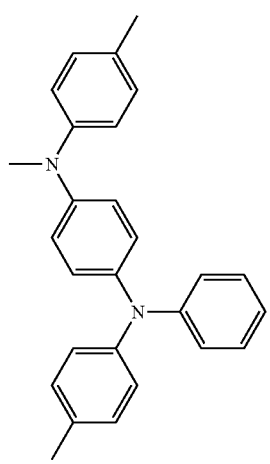
302
-continued
232
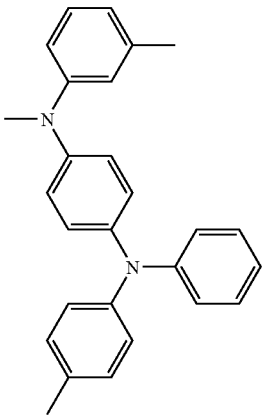
233
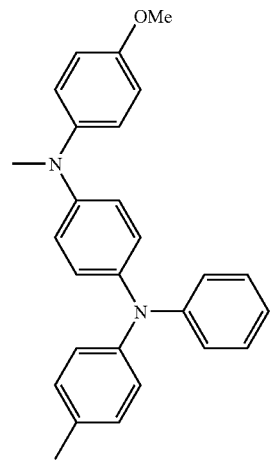
234
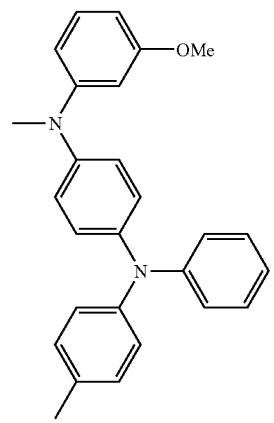

303
-continued
235
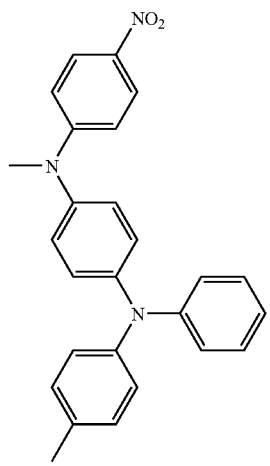
236
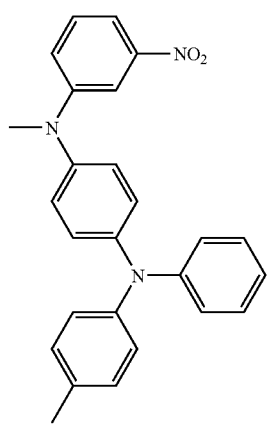
237
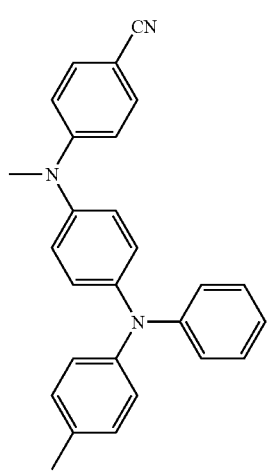
304
-continued
238
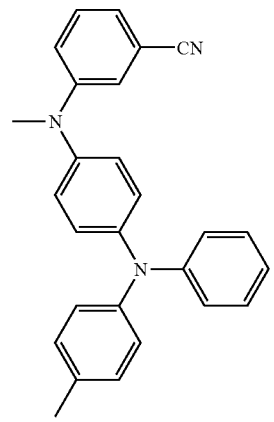
239
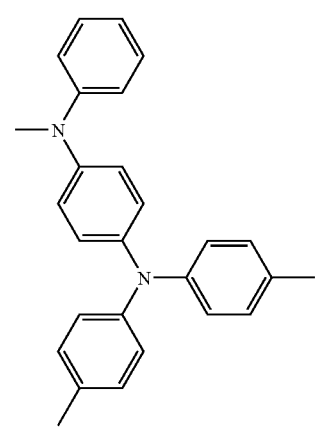
240
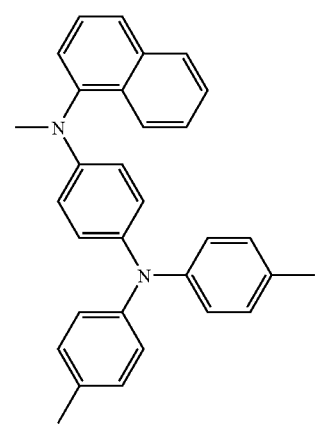

305
-continued
306
-continued
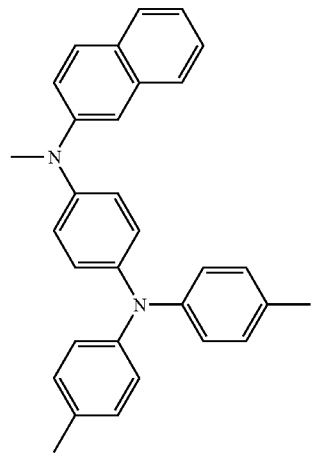
241
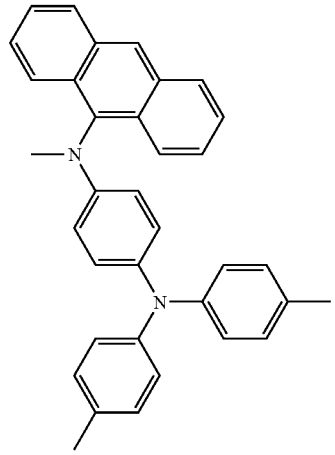
244
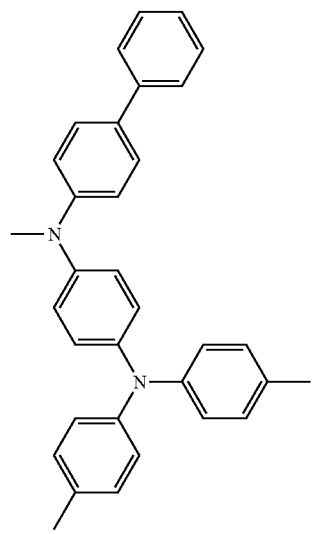
242
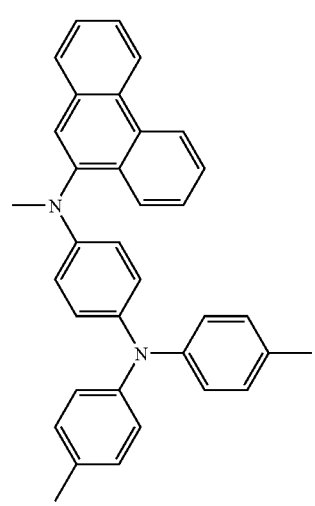
245
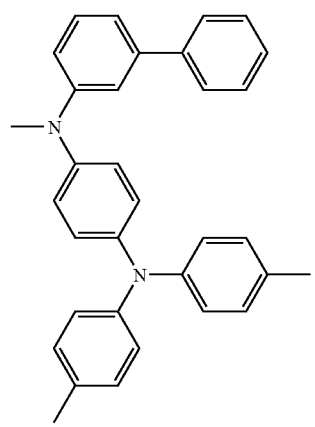
243
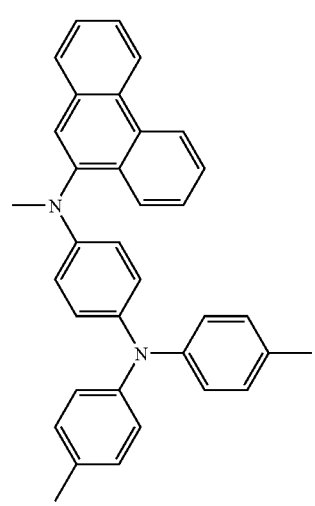
246

307
-continued
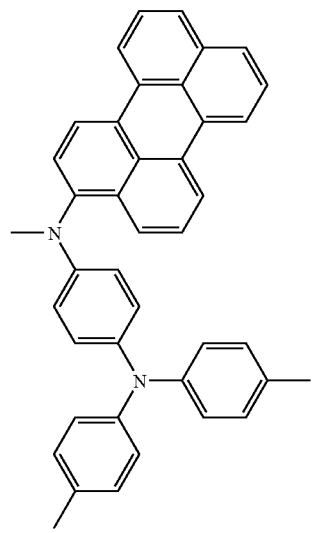
247
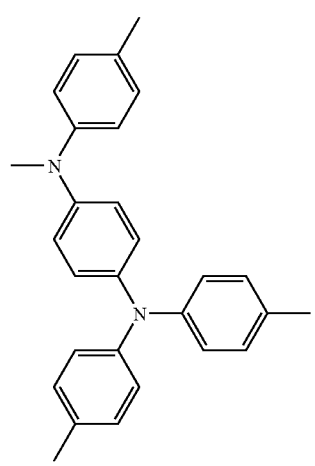
248
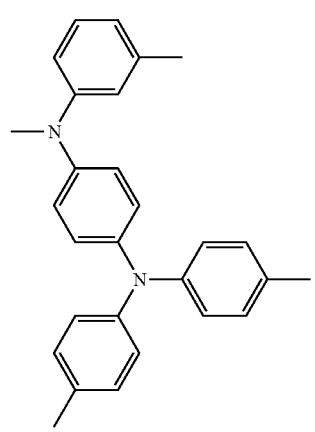
249
308
-continued
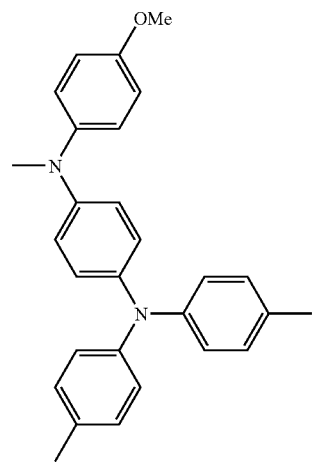
250
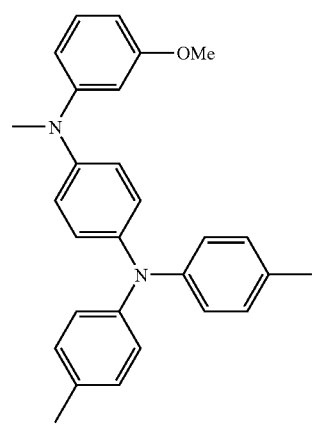
251
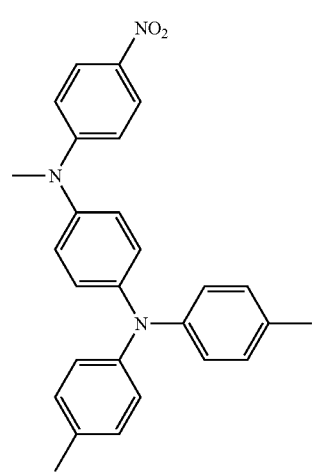
252

309
-continued
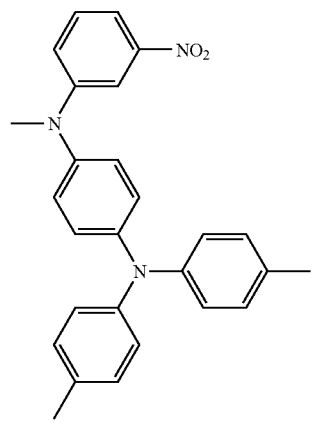
253
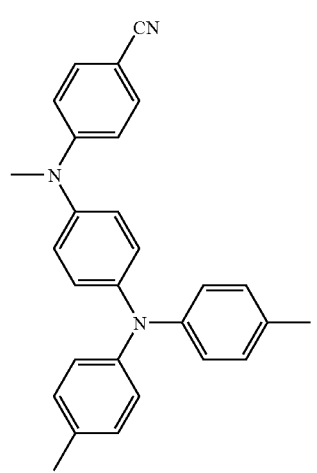
254
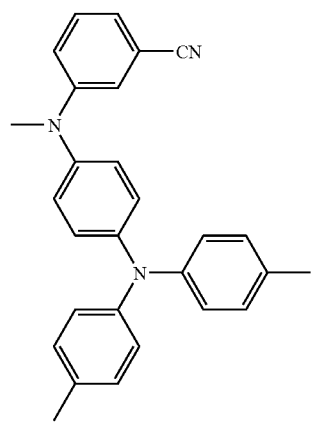
255
310
-continued
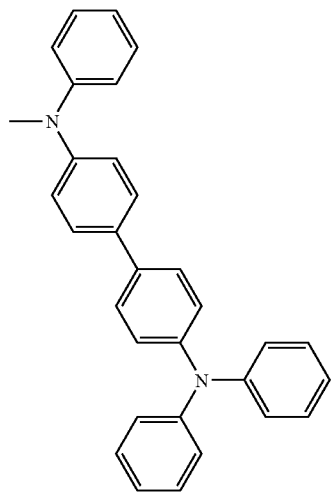
256
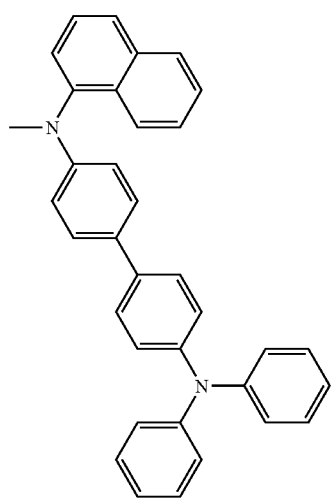
257
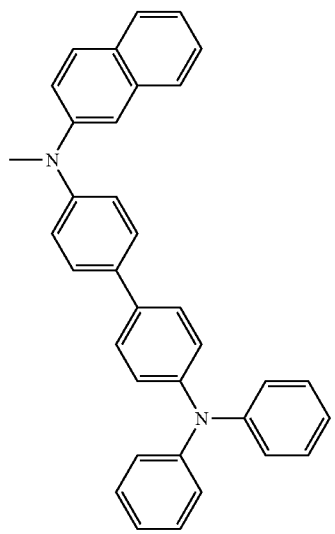
258

311
-continued
312
-continued
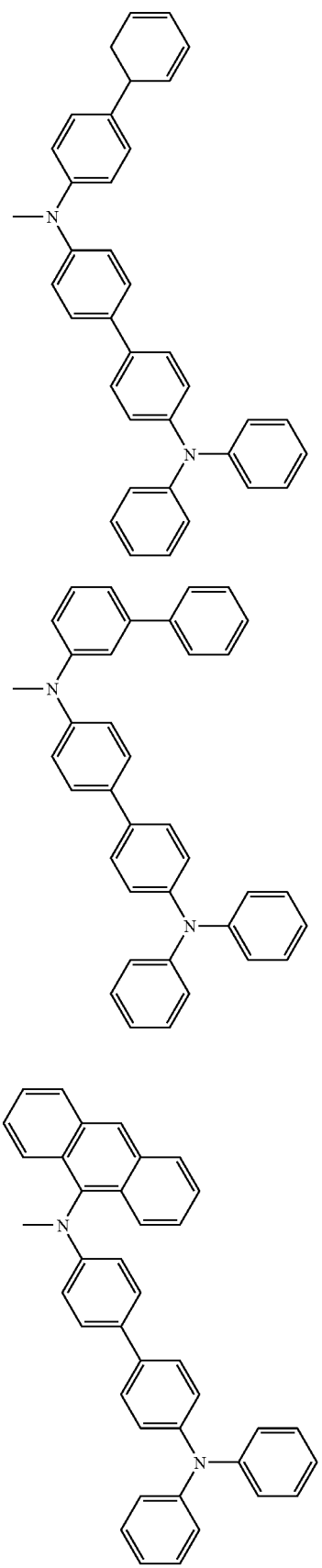
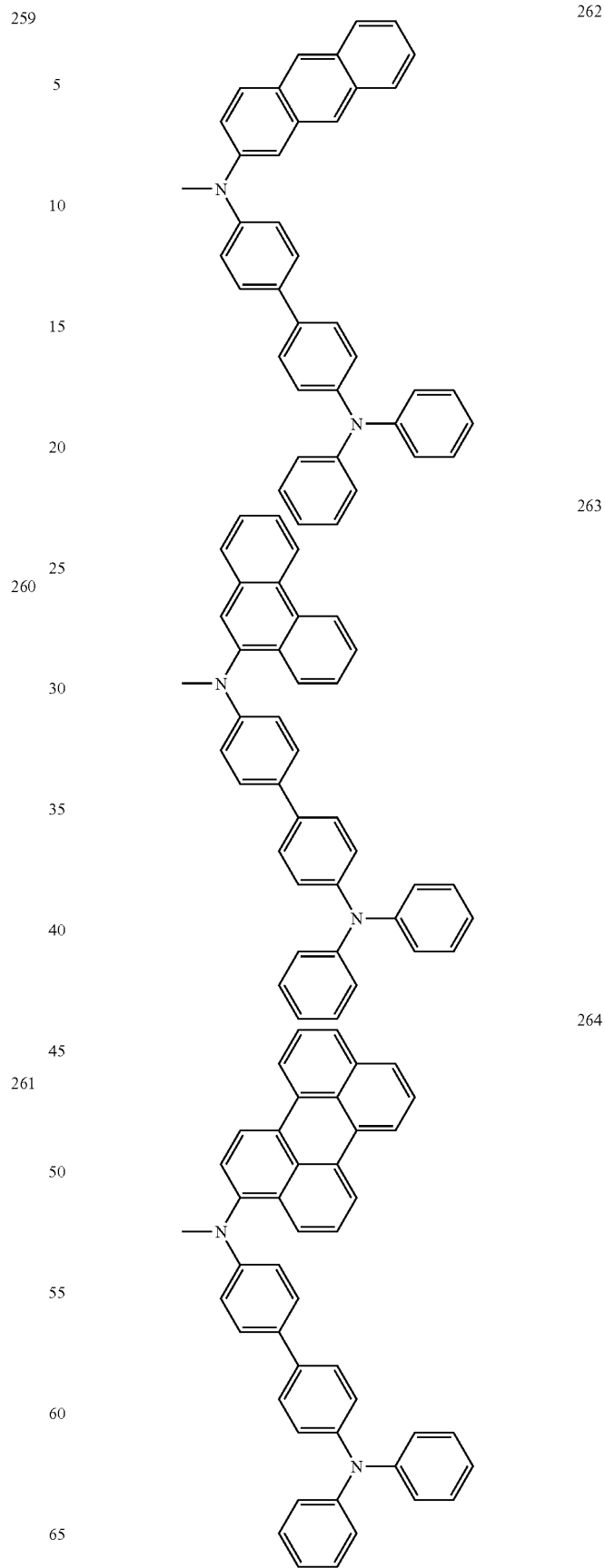

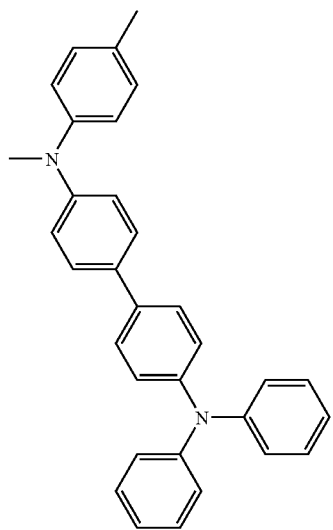
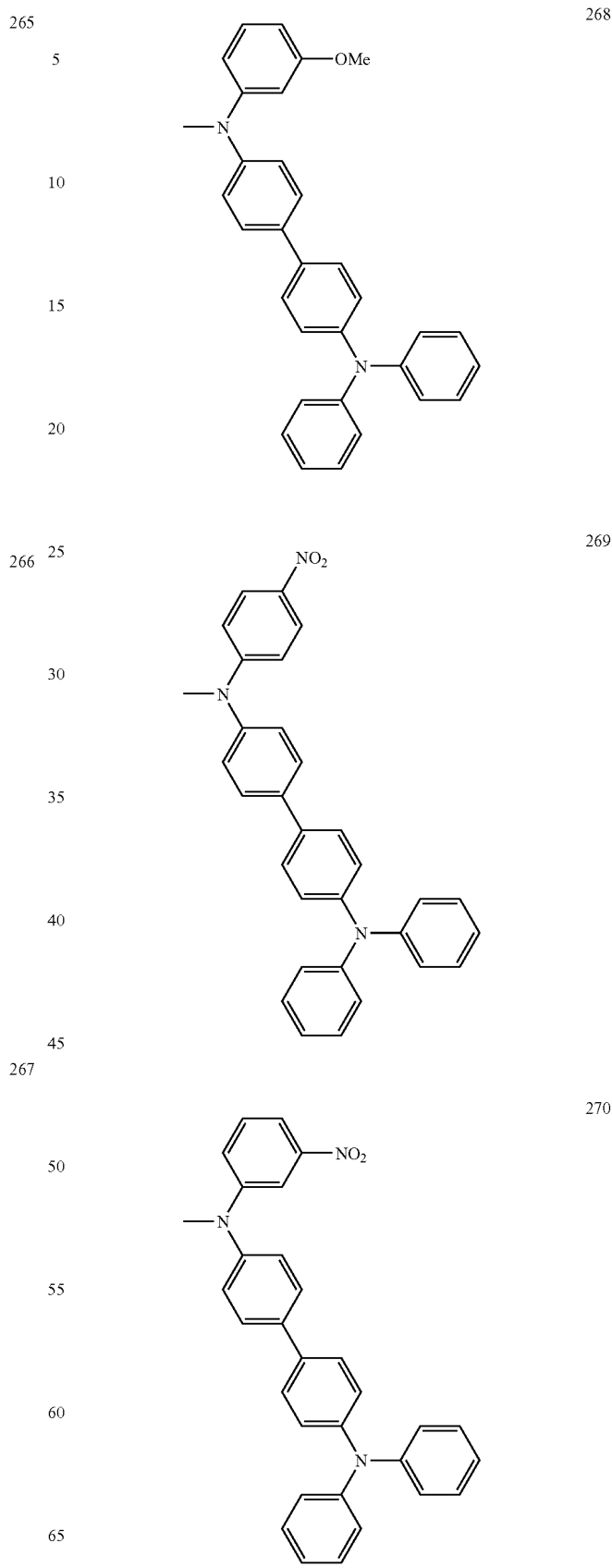

315
-continued
271
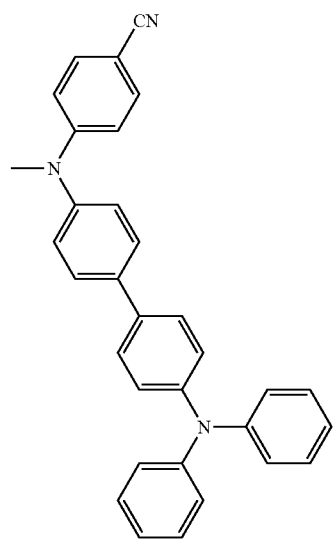
272
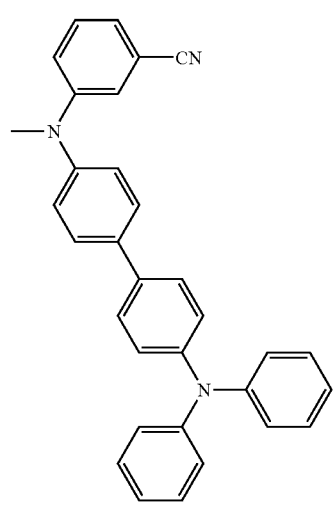
273
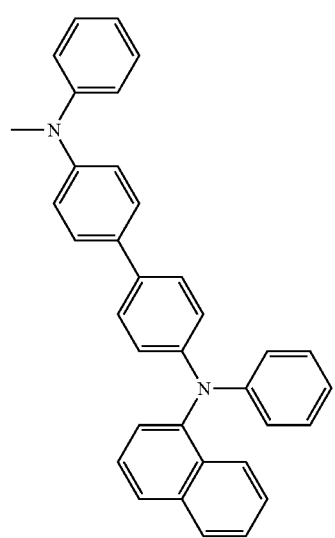
316
-continued
274
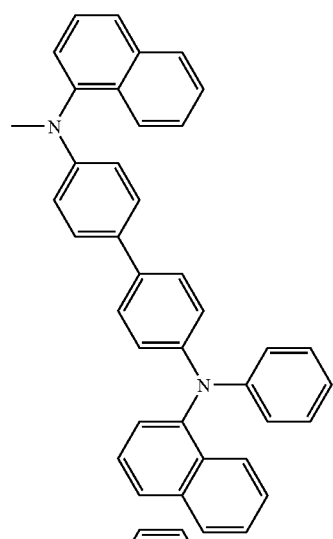
275
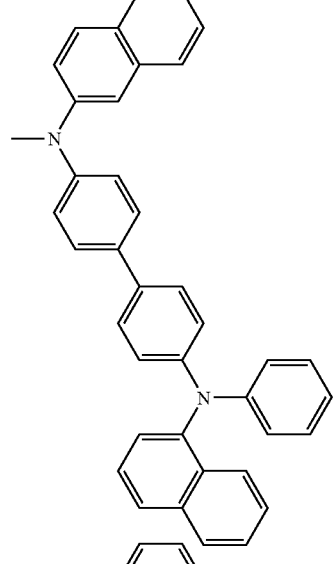
276
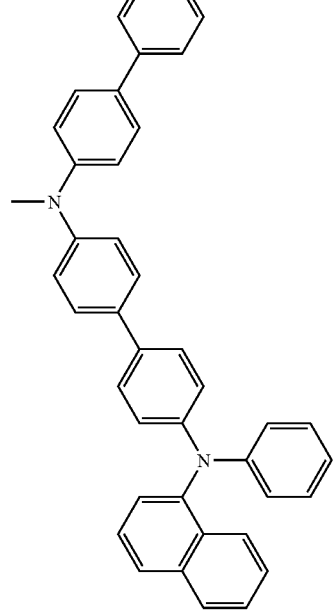

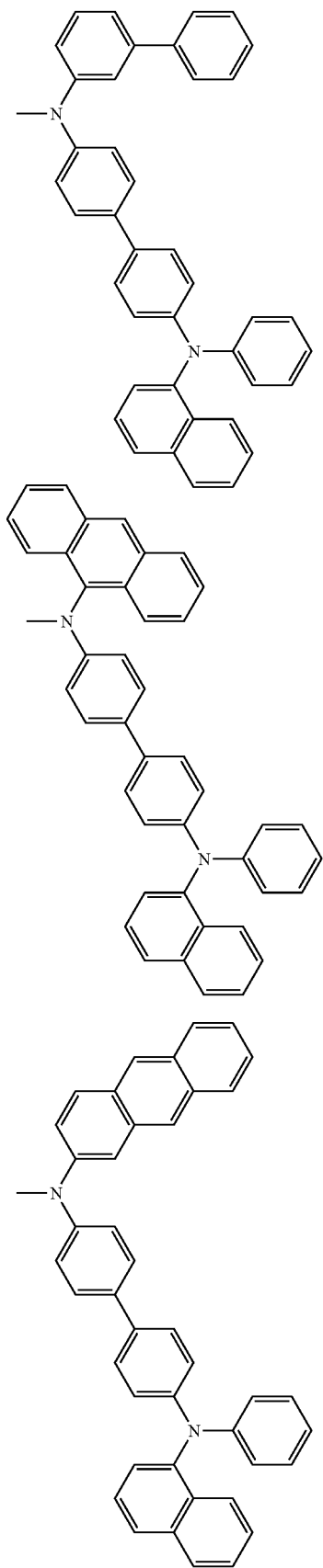

-continued
282
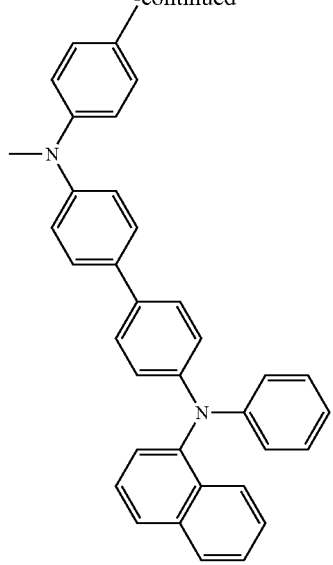
283
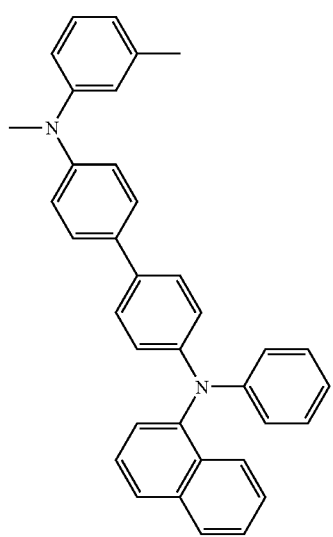
284
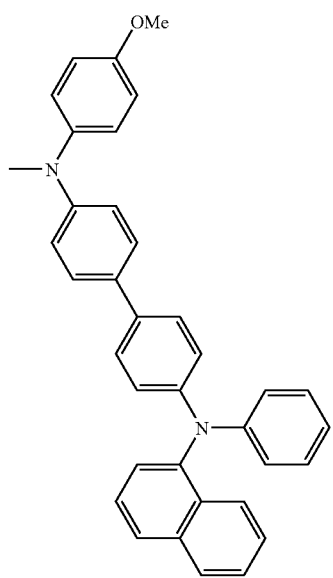
-continued
285
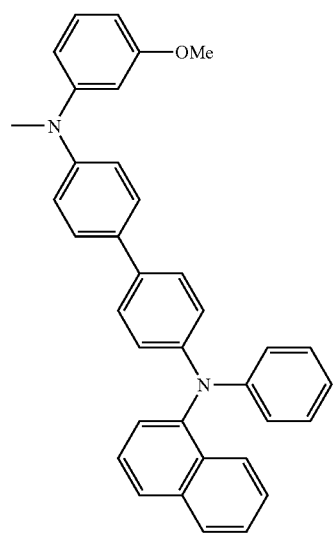
286
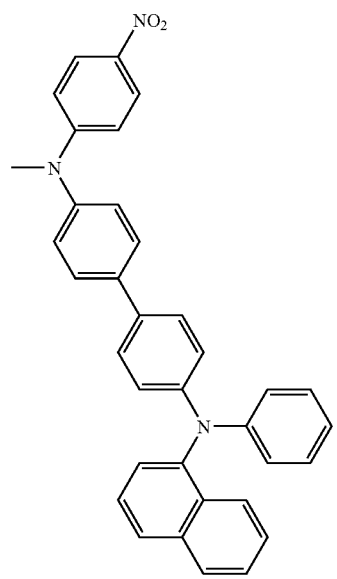
287
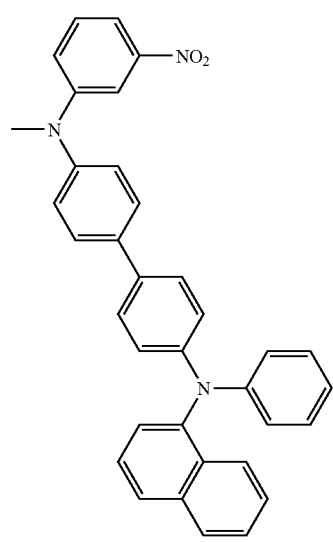

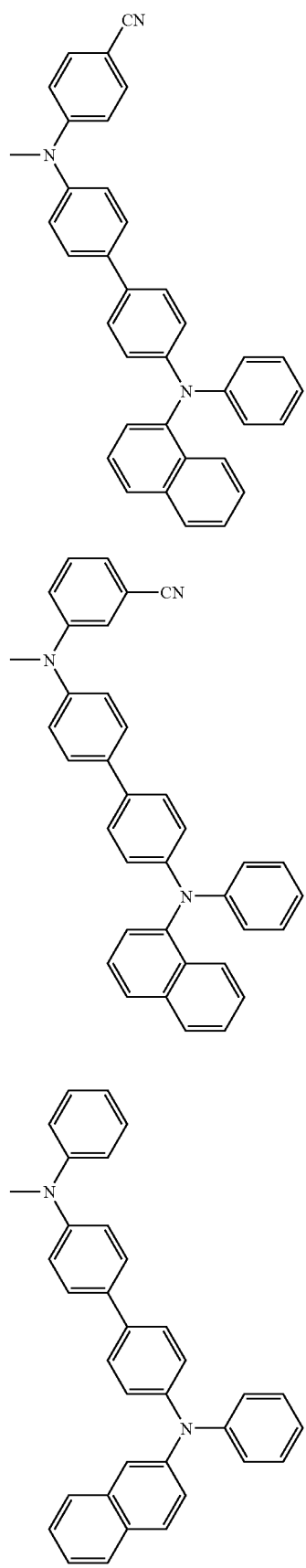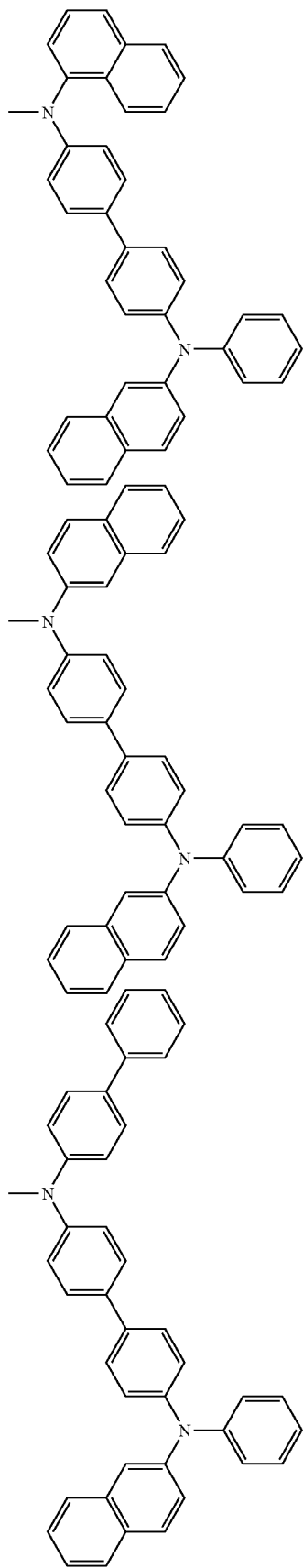

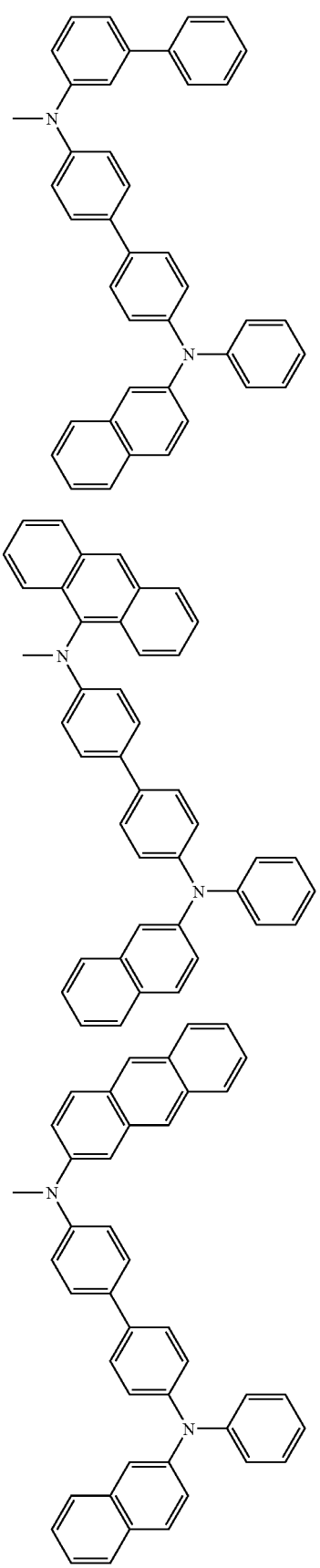

325
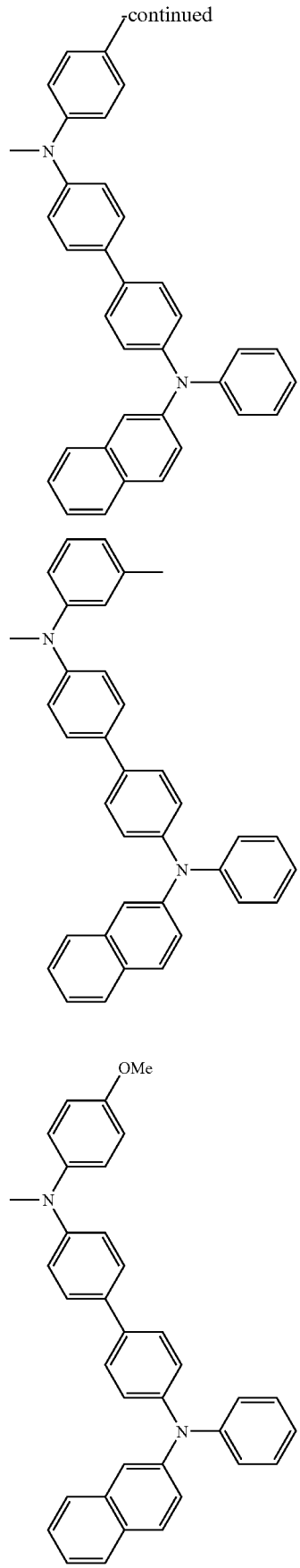
326
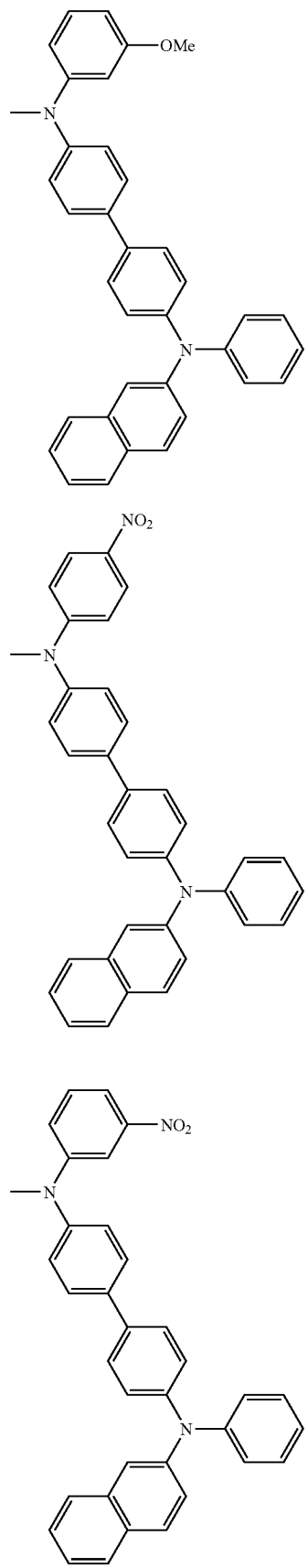

327
-continued
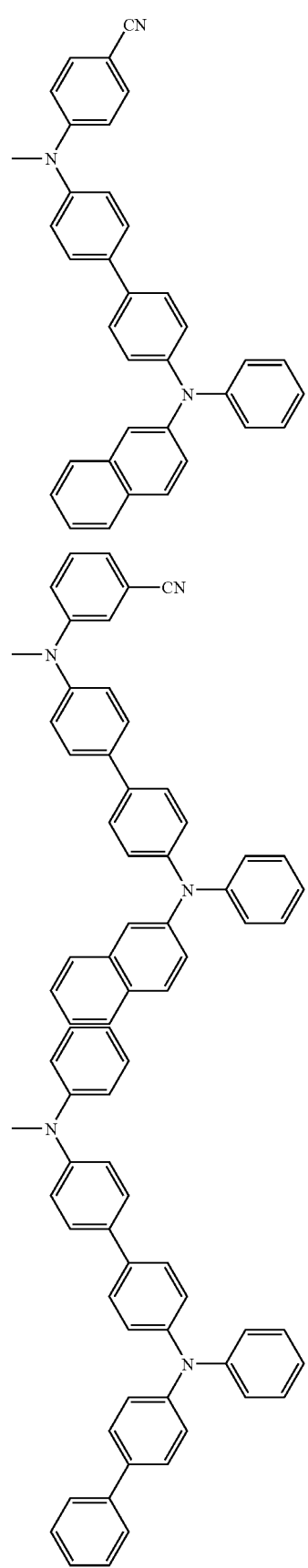
305
306
307
328
-continued
308
309

329
-continued
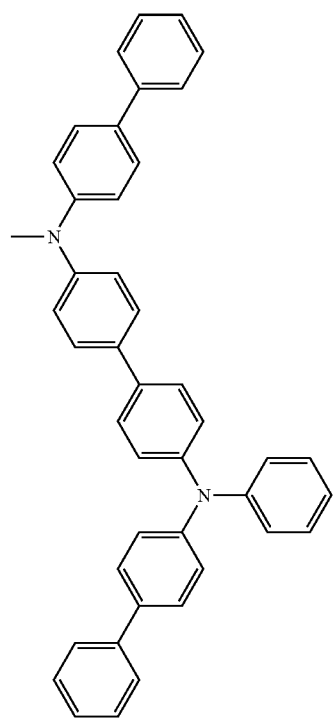
310
330
-continued
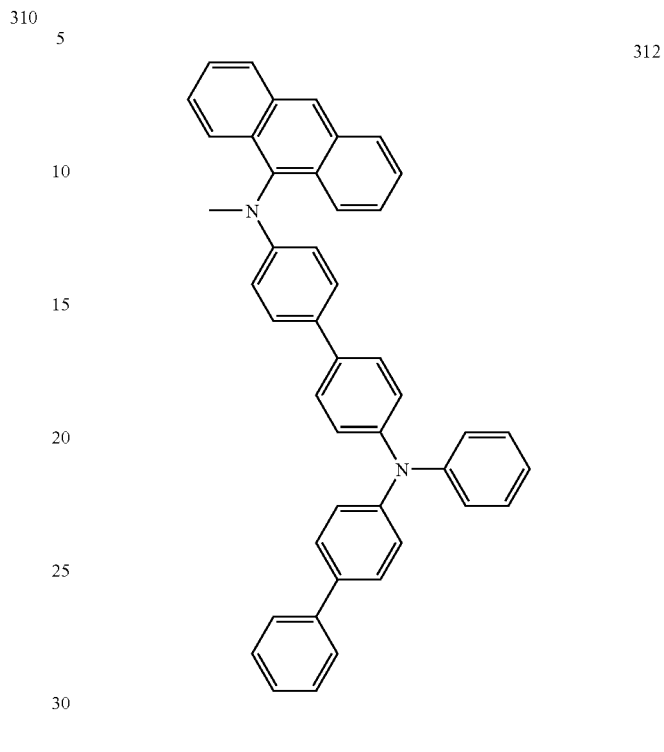
312
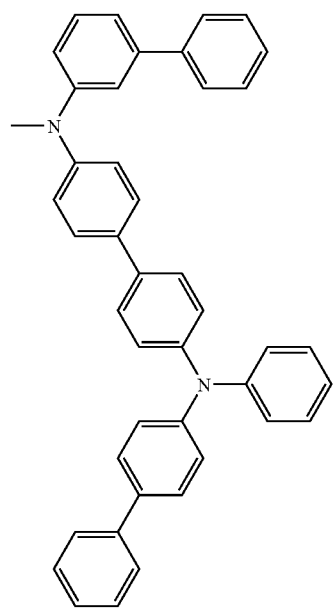
311
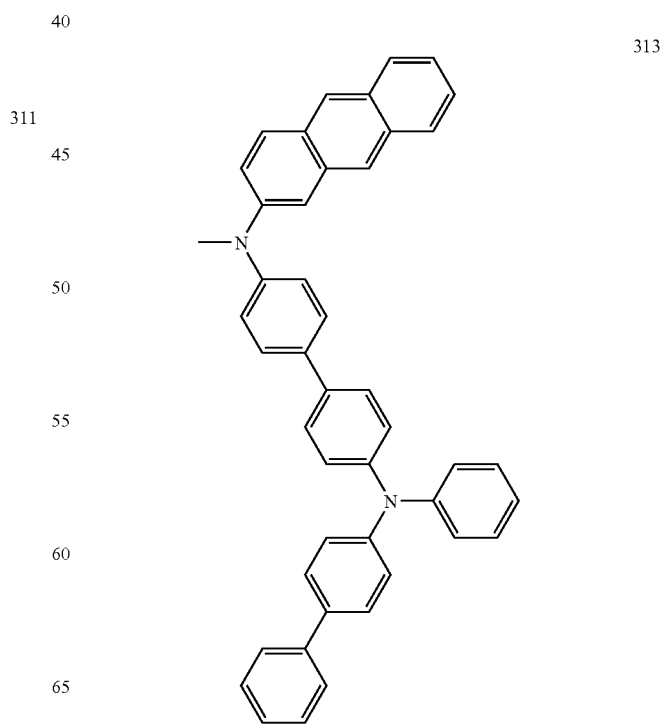
313

331
-continued
332
-continued
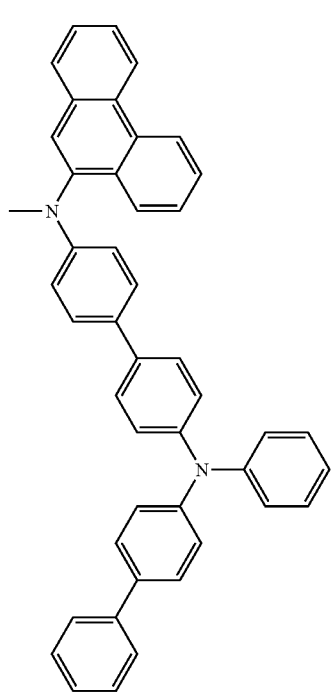
314
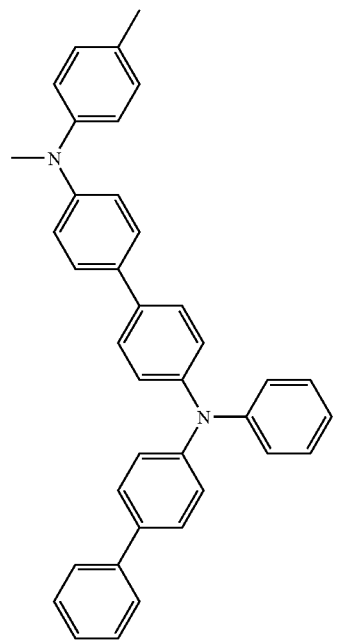
316
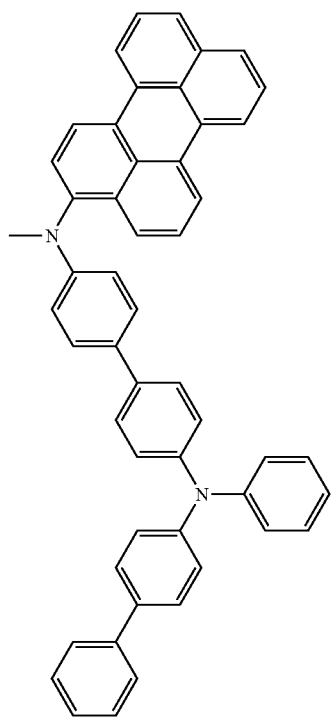
315
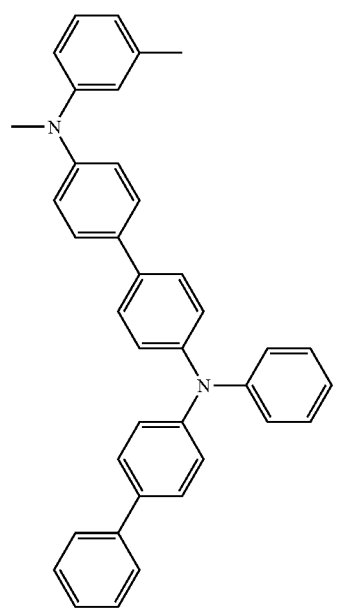
317

333
-continued
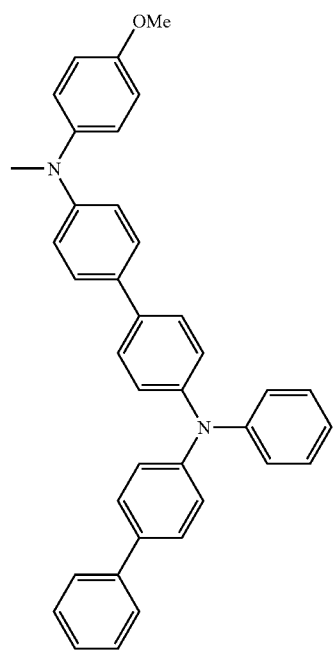
318
334
-continued
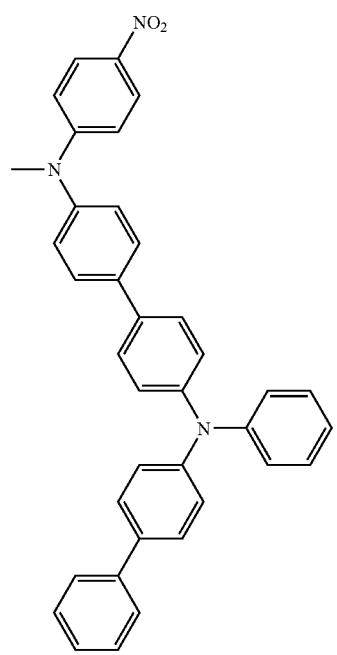
320
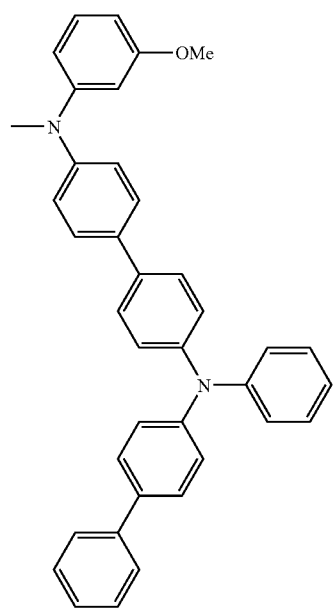
319
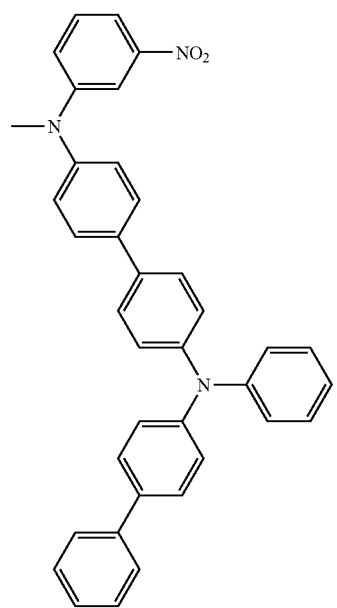
321

335
-continued
336
-continued
322
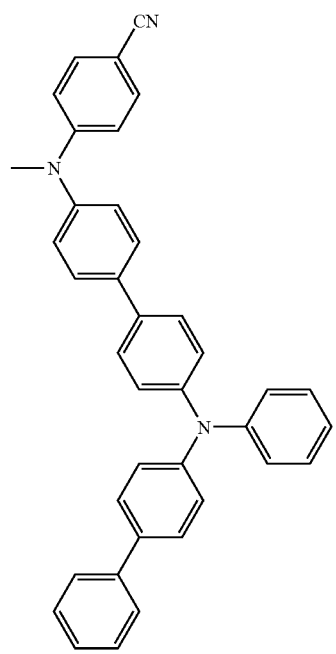
324
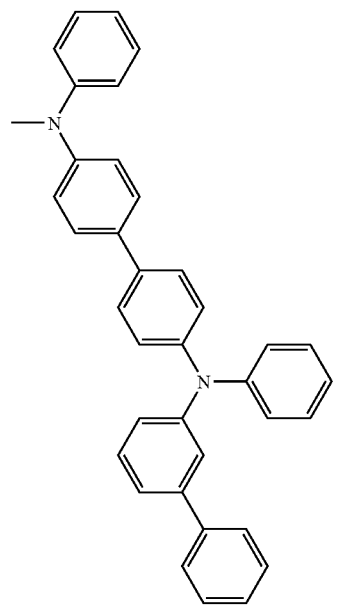
323
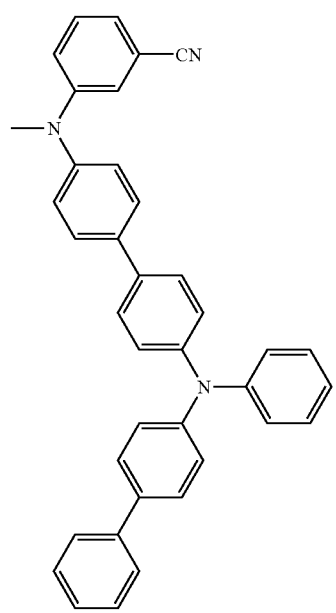
325
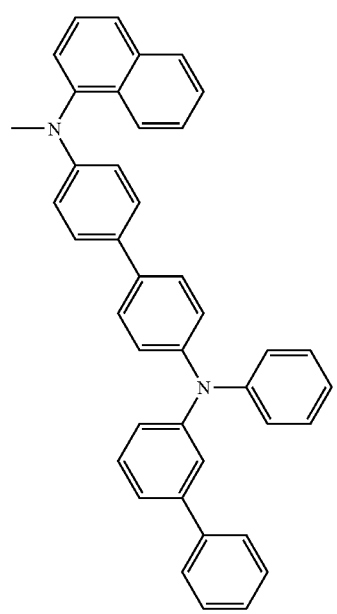

337
-continued
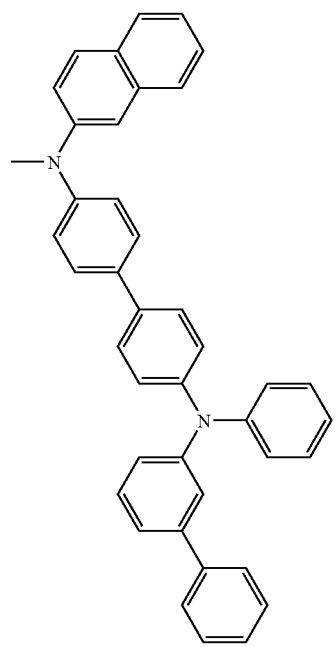
326
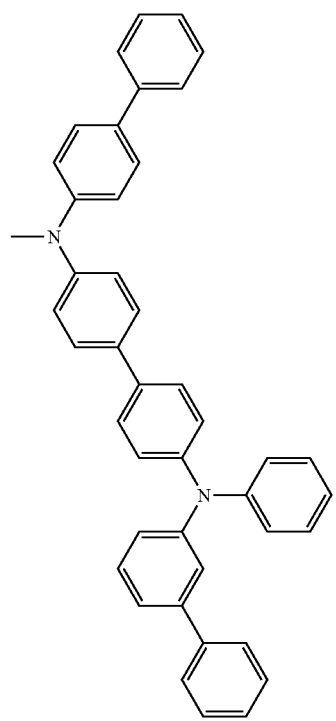
327
338
-continued
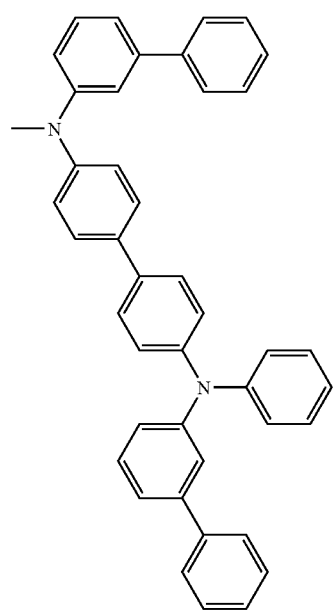
328
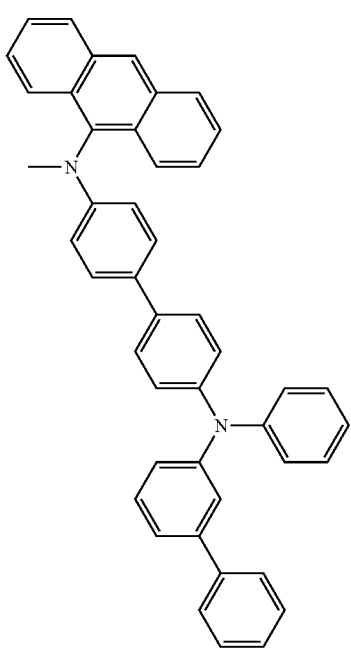
329

339
-continued
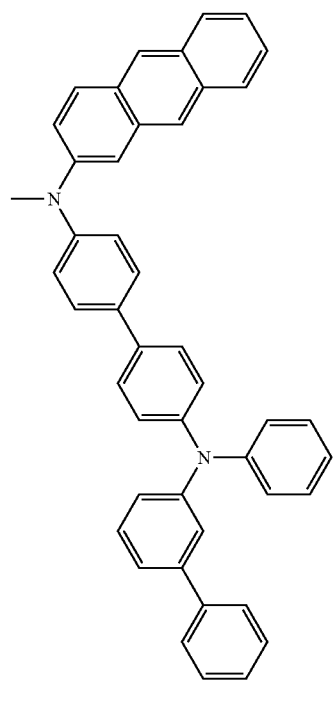
330
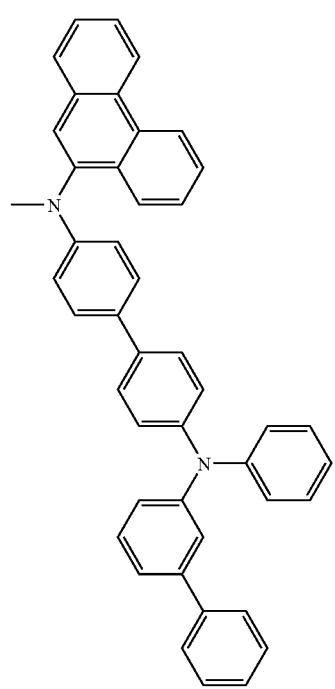
331
340
-continued
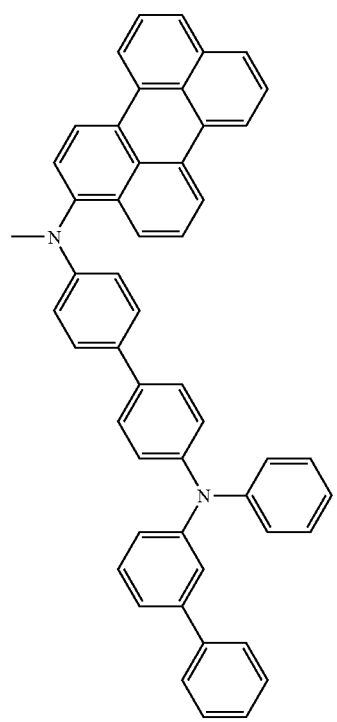
332
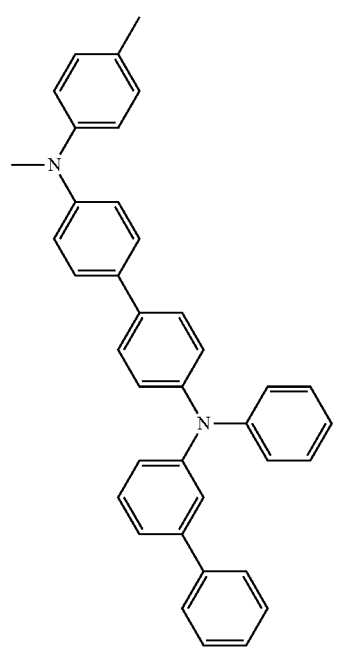
333

341
-continued
334
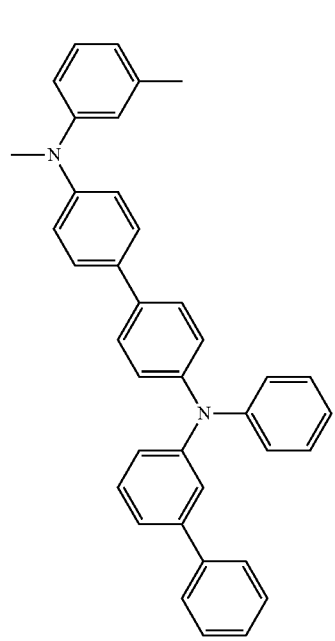
335
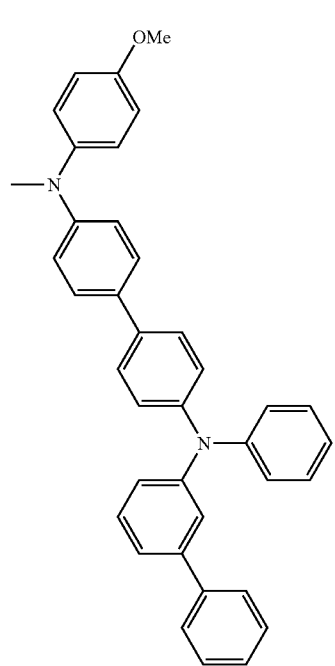
342
-continued
336
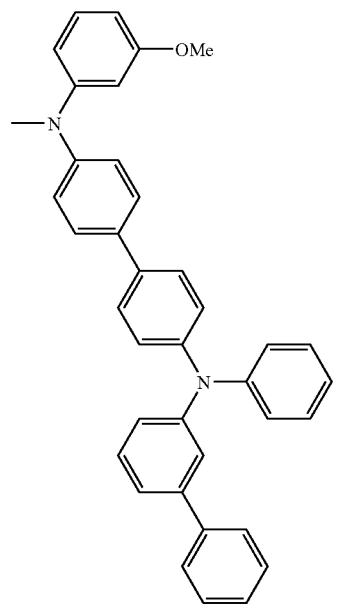
337
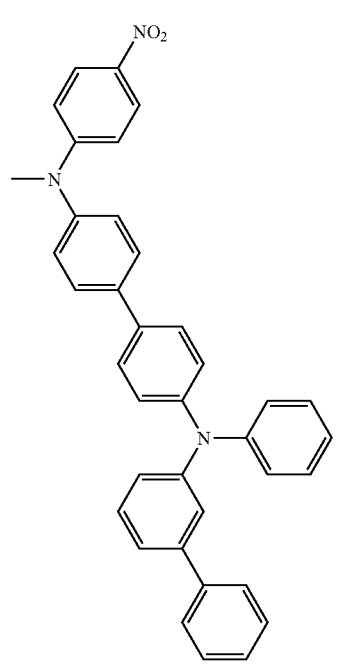

343
338
339
344
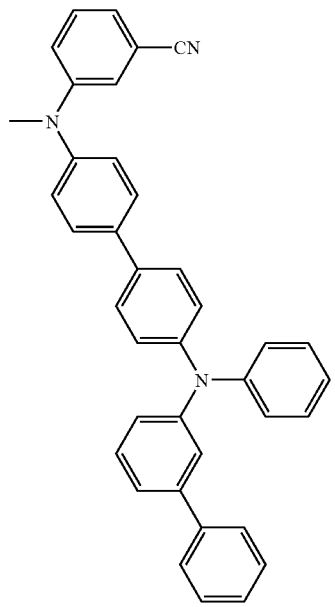
340
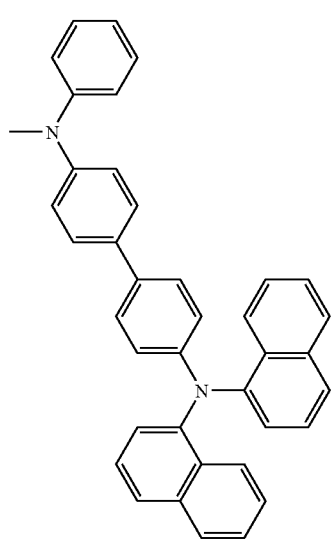
341
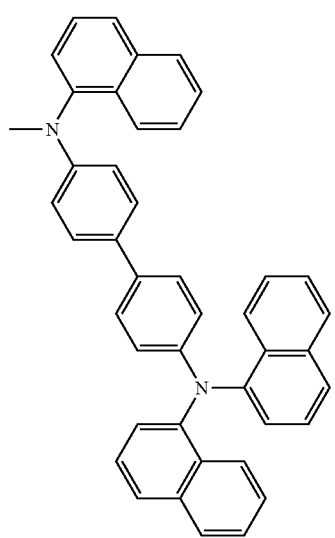
342

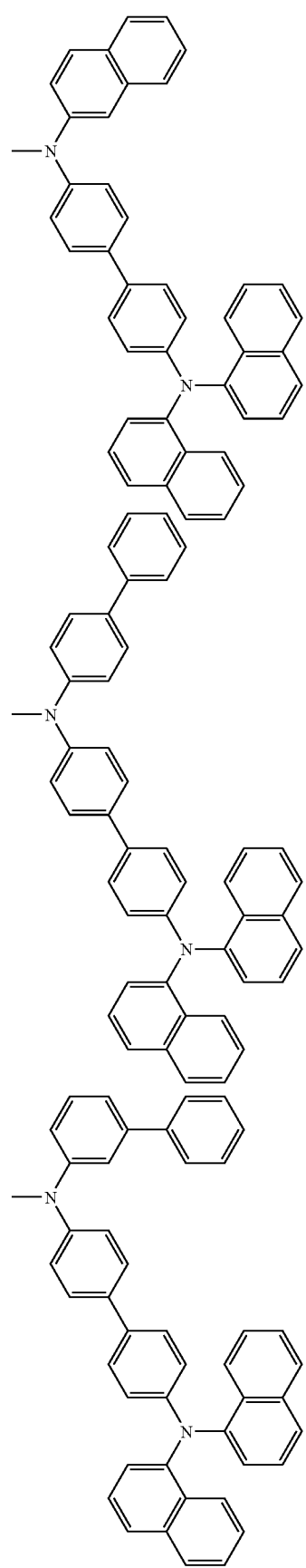
343
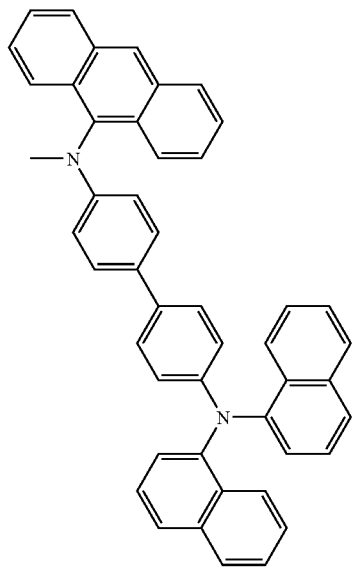
346
344
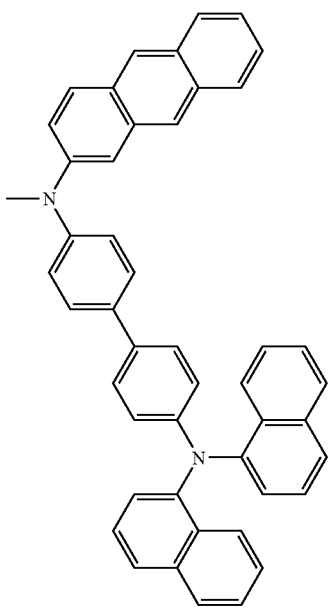
347
345

347
-continued
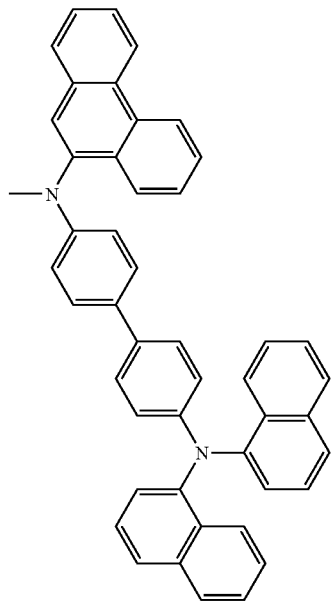
348
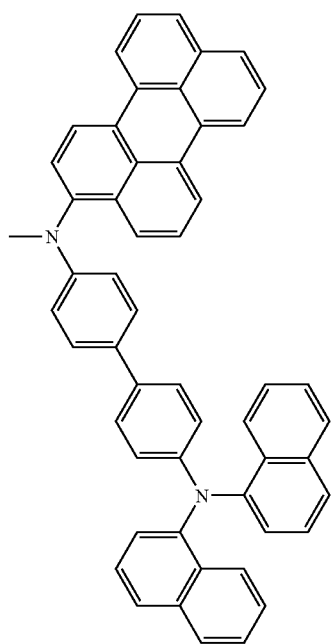
349
348
-continued
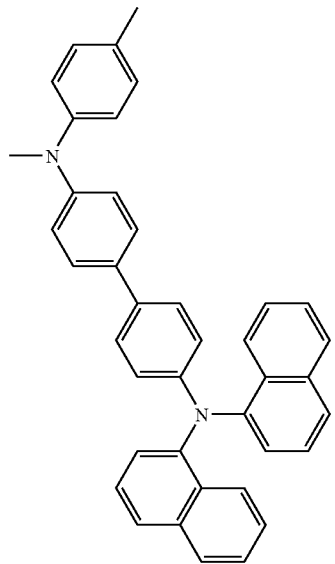
350
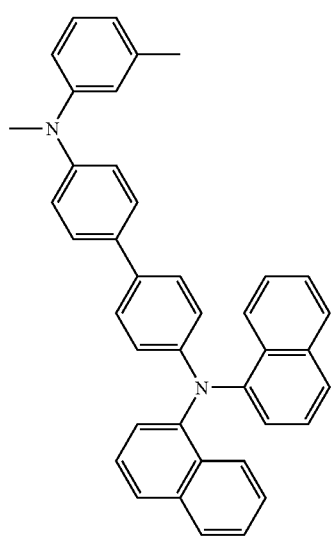
351
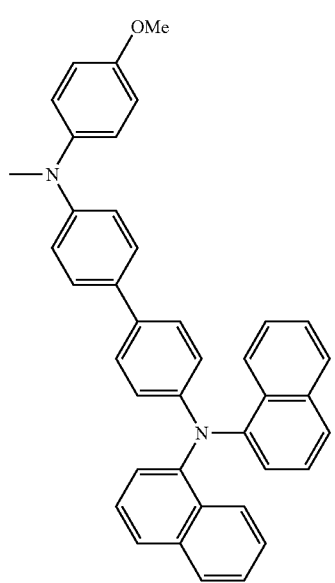
352

349
-continued
| | |
|---|---|
| 353 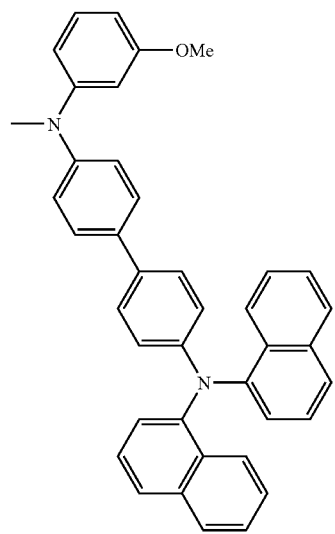 | 356 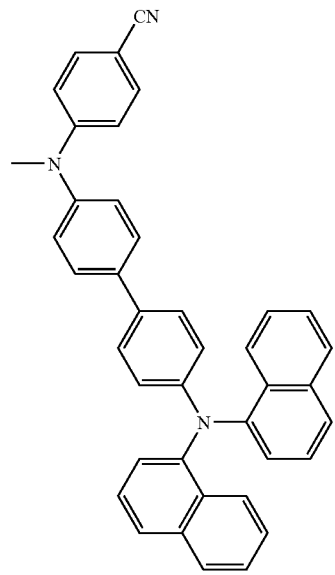 |
| 354 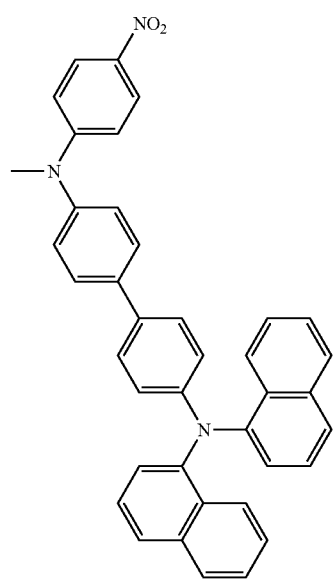 | 357 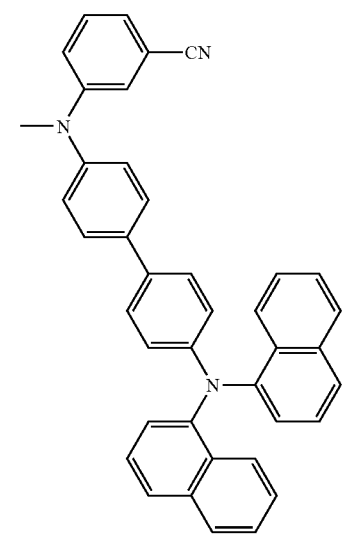 |
| 355 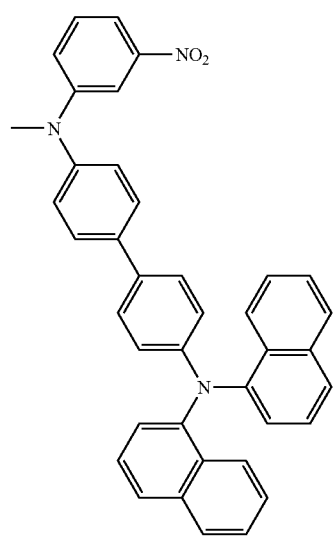 | 358 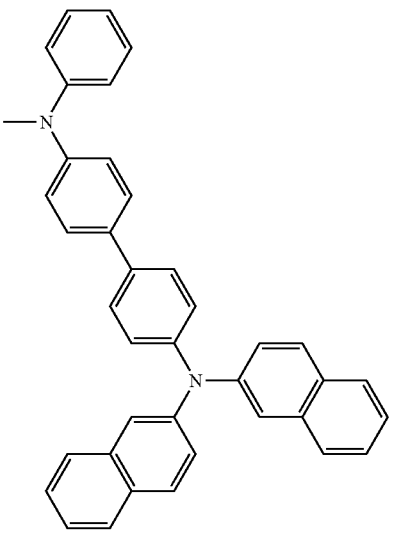 |
350
-continued

351
-continued
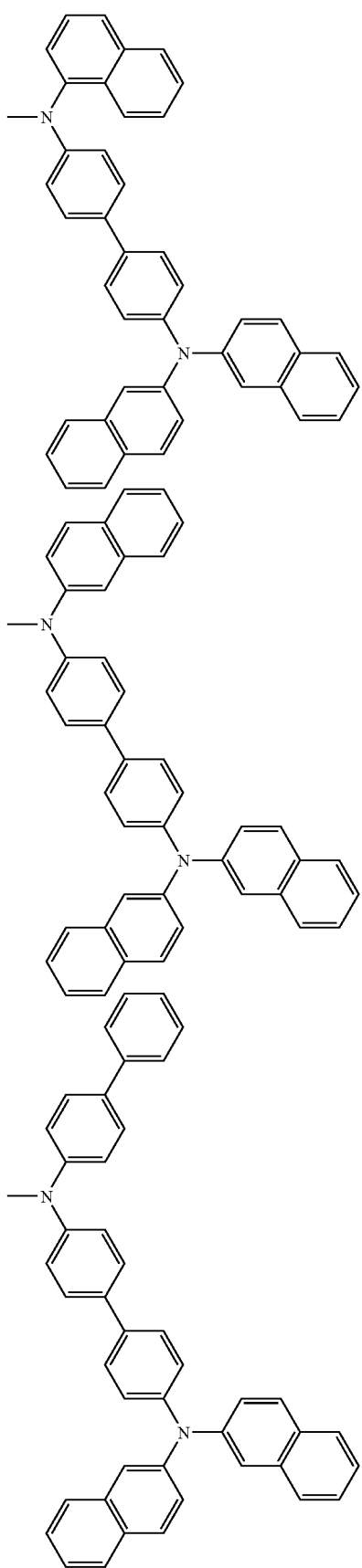
359
360
361
352
-continued
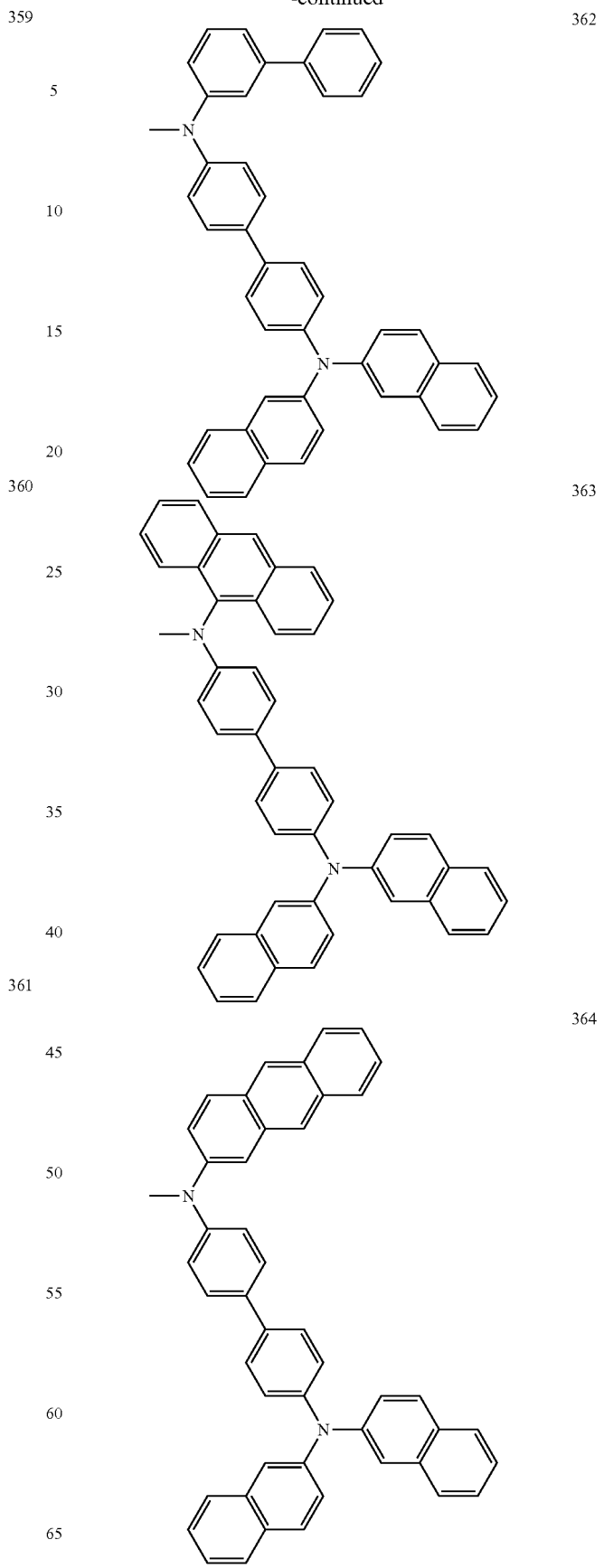
362
363
364

353
-continued
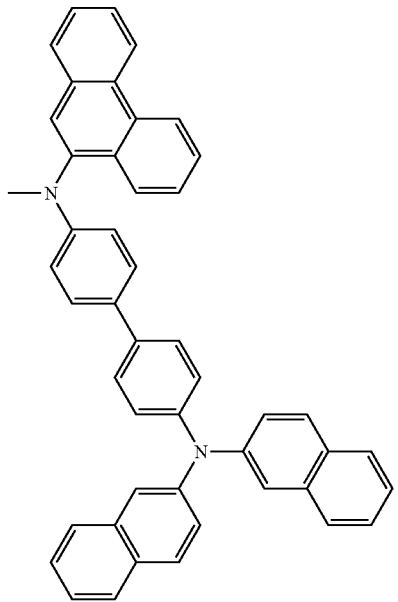
365
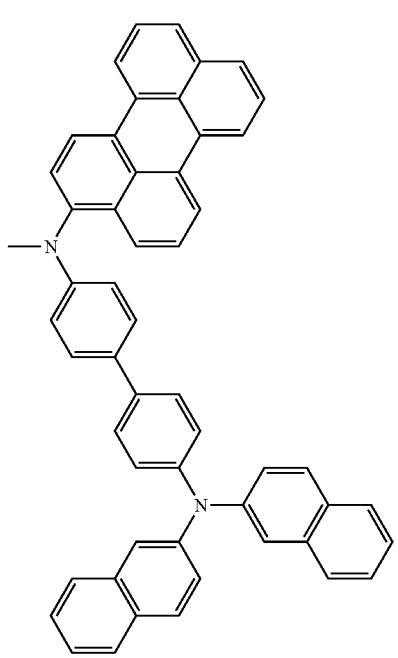
366
354
-continued
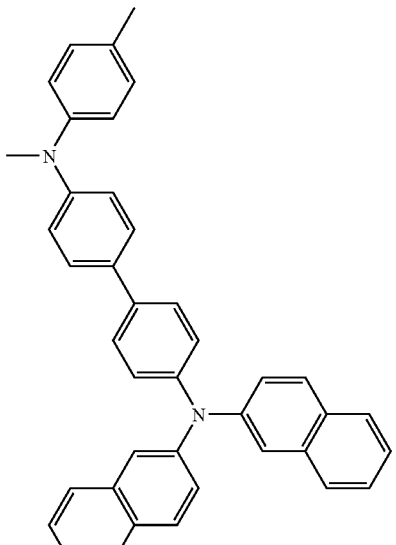
367
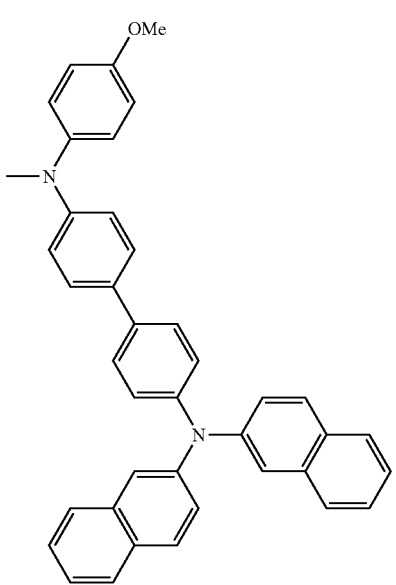
369

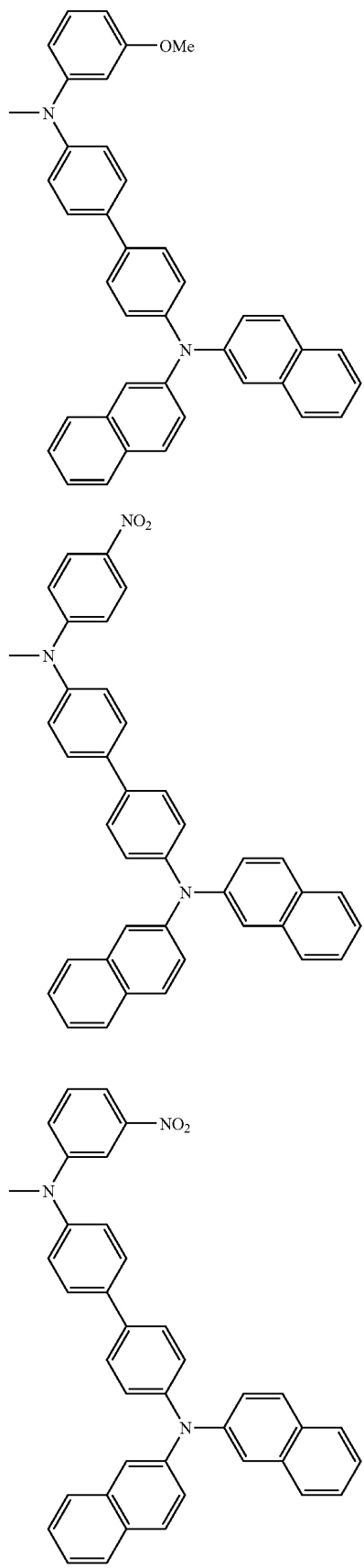
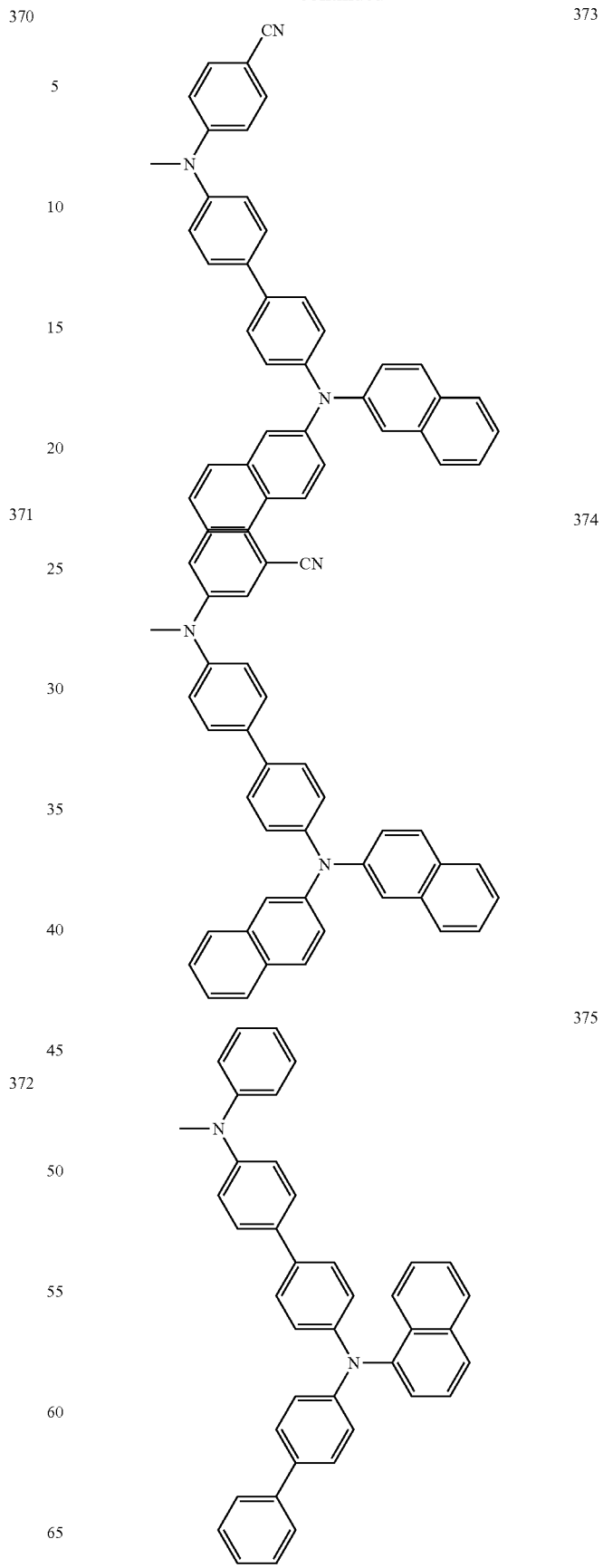

357
-continued
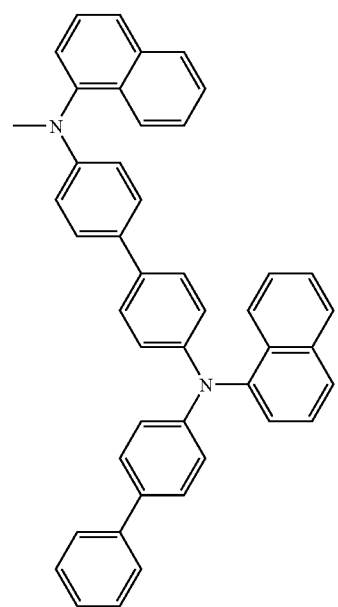
376
377
358
-continued
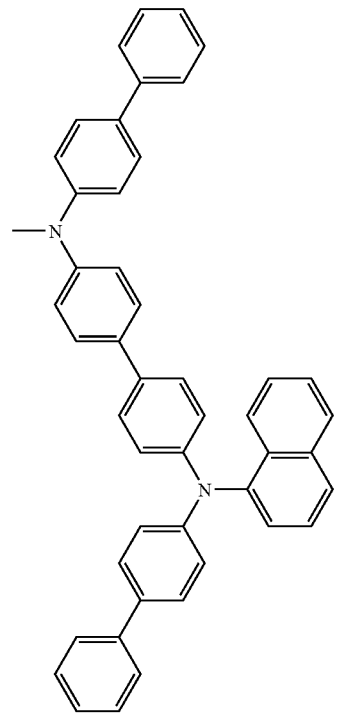
378
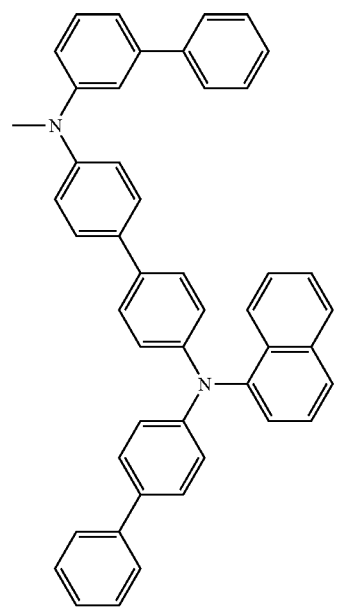
379
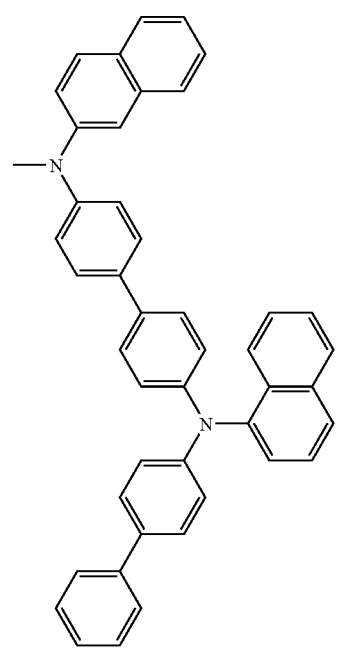

359
-continued
380
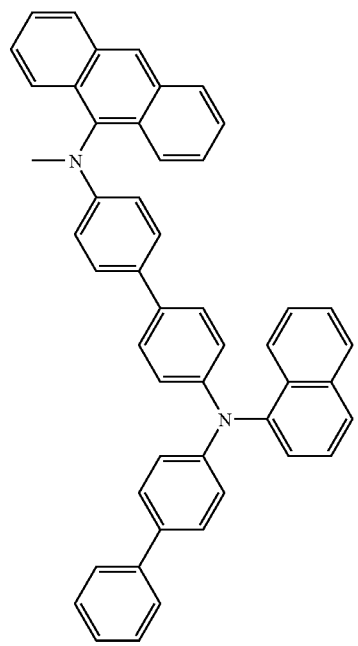
381
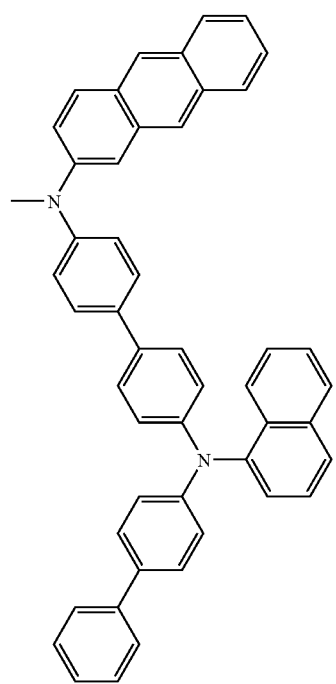
360
-continued
382
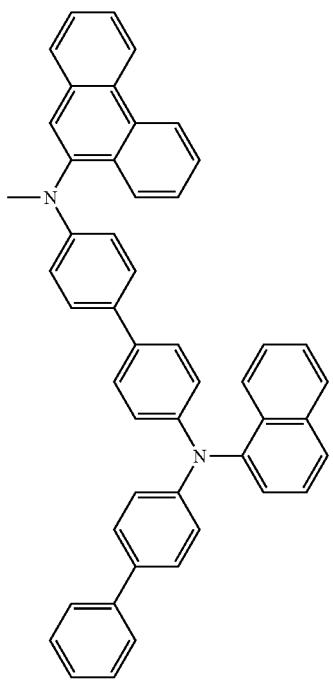
383
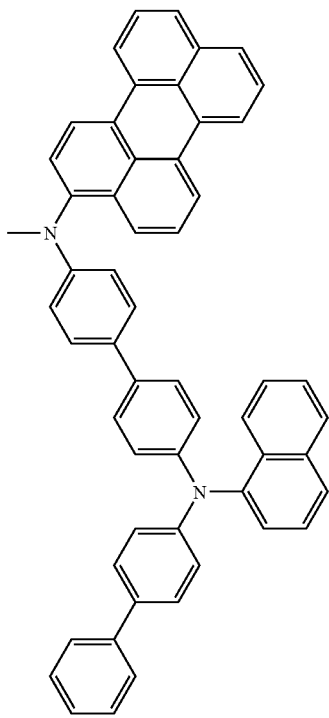

361
-continued
362
-continued
384
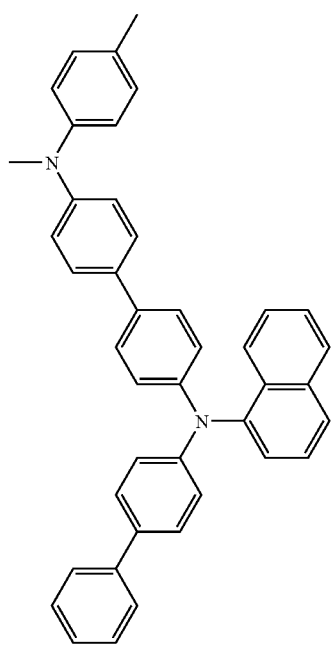
386
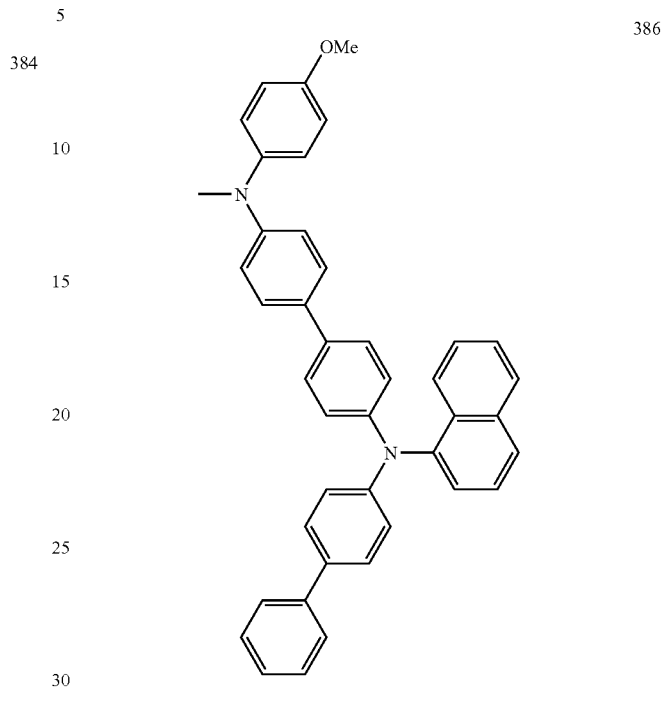
385
387
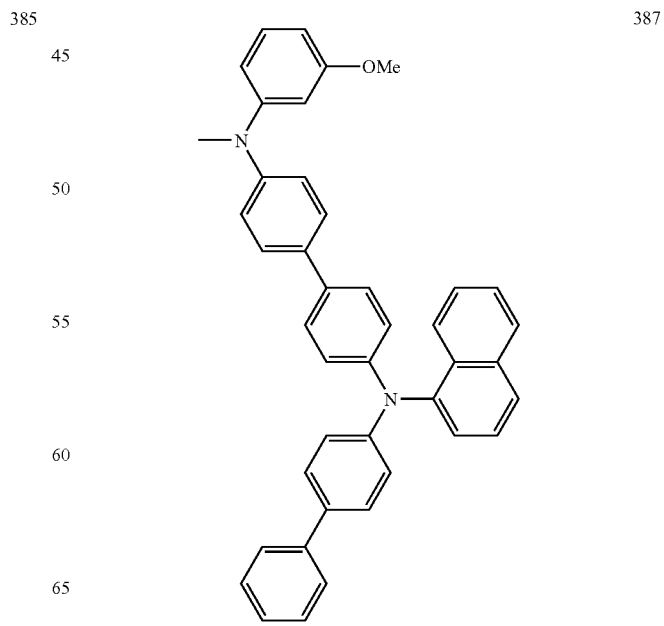

363
-continued
364
-continued
388
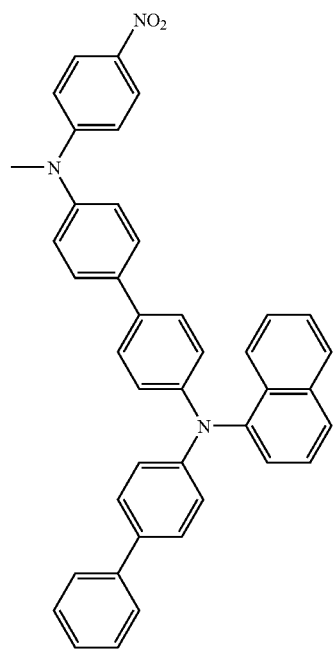
390
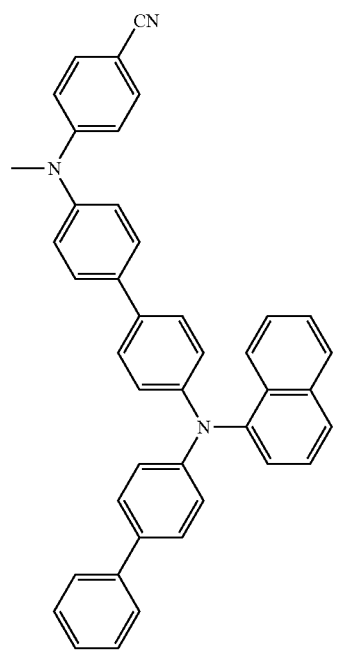
389
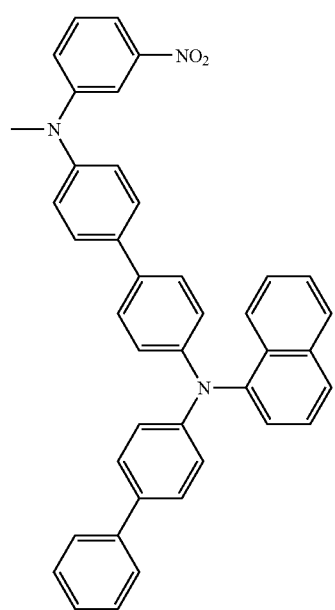
391
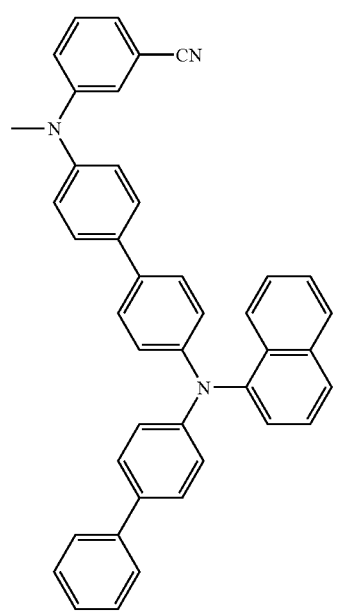

365
-continued
392
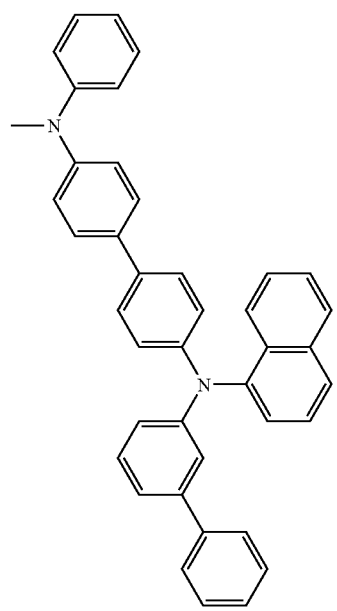
393
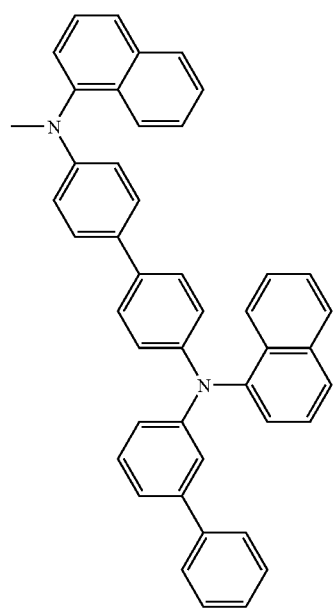
366
-continued
394
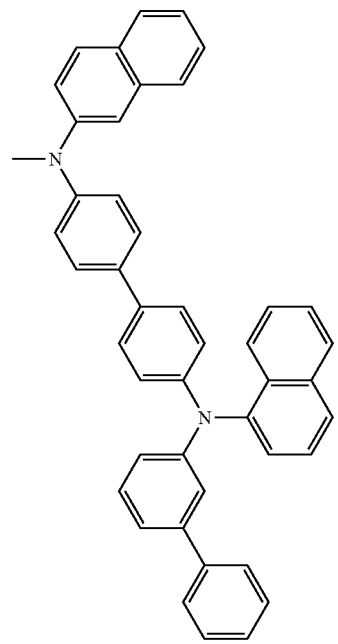
395
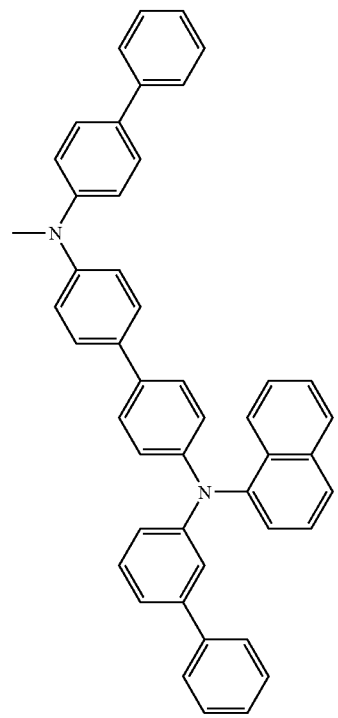

367
-continued
368
-continued
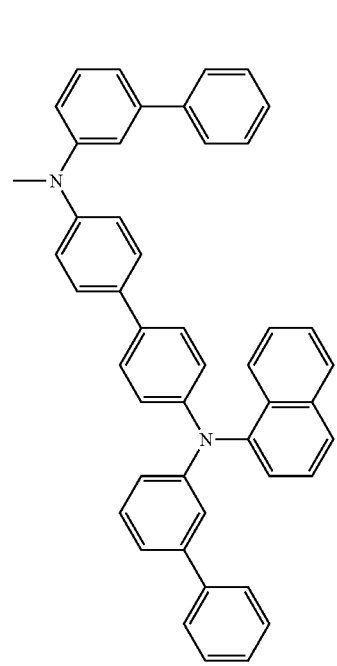
396
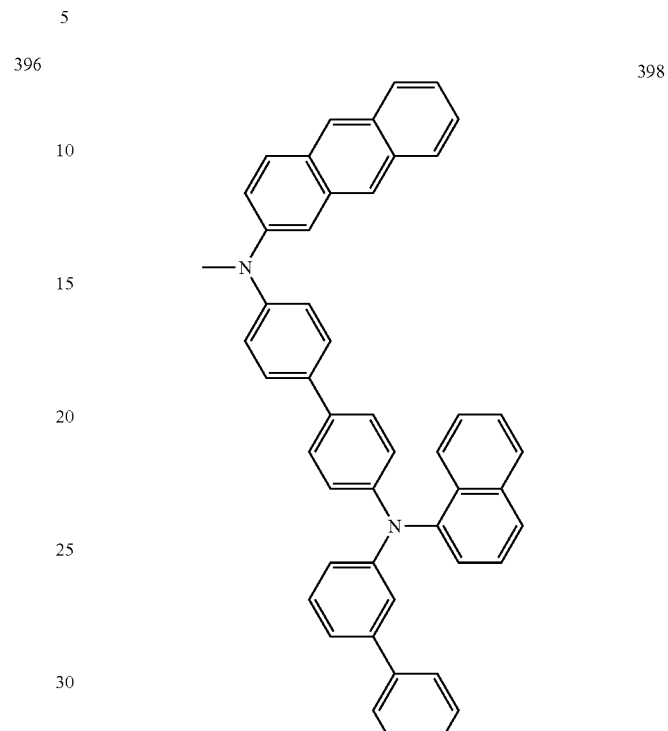
397
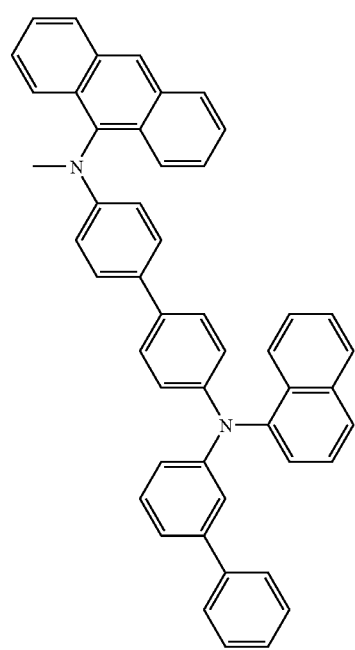
398
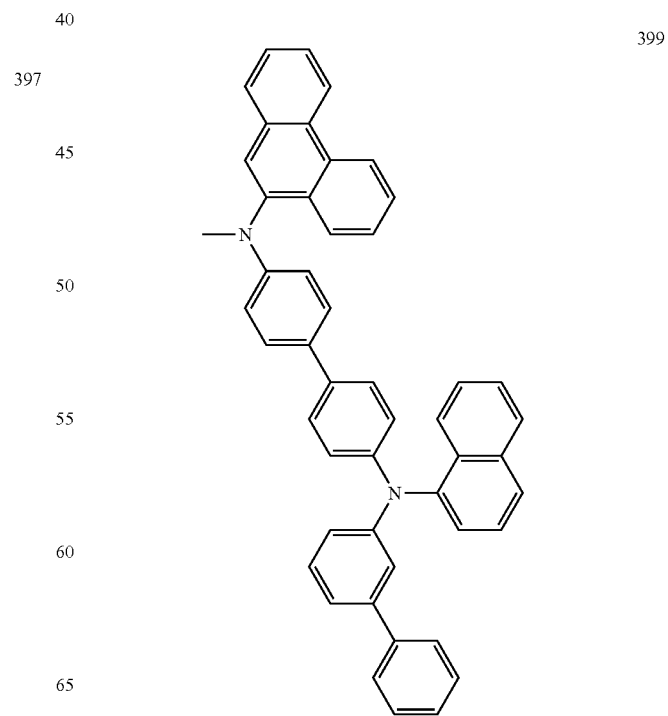
399

369
-continued
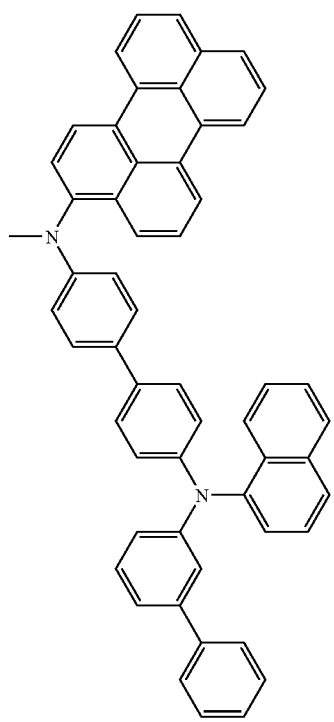
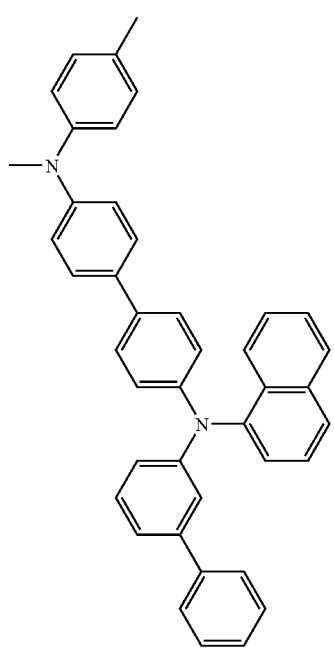
401
370
-continued
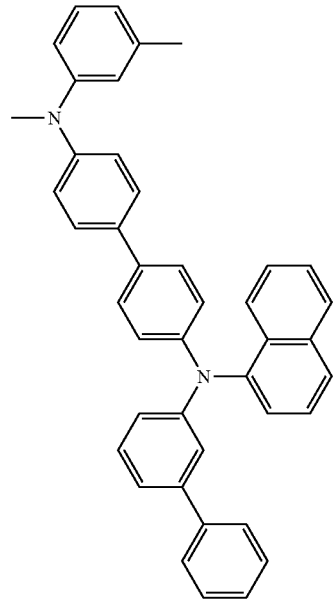
400
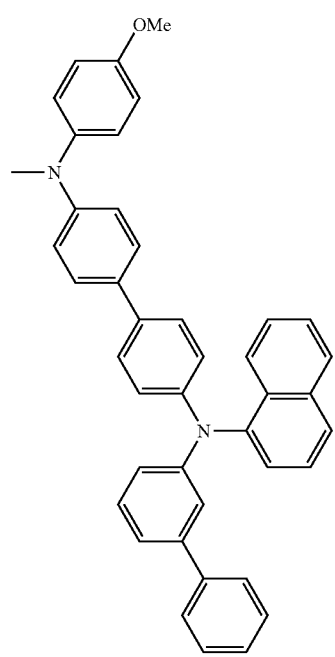
402
403

371
-continued
404
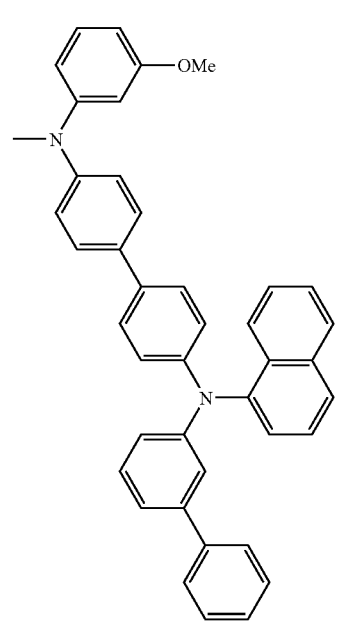
405
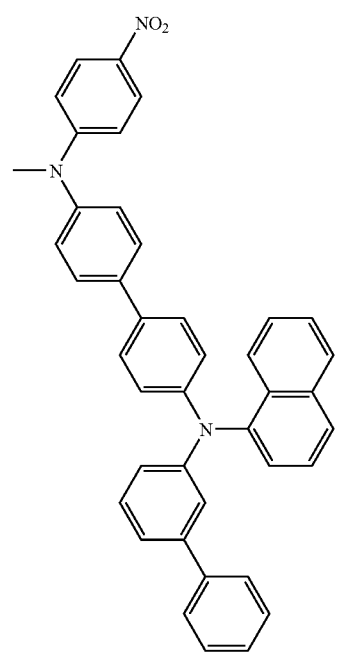
372
-continued
406
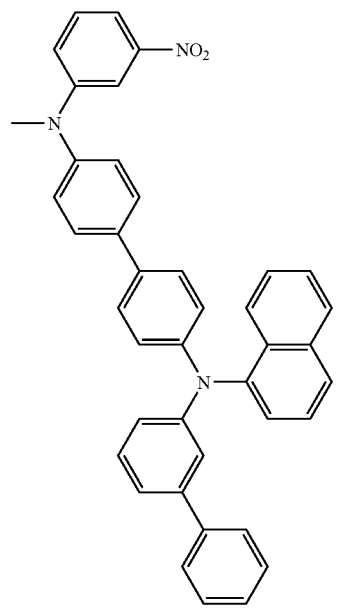
407
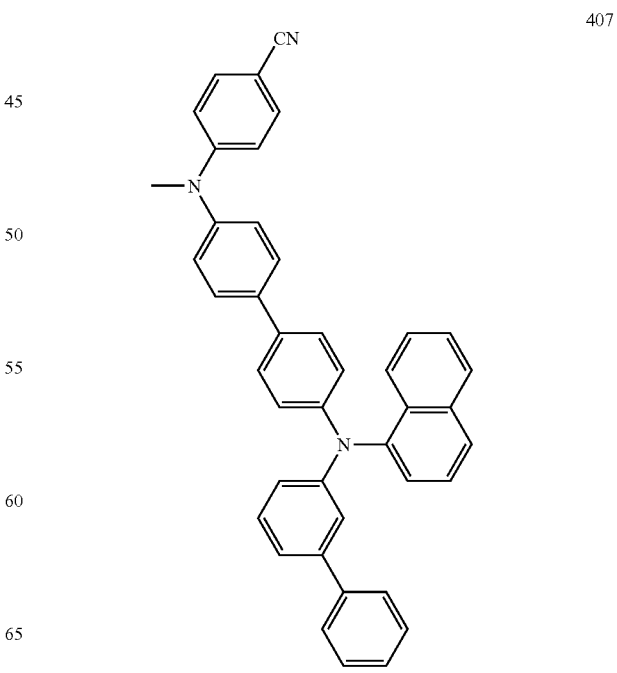

373
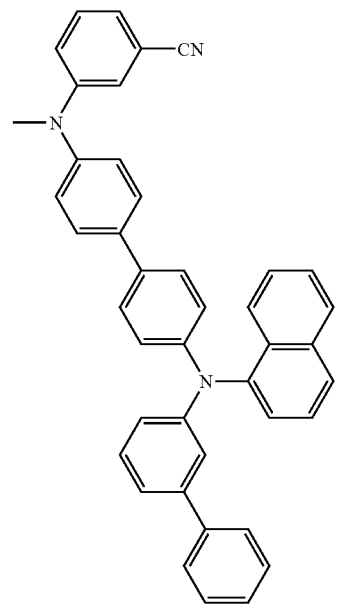
374
408
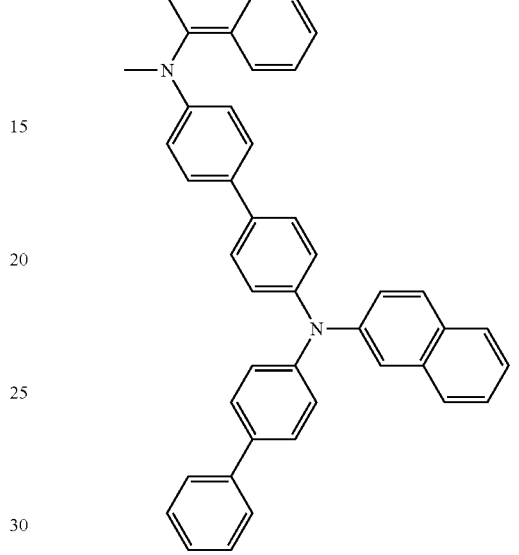
409
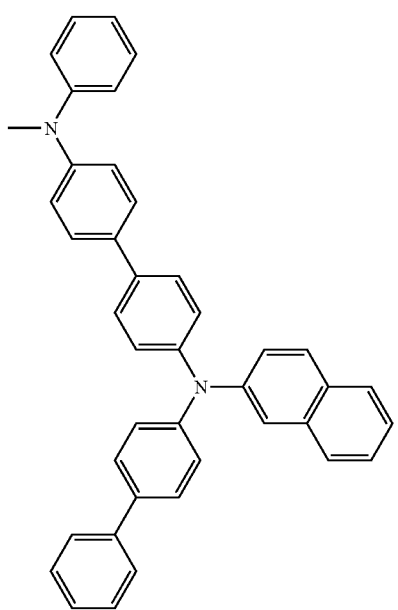
410
411
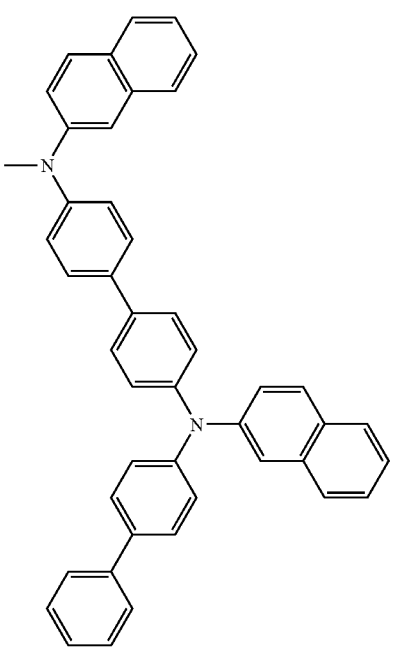

412
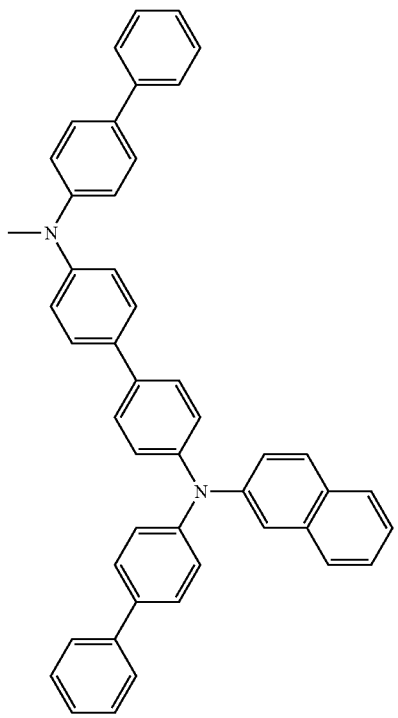
414
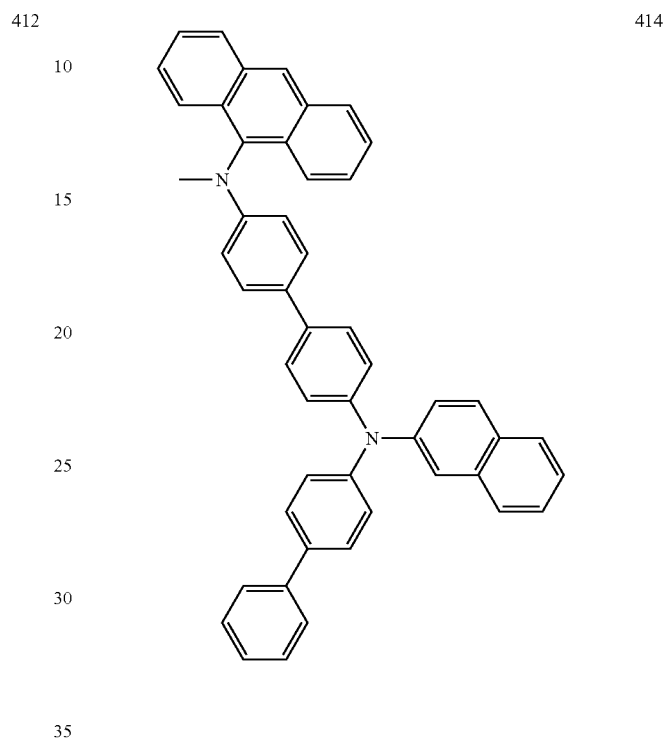
413
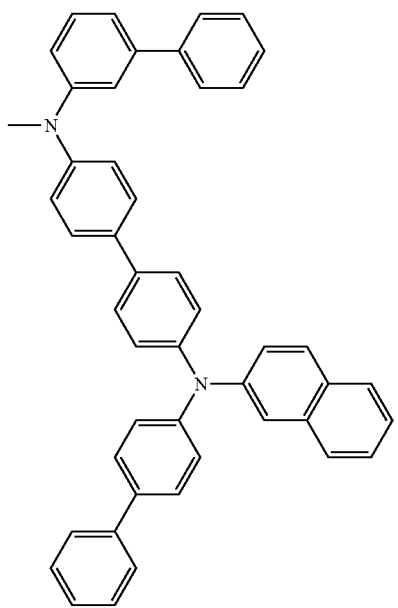
415
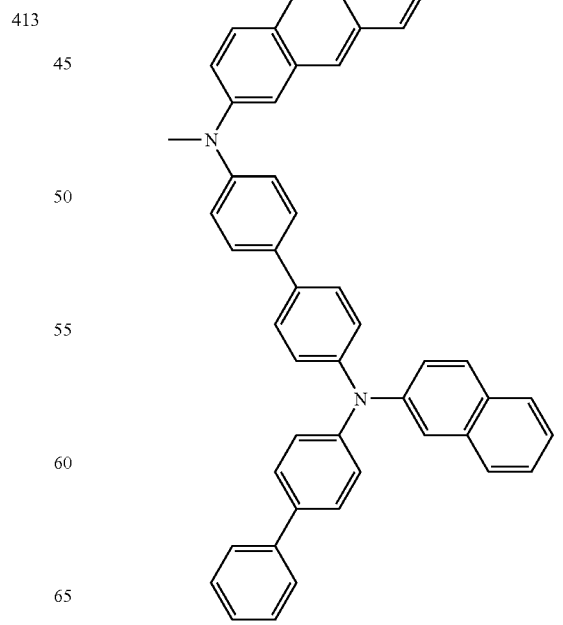

377
-continued
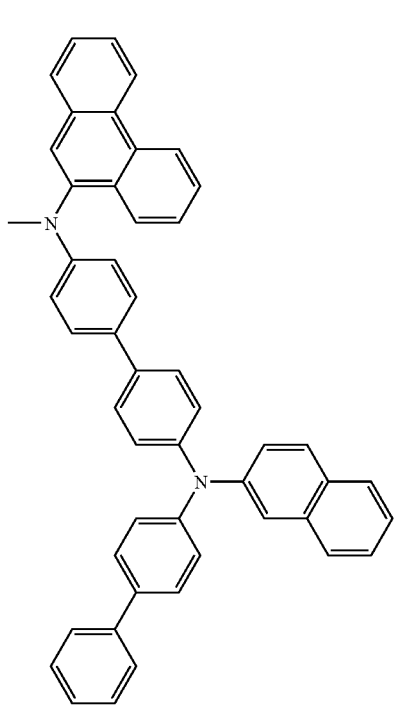
416
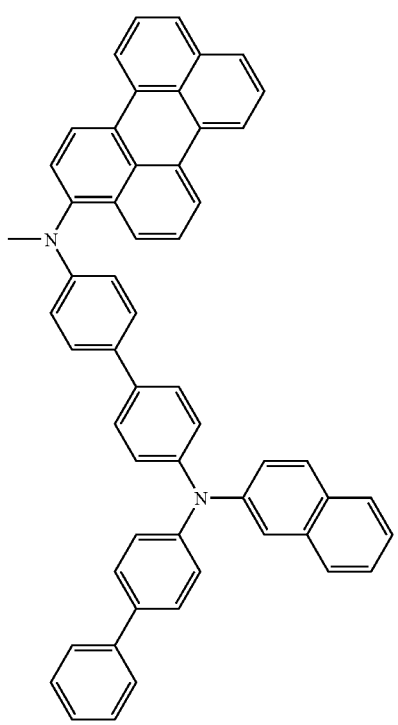
417
378
-continued
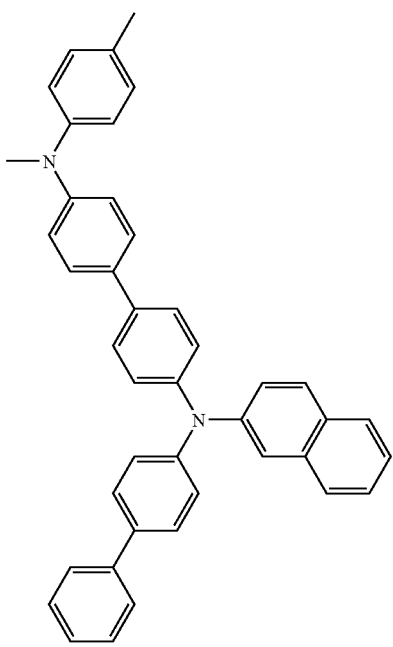
418
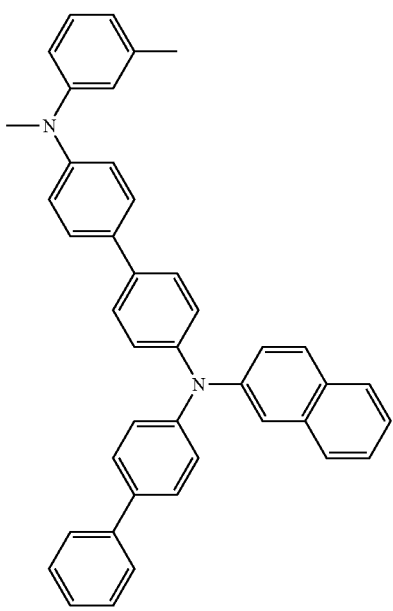
419

379
420 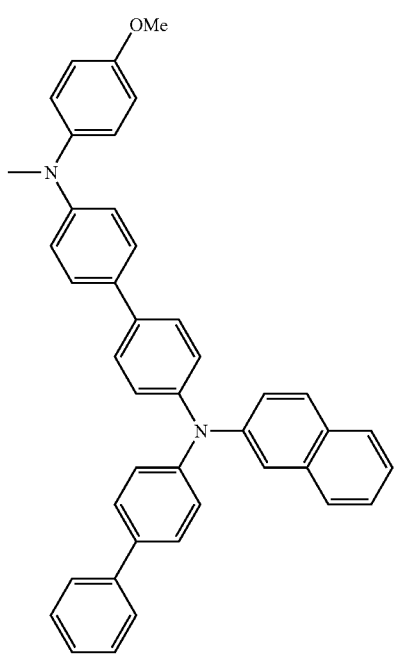
421 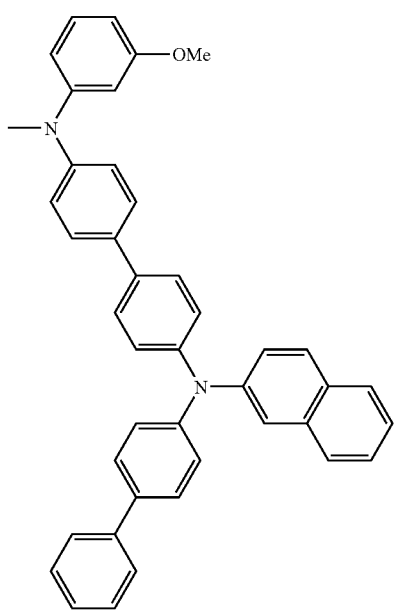
422 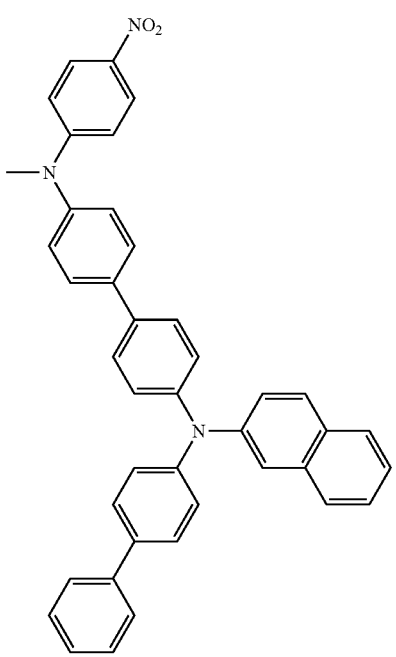
423

381
-continued
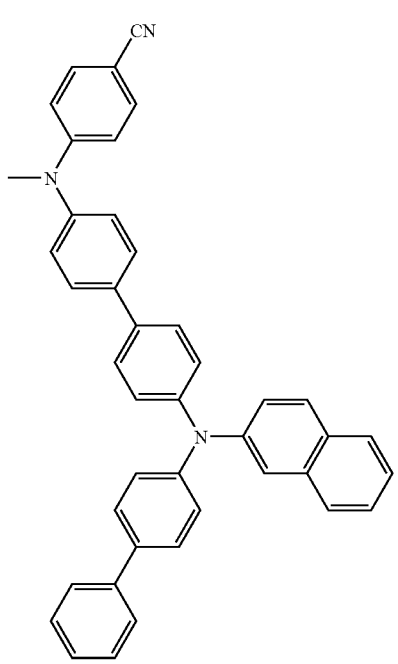
424
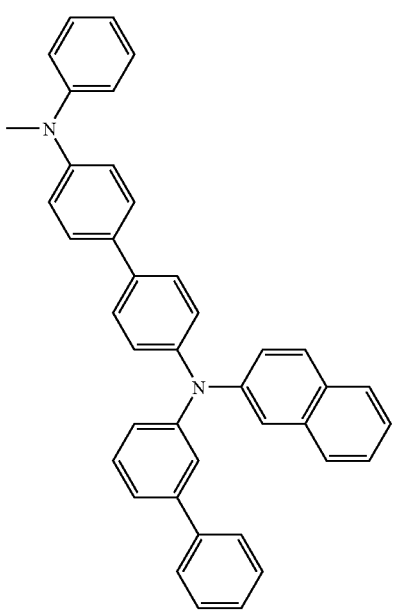
382
-continued
426
425
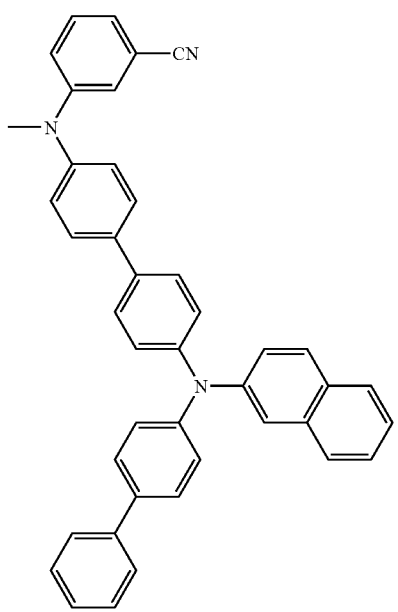
427

383
-continued
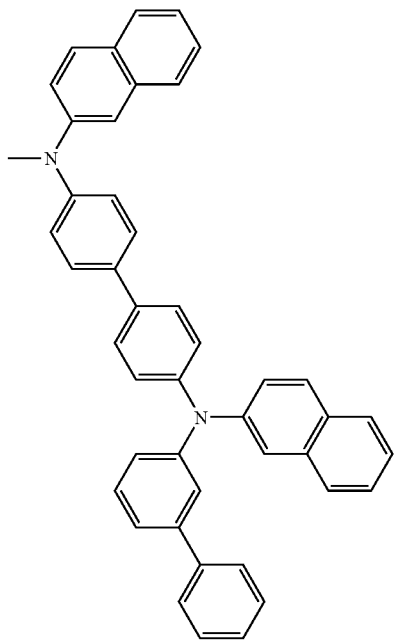
428
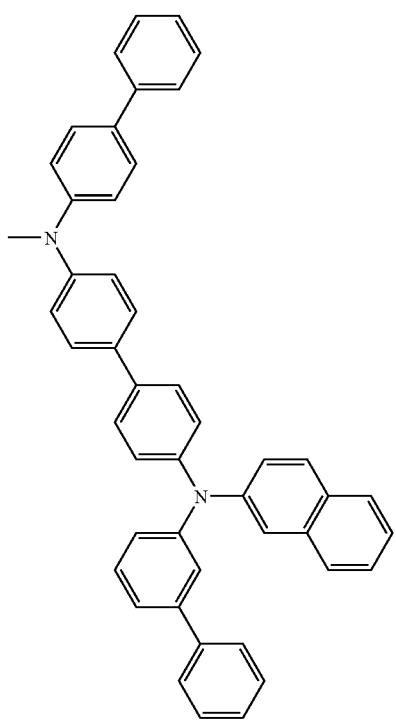
429
384
-continued
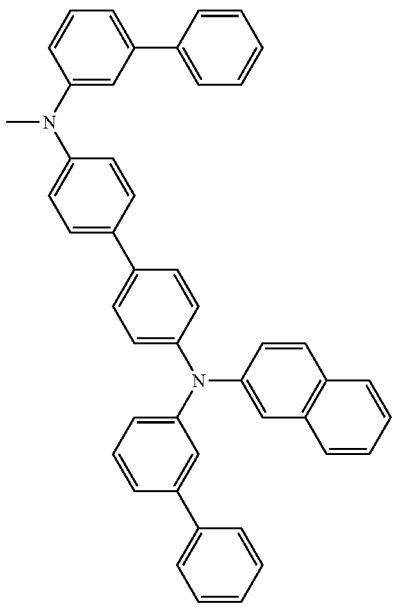
430
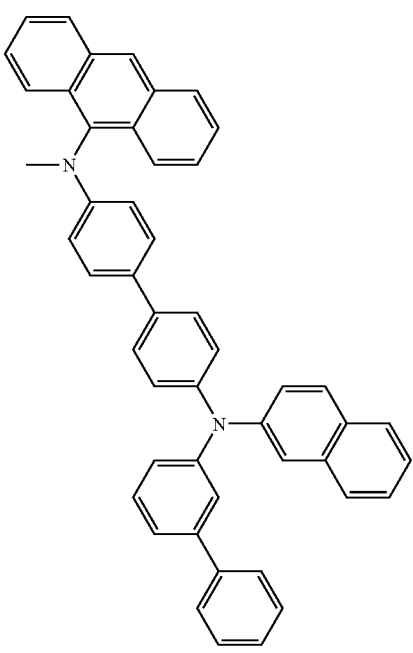
431

-continued
432
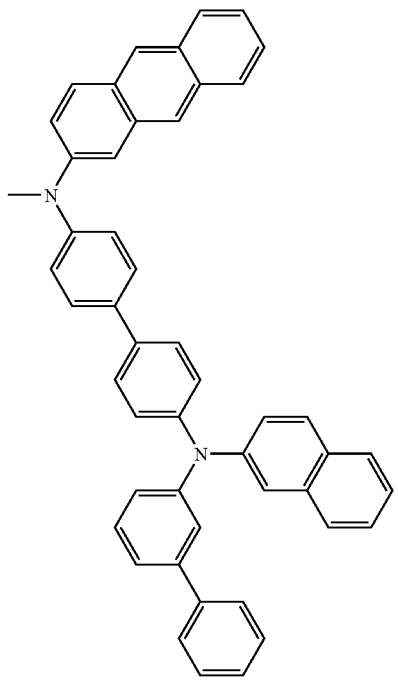
433
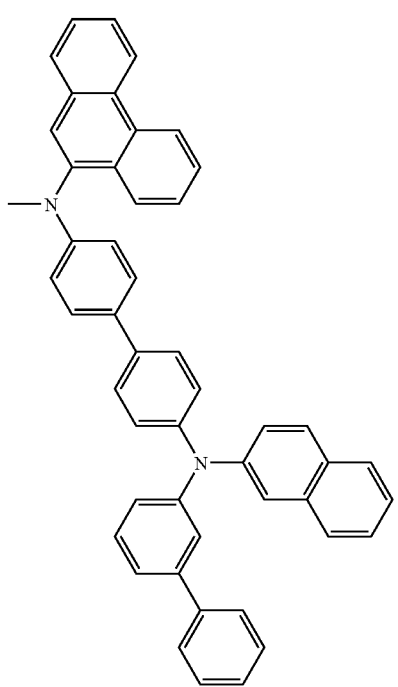
-continued
434
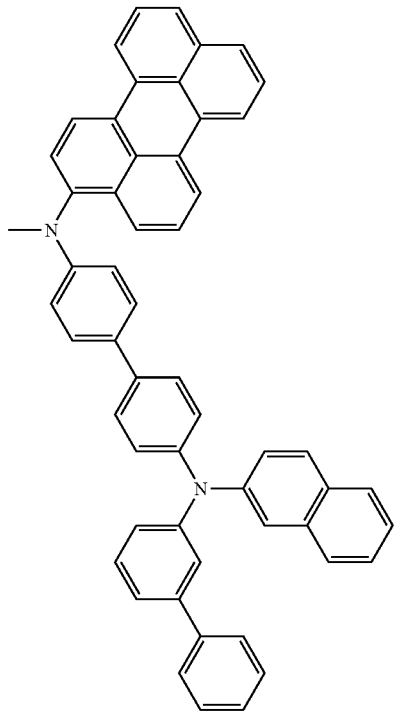
435
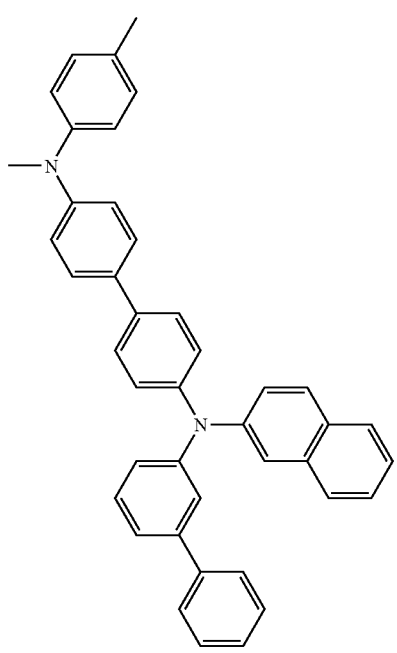

436
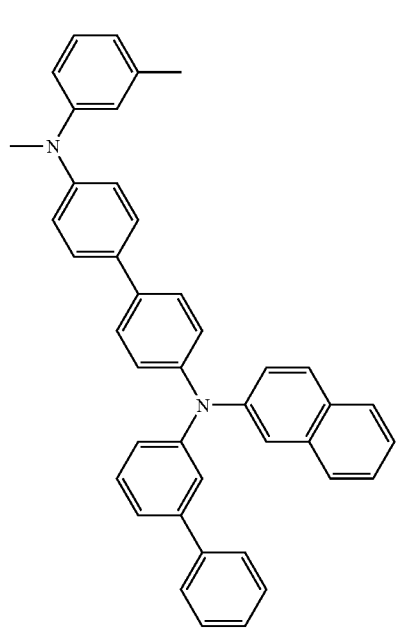
387
-continued
438
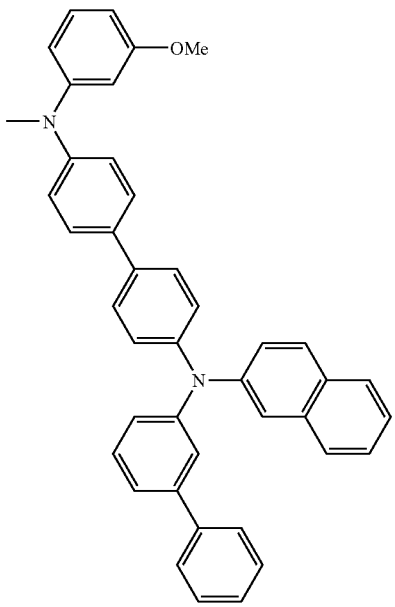
388
-continued
437
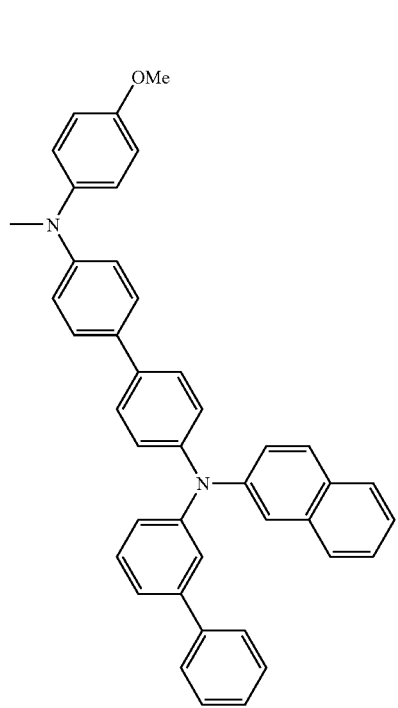
439
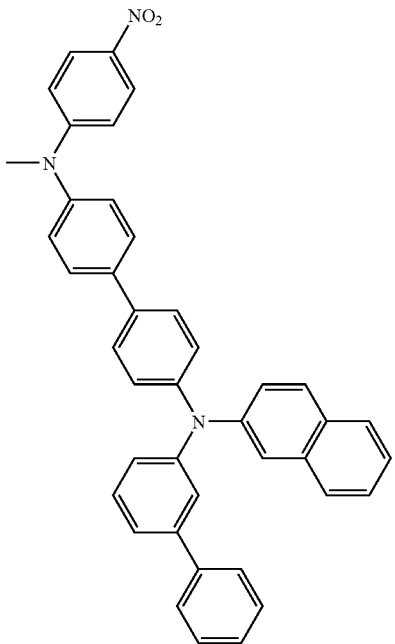

389
-continued
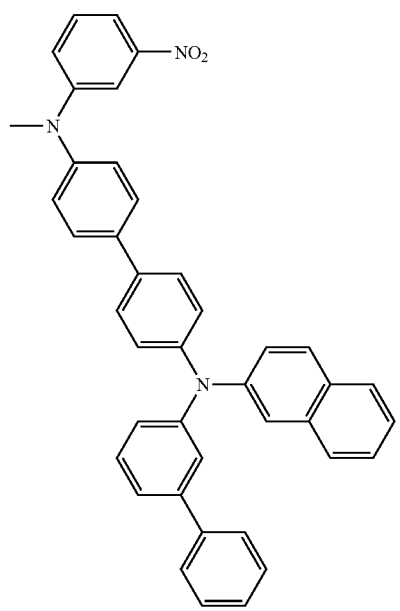
440
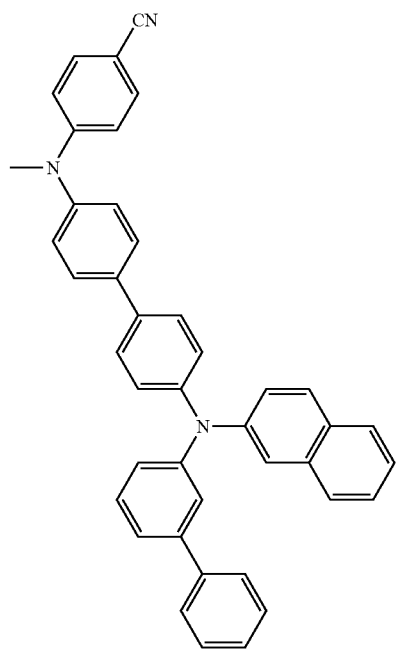
441
390
-continued
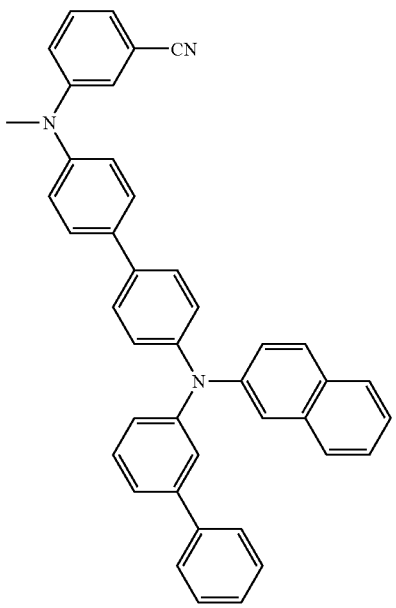
442
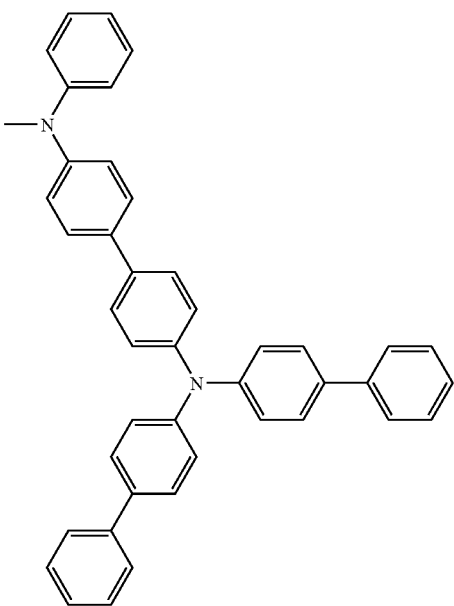
443

391
-continued
392
-continued
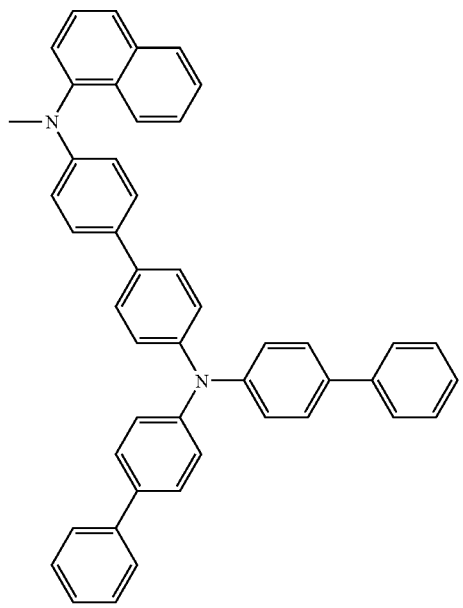
444
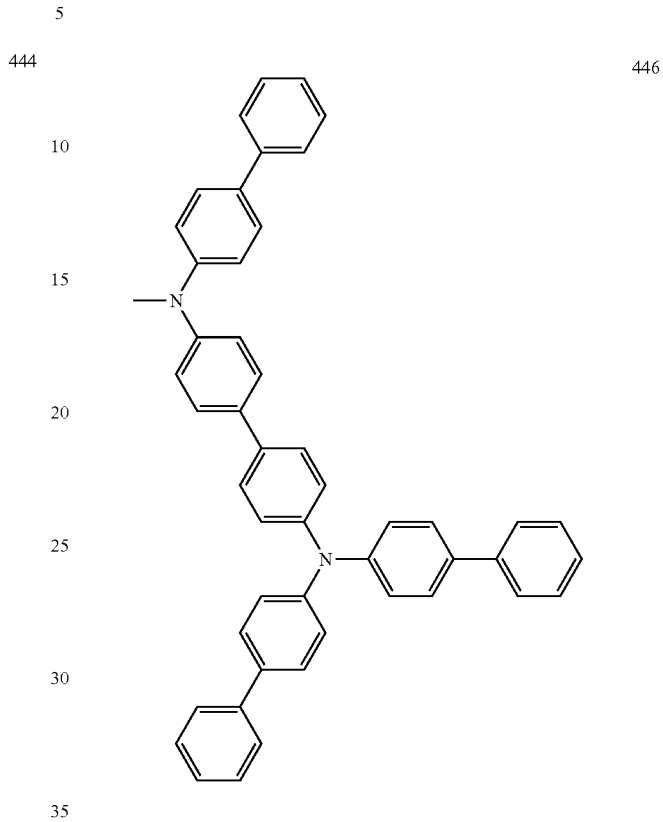
446
445
447
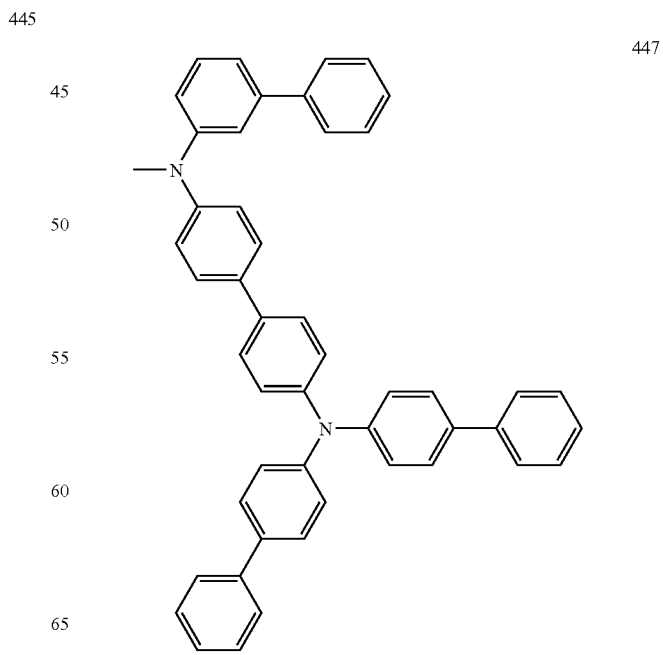

393
-continued
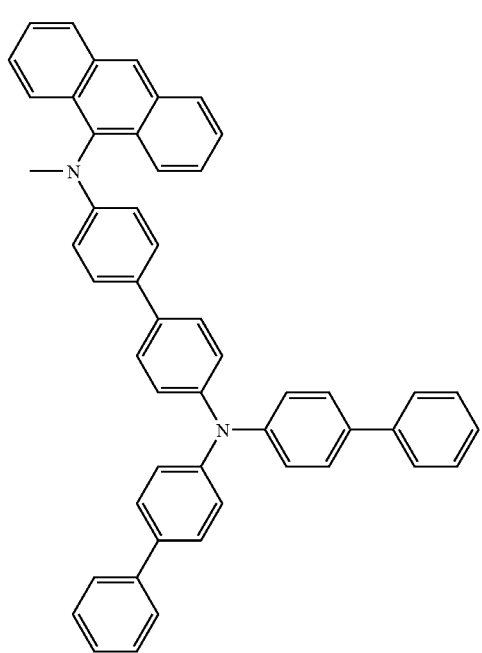
448
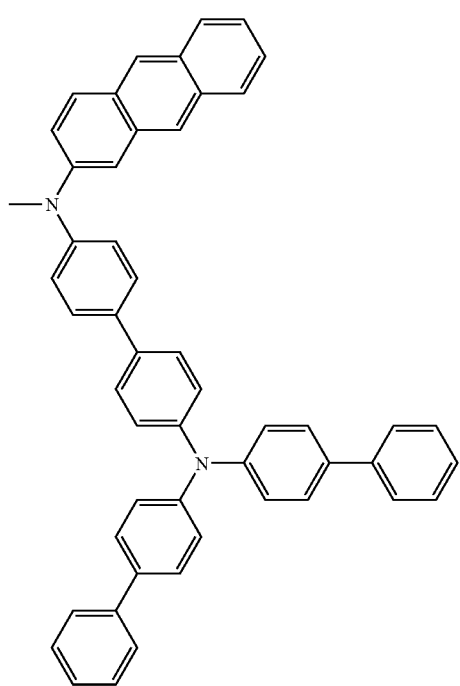
449
394
-continued
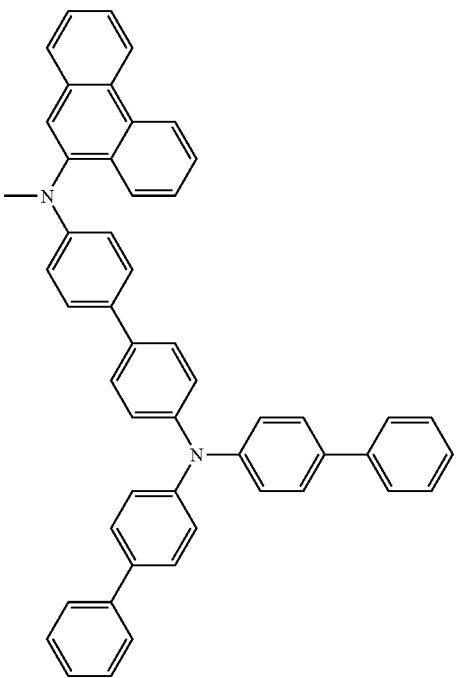
450
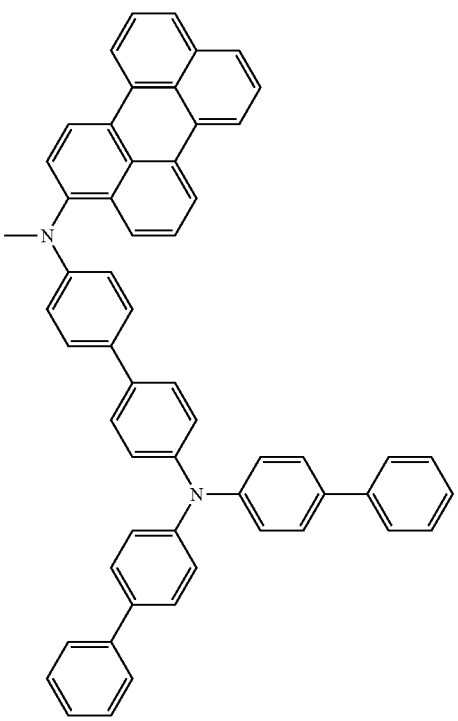
451

395
-continued
396
-continued
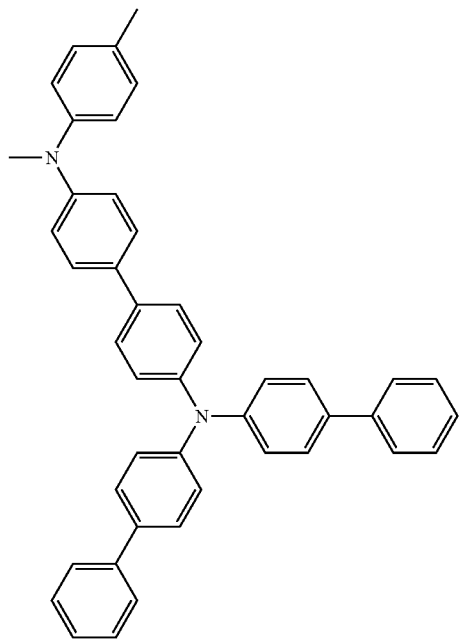
452
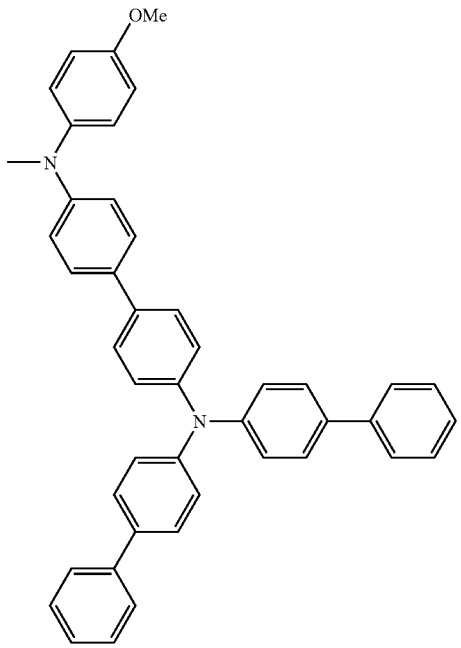
454
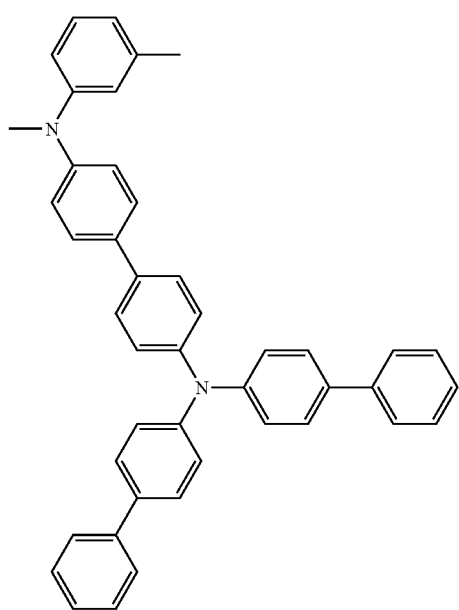
453
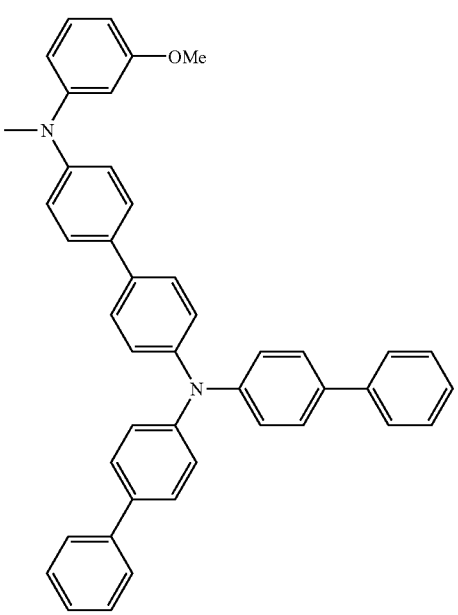
455

397
-continued
456
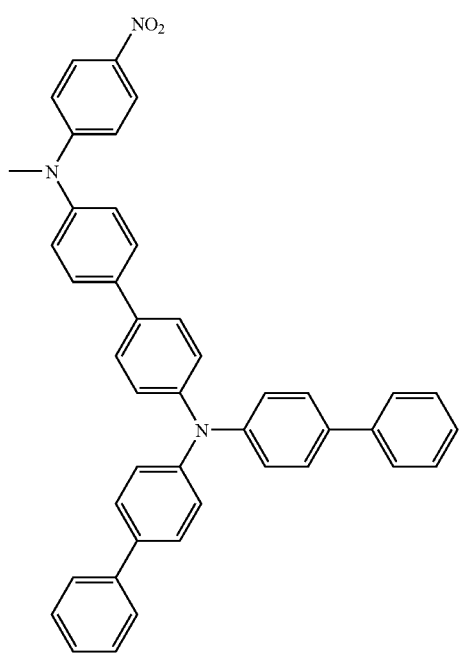
457
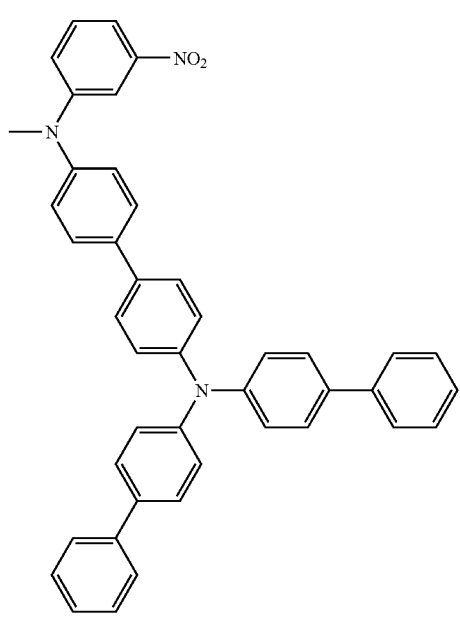
398
-continued
458
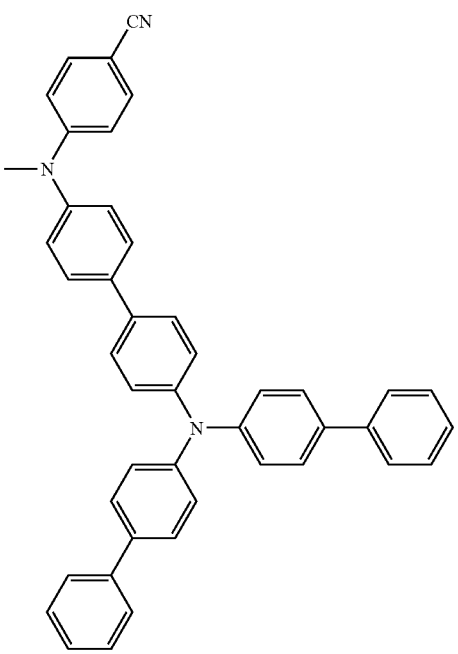
459
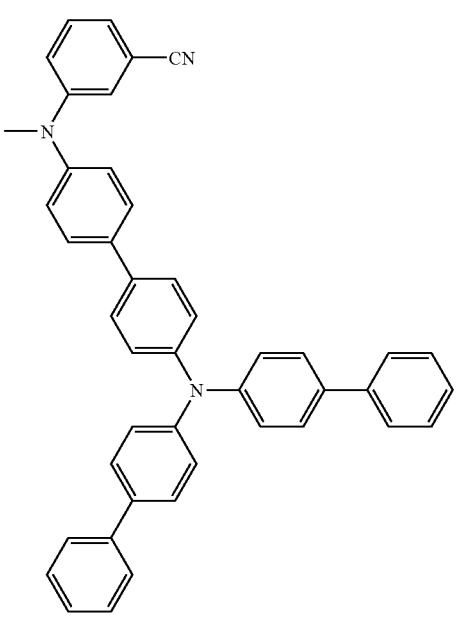

399
-continued
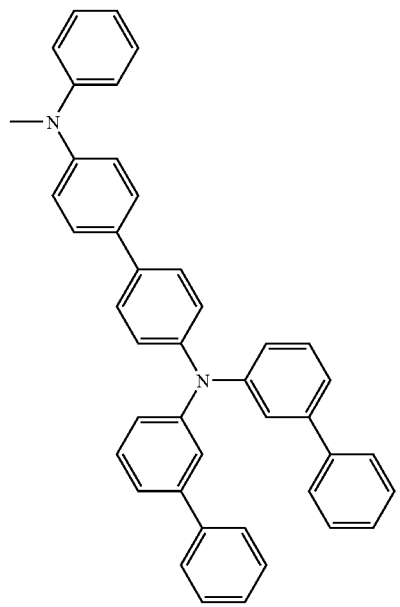
460
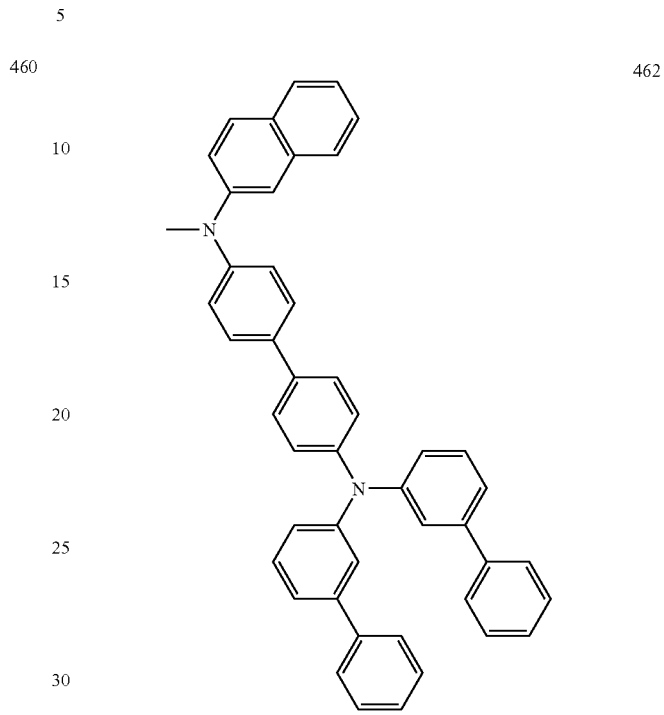
461
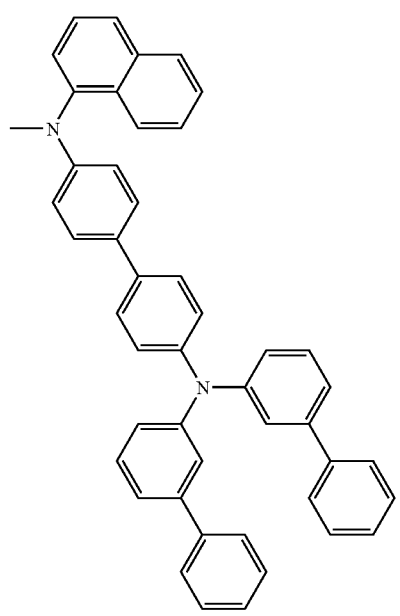
462
463
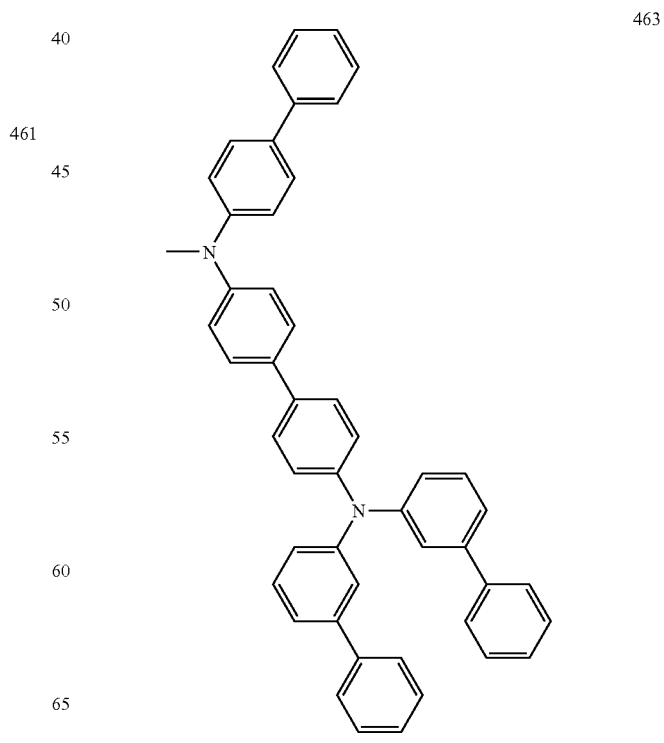

401
-continued
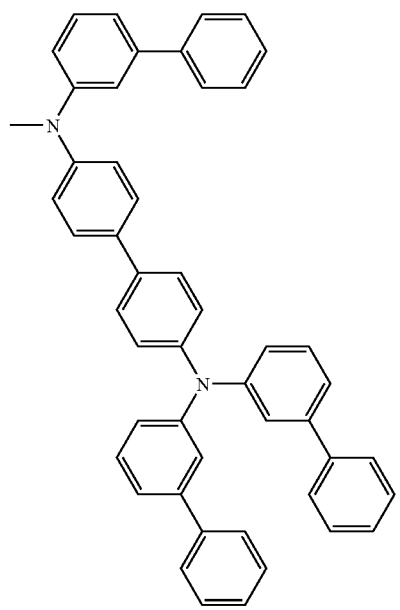
464
402
-continued
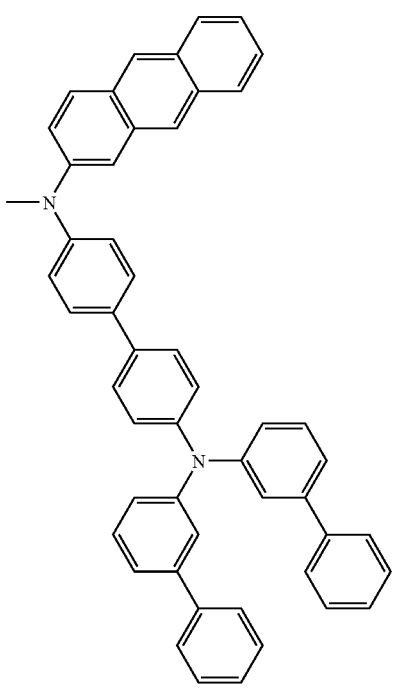
466
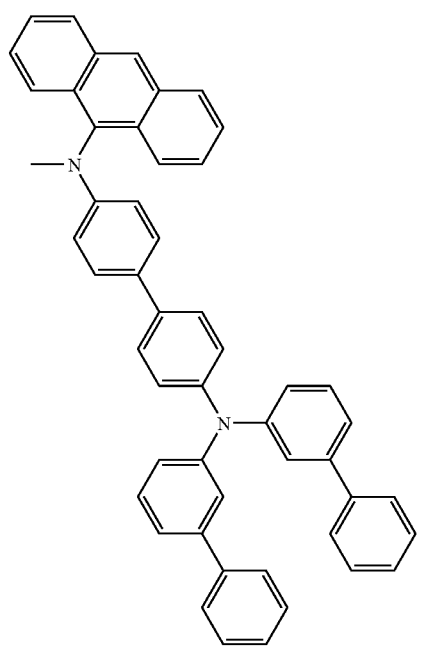
465
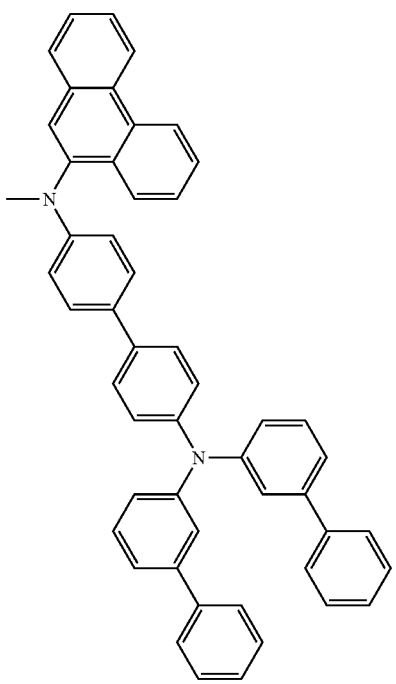
467

403
-continued
468
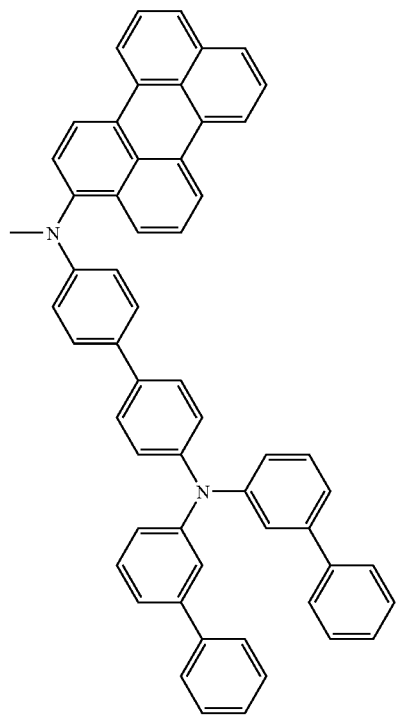
469
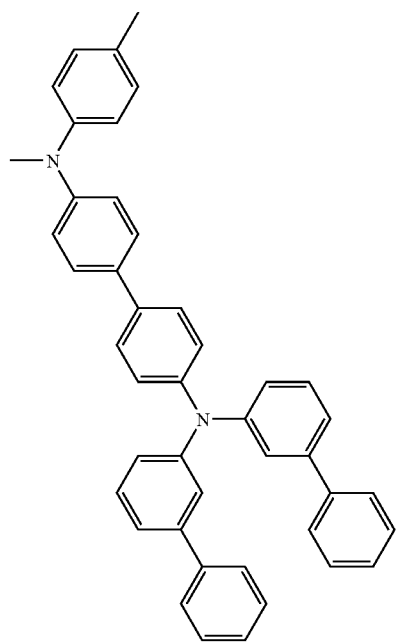
404
-continued
470
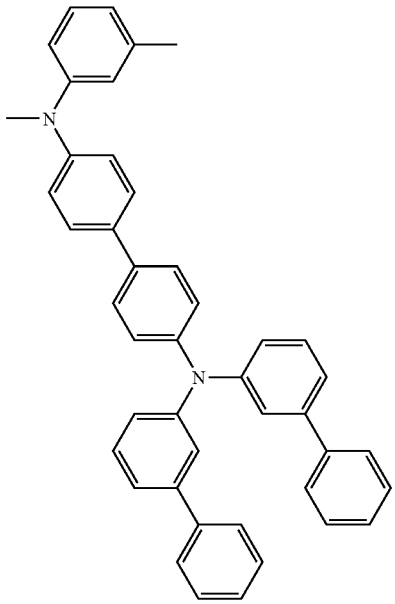
471
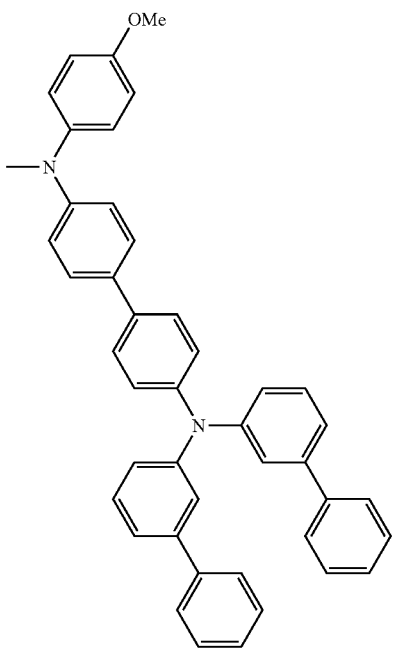

405
-continued
472
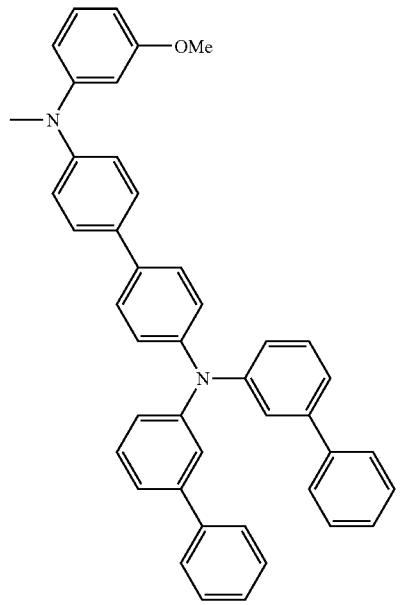
473
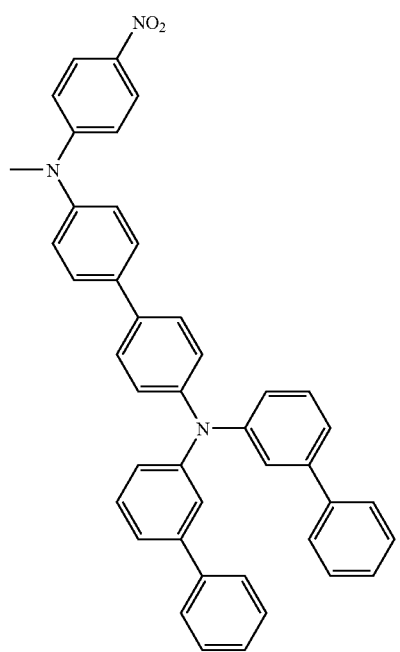
406
-continued
474
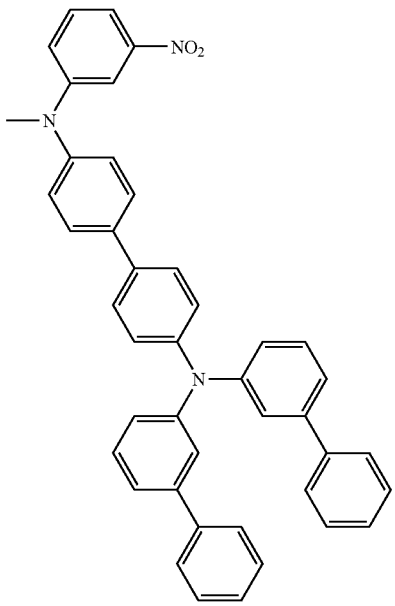
475
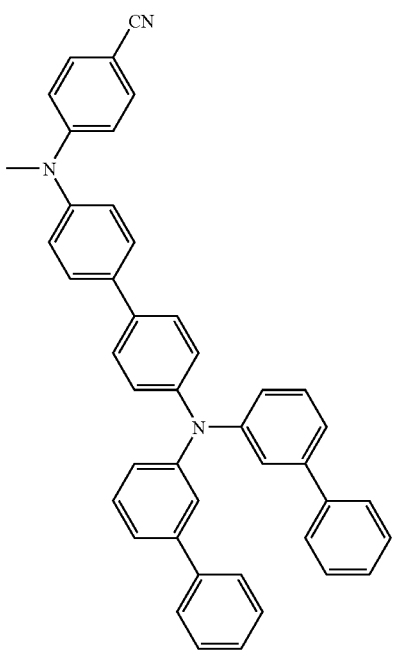

407
-continued
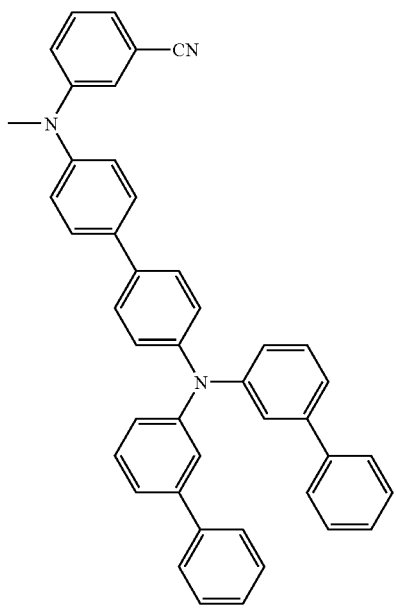
476
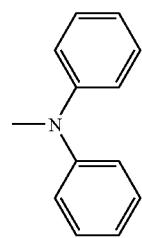
477
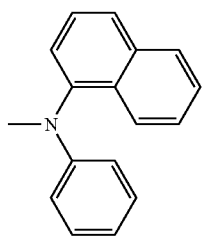
478
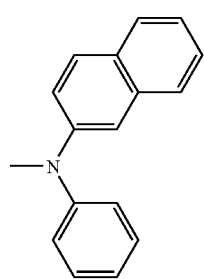
479
408
-continued
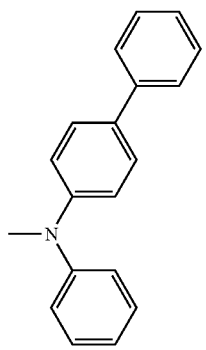
480
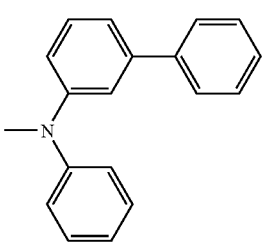
481
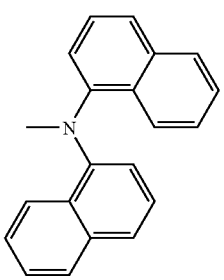
482
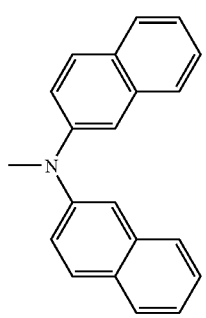
483
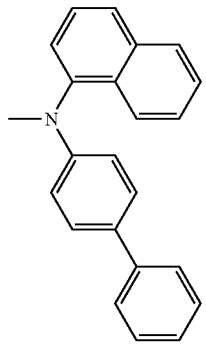
484

409
-continued
485
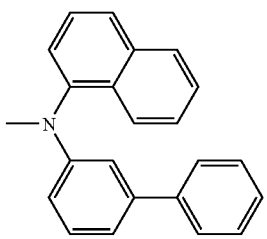
486
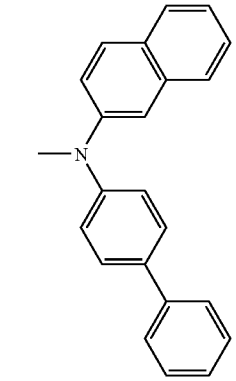
487
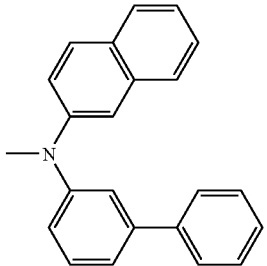
488
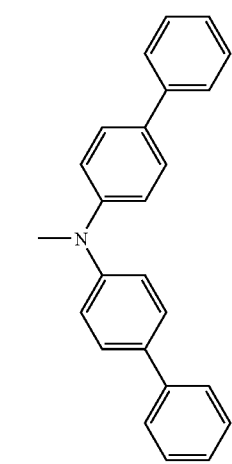
410
-continued
489
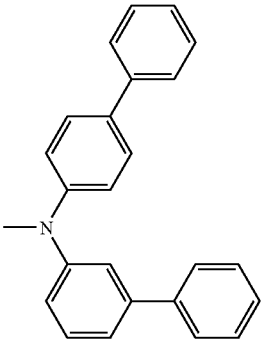
490
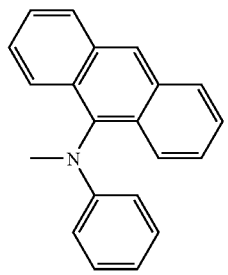
491
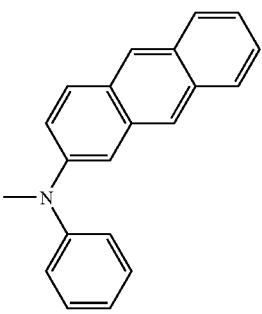
492
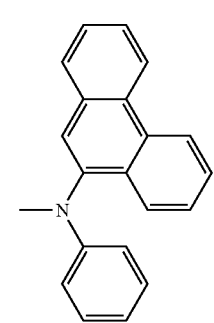
493
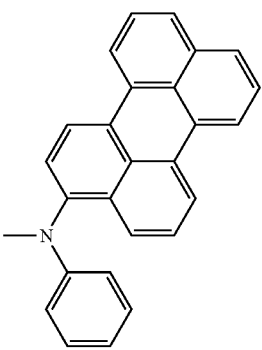

| | | | |
|---|---|---|---|
| 494 | 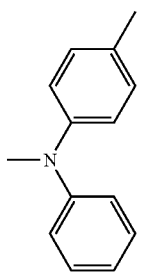 | 499 | 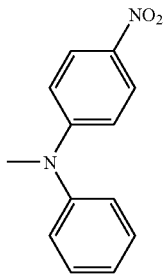 |
| 495 | 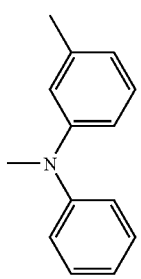 | 500 | 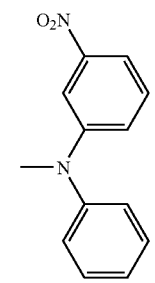 |
| 496 | 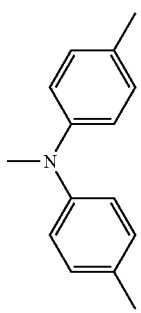 | 501 | 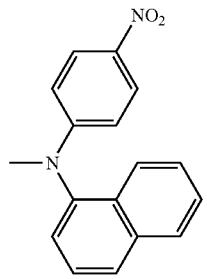 |
| 497 | 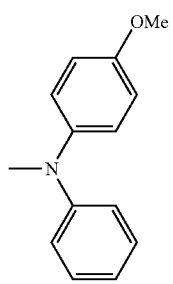 | 502 | 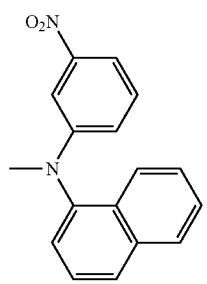 |
| 498 | 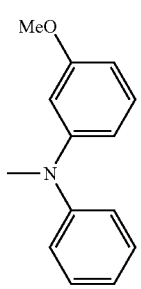 | 503 | 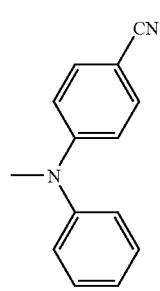 |

| 504 | 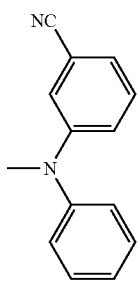 | 509 | 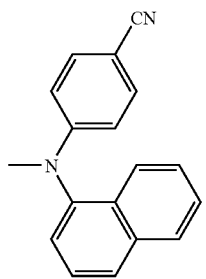 |
| 505 | 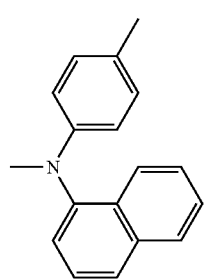 | 510 | 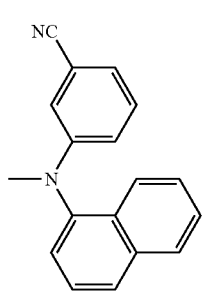 |
| 506 | 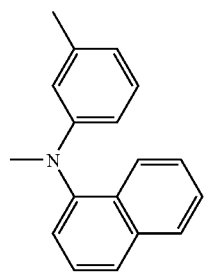 | 511 | 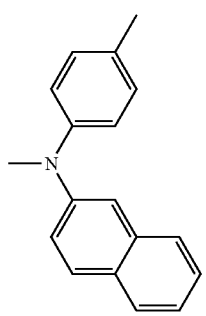 |
| 507 | 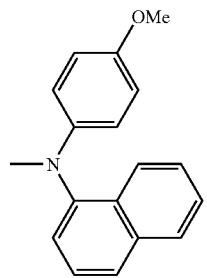 | 512 | 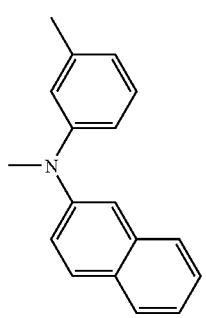 |
| 508 | 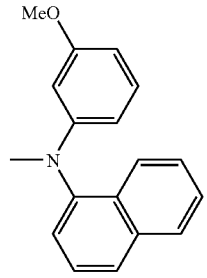 | 513 | 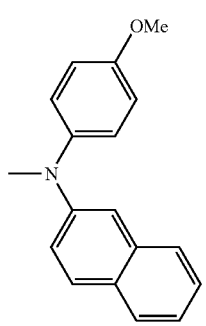 |

415
-continued
514
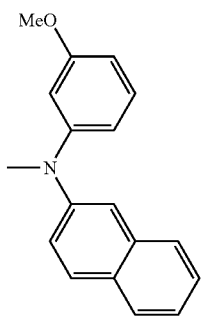
515
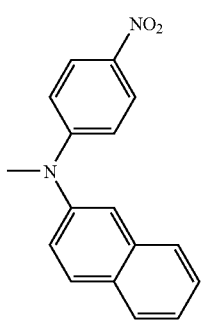
516
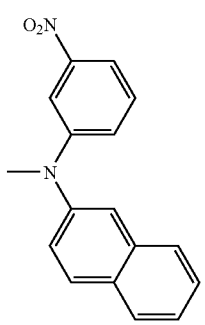
517
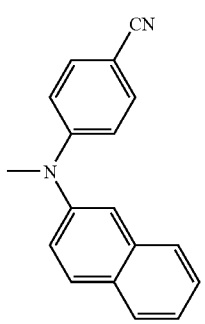
518
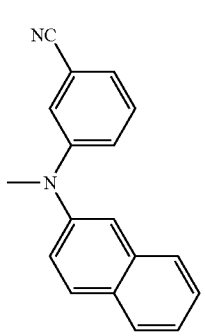
416
-continued
519
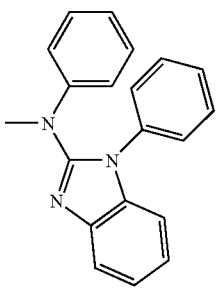
520
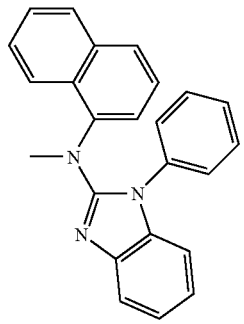
521
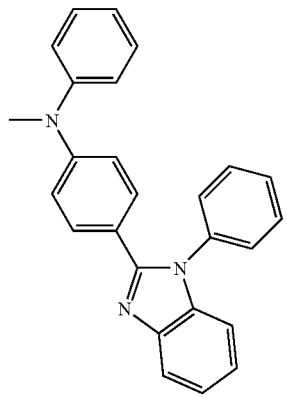
522
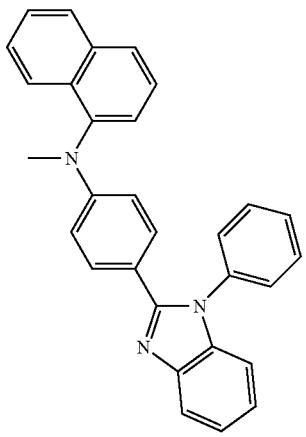

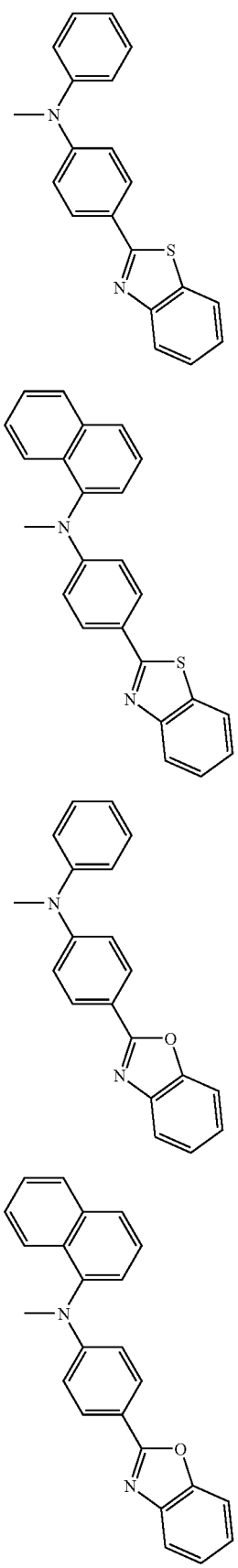
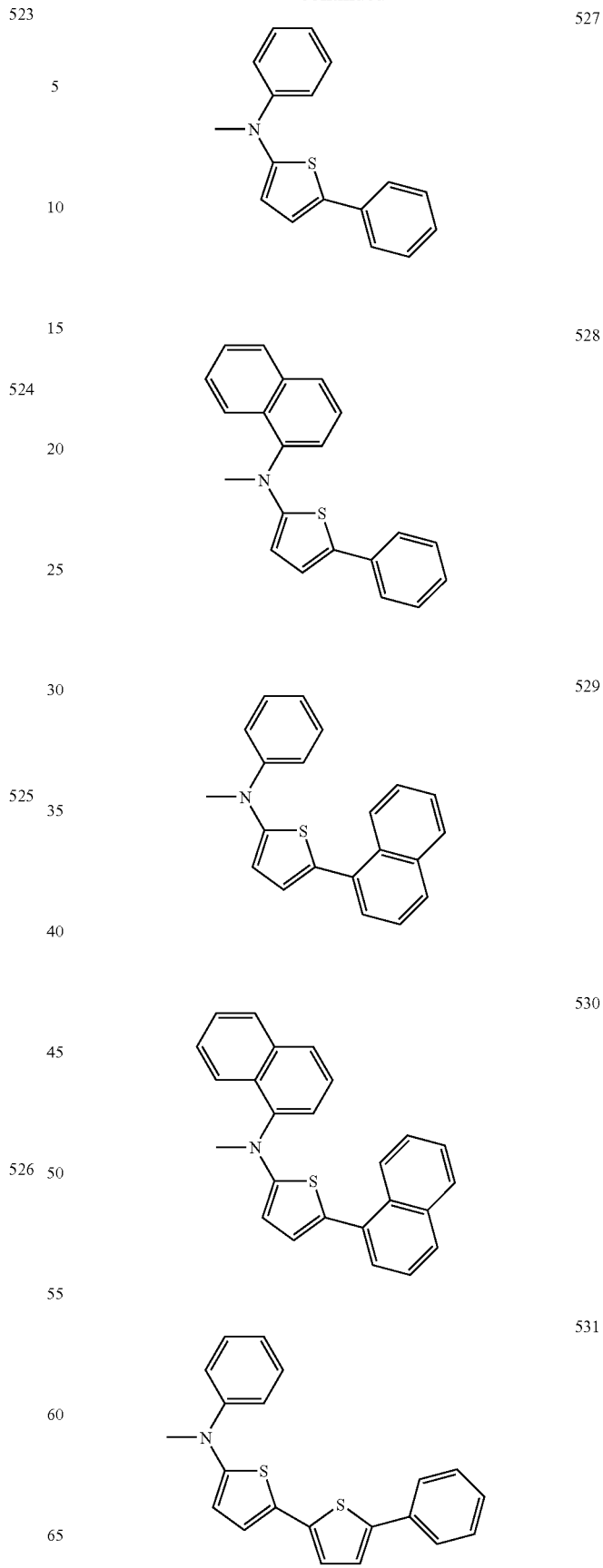

419
-continued

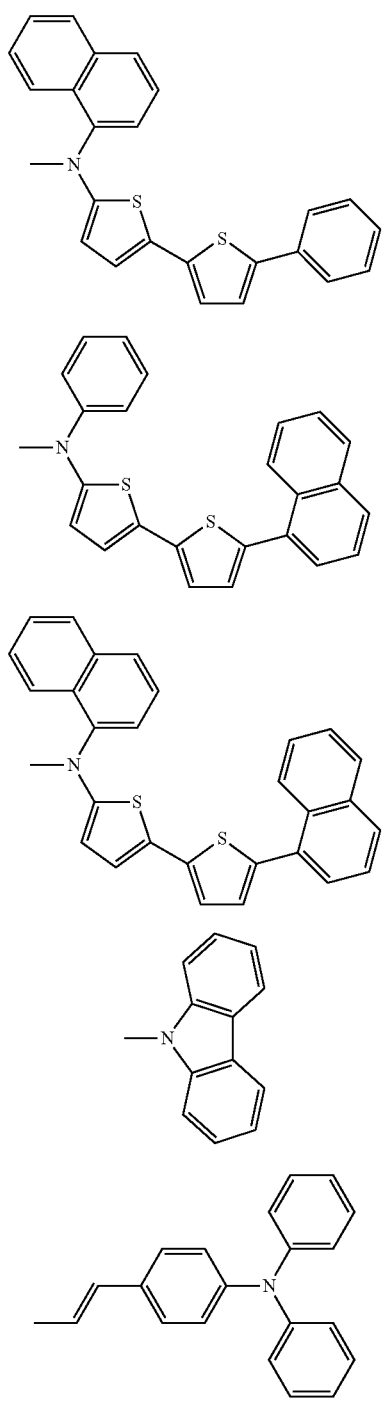

420
-continued

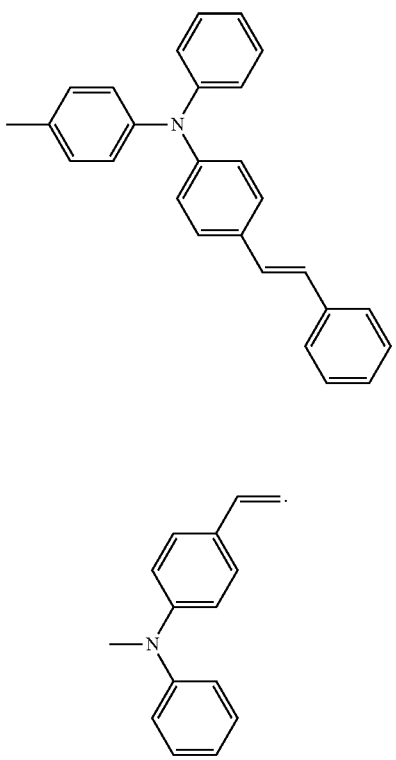

13. An organic light emitting diode comprising a first electrode, at least one organic material layer, and a second electrode, wherein the first electrode, the organic material layer(s), and the second electrode form a layered structure and at least one layer of the organic material layers comprises the compound of claim 1.

14. The organic light emitting diode according to claim 13, wherein the organic material layer comprises a hole transport layer, and the hole transport layer contains the compound.

15. The organic light emitting diode according to claim 13, wherein the organic material layer comprises a hole injection layer, and the hole injection layer contains the compound.

16. The organic light emitting diode according to claim 13, wherein the organic material layer comprises a hole injection and transport layer, and the hole injection and transport layer contains the compound.

* * * * *